US011786589B2

(12) United States Patent
Jiang et al.

(10) Patent No.: US 11,786,589 B2
(45) Date of Patent: Oct. 17, 2023

(54) HUMAN ROTAVIRUS STRAINS AND VACCINES

(71) Applicant: THE UNITED STATES OF AMERICA, as represented by the Secretary, Department of Health and Human Services, Bethesda, MD (US)

(72) Inventors: Baoming Jiang, Duluth, GA (US); Roger I. Glass, Atlanta, GA (US); Yuhuan Wang, Liburn, GA (US); Jon Gentsch, Atlanta, GA (US)

(73) Assignee: The United States of America, as Represented by the Secretary, Department of Health and Human Services, Bethesda, MD (US)

( * ) Notice: Subject to any disclaimer, the term of this patent is extended or adjusted under 35 U.S.C. 154(b) by 302 days.

(21) Appl. No.: 17/349,639

(22) Filed: Jun. 16, 2021

(65) Prior Publication Data

US 2021/0308254 A1 Oct. 7, 2021

Related U.S. Application Data

(60) Division of application No. 16/672,168, filed on Nov. 1, 2019, now Pat. No. 11,065,327, which is a continuation of application No. 15/956,662, filed on Apr. 18, 2018, now Pat. No. 10,500,269, which is a continuation of application No. 15/200,837, filed on Jul. 1, 2016, now Pat. No. 9,974,851, which is a continuation of application No. 14/461,663, filed on Aug. 18, 2014, now Pat. No. 9,498,526, which is a continuation of application No. 13/320,095, filed as application No. PCT/US2010/034537 on May 12, 2010, now Pat. No. 8,822,192.

(60) Provisional application No. 61/177,393, filed on May 12, 2009.

(51) Int. Cl.

| | |
|---|---|
| *A61K 39/15* | (2006.01) |
| *A61K 39/12* | (2006.01) |
| *C07K 16/10* | (2006.01) |
| *C07K 14/005* | (2006.01) |
| *C12N 7/00* | (2006.01) |
| *A61K 39/00* | (2006.01) |

(52) U.S. Cl.

CPC .............. *A61K 39/15* (2013.01); *A61K 39/12* (2013.01); *C07K 14/005* (2013.01); *C07K 16/10* (2013.01); *C12N 7/00* (2013.01); *A61K 2039/5252* (2013.01); *A61K 2039/5254* (2013.01); *A61K 2039/54* (2013.01); *A61K 2039/545* (2013.01); *A61K 2039/55505* (2013.01); *C12N 2720/12334* (2013.01); *C12N 2720/12361* (2013.01)

(58) Field of Classification Search

None

See application file for complete search history.

(56) References Cited

U.S. PATENT DOCUMENTS

| | | | |
|---|---|---|---|
| 5,474,773 | A | 12/1995 | Ward |
| 5,626,851 | A | 5/1997 | Clark et al. |
| 5,695,767 | A | 12/1997 | Ward |
| 5,750,109 | A | 5/1998 | Clark et al. |
| 5,773,009 | A | 6/1998 | Glass et al. |
| 6,113,910 | A | 9/2000 | Clark et al. |
| 6,290,968 | B1 | 9/2001 | Clark et al. |
| 6,506,385 | B1 | 1/2003 | Poston et al. |
| 6,616,931 | B1 | 9/2003 | Burke et al. |
| 6,673,355 | B1 | 1/2004 | Estes et al. |
| 6,780,630 | B1 | 8/2004 | Estes et al. |
| 7,150,984 | B2 | 12/2006 | Hoshino et al. |
| 8,822,192 | B2 | 9/2014 | Jiang et al. |
| 2002/0058043 | A1 | 5/2002 | Hoshino et al. |
| 2003/0166139 | A1 | 9/2003 | Choi et al. |
| 2004/0009187 | A1 | 1/2004 | Choi et al. |
| 2005/0048083 | A1 | 3/2005 | Colau et al. |
| 2007/0276130 | A1 | 11/2007 | Dormitzer et al. |

FOREIGN PATENT DOCUMENTS

| | | |
|---|---|---|
| CA | 2379196 | 2/2001 |
| WO | WO-1996/01651 | 1/1996 |
| WO | WO-200006196 | 2/2000 |
| WO | WO-2004/009115 | 1/2004 |
| WO | WO-2006/087205 | 8/2006 |
| WO | WO-2007008905 | 1/2007 |
| WO | WO-2009032913 | 3/2009 |

OTHER PUBLICATIONS

Bernstein, D. et al., Second-Year Follow-up Evaluation of Live, Attenuated Human Rotavirus Vaccine 89-12 in Healthy infants, *The Journal of infectious Diseases*, 186:1487-9, Nov. 15, 2002.

Crawford, S. et al., Characterization of Virus-Like Particles Produced by the Expression of Rotavirus Capsid Proteins in Insect Cells, *Journal of Virology*, 68(9): 5945-52, Sep. 1994.

Mascarenhas, J., Rotavirus G Serotypes and P□,G Genotypes Identified in Cases of Reinfection Among Children Participating in a Trial with Rhesus-human Reassortant Tetravalent Vaccine (RRV-TV) in Belem, Brazil, *Journal of Tropical Pediatrics*, 48(2): 93-97, 2002 (Abstract).

Esona, M. et al., Molecular characterization of human rotavirus vaccine strain CDC-9 during sequential passages in Vero cells, *Human Vaccines*, 6(3): 247-53, 2009.

(Continued)

*Primary Examiner* — Stacy B Chen

(74) *Attorney, Agent, or Firm* — Klarquist Sparkman, LLP

(57) ABSTRACT

A vaccine composition and method of vaccination are provided useful for immunizing a subject against a rotavirus. The vaccines include rotavirus strains CDC-9 and CDC-66, fragments thereof, homologues thereof, or combinations thereof. Inventive vaccines may include a fragment of CDC-9, CDC-66, homologues thereof, or combinations thereof. Methods of inducing an immunological response are provided by administering an inventive vaccine.

20 Claims, 7 Drawing Sheets

Specification includes a Sequence Listing.

(56) References Cited

OTHER PUBLICATIONS

Gentsch, J. et al., Serotype Diversity and Reassortment between Human and Animal Rotavirus Strains: Implications for Rotavirus Vaccine Programs, *Journal of Infectious Diseases*, Suppl. 1, 192: S146-159, 2005.
Gentsch, J. et al., G and P Types of Circulating Rotavirus Strains in the United States during 1996-2005: Nine Years of Prevaccine Data, *Journal of Infectious Diseases*, 200: S99-105, 2009.
Gerna, G. et al., Rapid Serotyping of Human Rotavirus Strains by Solid-Phase Immune Electronic Microscopy, *Journal of Clinical Microbiology*, 19(2): 273-78, Feb. 1984.
Glass, R., New Hope for Defeating Rotavirus, *Scientific American*, 294: 46-55, 2006.
Glass, R. et al., Rotavirus vaccines: past, present, and future, *Archives de pediatrie*, 12: 844-47, 2005.
Glass, R. et al., Rotavirus vaccines: current prospects and future challenges, *The Lancet*, 368: 323-32, 2006.
Jiang, B., Information for Keystone Meeting, Keystone Symposia: Malnutrition, Gut-microbial Interactions for Mucosal Immunity to Vaccines, New Delhi, India, Nov. 2011.
Jiang, B. et al., Immunogenicity of a thermally inactivated rotavirus vaccine in mice, Human Vaccines, 4(2): 143-47, Mar./Apr. 2008.
Jiang, B. et al., Inactivated rotavirus vaccines: A priority for accelerated vaccine development, Vaccine, 26: 6754-58, 2008.
Jiang, B., Should we consider non live-oral rotavirus vaccines?, Presented at the 9th International Rotavirus Symposium, Johannesburg, South Africa, Aug. 2010 (abstract).
Jiang, B. et al., Inactivated Rotavirus Vaccine: An Update and Pathway Forward, The 6th International Conference on Vaccines for Enteric Diseases, Cannes, France, Sep. 2011 (abstract).
Jiang, B., Vaccination against rotavirus using microneedles, Skin Vaccination Summit, Washington, D.C., Oct. 2011 (abstract).
Jiang, B. et al., The Role of Serum Antibodies in the Protection against Rotavirus Disease: An Overview, *Clinical Infectious Diseases*, 34(10): 1351-61, May 15, 2002.
Jiang, B. et al., Synthesis of Rotavirus-Like Particles in Insect Cells: Comparative and Quantitative Analysis, *Biotechnology and Bioengineering*, 60(3): 369-74, Nov. 5, 1998.
Jiang, B. et al., Heterotypic protection from rotavirus infection in mice vaccinated with virus-like particles, *Vaccine*, 17:1005-13, 1999.
Jiang, B. et al., Rotavirus vaccines for global use, *Human Vaccines*, 6(5): 1-3, May 2010.
Jiang, B. et al., Parenteral Rotavirus Vaccines, Chinese Journal of Vaccines and Immunization, 11:77-79, 2005.
Jiang, B. et al., Dose sparing of and enhanced immune response to inactivated rotavirus vaccine by skin vaccination using microneedles in mice, presented at Microneedles 2012, Cork, Ireland, May 2012 (Abstract).
Kapikian, Z., A rotavirus vaccine for prevention of severe diarrhoea of infants and young children: development, utilization and withdrawal, Novaritis Found Symp, 238:153-71, 2001.
Leite, J. et al., Rotavirus G and P types circulating in Brazil: characterization by RT-PCR, probe hybridization, and sequence analysis, Arch Virol, 141(12): 2365-74, 1996 (Abstract).
Linhares, A. et al., Efficacy and safety of an oral live attenuated human rotavirus vaccine against rotavirus gastroenteritis during the first 2 years of life in Latin American infants: a randomised, double-blind, placebo-controlled phase III study, The Lancet, 371(9619): 1181-89, Apr. 5, 2008.
Moon, S. et al., Inhibitory Effect of Breast Milk on Infectivity of Live Oral Rotavirus Vaccines, The Pediatric Infectious Disease Journal, 29(10): 919-23, Oct. 2010.
O'Mahony, J. et al., VP4 and VP7 genotyping of rotavirus samples recovered from infected children in Ireland over a 3-year period, J Clin Microbiol, 37(6): 1699-1703. Jun. 1999 (Abstract).
Patel, M. et al., Oral Rotavirus Vaccines: How Well Will They Work Where They are Needed Most?, Journal of Infectious Diseases, 200 (Supp 1), S39-48, 2009.
Rahman et al., "Evolutionary history and global spread of the emerging g12 human rotaviruses," *Journal of Virology* 81(5): 2382-2390 (Epub Dec. 13, 2006).
Phua, K. et al., Evaluation of RIX4414, a live, attenuated rotavirus vaccine, in a randomized, double-blind, placebo-controlled phase 2 trial involving 2464 Singaporean infants, *J Infect Dis*, 192, Suppl 1: S1-5, Sep. 1, 2005 (Abstract).
Pichichero, E. et al., A comparative evaluation of the safety and immunogenicity of a single dose of unbuffered oral rhesus rotavirus serotype 3, rhesus/human reassortant serotypes 1,2 and 4 and combined (tetravalent) vaccines in healthy infants, *Vaccine*, 11(7): 747-53, 1993 (Abstract).
Piec, T. et al., Sequence comparison of the VP7 of serotype G2 rotaviruses from diverse geographical locations, DNA Seq, 9(5-6): 369-73, 1998.
Ruiz-Palacios, G. et al., Safety and Efficacy of an Attenuated Vaccine against Severe Rotavirus Gastroenteritis, 354(1): 11-22, Jan. 5, 2006.
Santos, N. et al., Global distribution of rotavirus serotypes/genotypes and its implication for the development and implementation of an effective rotavirus vaccine, Reviews in Medical Virology, 15(1): 29-56. 2005.
Vesikari, T. et al., Safety and Efficacy of a Pentavalent Human-Bovine (WC3) Reassortment Rotavirus Vaccine, The New England Journal of Medicine, 354: 23-33, Jan. 5, 2006.
Wang, Y. et al., Dose sparing of and enhanced immune response to inactivated rotavirus vaccine by skin vaccination using a microneedle patch in mice, The 6th International Conference on Vaccines for Enteric Diseases, Cannes, France, Sep. 2011 (Abstract).
Wang, Y. et al., Inactivated rotavirus vaccine induces protective immunity in gnotobiotic piglets, Vaccine, 28, S432-36, 2010.
Westerman, L. et al., Serum IgG mediates mucosal immunity against rotavirus infection, PNAS, 102(20): 7268-73, May 17, 2005.
Xu, J. et al., Serum Antibody Responses in Children with Rotavirus Diarrhea Can Serve as Proxy for Protection, Clinical and Diagnostic Laboratory Immunology, 12(2): 273-79, Feb. 2005.
Zeng, C. et al., Characterization and Replicase Activity of Double-Layered and Single-Layered Rotavirus-Like Particles Expressed from Baculovirus Recombinants, Journal of Virology, 70(5): 2736-42, May 1996.
(Author unknown) Suspension of rotavirus vaccine after reports of intussusception—United States, 1999, Centers for Disease Control and Prevention (CDC), Erratum in MMWR Morb Mortal Wkly Rep, 53(37): 879, Sep. 24, 2004.
(Author unknown) Erratum in MMWR Morb Mortal Wkly Rpt, 53(37): 786-9, Sep. 3, 2004, Suspension of rotavirus vaccine after reports of intussusception—United States, 1999.
Lytle, C. et al., Predicted Inactivation of Viruses of Relevance to Biodefense by Solar Radiation, *Journal of Virology*, 79(22): 14244-14252, Nov. 2005.
Moe, K. et al., The Effects of Relative Humidity and Temperature on the Survival of Human Rotavirus in Faeces, *Archives of Virology*, 72:179-186, 1982.
Wu, H. et al., Serological and genomic characterization of human rotaviruses detected in China, *Journal of Medical Virology*, 55(2): 168-176, Jun. 1998.
GenBank Accession No. BAB83820.1, Human rotavirus A NS-5, Mar. 12, 2003.
International Search Report and Written Opinion from parent PCT Application No. PCT/US2010/034537 11 pages (dated Apr. 27, 2011).

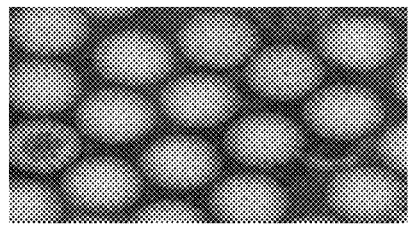
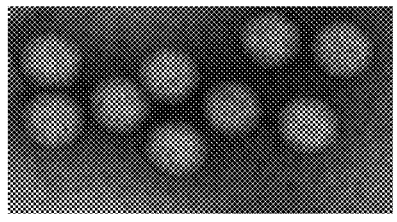
FIG. 1A　　　　　　FIG. 1B
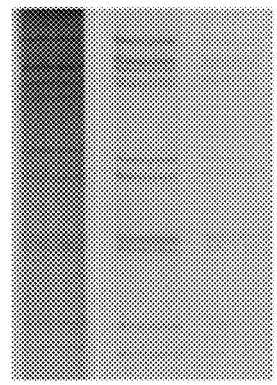
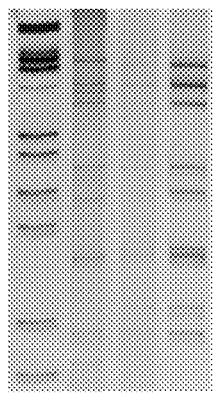
FIG. 2　　　　　　FIG. 3

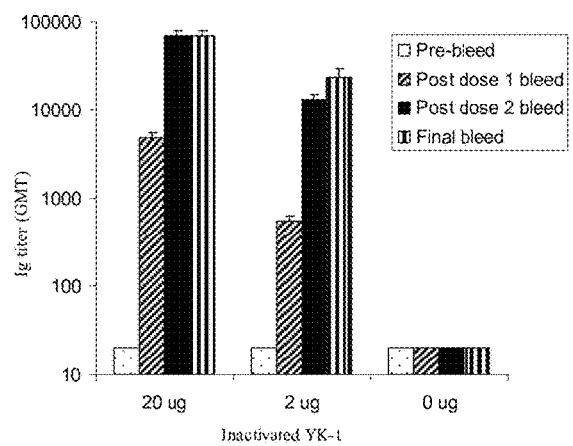 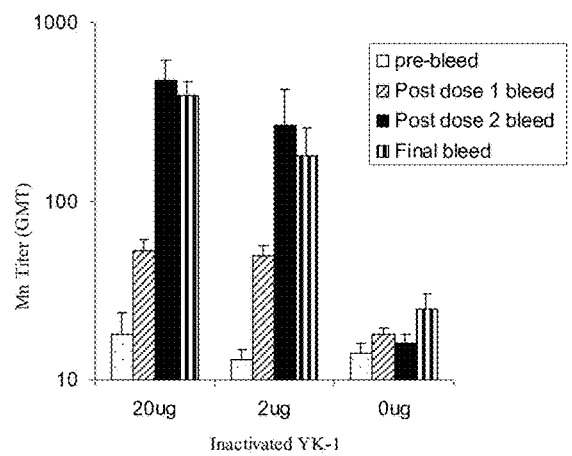
FIG. 5A  FIG. 5B
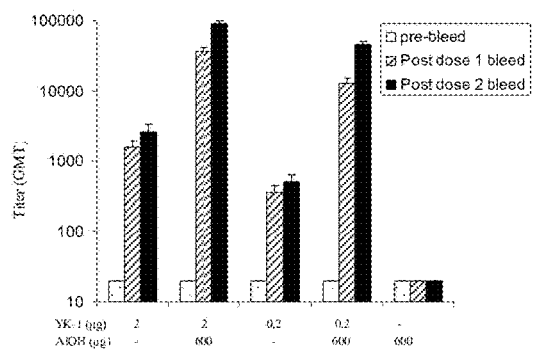
FIG. 6

SEQUENCE LISTING

```
<160> NUMBER OF SEQ ID NOS: 132

<210> SEQ ID NO 1
<211> LENGTH: 486
<212> TYPE: PRT
<213> ORGANISM: Human rotavirus

<400> SEQUENCE: 1

Met Ala Thr Phe Lys Asp Ala Cys Tyr Tyr Lys Arg Ile Asn Lys
1               5                   10                  15

Leu Asn His Ala Val Leu Lys Leu Gly Val Asn Asp Thr Trp Arg Pro
                20                  25                  30

Ser Pro Pro Thr Lys Tyr Lys Gly Trp Cys Leu Asp Cys Cys Gln His
            35                  40                  45

Thr Asp Leu Thr Tyr Cys Arg Gly Cys Thr Met Tyr His Val Cys Gln
        50                  55                  60

Trp Cys Ser Gln Tyr Asp Arg Cys Phe Leu Asp Asn Gln Pro His Leu
65                  70                  75                  80

Leu Arg Met Arg Thr Phe Lys Asn Glu Val Thr Lys Asn Asp Leu Met
                85                  90                  95

Asn Leu Ile Asp Met Tyr Asn Ile Leu Phe Pro Ile Asn Gln Arg Ile
                100                 105                 110

Val Asp Lys Phe Ile Ser Ser Thr Arg Gln His Lys Cys Arg Asn Glu
            115                 120                 125

Cys Met Thr Gln Trp Tyr Asn His Leu Leu Met Pro Ile Thr Leu Gln
        130                 135                 140

Ser Leu Ser Ile Glu Leu Asp Gly Asp Val Tyr Tyr Val Phe Gly Tyr
145                 150                 155                 160

Tyr Asp Ser Met Arg Asp Ile Asn Gln Thr Pro Phe Ser Phe Thr Asn
                165                 170                 175

Leu Ile Asp Met Tyr Asp Lys Leu Leu Leu Asp Asn Val Asn Phe Asn
                180                 185                 190
```

```
Arg Met Ser Phe Leu Pro Val Ala Leu Gln Gln Glu Tyr Ala Leu Arg
            195                 200                 205

Tyr Phe Ser Lys Ser Arg Phe Ile Ser Glu Lys Arg Lys Cys Ile Ser
210                 215                 220

Asp Leu His Phe Ser Thr Asn Val Ile Glu Asn Leu His Asn Pro Ser
225                 230                 235                 240

Phe Lys Ile Gln Ile Thr Arg Asn Cys Ser Glu Leu Ser Ser Asp Trp
            245                 250                 255

Asn Gly Ala Cys Lys Leu Val Lys Asp Met Ser Thr Tyr Phe Asn Val
                260                 265                 270

Leu Lys Thr Ser His Ile Glu Phe Tyr Ser Ile Ser Thr Arg Cys Arg
            275                 280                 285

Met Phe Thr Gln His Lys Leu Lys Ile Ala Ser Lys His Ile Lys Pro
290                 295                 300

Asn Tyr Val Thr Ser Asn His Arg Thr Ser Ala Thr Glu Val His Asn
305                 310                 315                 320

Cys Lys Trp Cys Ser Ile Asn Asn Gly Tyr Thr Val Trp Asn Asp Phe
                325                 330                 335

Arg Ile Lys Lys Ile Tyr Asp Asn Ile Phe Asn Phe Leu Arg Ala Leu
            340                 345                 350

Val Lys Ser Asn Ser Asn Ile Gly His Cys Ser Ser Gln Glu Lys Ile
            355                 360                 365

Tyr Glu His Ile Lys Asp Val Leu Asp Val Cys Asp Asp Glu Lys Trp
            370                 375                 380

Lys Met Ala Val Ala Glu Ile Phe Asn Cys Leu Glu Pro Val Glu Leu
385                 390                 395                 400

Asp Thr Val Lys Tyr Val Leu Phe Asn His Glu Val Asn Trp Asp Val
                405                 410                 415

Ile Asn Leu Leu Val Gln Ser Val Gly Lys Val Pro Gln Ile Leu Thr
            420                 425                 430

Leu Asn Asp Ile Ile Ile Ile Met Lys Ser Ile Ile Tyr Glu Trp Phe
            435                 440                 445

Asp Ile Arg Tyr Met Arg Asn Thr Pro Met Thr Thr Phe Thr Val Asp
450                 455                 460

Lys Leu Arg Gln Leu Cys Thr Gly Val Lys Thr Val Asp Tyr Asp Ser
465                 470                 475                 480

Gly Ile Ser Asp Val Glu
            485

<210> SEQ ID NO 2
<211> LENGTH: 486
<212> TYPE: PRT
<213> ORGANISM: Human rotavirus

<400> SEQUENCE: 2

Met Ala Thr Phe Lys Asp Ala Cys Tyr Tyr Lys Arg Ile Asn Lys
1               5                   10                  15

Leu Asn His Ala Val Leu Lys Leu Gly Val Asn Asp Thr Trp Arg Pro
                20                  25                  30

Ser Pro Pro Thr Lys Tyr Lys Gly Trp Cys Leu Asp Cys Cys Gln His
            35                  40                  45

Thr Asp Leu Thr Tyr Cys Arg Gly Cys Thr Met Tyr His Val Cys Gln
        50                  55                  60

Trp Cys Ser Gln Tyr Asp Arg Cys Phe Leu Asp Ser Gln Pro His Leu
65                  70                  75                  80
```

```
Leu Arg Met Arg Thr Phe Lys Asn Glu Val Thr Lys Asn Asp Leu Met
                85                  90                  95

Asn Leu Ile Asp Met Tyr Asn Ile Leu Phe Pro Ile Asn Gln Arg Ile
            100                 105                 110

Val Asp Lys Phe Ile Ser Ser Thr Arg Gln His Lys Cys Arg Asn Glu
            115                 120                 125

Cys Met Thr Gln Trp Tyr Asn His Leu Leu Met Pro Ile Thr Leu Gln
130                 135                 140

Ser Leu Ser Ile Glu Leu Asp Gly Asp Val Tyr Tyr Val Phe Gly Tyr
145                 150                 155                 160

Tyr Asp Ser Met Arg Asp Ile Asn Gln Thr Pro Phe Ser Phe Thr Asn
                165                 170                 175

Leu Ile Asp Met Tyr Asp Lys Leu Leu Leu Asp Asn Val Asn Phe Asn
            180                 185                 190

Arg Met Ser Phe Leu Pro Val Ala Leu Gln Gln Glu Tyr Ala Leu Arg
            195                 200                 205

Tyr Phe Ser Lys Ser Arg Phe Ile Ser Glu Lys Arg Lys Cys Ile Ser
210                 215                 220

Asp Leu His Phe Ser Thr Asn Val Ile Glu Asn Leu His Asn Pro Ser
225                 230                 235                 240

Phe Lys Ile Gln Ile Thr Arg Asn Cys Ser Glu Leu Ser Ser Asp Trp
                245                 250                 255

Asn Gly Ala Cys Lys Leu Val Lys Asp Met Ser Thr Tyr Phe Asn Val
            260                 265                 270

Leu Lys Thr Ser His Ile Glu Phe Tyr Ser Ile Ser Thr Arg Cys Arg
            275                 280                 285

Met Phe Thr Gln His Lys Leu Lys Ile Ala Ser Lys His Ile Lys Pro
290                 295                 300

Asn Tyr Val Thr Ser Asn His Arg Thr Ser Ala Thr Glu Val His Asn
305                 310                 315                 320

Cys Lys Trp Cys Ser Ile Asn Asn Gly Tyr Thr Val Trp Asn Asp Phe
                325                 330                 335

Arg Ile Lys Lys Ile Tyr Asp Asn Ile Phe Asn Phe Leu Arg Ala Leu
            340                 345                 350

Val Lys Ser Asn Ser Asn Ile Gly His Cys Ser Ser Gln Glu Lys Ile
            355                 360                 365

Tyr Glu His Ile Lys Asp Val Leu Asp Val Cys Asp Asp Glu Lys Trp
370                 375                 380

Lys Met Ala Val Ala Glu Ile Phe Asn Cys Leu Gly Pro Val Glu Leu
385                 390                 395                 400

Asp Thr Val Lys Tyr Val Met Phe Asn His Glu Val Asn Trp Asp Val
                405                 410                 415

Ile Asn Leu Leu Val Gln Ser Val Gly Lys Val Pro Gln Ile Leu Thr
            420                 425                 430

Leu Asn Asp Ile Ile Ile Ile Met Lys Ser Ile Ile Tyr Glu Trp Phe
            435                 440                 445

Asp Ile Arg Tyr Met Arg Asn Thr Pro Met Thr Thr Phe Thr Val Asp
450                 455                 460

Lys Leu Arg Gln Leu Cys Thr Gly Met Lys Thr Val Asp Tyr Asp Ser
465                 470                 475                 480

Gly Ile Ser Asp Val Glu
                485
```

```
<210> SEQ ID NO 3
<211> LENGTH: 486
<212> TYPE: PRT
<213> ORGANISM: Human rotavirus

<400> SEQUENCE: 3

Met Ala Thr Phe Lys Asp Ala Cys Tyr Tyr Lys Arg Ile Asn Lys
 1               5                  10                  15

Leu Asn His Ala Val Leu Lys Leu Gly Val Asn Asp Thr Trp Arg Pro
                20                  25                  30

Ser Pro Pro Thr Lys Tyr Lys Gly Trp Cys Leu Asp Cys Cys Gln His
                35                  40                  45

Thr Asp Leu Thr Tyr Cys Arg Gly Cys Thr Met Tyr His Val Cys Gln
 50                  55                  60

Trp Cys Ser Gln Tyr Asp Arg Cys Phe Leu Asp Ser Gln Pro His Leu
 65                  70                  75                  80

Leu Arg Met Arg Thr Phe Lys Asn Glu Val Thr Lys Asn Asp Leu Met
                85                  90                  95

Asn Leu Ile Asp Met Tyr Asn Ile Leu Phe Pro Ile Asn Gln Arg Ile
                100                 105                 110

Val Asp Lys Phe Ile Ser Ser Thr Arg Arg His Lys Cys Arg Asn Glu
                115                 120                 125

Cys Met Thr Gln Trp Tyr Asn His Leu Leu Met Pro Ile Thr Leu Gln
130                 135                 140

Ser Leu Ser Ile Glu Leu Asp Gly Asp Val Tyr Tyr Val Phe Gly Tyr
145                 150                 155                 160

Tyr Asp Ser Met Arg Asp Ile Asn Gln Thr Pro Phe Ser Phe Thr Asn
                165                 170                 175

Leu Ile Asp Met Tyr Asp Lys Leu Leu Leu Asp Asn Val Asn Phe Asn
                180                 185                 190

Arg Met Ser Phe Leu Pro Val Ala Leu Gln Gln Glu Tyr Ala Leu Arg
                195                 200                 205

Tyr Phe Ser Lys Ser Arg Phe Ile Ser Glu Lys Arg Lys Cys Ile Ser
                210                 215                 220

Asp Leu His Phe Ser Thr Asn Val Ile Glu Asn Leu His Asn Pro Ser
225                 230                 235                 240

Phe Lys Ile Gln Ile Thr Arg Asn Cys Ser Glu Leu Ser Ser Asp Trp
                245                 250                 255

Asn Gly Ala Cys Lys Leu Val Lys Asp Met Ser Thr Tyr Phe Asn Val
                260                 265                 270

Leu Lys Thr Ser His Ile Glu Phe Tyr Ser Ile Ser Thr Arg Cys Arg
                275                 280                 285

Met Phe Thr Gln His Lys Leu Lys Ile Ala Ser Lys His Ile Lys Pro
                290                 295                 300

Asn Tyr Val Thr Ser Asn His Arg Thr Ser Ala Thr Glu Val His Asn
305                 310                 315                 320

Cys Lys Trp Cys Ser Ile Asn Asn Gly Tyr Thr Val Trp Asn Asp Phe
                325                 330                 335

Arg Ile Lys Lys Ile Tyr Asp Asn Ile Phe Asn Phe Leu Arg Ala Leu
                340                 345                 350

Val Lys Ser Asn Ser Asn Ile Gly His Cys Ser Ser Gln Glu Lys Ile
                355                 360                 365

Tyr Glu His Ile Lys Asp Val Leu Asp Val Cys Asp Asp Glu Lys Trp
                370                 375                 380
```

```
Lys Met Ala Val Ala Glu Ile Phe Asn Cys Leu Gly Pro Val Glu Leu
385                 390                 395                 400

Asp Thr Val Lys Tyr Val Met Phe Asn His Glu Val Asn Trp Asp Val
                405                 410                 415

Ile Asn Leu Leu Val Gln Ser Val Gly Lys Val Pro Gln Ile Leu Thr
            420                 425                 430

Leu Asn Asp Ile Ile Ile Met Lys Ser Ile Ile Tyr Glu Trp Phe
        435                 440                 445

Asp Ile Arg Tyr Met Arg Asn Thr Pro Met Thr Thr Phe Thr Val Asp
    450                 455                 460

Lys Leu Arg Gln Leu Cys Thr Gly Met Lys Thr Val Asp Tyr Asp Ser
465                 470                 475                 480

Gly Ile Ser Asp Val Glu
                485

<210> SEQ ID NO 4
<211> LENGTH: 317
<212> TYPE: PRT
<213> ORGANISM: Human rotavirus

<400> SEQUENCE: 4

Met Ala Glu Leu Ala Cys Phe Cys Tyr Pro His Leu Glu Asn Asp Ser
1               5                   10                  15

Tyr Lys Phe Ile Pro Phe Asn Asn Leu Ala Ile Lys Cys Met Leu Thr
            20                  25                  30

Ala Lys Val Asp Lys Lys Asp Gln Asp Lys Phe Tyr Asn Ser Ile Ile
        35                  40                  45

Tyr Gly Ile Ala Pro Pro Pro Gln Phe Lys Lys Arg Tyr Asn Thr Asn
    50                  55                  60

Asp Asn Ser Arg Gly Met Asn Tyr Glu Thr Pro Met Leu Ile Lys Val
65                  70                  75                  80

Ala Ile Leu Ile Cys Glu Ala Leu Asn Ser Ile Lys Val Thr Gln Ser
                85                  90                  95

Asp Val Ala Asn Val Leu Ser Arg Val Val Ser Val Arg His Leu Glu
            100                 105                 110

Asn Leu Val Leu Arg Lys Glu Asn His Gln Asp Val Leu Phe His Ser
        115                 120                 125

Lys Glu Leu Leu Leu Lys Ser Val Leu Ile Ala Ile Gly Gln Ser Lys
    130                 135                 140

Glu Ile Glu Thr Thr Ala Thr Ala Glu Gly Gly Glu Ile Val Phe Gln
145                 150                 155                 160

Asn Val Ala Phe Thr Met Trp Lys Leu Thr Tyr Leu Asp His Lys Leu
                165                 170                 175

Met Pro Ile Leu Asp Gln Asn Phe Ile Glu Tyr Lys Ile Thr Met Asn
            180                 185                 190

Glu Asp Lys Pro Ile Ser Asp Val His Val Lys Glu Leu Ile Ala Glu
        195                 200                 205

Leu Arg Trp Gln Tyr Asn Arg Phe Ala Val Ile Thr His Gly Lys Gly
    210                 215                 220

His Tyr Arg Val Val Lys Tyr Ser Ser Val Ala Asn His Ala Asp Arg
225                 230                 235                 240

Val Phe Ala Thr Tyr Lys Asn Asn Ala Lys Ser Gly Asn Val Ile Asp
                245                 250                 255

Phe Asn Leu Leu Asp Gln Arg Ile Ile Trp Gln Asn Trp Tyr Ala Phe
```

```
                260                 265                 270
Thr Ser Ser Met Lys Gln Gly Phe Thr Leu Asp Val Cys Lys Lys Leu
            275                 280                 285

Leu Phe Gln Lys Met Lys Gln Glu Arg Asn Pro Phe Lys Gly Leu Ser
            290                 295                 300

Thr Asp Arg Lys Met Asp Glu Val Ser Arg Ile Gly Ile
305                 310                 315
```

<210> SEQ ID NO 5
<211> LENGTH: 317
<212> TYPE: PRT
<213> ORGANISM: Human rotavirus

<400> SEQUENCE: 5

```
Met Ala Glu Leu Ala Cys Phe Cys Tyr Pro His Leu Glu Asn Asp Ser
1               5                   10                  15

Tyr Lys Phe Ile Pro Phe Asn Asn Leu Ala Ile Lys Cys Met Leu Thr
                20                  25                  30

Ala Lys Val Asp Lys Lys Asp Gln Asp Lys Phe Tyr Asn Ser Ile Val
            35                  40                  45

Tyr Gly Ile Ala Pro Pro Gln Phe Arg Lys Arg Tyr Asn Thr Ser
50                  55                  60

Asp Asn Ser Arg Gly Met Asn Tyr Glu Thr Ile Met Phe Asn Lys Val
65                  70                  75                  80

Ala Ile Leu Ile Cys Glu Ala Leu Asn Ser Ile Lys Val Thr Gln Ser
                85                  90                  95

Glu Val Ala Asn Val Leu Ser Arg Val Val Ser Val Arg His Leu Glu
            100                 105                 110

Asn Leu Val Leu Arg Lys Glu Asn His Gln Asp Val Leu Phe His Ser
            115                 120                 125

Lys Glu Leu Leu Leu Lys Ser Val Leu Ile Ala Ile Gly Gln Ser Lys
            130                 135                 140

Glu Ile Glu Thr Thr Ala Thr Ala Glu Gly Gly Glu Ile Val Phe Gln
145                 150                 155                 160

Asn Ala Ala Phe Thr Met Trp Lys Leu Thr Tyr Leu Asp His Lys Leu
                165                 170                 175

Met Pro Ile Leu Asp Gln Asn Phe Ile Glu Tyr Lys Ile Thr Leu Asn
            180                 185                 190

Glu Asp Lys Pro Ile Ser Asp Val Cys Val Lys Glu Leu Val Ala Glu
            195                 200                 205

Leu Arg Trp Gln Tyr Asn Arg Phe Ala Val Ile Thr His Gly Lys Gly
            210                 215                 220

His Tyr Arg Val Val Lys Tyr Ser Ser Val Ala Asn His Ala Asp Arg
225                 230                 235                 240

Val Phe Ala Thr Tyr Lys Asn Asn Ala Lys Ser Gly Asn Thr Thr Asp
                245                 250                 255

Phe Asn Leu Leu Asp Gln Arg Ile Ile Trp Gln Asn Trp Tyr Ala Phe
            260                 265                 270

Thr Ser Ser Met Lys Gln Gly Asn Thr Ile Asp Val Cys Lys Lys Leu
            275                 280                 285

Leu Phe Gln Lys Met Lys Gln Glu Lys Asn Pro Phe Lys Gly Leu Ser
            290                 295                 300

Thr Asp Arg Lys Met Asp Glu Val Ser His Val Gly Ile
305                 310                 315
```

<210> SEQ ID NO 6
<211> LENGTH: 317
<212> TYPE: PRT
<213> ORGANISM: Human rotavirus

<400> SEQUENCE: 6

```
Met Ala Glu Leu Ala Cys Phe Cys Tyr Pro His Leu Glu Asn Asp Ser
1               5                   10                  15

Tyr Lys Phe Ile Pro Phe Asn Asn Leu Ala Ile Lys Cys Met Leu Thr
            20                  25                  30

Ala Lys Val Asp Lys Lys Asp Gln Asp Lys Phe Tyr Asn Ser Ile Val
        35                  40                  45

Tyr Gly Ile Ala Pro Pro Gln Phe Arg Lys Arg Tyr Asn Thr Ser
    50                  55                  60

Asp Asn Ser Arg Gly Met Asn Tyr Glu Thr Ile Met Phe Asn Lys Val
65                  70                  75                  80

Ala Ile Leu Ile Cys Glu Ala Leu Asn Ser Ile Lys Val Thr Gln Ser
                85                  90                  95

Glu Val Ala Asn Val Leu Ser Arg Val Val Ser Val Arg His Leu Glu
            100                 105                 110

Asn Leu Val Leu Arg Lys Glu Asn His Gln Asp Val Leu Phe His Ser
        115                 120                 125

Lys Glu Leu Leu Leu Lys Ser Val Leu Ile Ala Ile Gly Gln Ser Lys
    130                 135                 140

Glu Ile Glu Thr Thr Ala Thr Ala Glu Gly Gly Glu Ile Val Phe Gln
145                 150                 155                 160

Asn Ala Ala Phe Thr Met Trp Lys Leu Thr Tyr Leu Asp His Lys Leu
                165                 170                 175

Met Pro Ile Leu Asp Gln Asn Phe Ile Glu Tyr Lys Ile Thr Leu Asn
            180                 185                 190

Glu Asp Lys Pro Ile Ser Asp Val Cys Val Lys Glu Leu Val Ala Glu
        195                 200                 205

Leu Arg Trp Gln Tyr Asn Arg Phe Ala Val Ile Thr His Gly Lys Gly
    210                 215                 220

His Tyr Arg Val Val Lys Tyr Ser Ser Val Ala Asn His Ala Asp Arg
225                 230                 235                 240

Val Phe Ala Thr Tyr Lys Asn Asn Ala Lys Ser Gly Asn Thr Thr Asp
                245                 250                 255

Phe Asn Leu Leu Asp Gln Arg Ile Ile Trp Gln Asn Trp Tyr Ala Phe
            260                 265                 270

Thr Ser Ser Met Lys Gln Gly Asn Thr Ile Asp Val Cys Lys Lys Leu
        275                 280                 285

Leu Phe Gln Lys Met Lys Gln Glu Lys Asn Pro Phe Lys Gly Leu Ser
    290                 295                 300

Thr Asp Arg Lys Met Asp Glu Val Ser His Val Gly Ile
305                 310                 315
```

<210> SEQ ID NO 7
<211> LENGTH: 310
<212> TYPE: PRT
<213> ORGANISM: Human rotavirus

<400> SEQUENCE: 7

```
Met Glu Ser Thr Gln Gln Met Val Ser Ser Ile Ile Asn Thr Ser Phe
1               5                   10                  15
```

```
Glu Ala Ala Val Val Ala Ala Thr Ser Thr Leu Glu Leu Met Gly Ile
                20                  25                  30

Gln Tyr Asp Tyr Asn Glu Val Phe Thr Arg Val Lys Ser Lys Phe Asp
            35                  40                  45

Tyr Val Met Asp Asp Ser Gly Val Lys Asn Asn Leu Leu Gly Lys Ala
        50                  55                  60

Ile Thr Ile Gly Pro Ala Cys Asn Glu Lys Phe Gly Ser Ala Ile Arg
65                  70                  75                  80

Asn Arg Asn Trp Met Ile Asp Ser Lys Thr Val Ala Lys Leu Asp Glu
                85                  90                  95

Asp Val Asn Lys Leu Arg Met Thr Leu Ser Ser Lys Gly Ile Asp Gln
            100                 105                 110

Lys Met Arg Val Leu Asn Ala Cys Phe Ser Val Lys Arg Ile Pro Gly
        115                 120                 125

Lys Ser Ser Ile Ile Lys Cys Thr Arg Leu Met Lys Asp Lys Leu
130                 135                 140

Glu Arg Gly Glu Val Val Asp Asp Ser Tyr Val Asp Glu Lys Met
145                 150                 155                 160

Glu Ile Asp Thr Ile Asp Trp Lys Ser Arg Tyr Asp Gln Leu Glu Lys
                165                 170                 175

Arg Phe Glu Ser Leu Lys Gln Arg Val Asn Glu Lys Tyr Asn Ala Trp
            180                 185                 190

Val Gln Lys Ala Lys Lys Val Asn Glu Asn Met Tyr Ser Leu Gln Asn
        195                 200                 205

Val Ile Ser Gln Gln Gln Asn Gln Ile Ala Asp Leu Gln Gln Tyr Cys
210                 215                 220

Asn Lys Leu Glu Val Asp Leu Gln Gly Lys Phe Ser Ser Leu Val Ser
225                 230                 235                 240

Ser Val Glu Trp Tyr Leu Arg Ser Met Glu Leu Pro Asp Asp Val Lys
                245                 250                 255

Thr Asp Val Glu Gln Gln Leu Asn Ser Ile Asp Leu Ile Asn Pro Ile
            260                 265                 270

Gly Ala Ile Asp Asp Ile Glu Ser Leu Ile Arg Asn Leu Ile Gln Asp
        275                 280                 285

Tyr Asp Arg Thr Phe Leu Met Leu Lys Gly Leu Leu Lys Gln Cys Asn
290                 295                 300

Tyr Glu Tyr Ala Tyr Glu
305                 310

<210> SEQ ID NO 8
<211> LENGTH: 310
<212> TYPE: PRT
<213> ORGANISM: Human rotavirus

<400> SEQUENCE: 8

Met Glu Ser Thr Gln Gln Met Val Ser Ser Ile Ile Asn Thr Ser Phe
1               5                   10                  15

Glu Ala Ala Val Val Ala Ala Thr Ser Thr Leu Glu Leu Met Gly Ile
                20                  25                  30

Gln Tyr Asp Tyr Asn Glu Val Phe Thr Arg Val Lys Ser Lys Phe Asp
            35                  40                  45

Tyr Val Met Asp Asp Ser Gly Val Lys Asn Asn Leu Leu Gly Lys Ala
        50                  55                  60

Ile Thr Ile Asp Gln Ala Leu Asn Gly Lys Phe Gly Ser Ala Ile Arg
65                  70                  75                  80
```

```
Asn Arg Asn Trp Met Thr Asp Ser Lys Thr Val Ala Lys Leu Asp Glu
                85                  90                  95

Asp Val Asn Lys Leu Arg Met Thr Leu Ser Ser Lys Gly Ile Asp Gln
            100                 105                 110

Lys Met Arg Val Leu Asn Ala Cys Phe Ser Val Lys Arg Ile Pro Gly
        115                 120                 125

Lys Ser Ser Ser Ile Ile Lys Cys Thr Lys Leu Met Lys Asp Lys Ile
    130                 135                 140

Glu Arg Gly Glu Val Glu Val Asp Asp Ser Tyr Ile Asp Glu Lys Met
145                 150                 155                 160

Glu Ile Asp Thr Ile Asp Trp Lys Ser Arg Tyr Asp Gln Leu Glu Lys
                165                 170                 175

Arg Phe Glu Ser Leu Lys Gln Arg Val Thr Glu Lys Tyr Asn Thr Trp
            180                 185                 190

Val Gln Lys Ala Lys Lys Val Asn Glu Asn Met Tyr Ser Leu Gln Asn
        195                 200                 205

Val Ile Ser Gln Gln Gln Asn Gln Ile Ala Asp Leu Gln Gln Tyr Cys
    210                 215                 220

Asn Lys Leu Glu Thr Asp Leu Gln Gly Lys Phe Ser Ser Leu Val Ser
225                 230                 235                 240

Ser Val Glu Trp Tyr Leu Arg Ser Met Glu Leu Pro Asp Asp Val Lys
                245                 250                 255

Asn Asp Ile Glu Gln Gln Leu Asn Ser Ile Asp Leu Ile Asn Pro Ile
            260                 265                 270

Asn Ala Ile Asp Asp Ile Glu Ser Leu Val Arg Asn Leu Val Gln Asp
        275                 280                 285

Tyr Asp Arg Thr Phe Leu Met Leu Lys Gly Leu Leu Lys Gln Cys Asn
    290                 295                 300

Tyr Glu Tyr Val Tyr Glu
305                 310

<210> SEQ ID NO 9
<211> LENGTH: 310
<212> TYPE: PRT
<213> ORGANISM: Human rotavirus

<400> SEQUENCE: 9

Met Glu Ser Thr Gln Gln Met Val Ser Ser Ile Ile Asn Thr Ser Phe
1               5                   10                  15

Glu Ala Ala Val Val Ala Ala Thr Ser Thr Leu Glu Leu Met Gly Ile
            20                  25                  30

Gln Tyr Asp Tyr Asn Glu Val Phe Thr Arg Val Lys Ser Lys Phe Asp
        35                  40                  45

Tyr Val Met Asp Asp Ser Gly Val Lys Asn Asn Leu Leu Gly Lys Ala
    50                  55                  60

Ile Thr Ile Asp Gln Ala Leu Asn Gly Lys Phe Gly Ser Ala Ile Arg
65                  70                  75                  80

Asn Arg Asn Trp Met Thr Asp Ser Lys Thr Val Ala Lys Leu Asp Glu
                85                  90                  95

Asp Val Asn Lys Leu Arg Met Thr Leu Ser Ser Lys Gly Ile Asp Gln
            100                 105                 110

Lys Met Arg Val Leu Asn Ala Cys Phe Ser Val Lys Arg Ile Pro Gly
        115                 120                 125

Lys Ser Ser Ser Ile Ile Lys Cys Thr Lys Leu Met Lys Asp Lys Ile
```

```
                130             135             140
Glu Arg Gly Glu Val Glu Val Asp Asp Ser Tyr Ile Asp Glu Lys Met
145                 150                 155                 160

Glu Ile Asp Thr Ile Asp Trp Lys Ser Arg Tyr Asp Gln Leu Glu Lys
                165                 170                 175

Arg Phe Glu Ser Leu Lys Gln Arg Val Thr Glu Lys Tyr Asn Thr Trp
            180                 185                 190

Val Gln Lys Ala Lys Lys Val Asn Glu Asn Met Tyr Ser Leu Gln Asn
        195                 200                 205

Val Ile Ser Gln Gln Gln Asn Gln Ile Ala Asp Leu Gln Gln Tyr Cys
    210                 215                 220

Asn Lys Leu Glu Thr Asp Leu Gln Gly Lys Phe Ser Ser Leu Val Ser
225                 230                 235                 240

Ser Val Glu Trp Tyr Leu Arg Ser Met Glu Leu Pro Asp Asp Val Lys
                245                 250                 255

Asn Asp Ile Glu Gln Gln Leu Asn Ser Ile Asp Leu Ile Asn Pro Ile
            260                 265                 270

Asn Ala Ile Asp Asp Ile Glu Ser Leu Val Arg Asn Leu Val Gln Asp
        275                 280                 285

Tyr Asp Arg Thr Phe Leu Met Leu Lys Gly Leu Leu Lys Gln Cys Asn
    290                 295                 300

Tyr Glu Tyr Val Tyr Glu
305                 310

<210> SEQ ID NO 10
<211> LENGTH: 175
<212> TYPE: PRT
<213> ORGANISM: Human rotavirus

<400> SEQUENCE: 10

Met Asp Lys Leu Ala Asp Leu Asn Tyr Thr Leu Ser Val Ile Thr Leu
1               5                   10                  15

Met Asn Asp Thr Leu His Ser Ile Ile Gln Asp Pro Gly Met Ala Tyr
                20                  25                  30

Phe Thr Tyr Ile Ala Ser Val Leu Thr Val Leu Phe Thr Leu His Lys
            35                  40                  45

Ala Ser Ile Pro Thr Met Lys Ile Ala Leu Lys Thr Ser Lys Cys Ser
        50                  55                  60

Tyr Lys Val Ile Lys Tyr Cys Ile Val Thr Ile Ile Asn Thr Leu Leu
65                  70                  75                  80

Arg Leu Ala Gly Tyr Lys Glu Gln Val Thr Thr Lys Asp Glu Ile Glu
                85                  90                  95

Gln Gln Met Asp Arg Ile Val Lys Glu Met Arg Arg Gln Leu Glu Met
            100                 105                 110

Ile Asp Lys Leu Thr Thr Arg Glu Ile Glu Gln Val Glu Leu Leu Lys
        115                 120                 125

Ser Ile His Asp Asn Leu Ile Thr Arg Ser Val Asp Val Ile Asp Met
    130                 135                 140

Ser Lys Glu Phe Asn Gln Lys Asn Ile Lys Thr Leu Asp Glu Trp Glu
145                 150                 155                 160

Ser Gly Arg Asn Pro Tyr Glu Pro Ser Glu Val Thr Ala Ser Met
                165                 170                 175

<210> SEQ ID NO 11
<211> LENGTH: 175
```

```
<212> TYPE: PRT
<213> ORGANISM: Human rotavirus

<400> SEQUENCE: 11

Met Asp Lys Leu Ala Asp Leu Asn Tyr Thr Leu Ser Val Ile Thr Leu
1               5                   10                  15

Met Asn Asp Thr Leu His Ser Ile Ile Gln Asp Pro Gly Met Ala Tyr
                20                  25                  30

Phe Pro Tyr Ile Ala Ser Val Leu Thr Val Leu Phe Thr Leu His Lys
            35                  40                  45

Ala Ser Ile Pro Thr Met Lys Ile Ala Leu Lys Thr Ser Lys Cys Ser
        50                  55                  60

Tyr Lys Val Ile Lys Tyr Cys Ile Val Thr Ile Ile Asn Thr Leu Leu
65                  70                  75                  80

Lys Leu Ala Gly Tyr Lys Glu Gln Val Thr Thr Lys Asp Glu Ile Glu
                85                  90                  95

Gln Gln Met Asp Arg Ile Val Lys Glu Met Arg Arg Gln Leu Glu Met
                100                 105                 110

Ile Asp Lys Leu Thr Thr Arg Glu Ile Glu Gln Val Glu Leu Leu Lys
            115                 120                 125

Arg Ile Tyr Asp Asn Leu Ile Thr Arg Pro Val Asp Ile Val Asp Met
        130                 135                 140

Thr Lys Glu Phe Asn Gln Lys Asn Ile Lys Thr Leu Asp Glu Trp Glu
145                 150                 155                 160

Ser Gly Lys Asn Pro Tyr Glu Pro Ile Glu Val Thr Ala Ser Met
                165                 170                 175

<210> SEQ ID NO 12
<211> LENGTH: 175
<212> TYPE: PRT
<213> ORGANISM: Human rotavirus

<400> SEQUENCE: 12

Met Asp Lys Leu Ala Asp Leu Asn Tyr Thr Leu Ser Val Ile Thr Leu
1               5                   10                  15

Met Asn Asp Thr Leu His Ser Ile Ile Gln Asp Pro Gly Met Ala Tyr
                20                  25                  30

Phe Pro Tyr Ile Ala Ser Val Leu Thr Val Leu Phe Thr Leu His Lys
            35                  40                  45

Ala Ser Ile Pro Thr Met Lys Ile Ala Leu Lys Thr Ser Lys Cys Ser
        50                  55                  60

Tyr Lys Val Ile Lys Tyr Cys Ile Val Thr Ile Ile Asn Thr Leu Leu
65                  70                  75                  80

Lys Leu Ala Gly Tyr Lys Glu Gln Val Thr Thr Lys Asp Glu Ile Glu
                85                  90                  95

Gln Gln Met Asp Arg Ile Val Lys Glu Met Arg Arg Gln Leu Glu Met
                100                 105                 110

Ile Asp Lys Leu Thr Thr Arg Glu Ile Glu Gln Val Glu Leu Leu Lys
            115                 120                 125

Arg Ile Tyr Asp Asn Leu Ile Thr Arg Pro Val Asp Ile Val Asp Met
        130                 135                 140

Thr Lys Glu Phe Asn Gln Lys Asn Ile Lys Thr Leu Asp Glu Trp Glu
145                 150                 155                 160

Ser Gly Lys Asn Pro Tyr Glu Pro Ile Glu Val Thr Ala Ser Met
                165                 170                 175
```

<210> SEQ ID NO 13
<211> LENGTH: 197
<212> TYPE: PRT
<213> ORGANISM: Human rotavirus

<400> SEQUENCE: 13

```
Met Ser Leu Ser Ile Asp Val Thr Ser Leu Pro Ser Ile Ser Ser
1               5                   10                  15

Ile Phe Lys Asn Glu Ser Ser Thr Thr Ser Thr Leu Ser Gly Lys
                20                  25                  30

Ser Ile Gly Arg Asn Glu Gln Tyr Val Ser Pro Asp Ile Asp Ala Phe
        35                  40                  45

Asn Lys Tyr Met Leu Ser Lys Ser Pro Glu Asp Ile Gly Pro Ser Asp
    50                  55                  60

Ser Ala Ser Asn Asp Pro Leu Thr Ser Phe Ser Ile Arg Ser Asn Ala
65                  70                  75                  80

Val Lys Thr Asn Ala Asp Ala Gly Val Ser Met Asp Ser Ser Thr Gln
                85                  90                  95

Ser Arg Pro Ser Ser Asn Val Gly Cys Asp Gln Met Asp Phe Ser Leu
            100                 105                 110

Asn Lys Gly Ile Asn Val Ser Ala Ser Leu Asp Ser Cys Val Ser Ile
        115                 120                 125

Ser Thr Asn Gln Lys Lys Glu Lys Ser Lys Asp Lys Ser Arg Lys
    130                 135                 140

His Tyr Pro Arg Ile Glu Ala Asp Ser Asp Ser Glu Asp Tyr Val Leu
145                 150                 155                 160

Asp Asp Ser Asp Ser Asp Gly Lys Cys Lys Asn Cys Lys Tyr Lys
                165                 170                 175

Lys Lys Tyr Phe Ala Leu Arg Met Arg Met Lys Gln Val Ala Met Gln
            180                 185                 190

Leu Ile Glu Asp Leu
        195
```

<210> SEQ ID NO 14
<211> LENGTH: 197
<212> TYPE: PRT
<213> ORGANISM: Human rotavirus

<400> SEQUENCE: 14

```
Met Ser Leu Ser Ile Asp Val Thr Ser Leu Pro Ser Ile Ser Ser
1               5                   10                  15

Ile Phe Lys Asn Glu Ser Ser Thr Thr Ser Thr Leu Ser Gly Lys
                20                  25                  30

Ser Ile Gly Arg Ser Glu Gln Tyr Ile Ser Pro Asp Ala Glu Ala Phe
        35                  40                  45

Asn Lys Tyr Met Leu Ser Lys Ser Pro Glu Asp Ile Gly Pro Ser Asp
    50                  55                  60

Ser Ala Ser Asn Asp Pro Leu Thr Ser Phe Ser Ile Arg Ser Asn Ala
65                  70                  75                  80

Val Lys Thr Asn Ala Asp Ala Gly Val Ser Met Asp Ser Ser Thr Gln
                85                  90                  95

Ser Arg Pro Ser Ser Asn Val Gly Cys Asp Gln Leu Asp Phe Ser Leu
            100                 105                 110

Thr Lys Gly Ile Asn Val Ser Ala Asn Leu Asp Ser Cys Ile Ser Ile
        115                 120                 125
```

```
Ser Thr Asp His Lys Lys Glu Lys Ser Lys Lys Asp Lys Ser Arg Lys
    130                 135                 140
His Tyr Pro Arg Ile Glu Ala Asp Ser Asp Ser Glu Asp Tyr Val Leu
145                 150                 155                 160
Asp Asp Ser Asp Ser Asp Asp Gly Lys Cys Lys Asn Cys Lys Tyr Lys
                165                 170                 175
Lys Lys Tyr Phe Ala Leu Arg Met Arg Met Lys Arg Val Ala Met Gln
            180                 185                 190
Leu Ile Glu Asp Leu
        195

<210> SEQ ID NO 15
<211> LENGTH: 197
<212> TYPE: PRT
<213> ORGANISM: Human rotavirus

<400> SEQUENCE: 15

Met Ser Leu Ser Ile Asp Val Thr Ser Leu Pro Ser Ile Ser Ser Ser
1               5                   10                  15
Ile Phe Lys Asn Glu Ser Ser Ser Thr Thr Ser Thr Leu Ser Gly Lys
            20                  25                  30
Ser Ile Gly Arg Ser Glu Gln Tyr Ile Ser Pro Asp Val Glu Ala Phe
        35                  40                  45
Asn Lys Tyr Met Leu Ser Lys Ser Pro Glu Asp Ile Gly Pro Ser Asp
    50                  55                  60
Ser Ala Ser Asn Asp Pro Leu Thr Ser Phe Ser Ile Arg Ser Asn Ala
65                  70                  75                  80
Val Lys Thr Asn Ala Asp Ala Gly Val Ser Met Asp Ser Ser Thr Gln
                85                  90                  95
Ser Arg Pro Ser Ser Asn Val Gly Cys Asp Gln Leu Asp Phe Ser Leu
            100                 105                 110
Thr Lys Gly Ile Asn Val Ser Ala Asn Leu Asp Ser Cys Ile Ser Ile
        115                 120                 125
Ser Thr Asp His Lys Lys Glu Lys Ser Lys Lys Asp Lys Ser Arg Lys
    130                 135                 140
His Tyr Pro Arg Ile Glu Ala Asp Ser Asp Ser Glu Asp Tyr Val Leu
145                 150                 155                 160
Asp Asp Ser Asp Ser Asp Asp Gly Lys Cys Lys Asn Cys Lys Tyr Lys
                165                 170                 175
Lys Lys Tyr Phe Ala Leu Arg Met Arg Met Lys Arg Val Ala Met Gln
            180                 185                 190
Leu Ile Glu Asp Leu
        195

<210> SEQ ID NO 16
<211> LENGTH: 1088
<212> TYPE: PRT
<213> ORGANISM: Human rotavirus

<400> SEQUENCE: 16

Met Gly Lys Tyr Asn Leu Ile Leu Ser Glu Tyr Leu Ser Phe Val Tyr
1               5                   10                  15
Asn Ser Gln Ser Ala Val Gln Ile Pro Ile Tyr Tyr Ser Ser Asn Ser
            20                  25                  30
Glu Leu Glu Thr Arg Cys Ile Glu Phe His Ala Lys Cys Val Asp Asn
        35                  40                  45
```

```
Ser Lys Lys Gly Leu Ser Leu Lys Pro Leu Phe Glu Glu Tyr Lys Asp
 50                  55                  60

Val Thr Asp Asn Ala Thr Leu Leu Ser Ile Leu Ser Tyr Ser Tyr Asp
 65                  70                  75                  80

Lys Tyr Asn Ala Val Glu Arg Lys Leu Val Ser Tyr Ala Lys Gly Lys
                 85                  90                  95

Pro Leu Glu Ala Asp Leu Thr Ala Asn Glu Leu Asp Tyr Glu Asn Asn
            100                 105                 110

Lys Ile Thr Ser Glu Leu Phe Gln Ser Ala Glu Tyr Thr Asp Ser
             115                 120                 125

Leu Met Asp Pro Ala Ile Leu Thr Ser Leu Ser Ser Asn Leu Asn Ala
130                 135                 140

Val Met Phe Trp Leu Glu Arg His Ser Asn Asp Ile Ala Asp Ala Asn
145                 150                 155                 160

Lys Ile Tyr Lys Arg Arg Leu Asp Leu Phe Thr Ile Val Ala Ser Thr
                165                 170                 175

Ile Asn Lys Tyr Gly Val Pro Arg His Asn Glu Lys Tyr Arg Tyr Glu
            180                 185                 190

Tyr Glu Val Met Lys Asp Lys Pro Tyr Tyr Leu Val Thr Trp Ala Asn
            195                 200                 205

Ser Ser Ile Glu Met Leu Met Ser Val Phe Ser His Glu Asp Tyr Leu
210                 215                 220

Ile Ala Lys Glu Leu Ile Val Leu Ser Tyr Ser Asn Arg Ser Thr Leu
225                 230                 235                 240

Ala Lys Leu Val Ser Ser Pro Met Ser Ile Leu Val Ala Leu Ile Asp
                245                 250                 255

Ile Asn Gly Thr Phe Ile Thr Asn Glu Glu Leu Glu Leu Glu Phe Ser
            260                 265                 270

Asp Lys Tyr Val Lys Ala Ile Val Pro Asp Gln Thr Phe Asp Glu Leu
            275                 280                 285

Gln Glu Met Ile Asn Asn Met Lys Lys Ile Gly Leu Val Asp Ile Pro
290                 295                 300

Arg Met Ile Gln Glu Trp Leu Ile Asp Cys Ser Leu Glu Lys Phe Thr
305                 310                 315                 320

Leu Met Ser Lys Ile Tyr Ser Trp Ser Phe His Val Gly Phe Arg Lys
                325                 330                 335

Gln Lys Met Ile Asp Ala Ala Leu Asp Gln Leu Lys Thr Glu Tyr Thr
            340                 345                 350

Lys Asp Val Asp Asp Glu Met Tyr Asn Glu Tyr Thr Met Leu Ile Arg
            355                 360                 365

Asp Glu Ile Val Lys Met Leu Glu Ile Pro Val Lys His Asp Asp His
370                 375                 380

Leu Leu Arg Asp Ser Glu Leu Ala Gly Leu Leu Ser Met Ser Ser Ala
385                 390                 395                 400

Ser Asn Gly Glu Ser Arg Gln Ile Lys Phe Gly Arg Lys Thr Ile Phe
                405                 410                 415

Ser Thr Lys Lys Asn Met His Val Met Asp Asp Ile Ala His Gly Lys
            420                 425                 430

Tyr Thr Pro Gly Val Ile Pro Pro Val Asn Val Asp Lys Pro Ile Pro
            435                 440                 445

Leu Gly Arg Arg Asp Val Pro Gly Arg Arg Thr Arg Ile Ile Phe Ile
450                 455                 460

Leu Pro Tyr Glu Tyr Phe Ile Ala Gln His Ala Val Val Glu Lys Met
```

-continued

```
            465                 470                 475                 480
        Leu Leu Tyr Ala Lys His Thr Arg Glu Tyr Ala Glu Phe Tyr Ser Gln
                        485                 490                 495
        Ser Asn Gln Leu Leu Ser Tyr Gly Asp Val Thr Arg Phe Leu Ser Ser
                        500                 505                 510
        Asn Ser Met Val Leu Tyr Thr Asp Val Ser Gln Trp Asp Ser Ser Gln
                        515                 520                 525
        His Asn Thr Gln Pro Phe Arg Lys Gly Ile Ile Met Gly Leu Asp Met
                        530                 535                 540
        Leu Ser Asn Met Thr Asn Asp Pro Lys Val Val Gln Ala Leu Asn Leu
        545                 550                 555                 560
        Tyr Lys Gln Thr Gln Ile Asn Leu Met Asp Ser Tyr Val Gln Ile Pro
                        565                 570                 575
        Asp Gly Asn Val Ile Lys Lys Asn Gln Tyr Gly Ala Val Ala Ser Gly
                        580                 585                 590
        Glu Lys Gln Thr Lys Ala Ala Asn Ser Ile Ala Asn Leu Ala Leu Ile
                        595                 600                 605
        Lys Thr Val Leu Ser Arg Ile Ala Asn Lys Tyr Ser Phe Ile Thr Lys
                        610                 615                 620
        Ile Ile Arg Val Ser Gly Asp Asp Asn Tyr Ala Val Leu Gln Phe Asn
        625                 630                 635                 640
        Thr Asp Leu Thr Lys Gln Met Ile Gln Asp Val Ser Asn Asp Val Arg
                        645                 650                 655
        Tyr Ile Tyr Phe Arg Met Asn Ala Lys Val Lys Ala Leu Val Ser Thr
                        660                 665                 670
        Val Gly Ile Glu Ile Ala Lys Arg Tyr Leu Ala Gly Gly Lys Ile Phe
                        675                 680                 685
        Phe Arg Ala Gly Ile Asn Leu Leu Asn Asn Glu Lys Arg Gly Gln Ser
                        690                 695                 700
        Thr Gln Trp Asp Gln Ala Ala Ile Leu Tyr Ser Asn Tyr Ile Val Asn
        705                 710                 715                 720
        Lys Leu Arg Gly Phe Glu Thr Asp Arg Glu Phe Ile Leu Thr Lys Ile
                        725                 730                 735
        Ile Gln Met Thr Ser Val Ala Ile Thr Gly Ser Leu Arg Leu Phe Pro
                        740                 745                 750
        Ser Glu Arg Val Leu Thr Thr Asn Ser Thr Phe Lys Val Phe Asp Ser
                        755                 760                 765
        Glu Asp Phe Ile Ile Glu Tyr Gly Thr Thr Asp Asp Glu Val Tyr Ile
                        770                 775                 780
        Gln Arg Ala Phe Met Ser Leu Ser Ser Gln Lys Ser Gly Ile Ala Asp
        785                 790                 795                 800
        Glu Ile Ala Ser Ser Gln Thr Phe Lys Asn Tyr Val Ser Lys Leu Ser
                        805                 810                 815
        Asp Gln Leu Leu Val Ser Lys Asn Val Ile Val Ser Lys Gly Ile Ala
                        820                 825                 830
        Val Thr Glu Lys Ala Lys Leu Asn Ser Tyr Ala Pro Ile Tyr Leu Glu
                        835                 840                 845
        Lys Arg Arg Ala Gln Ile Ser Ala Leu Leu Thr Met Leu Gln Lys Pro
                        850                 855                 860
        Val Ser Phe Lys Ser Asn Lys Asn Thr Ile Asn Glu Ile Leu Arg Asp
        865                 870                 875                 880
        Ile Lys Pro Phe Phe Val Thr Thr Glu Asp Asn Leu Pro Ile Gln Tyr
                        885                 890                 895
```

-continued

```
Arg Lys Phe Met Pro Thr Leu Pro Asp Asn Val Gln Tyr Val Ile Gln
            900                 905                 910

Cys Ile Gly Ser Arg Thr Tyr Gln Ile Glu Asp Ser Gly Ser Lys Ser
            915                 920                 925

Ser Ile Ser Lys Leu Ile Ser Lys Tyr Ser Val Tyr Lys Pro Ser Ile
            930                 935                 940

Glu Glu Leu Tyr Lys Val Ile Ser Leu Arg Glu Gln Glu Ile Gln Leu
945                 950                 955                 960

Tyr Leu Val Ser Leu Gly Val Pro Leu Val Asp Ala Ser Ala Tyr Val
                965                 970                 975

Ala Ser Arg Ile Tyr Ser Gln Asp Lys Tyr Lys Ile Leu Glu Ser Tyr
            980                 985                 990

Val Tyr Asn Leu Leu Ser Ile Asn Tyr Gly Cys Tyr Gln Leu Phe Asp
            995                 1000                1005

Phe Asn Ser Pro Asp Leu Glu Lys Leu Ile Arg Ile Pro Phe Lys
        1010                1015                1020

Gly Lys Ile Pro Ala Val Thr Phe Ile Leu His Leu Tyr Ala Lys
        1025                1030                1035

Leu Glu Ile Ile Asn Tyr Ala Ile Lys Asn Arg Ala Trp Ile Ser
        1040                1045                1050

Val Phe Cys Asn Tyr Pro Lys Ser Glu Met Ile Lys Leu Trp Lys
        1055                1060                1065

Lys Met Trp Ser Ile Thr Ala Leu Arg Ser Pro Tyr Thr Ser Ala
        1070                1075                1080

Asn Phe Phe Gln Asp
        1085

<210> SEQ ID NO 17
<211> LENGTH: 1088
<212> TYPE: PRT
<213> ORGANISM: Human rotavirus

<400> SEQUENCE: 17

Met Gly Lys Tyr Asn Leu Ile Leu Ser Glu Tyr Leu Ser Phe Val Tyr
1               5                   10                  15

Asn Ser Gln Ser Ala Val Gln Ile Pro Ile Tyr Tyr Ser Ser Asn Ser
            20                  25                  30

Glu Leu Glu Lys Arg Cys Ile Glu Phe His Ala Lys Cys Val Asp Ser
        35                  40                  45

Ser Lys Lys Gly Met Ser Leu Lys Pro Leu Phe Glu Glu Tyr Lys Asp
    50                  55                  60

Val Ile Asp Asn Ala Thr Leu Leu Ser Ile Leu Ser Tyr Ser Tyr Asp
65                  70                  75                  80

Lys Tyr Asn Ala Val Glu Arg Lys Leu Val Asn Tyr Ala Lys Gly Lys
                85                  90                  95

Pro Leu Glu Ala Asp Leu Thr Ala Asn Glu Leu Asp Tyr Glu Asn Asn
            100                 105                 110

Lys Ile Thr Ser Glu Leu Phe Gln Ser Ala Glu Glu Tyr Thr Asp Ser
        115                 120                 125

Leu Met Asp Pro Ala Ile Leu Thr Ser Leu Ser Ser Asn Leu Asn Ala
    130                 135                 140

Val Met Phe Trp Leu Glu Arg His Ser Asn Asp Val Ala Asp Ala Asn
145                 150                 155                 160

Lys Ile Tyr Lys Arg Arg Leu Asp Leu Phe Thr Ile Val Ala Ser Thr
```

-continued

```
                165                 170                 175
Ile Asn Lys Tyr Gly Val Pro Arg His Asn Glu Lys Tyr Arg Tyr Glu
                180                 185                 190
Tyr Glu Val Met Lys Asp Lys Pro Tyr Tyr Leu Val Thr Trp Ala Asn
                195                 200                 205
Ser Ser Ile Glu Met Leu Met Ser Val Phe Ser His Glu Asp Tyr Leu
            210                 215                 220
Ile Ala Lys Glu Leu Ile Ile Leu Ser Tyr Ser Asn Arg Ser Thr Leu
225                 230                 235                 240
Ala Lys Leu Val Ser Ser Pro Met Ser Ile Leu Val Ala Leu Ile Asp
                245                 250                 255
Ile Asn Gly Thr Phe Ile Thr Asn Glu Glu Leu Glu Leu Glu Phe Ser
                260                 265                 270
Asp Lys Tyr Val Lys Ala Ile Val Pro Asp Gln Ile Phe Asp Glu Leu
                275                 280                 285
Gln Glu Met Ile Asp Asn Met Lys Lys Val Gly Leu Val Asp Ile Pro
            290                 295                 300
Arg Met Ile Gln Glu Trp Leu Val Asp Cys Ser Leu Glu Lys Phe Thr
305                 310                 315                 320
Leu Met Ser Lys Ile Tyr Ser Trp Ser Phe His Val Gly Phe Arg Lys
                325                 330                 335
Gln Lys Met Ile Asp Ala Ala Leu Asp Gln Leu Lys Thr Glu Tyr Thr
                340                 345                 350
Glu Asp Val Asp Gly Glu Met Tyr Asn Glu Tyr Thr Met Leu Ile Arg
            355                 360                 365
Asp Glu Ile Val Lys Met Leu Glu Val Pro Val Lys His Asp Asp His
        370                 375                 380
Leu Leu Arg Asp Ser Glu Leu Ala Gly Leu Leu Ser Met Ser Ser Ala
385                 390                 395                 400
Ser Asn Gly Glu Ser Arg Gln Leu Lys Phe Gly Leu Lys Thr Ile Phe
                405                 410                 415
Ser Thr Lys Lys Asn Met His Val Met Asp Asp Ile Ala His Gly Arg
                420                 425                 430
Tyr Thr Pro Gly Ile Ile Pro Pro Val Asn Val Asp Arg Pro Ile Pro
            435                 440                 445
Leu Gly Arg Arg Asp Val Pro Gly Arg Arg Thr Arg Ile Ile Phe Ile
450                 455                 460
Leu Pro Tyr Glu Tyr Phe Ile Ala Gln His Ala Val Val Glu Lys Met
465                 470                 475                 480
Leu Ser Tyr Ala Lys His Thr Arg Glu Tyr Ala Glu Phe Tyr Ser Gln
                485                 490                 495
Ser Asn Gln Leu Leu Ser Tyr Gly Asp Val Thr Arg Phe Leu Ser Ser
            500                 505                 510
Asn Ser Met Val Leu Tyr Thr Asp Val Ser Gln Trp Asp Ser Ser Gln
            515                 520                 525
His Asn Thr Gln Pro Phe Arg Lys Gly Ile Ile Met Gly Leu Asp Met
        530                 535                 540
Leu Ser Asn Met Thr Asn Asp Pro Lys Val Ile Gln Thr Leu Asn Leu
545                 550                 555                 560
Tyr Lys Gln Thr Gln Ile Asn Leu Met Asp Ser Tyr Val Gln Ile Pro
                565                 570                 575
Asp Gly Asn Val Ile Lys Lys Ile Gln Tyr Gly Ala Val Ala Ser Gly
            580                 585                 590
```

```
Glu Lys Gln Thr Lys Ala Ala Asn Ser Ile Ala Asn Leu Ala Leu Ile
        595                 600                 605
Lys Thr Val Leu Ser Arg Ile Ala Asn Lys Tyr Ser Phe Ile Thr Lys
        610                 615                 620
Ile Ile Arg Val Asp Gly Asp Asn Tyr Ala Val Leu Gln Phe Asn
625                 630                 635                 640
Thr Asp Val Thr Lys Gln Met Val Gln Asp Val Ser Asn Asp Val Arg
                645                 650                 655
His Ile Tyr Ser Arg Met Asn Ala Lys Val Lys Ala Leu Val Ser Thr
                660                 665                 670
Val Gly Ile Glu Ile Ala Lys Arg Tyr Ile Ala Gly Lys Ile Phe
        675                 680                 685
Phe Arg Ala Gly Ile Asn Leu Leu Asn Asn Glu Lys Arg Gly Gln Ser
        690                 695                 700
Thr Gln Trp Asp Gln Ala Ala Ile Leu Tyr Ser Asn Tyr Ile Val Asn
705                 710                 715                 720
Lys Leu Arg Gly Phe Glu Thr Asp Arg Glu Phe Ile Leu Thr Lys Ile
                725                 730                 735
Ile Gln Met Thr Ser Val Ala Ile Thr Gly Ser Leu Arg Leu Phe Pro
            740                 745                 750
Ser Glu Arg Val Leu Thr Thr Asn Ser Thr Phe Lys Val Phe Asp Ser
            755                 760                 765
Glu Asp Phe Ile Ile Glu Tyr Gly Thr Thr Asp Glu Val Tyr Ile
770                 775                 780
Gln Arg Ala Phe Met Ser Leu Ser Ser Gln Lys Ser Gly Ile Ala Asp
785                 790                 795                 800
Glu Ile Ala Ser Ser Gln Thr Phe Lys Asn Tyr Val Asn Lys Leu Ser
                805                 810                 815
Asp Gln Leu Leu Ile Ser Lys Asn Val Ile Ser Lys Gly Ile Ala
            820                 825                 830
Val Thr Glu Lys Ala Lys Leu Asn Ser Tyr Ala Pro Val Tyr Leu Glu
        835                 840                 845
Lys Arg Arg Ala Gln Ile Ser Ala Leu Leu Thr Met Leu Gln Lys Pro
        850                 855                 860
Val Ser Phe Lys Ser Asn Lys Ile Thr Ile Asn Asp Ile Leu Arg Asp
865                 870                 875                 880
Ile Lys Pro Phe Phe Val Thr Ser Glu Ala Asn Leu Pro Ile Gln Tyr
                885                 890                 895
Arg Lys Phe Met Pro Thr Leu Pro Asp Asn Val Gln Tyr Val Ile Gln
                900                 905                 910
Cys Ile Gly Ser Arg Thr Tyr Gln Ile Glu Asp Ser Gly Ser Lys Ser
        915                 920                 925
Ser Ile Ser Lys Leu Ile Ser Lys Tyr Ser Val Tyr Lys Pro Ser Ile
        930                 935                 940
Glu Glu Leu Tyr Lys Val Ile Ser Leu Arg Glu Gln Glu Ile Gln Leu
945                 950                 955                 960
Tyr Leu Val Ser Leu Gly Val Pro Pro Val Asp Ala Gly Thr Tyr Val
                965                 970                 975
Gly Ser Arg Ile Tyr Ser Gln Asp Lys Tyr Lys Ile Leu Glu Ser Tyr
            980                 985                 990
Val Tyr Asn Leu Leu Ser Ile Asn  Tyr Gly Cys Tyr Gln  Leu Phe Asp
        995                 1000                1005
```

Phe Asn Ser Pro Asp Leu Glu Lys Leu Ile Arg Ile Pro Phe Lys
1010              1015                 1020

Gly Lys Ile Pro Ala Val Thr Phe Ile Leu His Leu Tyr Ala Lys
1025              1030                 1035

Leu Glu Ile Ile Asn His Ala Ile Lys Asn Gly Ala Trp Ile Ser
1040              1045                 1050

Leu Phe Cys Asn Tyr Pro Lys Ser Glu Met Ile Lys Leu Trp Lys
1055              1060                 1065

Lys Met Trp Asn Ile Thr Ala Leu Arg Ser Pro Tyr Thr Ser Ala
1070              1075                 1080

Asn Phe Phe Gln Asp
1085

<210> SEQ ID NO 18
<211> LENGTH: 1088
<212> TYPE: PRT
<213> ORGANISM: Human rotavirus

<400> SEQUENCE: 18

Met Gly Lys Tyr Asn Leu Ile Leu Ser Glu Tyr Leu Ser Phe Val Tyr
1               5                   10                  15

Asn Ser Gln Ser Ala Val Gln Ile Pro Ile Tyr Tyr Ser Ser Asn Ser
                20                  25                  30

Glu Leu Glu Lys Arg Cys Ile Glu Phe His Ala Lys Cys Val Asp Ser
            35                  40                  45

Ser Lys Lys Gly Met Ser Leu Lys Pro Leu Phe Glu Glu Tyr Lys Asp
        50                  55                  60

Val Ile Asp Asn Ala Thr Leu Leu Ser Ile Leu Ser Tyr Ser Tyr Asp
65                  70                  75                  80

Lys Tyr Asn Ala Val Glu Arg Lys Leu Val Asn Tyr Ala Lys Gly Lys
                85                  90                  95

Pro Leu Glu Ala Asp Leu Thr Ala Asn Glu Leu Asp Tyr Glu Asn Asn
            100                 105                 110

Lys Ile Thr Ser Glu Leu Phe Gln Ser Ala Glu Glu Tyr Thr Asp Ser
        115                 120                 125

Leu Met Asp Pro Ala Ile Leu Thr Ser Leu Ser Ser Asn Leu Asn Ala
    130                 135                 140

Val Met Phe Trp Leu Glu Arg His Ser Asn Asp Val Ala Asp Ala Asn
145                 150                 155                 160

Lys Ile Tyr Lys Arg Arg Leu Asp Leu Phe Thr Ile Val Ala Ser Thr
                165                 170                 175

Ile Asn Lys Tyr Gly Val Pro Arg His Asn Glu Lys Tyr Arg Tyr Glu
            180                 185                 190

Tyr Glu Val Met Lys Asp Lys Pro Tyr Tyr Leu Val Thr Trp Ala Asn
        195                 200                 205

Ser Ser Ile Glu Met Leu Met Ser Val Phe Ser His Glu Asp Tyr Leu
    210                 215                 220

Ile Ala Lys Glu Leu Ile Ile Leu Ser Tyr Ser Asn Arg Ser Thr Leu
225                 230                 235                 240

Ala Lys Leu Val Ser Ser Pro Met Ser Ile Leu Val Ala Leu Ile Asp
                245                 250                 255

Ile Asn Gly Thr Phe Ile Thr Asn Glu Glu Leu Glu Leu Glu Phe Ser
            260                 265                 270

Asp Lys Tyr Val Lys Ala Ile Val Pro Asp Gln Ile Phe Asp Glu Leu
        275                 280                 285

-continued

```
Gln Glu Met Ile Asp Asn Met Lys Lys Val Gly Leu Val Asp Ile Pro
    290                 295                 300
Arg Met Ile Gln Glu Trp Leu Val Asp Cys Ser Leu Glu Lys Phe Thr
305                 310                 315                 320
Leu Met Ser Lys Ile Tyr Ser Trp Ser Phe His Val Gly Phe Arg Lys
                325                 330                 335
Gln Lys Met Ile Asp Ala Ala Leu Asp Gln Leu Lys Thr Glu Tyr Thr
            340                 345                 350
Glu Asp Val Asp Gly Glu Met Tyr Asn Glu Tyr Thr Met Leu Ile Arg
        355                 360                 365
Asp Glu Ile Val Lys Met Leu Glu Val Pro Val Lys His Asp Asp His
    370                 375                 380
Leu Leu Arg Asp Ser Glu Leu Ala Gly Leu Leu Ser Met Ser Ser Ala
385                 390                 395                 400
Ser Asn Gly Glu Ser Arg Gln Leu Lys Phe Gly Leu Lys Thr Ile Phe
                405                 410                 415
Ser Thr Lys Lys Asn Met His Val Met Asp Asp Ile Ala His Gly Arg
            420                 425                 430
Tyr Thr Pro Gly Ile Ile Pro Pro Val Asn Val Asp Arg Pro Ile Pro
        435                 440                 445
Leu Gly Arg Arg Asp Val Pro Gly Arg Arg Thr Arg Ile Ile Phe Ile
    450                 455                 460
Leu Pro Tyr Glu Tyr Phe Ile Ala Gln His Ala Val Val Glu Lys Met
465                 470                 475                 480
Leu Ser Tyr Ala Lys His Thr Arg Glu Tyr Ala Glu Phe Tyr Ser Gln
                485                 490                 495
Ser Asn Gln Leu Leu Ser Tyr Gly Asp Val Thr Arg Phe Leu Ser Ser
            500                 505                 510
Asn Ser Met Val Leu Tyr Thr Asp Val Ser Gln Trp Asp Ser Ser Gln
        515                 520                 525
His Asn Thr Gln Pro Phe Arg Lys Gly Ile Ile Met Gly Leu Asp Met
    530                 535                 540
Leu Ser Asn Met Thr Asn Asp Pro Lys Val Ile Gln Thr Leu Asn Leu
545                 550                 555                 560
Tyr Lys Gln Thr Gln Ile Asn Leu Met Asp Ser Tyr Val Gln Ile Pro
                565                 570                 575
Asp Gly Asn Val Ile Lys Lys Ile Gln Tyr Gly Ala Val Ala Ser Gly
            580                 585                 590
Glu Lys Gln Thr Lys Ala Ala Asn Ser Ile Ala Asn Leu Ala Leu Ile
        595                 600                 605
Lys Thr Val Leu Ser Arg Ile Ala Asn Lys Tyr Ser Phe Ile Thr Lys
    610                 615                 620
Ile Ile Arg Val Asp Gly Asp Asp Asn Tyr Ala Val Leu Gln Phe Asn
625                 630                 635                 640
Thr Asp Val Thr Lys Gln Met Val Gln Asp Val Ser Asn Asp Val Arg
                645                 650                 655
His Ile Tyr Ser Arg Met Asn Ala Lys Val Lys Ala Leu Val Ser Thr
            660                 665                 670
Val Gly Ile Glu Ile Ala Lys Arg Tyr Ile Ala Gly Lys Ile Phe
        675                 680                 685
Phe Arg Ala Gly Ile Asn Leu Leu Asn Asn Glu Lys Arg Gly Gln Ser
    690                 695                 700
```

-continued

Thr Gln Trp Asp Gln Ala Ala Ile Leu Tyr Ser Asn Tyr Ile Val Asn
705                 710                 715                 720

Lys Leu Arg Gly Phe Glu Thr Asp Arg Glu Phe Ile Leu Thr Lys Ile
            725                 730                 735

Ile Gln Met Thr Ser Val Ala Ile Thr Gly Ser Leu Arg Leu Phe Pro
            740                 745                 750

Ser Glu Arg Val Leu Thr Thr Asn Ser Thr Phe Lys Val Phe Asp Ser
            755                 760                 765

Glu Asp Phe Ile Ile Glu Tyr Gly Thr Thr Asp Glu Val Tyr Ile
    770                 775                 780

Gln Arg Ala Phe Met Ser Leu Ser Ser Gln Lys Ser Gly Ile Ala Asp
785                 790                 795                 800

Glu Ile Ala Ser Ser Gln Thr Phe Lys Asn Tyr Val Asn Lys Leu Ser
            805                 810                 815

Asp Gln Leu Leu Ile Ser Lys Asn Val Ile Val Ser Lys Gly Ile Ala
            820                 825                 830

Val Thr Glu Lys Ala Lys Leu Asn Ser Tyr Ala Pro Val Tyr Leu Glu
            835                 840                 845

Lys Arg Arg Ala Gln Ile Ser Ala Leu Leu Thr Met Leu Gln Lys Pro
850                 855                 860

Val Ser Phe Lys Ser Asn Lys Ile Thr Ile Asn Asp Ile Leu Arg Asp
865                 870                 875                 880

Ile Lys Pro Phe Phe Val Thr Ser Glu Ala Asn Leu Pro Ile Gln Tyr
            885                 890                 895

Arg Lys Phe Met Pro Thr Leu Pro Asp Asn Val Gln Tyr Val Ile Gln
            900                 905                 910

Cys Ile Gly Ser Arg Thr Tyr Gln Ile Glu Asp Ser Gly Ser Lys Ser
            915                 920                 925

Ser Ile Ser Lys Leu Ile Ser Lys Tyr Ser Val Tyr Lys Pro Ser Ile
930                 935                 940

Glu Glu Leu Tyr Lys Val Ile Ser Leu Arg Gln Glu Ile Gln Leu
945                 950                 955                 960

Tyr Leu Val Ser Leu Gly Val Pro Pro Val Asp Ala Gly Thr Tyr Val
            965                 970                 975

Gly Ser Arg Ile Tyr Ser Gln Asp Lys Tyr Lys Ile Leu Glu Ser Tyr
            980                 985                 990

Val Tyr Asn Leu Leu Ser Ile Asn  Tyr Gly Cys Tyr Gln  Leu Phe Asp
            995                 1000                1005

Phe Asn  Ser Pro Asp Leu Glu  Lys Leu Ile Arg Ile  Pro Phe Lys
    1010                1015                1020

Gly Lys  Ile Pro Ala Val Thr  Phe Ile Leu His Leu  Tyr Ala Lys
    1025                1030                1035

Leu Glu  Ile Ile Asn His Ala  Ile Lys Asn Gly Ala  Trp Ile Ser
    1040                1045                1050

Leu Phe  Cys Asn Tyr Pro Lys  Ser Glu Met Ile Lys  Leu Trp Lys
    1055                1060                1065

Lys Met  Trp Asn Ile Thr Ala  Leu Arg Ser Pro Tyr  Thr Ser Ala
    1070                1075                1080

Asn Phe  Phe Gln Asp
    1085

<210> SEQ ID NO 19
<211> LENGTH: 900
<212> TYPE: PRT

<213> ORGANISM: Human rotavirus

<400> SEQUENCE: 19

Met Ala Tyr Arg Lys Arg Gly Thr Lys Arg Glu Asp Leu Pro Gln Gln
1               5                   10                  15

Asn Glu Arg Leu Gln Glu Lys Glu Ile Glu Asn Asn Ile Asp Val Thr
            20                  25                  30

Met Glu Asn Lys Asn Lys Asn Ile Asn Lys Asn Asn Lys Asn Asn
        35                  40                  45

Asn Arg Lys Gln Gln Leu Ser Asp Lys Val Leu Leu Gln Lys Glu Glu
    50                  55                  60

Ile Ile Thr Asp Val Gln Asp Asp Ile Lys Ile Thr Asp Glu Val Lys
65                  70                  75                  80

Lys Ser Ser Lys Glu Glu Ser Lys Gln Leu Leu Glu Ile Leu Lys Thr
                85                  90                  95

Lys Glu Asp His Gln Lys Glu Val Gln Tyr Glu Ile Leu Gln Lys Thr
            100                 105                 110

Ile Pro Thr Phe Glu Pro Lys Glu Ser Ile Leu Lys Lys Leu Glu Asp
        115                 120                 125

Ile Arg Pro Glu Gln Ala Lys Lys Gln Met Lys Leu Phe Arg Ile Phe
130                 135                 140

Glu Pro Arg Gln Leu Pro Ile Tyr Arg Ala Asn Gly Glu Lys Glu Leu
145                 150                 155                 160

Arg Asn Arg Trp Tyr Trp Lys Leu Lys Lys Asp Thr Leu Pro Asp Gly
                165                 170                 175

Asp Tyr Asp Val Arg Glu Tyr Phe Leu Asn Leu Tyr Asp Gln Ile Leu
            180                 185                 190

Ile Glu Met Pro Asp Tyr Leu Leu Leu Lys Asp Met Ala Val Glu Asn
        195                 200                 205

Lys Asn Ser Arg Asp Ala Gly Lys Val Val Asp Ser Glu Thr Ala Ser
    210                 215                 220

Ile Cys Asp Ala Ile Phe Gln Asp Glu Glu Thr Glu Gly Val Ile Arg
225                 230                 235                 240

Arg Phe Ile Ala Asp Met Arg Gln Gln Ile Gln Ala Asp Arg Asn Ile
                245                 250                 255

Val Asn Tyr Pro Ser Ile Leu His Pro Ile Asp His Ala Phe Asn Glu
            260                 265                 270

Tyr Phe Leu Asn His Gln Leu Val Glu Pro Leu Asn Asn Asp Ile Ile
        275                 280                 285

Phe Asn Tyr Ile Pro Glu Arg Ile Arg Asn Asp Val Asn Tyr Ile Leu
    290                 295                 300

Asn Met Asp Met Asn Leu Pro Ser Thr Ala Arg Tyr Ile Arg Pro Asn
305                 310                 315                 320

Leu Leu Gln Asp Arg Leu Asn Leu His Asp Asn Phe Glu Ser Leu Trp
                325                 330                 335

Asp Thr Ile Thr Thr Ser Asn Tyr Ile Leu Ala Arg Ser Val Val Pro
            340                 345                 350

Asp Leu Lys Glu Lys Glu Leu Val Ser Thr Glu Ala Gln Ile Gln Lys
        355                 360                 365

Met Ser Gln Asp Leu Gln Leu Glu Ala Leu Thr Ile Gln Ser Glu Thr
    370                 375                 380

Gln Phe Leu Ala Gly Ile Asn Ser Gln Ala Ala Asn Asp Cys Phe Lys
385                 390                 395                 400

-continued

```
Thr Leu Ile Ala Ala Met Leu Ser Gln Arg Thr Met Ser Leu Asp Phe
                405                 410                 415
Val Thr Thr Asn Tyr Met Ser Leu Ile Ser Gly Met Trp Leu Leu Thr
            420                 425                 430
Val Ile Pro Asn Asp Met Phe Leu Arg Glu Ser Leu Val Ala Cys Glu
        435                 440                 445
Leu Ala Ile Ile Asn Thr Ile Val Tyr Pro Ala Phe Gly Met Gln Arg
    450                 455                 460
Met His Tyr Arg Asn Gly Asp Pro Gln Thr Pro Phe Gln Ile Ala Glu
465                 470                 475                 480
Gln Gln Ile Gln Asn Phe Gln Val Ala Asn Trp Leu His Phe Ile Asn
                485                 490                 495
Asn Asn Arg Phe Arg Gln Val Val Ile Asp Gly Val Leu Asn Gln Thr
            500                 505                 510
Leu Asn Asp Asn Ile Arg Asn Gly Gln Val Ile Asn Gln Leu Met Glu
        515                 520                 525
Ala Leu Met Gln Leu Ser Arg Gln Gln Phe Pro Thr Met Pro Val Asp
    530                 535                 540
Tyr Lys Arg Ser Ile Gln Arg Gly Ile Leu Leu Ser Asn Arg Leu
545                 550                 555                 560
Gly Gln Leu Val Asp Leu Thr Arg Leu Leu Ser Tyr Asn Tyr Glu Thr
                565                 570                 575
Leu Met Ala Cys Ile Thr Met Asn Met Gln His Val Gln Thr Leu Thr
            580                 585                 590
Thr Glu Arg Leu Gln Leu Thr Ser Val Thr Ser Leu Cys Met Leu Ile
        595                 600                 605
Gly Asn Thr Thr Val Ile Pro Ser Pro Gln Thr Leu Phe His Tyr Tyr
    610                 615                 620
Asn Ile Asn Val Asn Phe His Ser Asn Tyr Asn Glu Arg Ile Asn Asp
625                 630                 635                 640
Ala Val Ala Ile Ile Thr Ala Ala Asn Arg Leu Asn Leu Tyr Gln Lys
                645                 650                 655
Lys Met Lys Ser Ile Val Glu Asp Phe Leu Lys Arg Leu Gln Ile Phe
            660                 665                 670
Asp Val Pro Arg Val Pro Asp Asp Gln Met Tyr Arg Leu Arg Asp Arg
        675                 680                 685
Leu Arg Leu Leu Pro Val Glu Arg Arg Leu Asp Ile Phe Asn Leu
    690                 695                 700
Ile Leu Met Asn Met Glu Gln Ile Glu Arg Ala Ser Asp Lys Ile Ala
705                 710                 715                 720
Gln Gly Val Ile Ile Ala Tyr Arg Asp Met Gln Leu Glu Arg Asp Glu
                725                 730                 735
Met Tyr Gly Phe Val Asn Ile Ala Arg Asn Leu Asp Gly Tyr Gln Gln
            740                 745                 750
Ile Asn Leu Glu Glu Leu Met Arg Thr Gly Asp Tyr Gly Gln Ile Thr
        755                 760                 765
Thr Met Leu Leu Asn Asn Gln Pro Val Ala Leu Val Gly Ala Leu Pro
    770                 775                 780
Phe Val Thr Asp Ser Ser Val Ile Ser Leu Ile Ala Lys Leu Asp Ala
785                 790                 795                 800
Thr Val Phe Ala Gln Ile Val Lys Leu Arg Lys Val Asp Thr Leu Lys
                805                 810                 815
Pro Ile Leu Tyr Lys Ile Asn Ser Asp Ser Asn Asp Phe Tyr Leu Val
```

```
                    820                 825                 830
Ala Asn Tyr Asp Trp Ile Pro Thr Ser Thr Thr Lys Val Tyr Lys Gln
                835                 840                 845

Val Pro Gln Pro Phe Asp Phe Arg Ala Ser Met His Met Leu Thr Ser
            850                 855                 860

Asn Leu Thr Phe Thr Val Tyr Ser Asp Leu Leu Ser Phe Val Ser Ala
865                 870                 875                 880

Asp Thr Val Glu Pro Ile Asn Ala Ile Ala Phe Asp Asn Met Arg Ile
                885                 890                 895

Met Asn Glu Leu
            900

<210> SEQ ID NO 20
<211> LENGTH: 900
<212> TYPE: PRT
<213> ORGANISM: Human rotavirus

<400> SEQUENCE: 20

Met Ala Tyr Arg Lys Arg Gly Thr Lys Arg Glu Asp Leu Pro Gln Gln
1               5                   10                  15

Asn Glu Arg Leu Gln Glu Lys Glu Ile Glu Asn Asn Ile Asp Val Thr
            20                  25                  30

Met Glu Asn Lys Asn Lys Asn Ile Asn Lys Asn Asn Asn Arg Asn Asn
        35                  40                  45

Asn Arg Lys Gln Gln Leu Ser Asp Lys Val Leu Ser Gln Lys Glu Glu
    50                  55                  60

Ile Ile Thr Asp Val Gln Asp Ile Lys Ile Thr Asp Glu Val Lys
65                  70                  75                  80

Lys Ser Ser Lys Glu Glu Ser Lys Gln Leu Leu Glu Ile Leu Lys Thr
                85                  90                  95

Lys Glu Asp His Gln Lys Glu Val Gln Tyr Glu Ile Leu Gln Lys Thr
            100                 105                 110

Ile Pro Thr Phe Glu Pro Lys Glu Ser Ile Leu Lys Lys Leu Glu Asp
        115                 120                 125

Ile Arg Pro Glu Gln Ala Lys Lys Gln Met Lys Leu Phe Arg Ile Phe
    130                 135                 140

Glu Pro Arg Gln Leu Pro Ile Tyr Arg Ala Asn Gly Glu Lys Glu Leu
145                 150                 155                 160

Arg Asn Arg Trp Tyr Trp Lys Leu Lys Lys Asp Thr Leu Pro Asp Gly
                165                 170                 175

Asp Tyr Asp Val Arg Glu Tyr Phe Leu Asn Leu Tyr Asp Gln Ile Leu
            180                 185                 190

Ile Glu Met Pro Asp Tyr Leu Leu Leu Lys Asp Met Ala Val Glu Asn
        195                 200                 205

Lys Asn Ser Arg Asp Ala Gly Lys Val Val Asp Ser Glu Thr Ala Ser
    210                 215                 220

Ile Cys Asp Ala Ile Phe Gln Asp Glu Glu Thr Glu Gly Val Ile Arg
225                 230                 235                 240

Arg Phe Ile Ala Asp Met Arg Gln Gln Ile Gln Ala Asp Arg Asn Ile
                245                 250                 255

Val Asn Tyr Pro Ser Ile Leu His Pro Ile Asp His Ala Phe Asn Glu
            260                 265                 270

Tyr Phe Leu Asn His Gln Leu Val Glu Pro Leu Asn Asn Asp Ile Ile
        275                 280                 285
```

-continued

```
Phe Asn Tyr Ile Pro Glu Arg Ile Arg Asn Asp Val Asn Tyr Ile Leu
    290                 295                 300
Asn Met Asp Met Asn Leu Pro Ser Thr Ala Arg Tyr Ile Arg Pro Asn
305                 310                 315                 320
Leu Leu Gln Asp Arg Leu Asn Leu His Asp Asn Phe Glu Ser Leu Trp
                325                 330                 335
Asp Thr Ile Thr Thr Ser Asn Tyr Ile Leu Ala Arg Ser Val Val Pro
                340                 345                 350
Asp Leu Lys Glu Lys Glu Leu Val Ser Thr Glu Ala Gln Ile Gln Lys
                355                 360                 365
Met Ser Gln Asp Leu Gln Leu Glu Ala Leu Thr Ile Gln Ser Glu Thr
370                 375                 380
Gln Phe Leu Ala Gly Ile Asn Ser Gln Ala Ala Asn Asp Cys Phe Lys
385                 390                 395                 400
Thr Leu Ile Ala Ala Met Leu Ser Gln Arg Thr Met Ser Leu Asp Phe
                405                 410                 415
Val Thr Thr Asn Tyr Met Ser Leu Ile Ser Gly Met Trp Leu Leu Thr
                420                 425                 430
Val Ile Pro Asn Asp Met Phe Leu Arg Glu Ser Leu Val Ala Cys Glu
                435                 440                 445
Leu Ala Ile Ile Asn Thr Ile Val Tyr Pro Ala Phe Gly Met Gln Arg
450                 455                 460
Met His Tyr Arg Asn Gly Asp Pro Gln Thr Pro Phe Gln Ile Ala Glu
465                 470                 475                 480
Gln Gln Ile Gln Asn Phe Gln Val Ala Asn Trp Leu His Phe Ile Asn
                485                 490                 495
Asn Asn Arg Phe Arg Gln Val Val Ile Asp Gly Val Leu Asn Gln Thr
                500                 505                 510
Leu Asn Asp Asn Ile Arg Asn Gly Gln Val Ile Asn Gln Leu Met Glu
                515                 520                 525
Ala Leu Met Gln Leu Ser Arg Gln Gln Phe Pro Thr Met Pro Val Asp
530                 535                 540
Tyr Lys Arg Ser Ile Gln Arg Gly Ile Leu Leu Leu Ser Asn Arg Leu
545                 550                 555                 560
Gly Gln Leu Val Asp Leu Thr Arg Leu Leu Ser Tyr Asn Tyr Glu Thr
                565                 570                 575
Leu Met Ala Cys Ile Thr Met Asn Met Gln His Val Gln Thr Leu Thr
                580                 585                 590
Thr Glu Arg Leu Gln Leu Thr Ser Val Thr Ser Leu Cys Met Leu Ile
                595                 600                 605
Gly Asn Thr Thr Val Ile Pro Ser Pro Gln Thr Leu Phe His Tyr Tyr
610                 615                 620
Asn Val Asn Val Asn Phe His Ser Asn Tyr Asn Glu Arg Ile Asn Asp
625                 630                 635                 640
Ala Val Ala Ile Ile Thr Ala Ala Asn Arg Leu Asn Leu Tyr Gln Lys
                645                 650                 655
Lys Met Lys Ser Ile Val Glu Asp Phe Leu Lys Arg Leu Gln Ile Phe
                660                 665                 670
Asp Val Pro Arg Val Pro Asp Asp Gln Met Tyr Arg Leu Arg Asp Arg
                675                 680                 685
Leu Arg Leu Leu Pro Val Glu Arg Arg Leu Asp Ile Phe Asn Leu
690                 695                 700
Ile Leu Met Asn Met Glu Gln Ile Glu Arg Ala Ser Asp Lys Ile Ala
```

```
                705                 710                 715                 720
        Gln Gly Val Ile Ile Ala Tyr Arg Asp Met Gln Leu Glu Arg Asp Glu
                        725                 730                 735

Met Tyr Gly Phe Val Asn Ile Ala Arg Asn Leu Asp Gly Tyr Gln Gln
                        740                 745                 750

Ile Asn Leu Glu Glu Leu Met Arg Thr Gly Asp Tyr Gly Gln Ile Thr
                        755                 760                 765

Thr Met Leu Leu Asn Asn Gln Pro Val Ala Leu Val Gly Ala Leu Pro
                        770                 775                 780

Phe Val Thr Asp Ser Ser Val Ile Ser Leu Ile Ala Lys Leu Asp Ala
        785                 790                 795                 800

Thr Val Phe Ala Gln Ile Val Lys Leu Arg Lys Val Asp Thr Leu Lys
                        805                 810                 815

Pro Ile Leu Tyr Lys Ile Asn Ser Asp Ser Asn Asp Phe Tyr Leu Val
                        820                 825                 830

Ala Asn Tyr Asp Trp Ile Pro Thr Ser Thr Lys Val Tyr Lys Gln
                        835                 840                 845

Val Pro Gln Pro Phe Asp Phe Arg Ala Ser Met His Met Leu Thr Ser
        850                 855                 860

Asn Leu Thr Phe Thr Val Tyr Ser Asp Leu Leu Ser Phe Val Ser Ala
        865                 870                 875                 880

Asp Thr Val Glu Pro Ile Asn Ala Ile Ala Phe Asp Asn Met Arg Ile
                        885                 890                 895

Met Asn Glu Leu
                        900

<210> SEQ ID NO 21
<211> LENGTH: 900
<212> TYPE: PRT
<213> ORGANISM: Human rotavirus

<400> SEQUENCE: 21

Met Ala Tyr Arg Lys Arg Gly Thr Lys Arg Glu Asp Leu Pro Gln Gln
        1               5                   10                  15

Asn Glu Arg Leu Gln Glu Lys Glu Ile Glu Asn Asn Ile Asp Val Thr
                        20                  25                  30

Met Glu Asn Lys Asn Lys Asn Ile Asn Lys Asn Asn Arg Asn Asn
                        35                  40                  45

Asn Arg Lys Gln Gln Leu Ser Asp Lys Val Leu Ser Gln Lys Glu Glu
        50                  55                  60

Ile Ile Thr Asp Val Gln Asp Ile Lys Ile Thr Asp Glu Val Lys
        65                  70                  75                  80

Lys Ser Ser Lys Glu Glu Ser Lys Gln Leu Leu Glu Ile Leu Lys Thr
                        85                  90                  95

Lys Glu Asp His Gln Lys Glu Val Gln Tyr Glu Ile Leu Gln Lys Thr
                        100                 105                 110

Ile Pro Thr Phe Glu Pro Lys Glu Ser Ile Leu Lys Lys Leu Glu Asp
                        115                 120                 125

Ile Arg Pro Glu Gln Ala Lys Lys Gln Met Lys Leu Phe Arg Ile Phe
        130                 135                 140

Glu Pro Arg Gln Leu Pro Ile Tyr Arg Ala Asn Gly Glu Lys Glu Leu
        145                 150                 155                 160

Arg Asn Arg Trp Tyr Trp Lys Leu Lys Lys Asp Thr Leu Pro Asp Gly
                        165                 170                 175
```

-continued

```
Asp Tyr Asp Val Arg Glu Tyr Phe Leu Asn Leu Tyr Asp Gln Ile Leu
            180                 185                 190

Ile Glu Met Pro Asp Tyr Leu Leu Leu Lys Asp Met Ala Val Glu Asn
        195                 200                 205

Lys Asn Ser Arg Asp Ala Gly Lys Val Val Asp Ser Glu Thr Ala Ser
    210                 215                 220

Ile Cys Asp Ala Ile Phe Gln Asp Glu Glu Thr Glu Gly Val Ile Arg
225                 230                 235                 240

Arg Phe Ile Ala Asp Met Arg Gln Gln Ile Gln Ala Asp Arg Asn Ile
                245                 250                 255

Val Asn Tyr Pro Ser Ile Leu His Pro Ile Asp His Ala Phe Asn Glu
            260                 265                 270

Tyr Phe Leu Asn His Gln Leu Val Glu Pro Leu Asn Asn Asp Ile Ile
        275                 280                 285

Phe Asn Tyr Ile Pro Glu Arg Ile Arg Asn Asp Val Asn Tyr Ile Leu
    290                 295                 300

Asn Met Asp Met Asn Leu Pro Ser Thr Ala Arg Tyr Ile Arg Pro Asn
305                 310                 315                 320

Leu Leu Gln Asp Arg Leu Asn Leu His Asp Asn Phe Glu Ser Leu Trp
                325                 330                 335

Asp Thr Ile Thr Thr Ser Asn Tyr Ile Leu Ala Arg Ser Val Val Pro
            340                 345                 350

Asp Leu Lys Glu Lys Glu Leu Val Ser Thr Glu Ala Gln Ile Gln Lys
        355                 360                 365

Met Ser Gln Asp Leu Gln Leu Glu Ala Leu Thr Ile Gln Ser Glu Thr
    370                 375                 380

Gln Phe Leu Ala Gly Ile Asn Ser Gln Ala Ala Asn Asp Cys Phe Lys
385                 390                 395                 400

Thr Leu Ile Ala Ala Met Leu Ser Gln Arg Thr Met Ser Leu Asp Phe
                405                 410                 415

Val Thr Thr Asn Tyr Met Ser Leu Ile Ser Gly Met Trp Leu Leu Thr
            420                 425                 430

Val Ile Pro Asn Asp Met Phe Leu Arg Glu Ser Leu Val Ala Cys Glu
        435                 440                 445

Leu Ala Ile Ile Asn Thr Ile Val Tyr Pro Ala Phe Gly Met Gln Arg
    450                 455                 460

Met His Tyr Arg Asn Gly Asp Pro Gln Thr Pro Phe Gln Ile Ala Glu
465                 470                 475                 480

Gln Gln Ile Gln Asn Phe Gln Val Ala Asn Trp Leu His Phe Ile Asn
                485                 490                 495

Asn Asn Arg Phe Arg Gln Val Val Ile Asp Gly Val Leu Asn Gln Thr
            500                 505                 510

Leu Asn Asp Asn Ile Arg Asn Gly Gln Val Ile Asn Gln Leu Met Glu
        515                 520                 525

Ala Leu Met Gln Leu Ser Arg Gln Gln Phe Pro Thr Met Pro Val Asp
    530                 535                 540

Tyr Lys Arg Ser Ile Gln Arg Gly Ile Leu Leu Leu Ser Asn Arg Leu
545                 550                 555                 560

Gly Gln Leu Val Asp Leu Thr Arg Leu Leu Ser Tyr Asn Tyr Glu Thr
                565                 570                 575

Leu Met Ala Cys Ile Thr Met Asn Met Gln His Val Gln Thr Leu Thr
            580                 585                 590

Thr Glu Arg Leu Gln Leu Thr Ser Val Thr Ser Leu Cys Met Leu Ile
```

```
              595                 600                 605
Gly Asn Thr Thr Val Ile Pro Ser Pro Gln Thr Leu Phe His Tyr Tyr
610                 615                 620

Asn Val Asn Val Asn Phe His Ser Asn Tyr Asn Glu Arg Ile Asn Asp
625                 630                 635                 640

Ala Val Ala Ile Ile Thr Ala Ala Asn Arg Leu Asn Leu Tyr Gln Lys
                645                 650                 655

Lys Met Lys Ser Ile Val Glu Asp Phe Leu Lys Arg Leu Gln Ile Phe
                660                 665                 670

Asp Val Pro Arg Val Pro Asp Asp Gln Met Tyr Arg Leu Arg Asp Arg
                675                 680                 685

Leu Arg Leu Leu Pro Val Glu Arg Arg Leu Asp Ile Phe Asn Leu
690                 695                 700

Ile Leu Met Asn Met Glu Gln Ile Glu Arg Ala Ser Asp Lys Ile Ala
705                 710                 715                 720

Gln Gly Val Ile Ile Ala Tyr Arg Asp Met Gln Leu Glu Arg Asp Glu
                725                 730                 735

Met Tyr Gly Phe Val Asn Ile Ala Arg Asn Leu Asp Gly Tyr Gln Gln
                740                 745                 750

Ile Asn Leu Glu Glu Leu Met Arg Thr Gly Asp Tyr Gly Gln Ile Thr
                755                 760                 765

Thr Met Leu Leu Asn Asn Gln Pro Val Ala Leu Val Gly Ala Leu Pro
770                 775                 780

Phe Val Thr Asp Ser Ser Val Ile Ser Leu Ile Ala Lys Leu Asp Ala
785                 790                 795                 800

Thr Val Phe Ala Gln Ile Val Lys Leu Arg Lys Val Asp Thr Leu Lys
                805                 810                 815

Pro Ile Leu Tyr Lys Ile Asn Ser Asp Ser Asn Asp Phe Tyr Leu Val
                820                 825                 830

Ala Asn Tyr Asp Trp Ile Pro Thr Ser Thr Lys Val Tyr Lys Gln
                835                 840                 845

Val Pro Gln Pro Phe Asp Phe Arg Ala Ser Met His Met Leu Thr Ser
850                 855                 860

Asn Leu Thr Phe Thr Val Tyr Ser Asp Leu Leu Ser Phe Val Ser Ala
865                 870                 875                 880

Asp Thr Val Glu Pro Ile Asn Ala Ile Ala Phe Asp Asn Met Arg Ile
                885                 890                 895

Met Asn Glu Leu
                900

<210> SEQ ID NO 22
<211> LENGTH: 835
<212> TYPE: PRT
<213> ORGANISM: Human rotavirus

<400> SEQUENCE: 22

Met Lys Val Leu Ala Leu Arg His Ser Val Ala Gln Ile Tyr Ala Asp
1               5                   10                  15

Thr Gln Val Tyr Thr His Asp Asp Ser Lys Asp Asp Tyr Glu Asn Ala
                20                  25                  30

Phe Leu Ile Ser Asn Leu Thr Thr His Asn Ile Leu Tyr Leu Asn Tyr
            35                  40                  45

Ser Val Lys Thr Leu Gln Ile Leu Asn Lys Ser Gly Ile Ala Ala Ile
        50                  55                  60
```

```
Glu Ile Gln Lys Ile Asp Glu Leu Phe Thr Leu Ile Arg Cys Asn Phe
 65                  70                  75                  80

Thr Tyr Asp Tyr Ile Asp Asp Val Val Tyr Leu His Asp Tyr Ser Tyr
                 85                  90                  95

Tyr Ala Asn Asn Glu Ile Arg Thr Asp Gln Tyr Trp Val Thr Lys Thr
            100                 105                 110

Asn Ile Glu Asp Tyr Leu Leu Pro Gly Trp Lys Leu Thr Tyr Val Gly
        115                 120                 125

Tyr Asn Gly Ser Asp Thr Arg Gly His Tyr Asn Phe Ser Phe Arg Cys
130                 135                 140

Gln Asn Ala Ala Thr Asp Asp Val Ile Ile Glu Tyr Ile Tyr Ser
145                 150                 155                 160

Asn Glu Leu Asp Phe Gln Asn Phe Ile Leu Lys Lys Ile Lys Glu Arg
                165                 170                 175

Met Thr Thr Ser Leu Pro Ile Ala Arg Leu Ser Asn Arg Val Phe Arg
            180                 185                 190

Asp Lys Leu Phe Lys Thr Leu Ser Val Asn His Asp Lys Val Val Asn
        195                 200                 205

Val Gly Pro Arg Asn Glu Ser Met Phe Thr Phe Leu Asp His Pro Ser
210                 215                 220

Ile Lys Gln Phe Ser Asn Gly Pro Tyr Leu Val Lys Asp Thr Ile Lys
225                 230                 235                 240

Leu Lys Gln Glu Arg Trp Leu Gly Lys Arg Leu Ser Gln Phe Asp Ile
                245                 250                 255

Gly Gln Tyr Lys Asn Met Leu Asn Val Leu Thr Thr Leu Tyr Gln Tyr
            260                 265                 270

Tyr Asp Met Tyr His Glu Lys Pro Ile Ile Tyr Met Ile Gly Ser Ala
        275                 280                 285

Pro Ser Tyr Trp Ile Tyr Asp Val Lys Gln Tyr Ser Asp Leu Lys Phe
290                 295                 300

Glu Thr Trp Asp Pro Leu Asp Thr Pro Tyr Ser Asn Leu His His Lys
305                 310                 315                 320

Glu Leu Phe Tyr Ile Asn Asp Val Gln Lys Leu Lys Asp Asn Ser Ile
                325                 330                 335

Leu Tyr Ile Asp Ile Arg Thr Asp Arg Gly Asn Met Asp Trp Lys Glu
            340                 345                 350

Trp Arg Lys Val Val Glu Gly Gln Thr Ala Asp Asn Leu His Ile Ala
        355                 360                 365

Tyr Lys Tyr Leu Ser Thr Gly Lys Ala Lys Ile Cys Cys Val Lys Met
370                 375                 380

Thr Ala Met Asp Val Glu Leu Pro Ile Ser Ala Lys Leu Leu His His
385                 390                 395                 400

Pro Thr Thr Glu Ile Arg Ser Glu Phe Tyr Leu Met Met Asp Ile Trp
                405                 410                 415

Asp Ser Lys Asn Ile Lys Arg Phe Ile Pro Lys Gly Val Leu Tyr Ser
            420                 425                 430

Tyr Ile Asn Asn Thr Ile Thr Glu Asn Val Phe Ile Gln Gln Pro Phe
        435                 440                 445

Lys Leu Lys Thr Leu Lys Asn Glu Tyr Val Ile Ala Leu Tyr Ala Leu
            450                 455                 460

Ser Asn Asp Leu Asn Asn Arg Glu Asp Val Val Lys Leu Ile Asn Asn
465                 470                 475                 480

Gln Lys Arg Ala Leu Ile Thr Val Arg Ile Asn Asn Thr Phe Lys Asp
```

```
                485                 490                 495
Glu Pro Lys Val Gly Phe Lys Asn Ile Tyr Asp Trp Thr Phe Leu Pro
            500                 505                 510

Thr Asp Phe Glu Met Asn Gly Ser Ile Ile Thr Ser Tyr Asp Gly Cys
            515                 520                 525

Leu Gly Ile Phe Gly Leu Ser Ile Ser Leu Ala Ser Lys Pro Thr Gly
            530                 535                 540

Asn Asn His Leu Phe Ile Leu Ser Gly Thr Asp Lys Tyr Phe Lys Leu
545                 550                 555                 560

Asp Gln Phe Ala Asn His Met Ser Ile Ser Arg Arg Ser His Gln Ile
                565                 570                 575

Arg Phe Ser Glu Ser Ala Thr Ser Tyr Ser Gly Tyr Ile Phe Arg Asp
            580                 585                 590

Leu Ser Asn Asn Asn Phe Asn Leu Ile Gly Thr Asn Val Glu Asn Ser
            595                 600                 605

Val Ser Gly His Val Tyr Asn Ala Leu Ile Tyr Tyr Arg Tyr Asn Tyr
            610                 615                 620

Ser Phe Asp Leu Lys Arg Trp Ile Tyr Leu His Ser Thr Gly Lys Ala
625                 630                 635                 640

Ser Ile Glu Gly Gly Lys Tyr Tyr Glu His Ala Pro Ile Glu Leu Ile
                645                 650                 655

Tyr Ala Cys Arg Ser Ala Arg Glu Phe Ala Lys Leu Gln Asp Asp Leu
            660                 665                 670

Thr Val Leu Arg Tyr Ser Asn Glu Ile Glu Asn Tyr Ile Asn Lys Val
            675                 680                 685

Tyr Ser Ile Thr Tyr Ala Asp Asp Pro Asn Tyr Phe Ile Gly Ile Lys
            690                 695                 700

Phe Lys Asn Ile Pro Tyr Lys Tyr Asn Val Lys Val Pro His Leu Thr
705                 710                 715                 720

Phe Gly Val Leu Asn Ile Ser Glu Gln Met Leu Pro Asp Ala Ile Ala
                725                 730                 735

Ile Leu Lys Lys Phe Lys Asn Glu Leu Phe Gly Met Asp Ile Thr Thr
            740                 745                 750

Ser Tyr Thr Tyr Met Leu Ser Asp Glu Val Tyr Val Ala Asn Ile Ser
            755                 760                 765

Gly Val Leu Ser Thr Tyr Phe Lys Ile Tyr Asn Ala Phe Tyr Lys Glu
            770                 775                 780

Gln Ile Thr Phe Gly Gln Ser Arg Met Phe Ile Pro His Val Thr Leu
785                 790                 795                 800

Ser Phe Ser Asn Glu Lys Thr Val Arg Ile Asp Thr Thr Lys Leu Tyr
                805                 810                 815

Ile Asp Ser Ile Tyr Leu Arg Lys Ile Lys Gly Asp Thr Val Phe Asp
            820                 825                 830

Met Thr Glu
        835

<210> SEQ ID NO 23
<211> LENGTH: 835
<212> TYPE: PRT
<213> ORGANISM: Human rotavirus

<400> SEQUENCE: 23

Met Lys Val Leu Ala Leu Arg His Ser Val Ala Gln Val Tyr Ala Asp
1               5                   10                  15
```

-continued

```
Thr Gln Val Tyr Thr His Asp Asp Ser Lys Asp Glu Tyr Glu Asn Ala
             20                  25                  30

Phe Leu Ile Ser Asn Leu Thr Thr His Asn Ile Leu Tyr Leu Asn Tyr
         35                  40                  45

Asn Val Lys Thr Leu Gln Ile Leu Asn Lys Ser Gly Ile Ala Ala Ile
     50                  55                  60

Glu Ile Gln Lys Ile Asp Glu Leu Phe Thr Leu Ile Arg Cys Asn Phe
 65                  70                  75                  80

Thr Tyr Asp Tyr Ile Asp Asn Val Val Tyr Leu His Asp Tyr Ser Tyr
                 85                  90                  95

Tyr Thr Asn Asn Glu Ile Arg Thr Asp Gln His Trp Ile Thr Lys Thr
                100                 105                 110

Asn Ile Glu Asp Tyr Leu Leu Pro Gly Trp Lys Leu Thr Tyr Val Gly
            115                 120                 125

Tyr Asn Gly Ser Asp Thr Arg Gly His Tyr Asn Phe Ser Phe Arg Cys
        130                 135                 140

Gln Asn Ala Ala Thr Asp Asp Ala Ile Ile Glu Tyr Ile Tyr Ser
145                 150                 155                 160

Asp Glu Leu Asp Phe Gln Ser Phe Ile Leu Lys Lys Ile Lys Glu Arg
                165                 170                 175

Met Thr Thr Ser Leu Pro Ile Ala Arg Leu Ser Asn Arg Val Phe Arg
            180                 185                 190

Asp Lys Leu Phe Lys Thr Leu Ser Val Asn His Asp Lys Val Val Asn
        195                 200                 205

Ile Gly Pro Arg Asn Glu Ser Met Phe Thr Phe Leu Asp Tyr Pro Ser
210                 215                 220

Ile Lys Gln Phe Ser Asn Gly Pro Tyr Leu Val Lys Asp Thr Ile Lys
225                 230                 235                 240

Leu Lys Gln Glu Arg Trp Leu Gly Lys Arg Leu Ser Gln Phe Asp Ile
                245                 250                 255

Gly Gln Tyr Lys Asn Met Leu Asn Val Leu Thr Thr Leu Tyr Gln Tyr
            260                 265                 270

Tyr Asp Ile Tyr His Glu Lys Pro Ile Val Tyr Met Ile Gly Ser Ala
        275                 280                 285

Pro Ser Tyr Trp Ile Tyr Asp Val Lys Gln Tyr Ser Asn Leu Lys Phe
    290                 295                 300

Glu Thr Trp Asp Pro Leu Asp Thr Pro Tyr Ser Asn Leu His His Lys
305                 310                 315                 320

Glu Leu Phe Tyr Met Asn Asp Val Gln Lys Leu Lys Asp Asn Ser Ile
                325                 330                 335

Leu Tyr Ile Asp Ile Arg Thr Asp Arg Gly Thr Val Asp Trp Lys Glu
            340                 345                 350

Trp Arg Lys Ile Val Glu Arg Gln Thr Ile Asp Asn Leu His Ile Ala
        355                 360                 365

Tyr Lys Tyr Leu Ser Thr Gly Lys Ala Lys Val Cys Cys Val Lys Met
    370                 375                 380

Thr Ala Met Asp Leu Glu Leu Pro Ile Ser Ala Lys Leu Leu His His
385                 390                 395                 400

Pro Thr Thr Glu Ile Arg Ser Glu Phe Tyr Leu Val Met Asp Ile Trp
                405                 410                 415

Asp Ser Lys Asn Ile Lys Arg Phe Ile Pro Lys Gly Val Leu Tyr Ser
            420                 425                 430

Tyr Ile Asn Asn Thr Ile Thr Glu Asn Val Phe Ile Gln Gln Pro Phe
```

```
            435                 440                 445
Lys Leu Lys Thr Leu Lys Asn Glu Tyr Ile Ile Ala Leu Tyr Ala Leu
450                 455                 460

Ser Asn Asp Phe Asn Asn Arg Glu Asp Val Val Lys Leu Ile Asn Asn
465                 470                 475                 480

Gln Lys Lys Ala Leu Met Thr Val Arg Ile Asn Asn Thr Phe Lys Asp
                485                 490                 495

Glu Pro Lys Val Gly Phe Lys Asn Ile Tyr Asp Trp Thr Phe Leu Pro
            500                 505                 510

Thr Asp Phe Glu Thr Asn Gly Ser Ile Ile Thr Ser Tyr Asp Gly Cys
        515                 520                 525

Leu Gly Ile Phe Gly Leu Ser Ile Ser Leu Ala Ser Lys Pro Thr Gly
    530                 535                 540

Asn Asn His Leu Phe Ile Leu Ser Gly Thr Asp Lys Tyr Phe Lys Leu
545                 550                 555                 560

Asp Gln Phe Ala Asn His Met Ser Ile Ser Arg Arg Ser His Gln Ile
                565                 570                 575

Arg Phe Ser Glu Ser Ala Thr Ser Tyr Ser Gly Tyr Ile Phe Arg Asp
            580                 585                 590

Leu Ser Asn Asn Phe Asn Leu Ile Gly Thr Asn Val Glu Asn Ser
        595                 600                 605

Val Ser Gly His Val Tyr Asn Ala Leu Ile Tyr Tyr Arg Tyr Asn Tyr
    610                 615                 620

Ser Phe Asp Leu Lys Arg Trp Ile Tyr Leu His Ser Thr Gly Lys Ala
625                 630                 635                 640

Ser Ile Glu Gly Gly Lys Tyr Tyr Glu His Ala Pro Ile Glu Leu Ile
                645                 650                 655

Tyr Ala Cys Arg Ser Ala Arg Glu Phe Ala Lys Leu Gln Asp Asp Leu
            660                 665                 670

Thr Val Leu Arg Tyr Ser Asn Glu Ile Glu Asn Tyr Ile Asn Arg Val
        675                 680                 685

Tyr Ser Ile Thr Tyr Ala Asp Asp Pro Asn Tyr Phe Ile Gly Val Lys
    690                 695                 700

Phe Lys Asn Ile Pro Tyr Lys Tyr Asn Val Lys Val Pro His Leu Thr
705                 710                 715                 720

Phe Gly Val Leu Asn Ile Ser Glu Gln Met Leu Pro Asp Val Ile Thr
                725                 730                 735

Ile Leu Lys Arg Phe Lys Asn Glu Leu Phe Gly Met Glu Val Thr Thr
            740                 745                 750

Ser Tyr Thr Tyr Met Leu Ser Asp Glu Val Tyr Val Ala Asn Ile Ser
        755                 760                 765

Gly Val Leu Ser Thr Tyr Phe Lys Ile Tyr Asn Ala Phe Tyr Lys Glu
    770                 775                 780

Gln Ile Thr Phe Gly Gln Ser Arg Met Phe Ile Pro His Val Thr Leu
785                 790                 795                 800

Ser Phe Ser Asn Glu Lys Thr Val Arg Ile Asp Thr Thr Lys Leu Tyr
                805                 810                 815

Ile Asp Ser Ile Tyr Leu Arg Lys Ile Lys Gly Asn Thr Val Phe Asp
            820                 825                 830

Met Thr Gly
        835

<210> SEQ ID NO 24
```

```
<211> LENGTH: 835
<212> TYPE: PRT
<213> ORGANISM: Human rotavirus

<400> SEQUENCE: 24

Met Lys Val Leu Ala Leu Arg His Ser Val Ala Gln Val Tyr Ala Asp
1               5                   10                  15

Thr Gln Val Tyr Thr His Asp Asp Ser Lys Asp Glu Tyr Glu Asn Ala
            20                  25                  30

Phe Leu Ile Ser Asn Leu Thr Thr His Asn Ile Leu Tyr Leu Asn Tyr
        35                  40                  45

Asn Val Lys Thr Leu Gln Ile Leu Asn Lys Ser Gly Ile Ala Ala Ile
    50                  55                  60

Glu Ile Gln Lys Ile Asp Glu Leu Phe Thr Leu Ile Arg Cys Asn Phe
65                  70                  75                  80

Thr Tyr Asp Tyr Ile Asp Asn Val Val Tyr Leu His Asp Tyr Ser Tyr
                85                  90                  95

Tyr Thr Asn Asn Glu Ile Arg Thr Asp Gln His Trp Ile Thr Lys Thr
            100                 105                 110

Asn Ile Glu Asp Tyr Leu Leu Pro Gly Trp Lys Leu Thr Tyr Val Gly
        115                 120                 125

Tyr Asn Gly Ser Asp Thr Arg Gly His Tyr Asn Phe Ser Phe Arg Cys
    130                 135                 140

Gln Asn Ala Ala Thr Asp Asp Ala Ile Ile Glu Tyr Ile Tyr Ser
145                 150                 155                 160

Asp Glu Leu Asp Phe Gln Ser Phe Ile Leu Lys Lys Ile Lys Glu Arg
                165                 170                 175

Met Thr Thr Ser Leu Pro Ile Ala Arg Leu Ser Asn Arg Val Phe Arg
            180                 185                 190

Asp Lys Leu Phe Lys Thr Leu Ser Val Asn His Asp Lys Val Val Asn
        195                 200                 205

Ile Gly Pro Arg Asn Glu Ser Met Phe Thr Phe Leu Asp Tyr Pro Ser
    210                 215                 220

Ile Lys Gln Phe Ser Asn Gly Pro Tyr Leu Val Lys Asp Thr Ile Lys
225                 230                 235                 240

Leu Lys Gln Glu Arg Trp Leu Gly Lys Arg Leu Ser Gln Phe Asp Ile
                245                 250                 255

Gly Gln Tyr Lys Asn Met Leu Asn Val Leu Thr Thr Leu Tyr Gln Tyr
            260                 265                 270

Tyr Asp Ile Tyr His Glu Lys Pro Ile Val Tyr Met Ile Gly Ser Ala
        275                 280                 285

Pro Ser Tyr Trp Ile Tyr Asp Val Lys Gln Tyr Ser Asn Leu Lys Phe
    290                 295                 300

Glu Thr Trp Asp Pro Leu Asp Thr Pro Tyr Ser Asn Leu His His Lys
305                 310                 315                 320

Glu Leu Phe Tyr Met Asn Asp Val Gln Lys Lys Asp Asn Ser Ile
                325                 330                 335

Leu Tyr Ile Asp Ile Arg Thr Asp Arg Gly Thr Val Asp Trp Lys Glu
            340                 345                 350

Trp Arg Lys Ile Val Glu Arg Gln Thr Ile Asp Asn Leu His Ile Ala
        355                 360                 365

Tyr Lys Tyr Leu Ser Thr Gly Lys Ala Lys Val Cys Cys Val Lys Met
    370                 375                 380

Thr Ala Met Asp Leu Glu Leu Pro Ile Ser Ala Lys Leu Leu His His
```

```
385                 390                 395                 400
Pro Thr Thr Glu Ile Arg Ser Glu Phe Tyr Leu Val Met Asp Ile Trp
                405                 410                 415

Asp Ser Lys Asn Ile Lys Arg Phe Ile Pro Lys Gly Val Leu Tyr Ser
                420                 425                 430

Tyr Ile Asn Asn Thr Ile Thr Glu Asn Val Phe Ile Gln Gln Pro Phe
                435                 440                 445

Lys Leu Lys Thr Leu Lys Asn Glu Tyr Ile Ile Ala Leu Tyr Ala Leu
                450                 455                 460

Ser Asn Asp Phe Asn Asn Arg Glu Asp Val Val Lys Leu Ile Asn Asn
465                 470                 475                 480

Gln Lys Lys Ala Leu Met Thr Val Arg Ile Asn Asn Thr Phe Lys Asp
                485                 490                 495

Glu Pro Lys Val Gly Phe Lys Asn Ile Tyr Asp Trp Thr Phe Leu Pro
                500                 505                 510

Thr Asp Phe Glu Thr Asn Gly Ser Ile Ile Thr Ser Tyr Asp Gly Cys
                515                 520                 525

Leu Gly Ile Phe Gly Leu Ser Ile Ser Leu Ala Ser Lys Pro Thr Gly
                530                 535                 540

Asn Asn His Leu Phe Ile Leu Ser Gly Thr Asp Lys Tyr Phe Lys Leu
545                 550                 555                 560

Asp Gln Phe Ala Asn His Met Ser Ile Ser Arg Arg Ser His Gln Ile
                565                 570                 575

Arg Phe Ser Glu Ser Ala Thr Ser Tyr Ser Gly Tyr Ile Phe Arg Asp
                580                 585                 590

Leu Ser Asn Asn Asn Phe Asn Leu Ile Gly Thr Asn Val Glu Asn Ser
                595                 600                 605

Val Ser Gly His Val Tyr Asn Ala Leu Ile Tyr Tyr Arg Tyr Asn Tyr
                610                 615                 620

Ser Phe Asp Leu Lys Arg Trp Ile Tyr Leu His Ser Thr Gly Lys Ala
625                 630                 635                 640

Ser Ile Glu Gly Gly Lys Tyr Tyr Glu His Ala Pro Ile Glu Leu Ile
                645                 650                 655

Tyr Ala Cys Arg Ser Ala Arg Glu Phe Ala Lys Leu Gln Asp Asp Leu
                660                 665                 670

Thr Val Leu Arg Tyr Ser Asn Glu Ile Glu Asn Tyr Ile Asn Arg Val
                675                 680                 685

Tyr Ser Ile Thr Tyr Ala Asp Asp Pro Asn Tyr Phe Ile Gly Val Lys
                690                 695                 700

Phe Lys Asn Ile Pro Tyr Lys Tyr Asn Val Lys Val Pro His Leu Thr
705                 710                 715                 720

Phe Gly Val Leu Asn Ile Ser Glu Gln Met Leu Pro Asp Val Ile Thr
                725                 730                 735

Ile Leu Lys Arg Phe Lys Asn Glu Leu Phe Gly Met Glu Val Thr Thr
                740                 745                 750

Ser Tyr Thr Tyr Met Leu Ser Asp Glu Val Tyr Val Ala Asn Ile Ser
                755                 760                 765

Gly Val Leu Ser Thr Tyr Phe Lys Ile Tyr Asn Ala Phe Tyr Lys Glu
                770                 775                 780

Gln Ile Thr Phe Gly Gln Ser Arg Met Phe Ile Pro His Val Thr Leu
785                 790                 795                 800

Ser Phe Ser Asn Glu Lys Thr Val Arg Ile Asp Thr Thr Lys Leu Tyr
                805                 810                 815
```

```
Ile Asp Ser Ile Tyr Leu Arg Lys Ile Lys Gly Asn Thr Val Phe Asp
            820                 825                 830

Met Thr Gly
        835

<210> SEQ ID NO 25
<211> LENGTH: 775
<212> TYPE: PRT
<213> ORGANISM: Human rotavirus

<400> SEQUENCE: 25

Met Ala Ser Leu Ile Tyr Arg Gln Leu Leu Thr Asn Ser Tyr Ser Val
1               5                   10                  15

Asp Leu His Asp Glu Ile Glu Gln Ile Gly Ser Glu Lys Thr Gln Asn
                20                  25                  30

Val Thr Val Asn Pro Gly Pro Phe Ala Gln Thr Arg Tyr Ala Pro Val
            35                  40                  45

Asn Trp Gly His Gly Glu Ile Asn Asp Ser Thr Thr Val Glu Pro Ile
        50                  55                  60

Leu Asp Gly Pro Tyr Gln Pro Thr Thr Phe Lys Pro Leu Thr Asp Tyr
65                  70                  75                  80

Trp Ile Leu Ile Asn Ser Asn Thr Asn Gly Val Val Tyr Glu Ser Thr
                85                  90                  95

Asn Asn Ser Asp Phe Trp Thr Ala Val Ala Val Glu Pro His Val
                100                 105                 110

Asn Pro Val Asp Arg Gln Tyr Thr Val Phe Gly Glu Asn Lys Gln Phe
            115                 120                 125

Asn Val Arg Asn Asp Ser Asp Lys Trp Lys Phe Leu Glu Met Phe Arg
        130                 135                 140

Gly Ser Ser Gln Asn Glu Phe Tyr Asn Arg Arg Thr Leu Thr Ser Asp
145                 150                 155                 160

Thr Lys Leu Val Gly Ile Leu Lys Tyr Gly Gly Arg Ile Trp Thr Phe
                165                 170                 175

His Gly Glu Thr Pro Arg Ala Thr Thr Asp Ser Ser Asn Thr Ala Asn
            180                 185                 190

Leu Asn Asp Ile Ser Ile Ile His Ser Glu Phe Tyr Ile Ile Pro
        195                 200                 205

Arg Ser Gln Glu Ser Lys Cys Asn Glu Tyr Ile Asn Asn Gly Leu Pro
210                 215                 220

Pro Ile Gln Asn Thr Arg Asn Val Val Pro Leu Ser Leu Ser Ser Arg
225                 230                 235                 240

Ser Ile Gln Tyr Lys Arg Ala Gln Val Asn Glu Asp Ile Thr Ile Ser
                245                 250                 255

Lys Thr Ser Leu Trp Lys Glu Met Gln Cys Asn Arg Asp Ile Ile Ile
            260                 265                 270

Arg Phe Lys Phe Gly Asn Ser Ile Val Lys Leu Gly Gly Leu Gly Tyr
        275                 280                 285

Lys Trp Ser Glu Ile Ser Tyr Lys Ala Ala Asn Tyr Gln Tyr Asn Tyr
            290                 295                 300

Leu Arg Asp Gly Glu Gln Val Thr Ala His Thr Thr Cys Ser Val Asn
305                 310                 315                 320

Gly Val Asn Asn Phe Ser Tyr Asn Gly Gly Ser Leu Pro Thr Asp Phe
                325                 330                 335

Ser Val Ser Arg Tyr Glu Val Ile Lys Glu Asn Ser Tyr Val Tyr Val
```

-continued

```
              340                 345                 350
Asp Tyr Trp Asp Asp Ser Lys Ala Phe Arg Asn Met Val Tyr Val Arg
            355                 360                 365

Ser Leu Ala Ala Asn Leu Asn Ser Val Lys Cys Thr Gly Gly Ser Tyr
        370                 375                 380

Asn Phe Ser Ile Pro Val Gly Ala Trp Pro Val Met Asn Gly Gly Ala
385                 390                 395                 400

Val Ser Leu His Phe Ala Gly Val Thr Leu Ser Thr Gln Phe Thr Asp
                405                 410                 415

Phe Val Ser Leu Asn Ser Leu Arg Phe Arg Phe Ser Leu Thr Val Asp
            420                 425                 430

Glu Pro Ser Phe Ser Ile Leu Arg Thr Arg Thr Val Asn Leu Tyr Gly
        435                 440                 445

Leu Pro Ala Ala Asn Pro Asn Asn Gly Asn Glu Tyr Tyr Glu Ile Ser
    450                 455                 460

Gly Arg Phe Ser Leu Ile Ser Leu Val Pro Thr Asn Asp Asp Tyr Gln
465                 470                 475                 480

Thr Pro Ile Met Asn Ser Val Thr Val Arg Gln Asp Leu Glu Arg Gln
                485                 490                 495

Leu Thr Asp Leu Arg Glu Glu Phe Asn Ser Leu Ser Gln Glu Ile Ala
            500                 505                 510

Met Ser Gln Leu Ile Asp Leu Ala Leu Leu Pro Leu Asp Met Phe Ser
        515                 520                 525

Met Phe Ser Gly Ile Lys Ser Thr Ile Asp Leu Thr Lys Ser Met Ala
    530                 535                 540

Thr Ser Val Met Lys Lys Phe Arg Lys Ser Lys Leu Ala Thr Ser Ile
545                 550                 555                 560

Ser Glu Met Thr Asn Ser Leu Ser Asp Ala Ala Ser Ser Ala Ser Arg
                565                 570                 575

Ser Val Ser Ile Arg Ser Asn Ile Ser Thr Ile Ser Asn Trp Thr Asn
            580                 585                 590

Val Ser Asn Asp Val Ser Asn Val Thr Asn Ser Leu Ser Asp Ile Ser
        595                 600                 605

Thr Gln Thr Ser Thr Ile Ser Lys Asn Leu Arg Leu Lys Glu Met Ile
    610                 615                 620

Thr Gln Thr Glu Gly Met Ser Phe Asp Asp Ile Ser Ala Ala Val Leu
625                 630                 635                 640

Lys Thr Lys Ile Asp Met Ser Thr Gln Ile Gly Lys Asn Thr Leu Pro
                645                 650                 655

Asp Ile Val Thr Glu Ala Ser Glu Lys Phe Ile Pro Lys Arg Ser Tyr
            660                 665                 670

Arg Ile Leu Lys Asp Asp Glu Val Met Glu Ile Asn Thr Glu Gly Lys
        675                 680                 685

Val Phe Ala Tyr Lys Ile Asp Thr Leu Asn Glu Val Pro Phe Asp Val
    690                 695                 700

Asn Lys Phe Ala Glu Leu Val Thr Asn Ser Pro Val Ile Ser Ala Ile
705                 710                 715                 720

Ile Asp Phe Lys Thr Leu Lys Asn Leu Asn Asp Asn Tyr Gly Ile Thr
                725                 730                 735

Arg Ile Glu Ala Leu Asn Leu Ile Lys Ser Asn Pro Asn Val Leu Arg
            740                 745                 750

Asn Phe Ile Asn Gln Asn Asn Pro Ile Ile Arg Asn Arg Ile Glu Gln
        755                 760                 765
```

```
Leu Ile Leu Gln Cys Lys Leu
    770             775

<210> SEQ ID NO 26
<211> LENGTH: 775
<212> TYPE: PRT
<213> ORGANISM: Human rotavirus

<400> SEQUENCE: 26

Met Ala Ser Leu Ile Tyr Arg Gln Leu Leu Thr Asn Ser Tyr Ser Val
1               5                   10                  15

Asp Leu Tyr Asp Glu Ile Glu Gln Ile Gly Ser Gly Lys Thr Gln Asn
                20                  25                  30

Val Thr Ile Asn Pro Gly Pro Phe Ala Gln Thr Arg Tyr Ala Pro Val
            35                  40                  45

Asn Trp Gly His Gly Glu Ile Asn Asp Ser Thr Thr Val Glu Pro Ile
50                  55                  60

Leu Asp Gly Pro Tyr Gln Pro Thr Thr Phe Thr Pro Pro Asn Asp Tyr
65                  70                  75                  80

Trp Ile Leu Ile Asn Ser Asn Thr Asn Gly Val Val Tyr Glu Ser Thr
                85                  90                  95

Asn Asn Ser Asp Phe Trp Thr Ala Val Val Ala Ile Glu Pro His Val
                100                 105                 110

Thr Pro Val Asp Arg Gln Tyr Met Ile Phe Gly Glu Ser Lys Gln Phe
            115                 120                 125

Asn Val Ser Asn Asp Ser Asn Lys Trp Lys Phe Leu Glu Met Phe Arg
130                 135                 140

Ser Ser Ser Gln Asn Glu Phe Tyr Asn Arg Arg Thr Leu Thr Ser Asp
145                 150                 155                 160

Thr Arg Leu Val Gly Ile Leu Lys Tyr Gly Gly Arg Val Trp Thr Phe
                165                 170                 175

His Gly Glu Thr Pro Arg Ala Thr Thr Asp Ser Ser Ser Thr Ala Asn
            180                 185                 190

Leu Asn Asn Ile Ser Ile Thr Ile His Ser Glu Phe Tyr Ile Ile Pro
            195                 200                 205

Arg Ser Gln Glu Ser Lys Cys Asn Glu Tyr Ile Asn Asn Gly Leu Pro
210                 215                 220

Pro Ile Gln Asn Thr Arg Asn Val Val Pro Leu Pro Leu Ser Ser Arg
225                 230                 235                 240

Ser Ile Gln Tyr Lys Arg Ala Gln Val Asp Glu Asp Ile Ile Val Ser
                245                 250                 255

Lys Thr Ser Leu Trp Lys Glu Met Gln Tyr Asn Arg Asp Ile Ile Ile
            260                 265                 270

Arg Phe Lys Phe Gly Asn Ser Ile Val Lys Met Gly Gly Leu Gly Tyr
            275                 280                 285

Lys Trp Ser Glu Ile Ser Tyr Lys Ala Ala Asn Tyr Gln Tyr Asn Tyr
        290                 295                 300

Leu Arg Asp Gly Glu Gln Val Thr Ala His Thr Thr Cys Ser Val Asn
305                 310                 315                 320

Gly Val Asn Asn Phe Ser Tyr Asn Gly Gly Ser Leu Pro Thr Asp Phe
                325                 330                 335

Gly Ile Ser Arg Tyr Glu Val Ile Lys Glu Asn Ser Tyr Val Tyr Val
            340                 345                 350

Asp Tyr Trp Asp Asp Ser Lys Ala Phe Arg Asn Met Val Tyr Val Arg
```

```
                355                 360                 365
Ser Leu Ala Ala Asn Leu Asn Ser Val Arg Cys Thr Gly Ser Tyr
    370                 375                 380

Asp Phe Ser Ile Pro Val Gly Ala Trp Pro Val Ile Asn Gly Gly Ala
385                 390                 395                 400

Val Ser Leu His Phe Ala Gly Val Thr Leu Ser Thr Gln Phe Thr Asp
            405                 410                 415

Phe Val Ser Leu Asn Ser Leu Arg Phe Arg Phe Ser Leu Thr Val Asp
                420                 425                 430

Glu Pro Pro Phe Ser Ile Leu Arg Thr Arg Thr Val Asn Leu Tyr Gly
            435                 440                 445

Leu Pro Ala Ala Asn Pro Asn Gly Asn Glu Tyr Tyr Glu Ile Ser
    450                 455                 460

Gly Arg Phe Ser Leu Ile Ser Leu Val Pro Thr Asn Asp Asp Tyr Gln
465                 470                 475                 480

Thr Pro Ile Met Asn Ser Val Thr Val Arg Gln Asp Leu Glu Arg Gln
            485                 490                 495

Leu Thr Asp Leu Arg Glu Glu Phe Asn Ser Leu Ser Gln Glu Ile Ala
                500                 505                 510

Met Ala Gln Leu Ile Asp Leu Ala Leu Leu Pro Leu Asp Met Phe Ser
            515                 520                 525

Met Phe Ser Gly Ile Lys Ser Thr Ile Asp Leu Thr Lys Ser Met Ala
            530                 535                 540

Thr Ser Val Met Lys Lys Phe Arg Lys Ser Lys Leu Ala Thr Ser Ile
545                 550                 555                 560

Ser Glu Met Thr Asn Ser Leu Ser Asp Ala Ala Ser Ser Ala Ser Arg
                565                 570                 575

Asn Val Ser Ile Arg Ser Asn Leu Ser Ala Ile Ser Asn Trp Thr Asn
                580                 585                 590

Val Ser Asn Asp Val Ser Asn Val Thr Asn Ser Leu Asn Asp Ile Ser
            595                 600                 605

Thr Gln Thr Ser Thr Ile Gly Lys Lys Leu Arg Leu Lys Glu Met Ile
            610                 615                 620

Thr Gln Thr Glu Gly Met Ser Phe Asp Asp Ile Ser Ala Ala Val Leu
625                 630                 635                 640

Lys Thr Lys Ile Asp Met Ser Thr Gln Ile Gly Lys Asn Thr Leu Pro
            645                 650                 655

Asp Ile Val Thr Glu Ala Ser Glu Lys Phe Ile Pro Lys Arg Ser Tyr
                660                 665                 670

Arg Ile Leu Lys Asp Asp Glu Val Met Glu Ile Asn Thr Glu Gly Lys
            675                 680                 685

Phe Phe Ala Tyr Lys Ile Asn Thr Phe Asp Glu Val Pro Phe Asp Val
            690                 695                 700

Asn Lys Phe Ala Glu Leu Val Thr Asp Ser Pro Val Ile Ser Ala Ile
705                 710                 715                 720

Ile Asp Phe Lys Thr Leu Lys Asn Leu Asn Asp Asn Tyr Gly Ile Thr
                725                 730                 735

Arg Thr Glu Ala Leu Asn Leu Ile Lys Ser Asn Pro Asn Met Leu Arg
            740                 745                 750

Asn Phe Ile Asn Gln Asn Asn Pro Ile Ile Arg Asn Arg Ile Glu Gln
            755                 760                 765

Leu Ile Leu Gln Cys Lys Leu
            770                 775
```

<210> SEQ ID NO 27
<211> LENGTH: 775
<212> TYPE: PRT
<213> ORGANISM: Human rotavirus

<400> SEQUENCE: 27

```
Met Ala Ser Leu Ile Tyr Arg Gln Leu Leu Thr Asn Ser Tyr Ser Val
1               5                   10                  15

Asp Leu Tyr Asp Glu Ile Glu Gln Ile Gly Ser Gly Lys Thr Gln Asn
                20                  25                  30

Val Thr Ile Asn Pro Gly Pro Phe Ala Gln Thr Arg Tyr Ala Pro Val
            35                  40                  45

Asn Trp Asp His Gly Glu Ile Asn Asp Ser Thr Thr Val Glu Pro Ile
        50                  55                  60

Leu Asp Gly Pro Tyr Gln Pro Thr Thr Phe Thr Pro Pro Asn Asp Tyr
65                  70                  75                  80

Trp Ile Leu Ile Asn Ser Asn Thr Asn Gly Val Val Tyr Glu Ser Thr
                85                  90                  95

Asn Asn Ser Asp Phe Trp Thr Ala Val Val Ala Ile Glu Pro His Val
                100                 105                 110

Thr Pro Val Asp Arg Gln Tyr Met Ile Phe Gly Glu Ser Lys Gln Phe
            115                 120                 125

Asn Val Ser Asn Asp Ser Asn Lys Trp Lys Phe Leu Glu Met Phe Arg
        130                 135                 140

Ser Ser Ser Gln Asn Glu Phe Tyr Asn Arg Arg Thr Leu Thr Ser Asp
145                 150                 155                 160

Thr Arg Leu Val Gly Ile Leu Lys Tyr Gly Gly Arg Val Trp Thr Phe
                165                 170                 175

His Gly Glu Thr Pro Arg Ala Thr Thr Asp Ser Ser Ser Thr Ala Asn
                180                 185                 190

Leu Asn Asn Ile Ser Ile Thr Ile His Ser Glu Phe Tyr Ile Ile Pro
            195                 200                 205

Arg Ser Gln Glu Ser Lys Cys Asn Glu Tyr Ile Asn Asn Gly Leu Pro
        210                 215                 220

Pro Ile Gln Asn Thr Arg Asn Val Val Pro Leu Pro Leu Ser Ser Arg
225                 230                 235                 240

Ser Ile Gln Tyr Lys Arg Ala Gln Val Asp Glu Asp Ile Ile Val Ser
                245                 250                 255

Lys Thr Ser Leu Trp Lys Glu Met Gln Tyr Asn Arg Asp Ile Ile Ile
                260                 265                 270

Arg Phe Lys Phe Gly Asn Ser Ile Val Lys Met Gly Gly Leu Gly Tyr
            275                 280                 285

Lys Trp Ser Glu Ile Ser Tyr Lys Ala Ala Asn Tyr Gln Tyr Asn Tyr
        290                 295                 300

Leu Arg Asp Gly Glu Gln Val Thr Ala His Thr Thr Cys Ser Val Asn
305                 310                 315                 320

Gly Val Asn Asn Phe Ser Tyr Asn Gly Gly Phe Leu Pro Thr Asp Phe
                325                 330                 335

Gly Ile Ser Arg Tyr Glu Val Ile Lys Glu Asn Ser Tyr Val Tyr Val
                340                 345                 350

Asp Tyr Trp Asp Asp Ser Lys Ala Phe Arg Asn Ile Val Tyr Val Arg
            355                 360                 365

Ser Leu Ala Ala Asn Leu Asn Ser Val Arg Cys Thr Gly Gly Ser Tyr
```

```
            370                 375                 380
His Phe Ser Leu Pro Val Gly Ala Trp Pro Val Ile Asn Gly Gly Ala
385                 390                 395                 400

Val Ser Leu His Phe Ala Gly Val Thr Leu Ser Thr Gln Phe Thr Asp
                405                 410                 415

Phe Val Ser Leu Asn Ser Leu Arg Phe Arg Phe Ser Leu Thr Val Asp
                420                 425                 430

Glu Pro Pro Phe Ser Ile Leu Arg Thr Arg Thr Val Asn Leu Tyr Gly
            435                 440                 445

Leu Pro Ala Ala Asn Pro Asn Asn Gly Asn Glu Tyr Tyr Glu Ile Ser
450                 455                 460

Gly Arg Phe Ser Leu Ile Ser Leu Val Pro Thr Asn Asp Asp Tyr Gln
465                 470                 475                 480

Thr Pro Ile Met Asn Ser Val Thr Val Arg Gln Asp Leu Glu Arg Gln
                485                 490                 495

Leu Thr Asp Leu Arg Glu Glu Phe Asn Ser Leu Ser Gln Glu Ile Ala
                500                 505                 510

Met Ala Gln Leu Ile Asp Leu Ala Leu Leu Pro Leu Asp Met Phe Ser
            515                 520                 525

Met Phe Ser Gly Ile Lys Ser Thr Ile Asp Leu Thr Lys Ser Met Ala
530                 535                 540

Thr Ser Val Met Lys Lys Phe Arg Lys Ser Lys Leu Ala Thr Ser Ile
545                 550                 555                 560

Ser Glu Met Thr Asn Ser Leu Ser Asp Ala Ala Ser Ser Ala Ser Arg
                565                 570                 575

Asn Val Ser Ile Arg Ser Asn Leu Ser Ala Ile Ser Asn Trp Thr Asn
                580                 585                 590

Val Ser Asn Asp Val Ser Asn Val Thr Asn Ser Leu Asn Asp Ile Ser
            595                 600                 605

Thr Gln Thr Ser Thr Ile Gly Lys Lys Leu Arg Leu Lys Glu Met Ile
            610                 615                 620

Thr Gln Thr Glu Gly Met Ser Phe Asp Asp Ile Ser Ala Ala Val Leu
625                 630                 635                 640

Lys Thr Lys Ile Asp Met Ser Thr Gln Ile Gly Lys Asn Thr Leu Pro
                645                 650                 655

Asp Ile Val Thr Glu Ala Ser Glu Lys Phe Ile Pro Lys Arg Ser Tyr
                660                 665                 670

Arg Ile Leu Lys Asp Asp Glu Val Met Glu Ile Asn Thr Glu Gly Lys
            675                 680                 685

Phe Phe Ala Tyr Lys Ile Asn Thr Phe Asp Glu Val Pro Phe Asp Val
690                 695                 700

Asn Lys Phe Ala Glu Leu Val Thr Asp Ser Pro Val Ile Ser Ala Ile
705                 710                 715                 720

Ile Asp Phe Lys Thr Leu Lys Asn Leu Asn Asp Asn Tyr Gly Ile Thr
                725                 730                 735

Arg Thr Glu Ala Leu Asn Leu Ile Lys Ser Asn Pro Asn Met Leu Arg
                740                 745                 750

Asn Phe Ile Asn Gln Asn Pro Ile Ile Arg Asn Arg Ile Glu Gln
            755                 760                 765

Leu Ile Leu Gln Cys Lys Leu
            770                 775

<210> SEQ ID NO 28
```

```
<211> LENGTH: 397
<212> TYPE: PRT
<213> ORGANISM: Human rotavirus

<400> SEQUENCE: 28

Met Glu Val Leu Tyr Ser Leu Ser Lys Thr Leu Lys Asp Ala Arg Asp
1               5                   10                  15

Lys Ile Val Glu Gly Thr Leu Tyr Ser Asn Val Ser Asp Leu Ile Gln
            20                  25                  30

Gln Phe Asn Gln Met Ile Val Thr Met Asn Gly Asn Asp Phe Gln Thr
        35                  40                  45

Gly Gly Ile Gly Asn Leu Pro Ile Arg Asn Trp Thr Phe Asp Phe Gly
50                  55                  60

Leu Leu Gly Thr Thr Leu Leu Asn Leu Asp Ala Asn Tyr Val Glu Asn
65                  70                  75                  80

Ala Arg Thr Thr Ile Glu Tyr Phe Ile Asp Phe Ile Asp Asn Val Cys
                85                  90                  95

Met Asp Glu Met Ala Arg Glu Ala Gln Arg Asn Gly Val Ala Pro Gln
            100                 105                 110

Ser Glu Ala Leu Gly Lys Leu Ala Gly Ile Lys Phe Lys Arg Ile Asn
        115                 120                 125

Phe Asp Asn Ser Ser Glu Tyr Ile Glu Asn Trp Asn Leu Gln Asn Arg
130                 135                 140

Arg Gln Arg Thr Gly Phe Val Phe His Lys Pro Asn Ile Phe Pro Tyr
145                 150                 155                 160

Ser Ala Ser Phe Thr Leu Asn Arg Ser Gln Pro Met His Asp Asn Leu
                165                 170                 175

Met Gly Thr Met Trp Leu Asn Ala Gly Ser Glu Ile Gln Val Ala Gly
            180                 185                 190

Phe Asp Tyr Ser Cys Ala Ile Asn Ala Pro Ala Asn Ile Gln Gln Phe
        195                 200                 205

Glu His Ile Val Gln Leu Arg Arg Ala Leu Thr Thr Ala Thr Ile Thr
210                 215                 220

Leu Leu Pro Asp Ala Glu Arg Phe Ser Phe Pro Arg Val Ile Asn Ser
225                 230                 235                 240

Ala Asp Gly Ala Thr Thr Trp Phe Phe Asn Pro Val Ile Leu Arg Pro
                245                 250                 255

Asn Asn Val Glu Val Glu Phe Leu Leu Asn Gly Gln Ile Ile Asn Thr
            260                 265                 270

Tyr Gln Ala Arg Phe Gly Thr Ile Ile Ala Arg Asn Phe Asp Thr Ile
        275                 280                 285

Arg Ser Leu Phe Gln Leu Met Arg Pro Pro Asn Met Thr Pro Ala Val
290                 295                 300

Asn Ala Leu Phe Pro Gln Ala Gln Pro Phe Gln His His Ala Thr Val
305                 310                 315                 320

Gly Leu Thr Leu Arg Ile Glu Ser Ala Val Cys Glu Ser Val Leu Ala
                325                 330                 335

Asp Ala Asn Glu Thr Leu Leu Ala Asn Val Thr Ala Val Arg Gln Glu
            340                 345                 350

Tyr Ala Ile Pro Val Gly Pro Val Phe Pro Pro Gly Met Asn Trp Thr
        355                 360                 365

Glu Leu Ile Thr Asn Tyr Ser Pro Ser Arg Glu Asp Asn Leu Gln Arg
370                 375                 380

Val Phe Thr Val Ala Ser Ile Arg Ser Met Leu Ile Lys
```

<210> SEQ ID NO 29
<211> LENGTH: 397
<212> TYPE: PRT
<213> ORGANISM: Human rotavirus

<400> SEQUENCE: 29

| | | | | | | | | | | | | | | |
|---|---|---|---|---|---|---|---|---|---|---|---|---|---|---|
| Met | Glu | Val | Leu | Tyr | Ser | Leu | Ser | Lys | Thr | Leu | Lys | Asp | Ala | Arg | Asp |
| 1 | | | | 5 | | | | | 10 | | | | | 15 | |
| Lys | Ile | Val | Glu | Gly | Thr | Leu | Tyr | Ser | Asn | Val | Ser | Asp | Leu | Ile | Gln |
| | | | 20 | | | | | 25 | | | | | 30 | | |
| Gln | Phe | Asn | Gln | Met | Ile | Val | Thr | Met | Asn | Gly | Asn | Asp | Phe | Gln | Thr |
| | | 35 | | | | | 40 | | | | | 45 | | | |
| Gly | Gly | Ile | Gly | Asn | Leu | Pro | Ile | Arg | Asn | Trp | Thr | Phe | Asp | Phe | Gly |
| 50 | | | | | 55 | | | | | 60 | | | | | |
| Leu | Leu | Gly | Thr | Thr | Leu | Leu | Asn | Leu | Asp | Ala | Asn | Tyr | Val | Glu | Thr |
| 65 | | | | | 70 | | | | | 75 | | | | | 80 |
| Ala | Arg | Thr | Thr | Ile | Glu | Tyr | Phe | Ile | Asp | Phe | Ile | Asp | Asn | Val | Cys |
| | | | | 85 | | | | | 90 | | | | | 95 | |
| Met | Asp | Glu | Met | Ala | Arg | Glu | Ser | Gln | Arg | Asn | Gly | Val | Ala | Pro | Gln |
| | | | 100 | | | | | 105 | | | | | 110 | | |
| Ser | Glu | Ala | Leu | Arg | Lys | Leu | Ala | Gly | Ile | Lys | Phe | Lys | Arg | Ile | Asn |
| | | 115 | | | | | 120 | | | | | 125 | | | |
| Phe | Asn | Asn | Ser | Ser | Glu | Tyr | Ile | Glu | Asn | Trp | Asn | Leu | Gln | Asn | Arg |
| 130 | | | | | 135 | | | | | 140 | | | | | |
| Arg | Gln | Arg | Thr | Gly | Phe | Val | Phe | His | Lys | Pro | Asn | Ile | Phe | Pro | Tyr |
| 145 | | | | | 150 | | | | | 155 | | | | | 160 |
| Ser | Ala | Ser | Phe | Thr | Leu | Asn | Arg | Ser | Gln | Pro | Met | His | Asp | Asn | Leu |
| | | | | 165 | | | | | 170 | | | | | 175 | |
| Met | Gly | Thr | Met | Trp | Leu | Asn | Ala | Gly | Ser | Glu | Ile | Gln | Val | Ala | Gly |
| | | | 180 | | | | | 185 | | | | | 190 | | |
| Phe | Asp | Tyr | Ser | Cys | Ala | Leu | Asn | Ala | Pro | Ala | Asn | Ile | Gln | Gln | Phe |
| | | 195 | | | | | 200 | | | | | 205 | | | |
| Glu | His | Ile | Val | Gln | Leu | Arg | Arg | Ala | Leu | Thr | Thr | Ala | Thr | Ile | Thr |
| 210 | | | | | 215 | | | | | 220 | | | | | |
| Leu | Leu | Pro | Asp | Ala | Glu | Arg | Phe | Ser | Phe | Pro | Arg | Val | Ile | Asn | Ser |
| 225 | | | | | 230 | | | | | 235 | | | | | 240 |
| Ala | Asp | Gly | Ala | Thr | Thr | Trp | Phe | Phe | Asn | Pro | Ile | Ile | Leu | Arg | Pro |
| | | | | 245 | | | | | 250 | | | | | 255 | |
| Asn | Asn | Val | Glu | Val | Glu | Phe | Leu | Leu | Asn | Gly | Gln | Ile | Ile | Asn | Thr |
| | | | 260 | | | | | 265 | | | | | 270 | | |
| Tyr | Gln | Ala | Arg | Phe | Gly | Thr | Ile | Val | Ala | Arg | Asn | Phe | Asp | Thr | Ile |
| | | 275 | | | | | 280 | | | | | 285 | | | |
| Arg | Leu | Ser | Phe | Gln | Leu | Met | Arg | Pro | Pro | Asn | Met | Thr | Pro | Ala | Val |
| 290 | | | | | 295 | | | | | 300 | | | | | |
| Asn | Ala | Leu | Phe | Pro | Gln | Ala | Gln | Pro | Phe | Gln | His | His | Ala | Thr | Val |
| 305 | | | | | 310 | | | | | 315 | | | | | 320 |
| Gly | Leu | Thr | Leu | Arg | Ile | Glu | Ser | Ala | Val | Cys | Glu | Ser | Val | Leu | Ala |
| | | | | 325 | | | | | 330 | | | | | 335 | |
| Asp | Ala | Asn | Glu | Thr | Leu | Leu | Ala | Asn | Val | Thr | Ala | Val | Arg | Gln | Glu |
| | | | 340 | | | | | 345 | | | | | 350 | | |
| Tyr | Ala | Ile | Pro | Val | Gly | Pro | Val | Phe | Pro | Pro | Gly | Met | Asn | Trp | Thr |
| | | 355 | | | | | 360 | | | | | 365 | | | |

Glu Leu Ile Thr Asn Tyr Ser Pro Ser Arg Glu Asp Asn Leu Gln Arg
370                 375                 380

Val Phe Thr Val Ala Ser Ile Arg Ser Met Leu Ile Lys
385                 390                 395

<210> SEQ ID NO 30
<211> LENGTH: 397
<212> TYPE: PRT
<213> ORGANISM: Human rotavirus

<400> SEQUENCE: 30

Met Glu Val Leu Tyr Ser Leu Ser Lys Thr Leu Lys Asp Ala Arg Asp
1               5                   10                  15

Lys Ile Val Glu Gly Thr Leu Tyr Ser Asn Val Ser Asp Leu Ile Gln
                20                  25                  30

Gln Phe Asn Gln Met Ile Val Thr Met Asn Gly Asn Asp Phe Gln Thr
            35                  40                  45

Gly Gly Ile Gly Asn Leu Pro Ile Arg Asn Trp Thr Phe Asp Phe Gly
50                  55                  60

Leu Leu Gly Thr Thr Leu Leu Asn Leu Asp Ala Asn Tyr Val Glu Thr
65                  70                  75                  80

Ala Arg Thr Thr Ile Glu Tyr Phe Ile Asp Phe Ile Asp Asn Val Cys
                85                  90                  95

Met Asp Glu Met Val Arg Glu Ser Gln Arg Asn Gly Val Ala Pro Gln
            100                 105                 110

Ser Glu Ala Leu Arg Lys Leu Ala Gly Ile Lys Phe Lys Arg Ile Asn
        115                 120                 125

Phe Asn Asn Ser Ser Glu Tyr Ile Glu Asn Trp Asn Leu Gln Asn Arg
130                 135                 140

Arg Gln Arg Thr Gly Phe Val Phe His Lys Pro Asn Ile Phe Pro Tyr
145                 150                 155                 160

Ser Ala Ser Phe Thr Leu Asn Arg Ser Gln Pro Met His Asp Asn Leu
                165                 170                 175

Met Gly Thr Met Trp Leu Asn Ala Gly Ser Glu Ile Gln Val Ala Gly
            180                 185                 190

Phe Asp Tyr Ser Cys Ala Leu Asn Ala Pro Ala Asn Ile Gln Gln Phe
        195                 200                 205

Glu His Ile Val Gln Leu Arg Arg Ala Leu Thr Thr Ala Thr Ile Thr
210                 215                 220

Leu Leu Pro Asp Ala Glu Arg Phe Ser Phe Pro Arg Val Ile Asn Ser
225                 230                 235                 240

Ala Asp Gly Ala Thr Thr Trp Phe Phe Asn Pro Ile Ile Leu Arg Pro
                245                 250                 255

Asn Asn Val Glu Val Glu Phe Leu Leu Asn Gly Gln Ile Ile Asn Thr
            260                 265                 270

Tyr Gln Ala Arg Phe Gly Thr Ile Val Ala Arg Asn Phe Asp Thr Ile
        275                 280                 285

Arg Leu Ser Phe Gln Leu Met Arg Pro Pro Asn Met Thr Pro Ala Val
290                 295                 300

Asn Ala Leu Phe Pro Gln Ala Gln Pro Phe Gln His His Ala Thr Val
305                 310                 315                 320

Gly Leu Thr Leu Arg Ile Glu Ser Ala Val Cys Glu Ser Val Leu Ala
                325                 330                 335

Asp Ala Asn Glu Thr Leu Leu Ala Asn Val Thr Ala Val Arg Gln Glu
            340                 345                 350

```
Tyr Ala Ile Pro Val Gly Pro Val Phe Pro Pro Gly Met Asn Trp Thr
        355                 360                 365

Glu Leu Ile Thr Asn Tyr Ser Pro Ser Arg Glu Asp Asn Leu Gln Arg
370                 375                 380

Val Phe Thr Val Ala Ser Ile Arg Ser Met Leu Ile Lys
385                 390                 395

<210> SEQ ID NO 31
<211> LENGTH: 346
<212> TYPE: PRT
<213> ORGANISM: Human rotavirus

<400> SEQUENCE: 31

Met Tyr Gly Ile Glu Tyr Thr Thr Ile Leu Ile Phe Leu Ile Ser Ile
1               5                   10                  15

Ile Leu Leu Asn Tyr Ile Leu Lys Ser Val Thr Arg Ile Met Asp Tyr
            20                  25                  30

Ile Ile Tyr Arg Phe Leu Leu Ile Thr Val Ala Leu Phe Ala Leu Thr
        35                  40                  45

Arg Ala Gln Asn Tyr Gly Leu Asn Leu Pro Ile Thr Gly Ser Met Asp
50                  55                  60

Thr Val Tyr Thr Asn Ser Thr Gln Glu Glu Val Phe Leu Thr Ser Thr
65                  70                  75                  80

Leu Cys Leu Tyr Tyr Pro Thr Glu Ala Ser Thr Gln Ile Asn Asp Gly
                85                  90                  95

Asp Trp Lys Asp Ser Leu Ser Gln Met Phe Leu Thr Lys Gly Trp Pro
            100                 105                 110

Thr Gly Ser Val Tyr Phe Lys Glu Tyr Ser Ser Ile Val Asp Phe Ser
        115                 120                 125

Val Asp Pro Gln Leu Tyr Cys Asp Tyr Asn Leu Val Leu Met Lys Tyr
130                 135                 140

Asp Gln Ser Leu Glu Leu Asp Met Ser Glu Leu Ala Asp Leu Ile Leu
145                 150                 155                 160

Asn Glu Trp Leu Cys Asn Pro Met Asp Ile Thr Leu Tyr Tyr Tyr Gln
                165                 170                 175

Gln Ser Gly Glu Ser Asn Lys Trp Ile Ser Met Gly Ser Ser Cys Thr
            180                 185                 190

Val Lys Val Cys Pro Leu Asn Thr Gln Thr Leu Gly Ile Gly Cys Gln
        195                 200                 205

Thr Thr Asn Val Asp Ser Phe Glu Met Val Ala Glu Asn Glu Lys Leu
210                 215                 220

Ala Ile Val Asp Val Val Asp Gly Ile Asn His Lys Ile Asn Leu Thr
225                 230                 235                 240

Thr Thr Thr Cys Thr Ile Arg Asn Cys Lys Lys Leu Gly Pro Arg Glu
                245                 250                 255

Asn Val Ala Val Ile Gln Val Gly Gly Ser Asn Val Leu Asp Ile Thr
            260                 265                 270

Ala Asp Pro Thr Thr Asn Pro Gln Thr Glu Arg Met Met Arg Val Asn
        275                 280                 285

Trp Lys Lys Trp Trp Gln Val Phe Tyr Thr Ile Val Asp Tyr Ile Asn
290                 295                 300

Gln Ile Val Gln Val Met Ser Lys Arg Ser Arg Ser Leu Asn Ser Ala
305                 310                 315                 320

Asp Tyr Ile Asn Gln Ile Val Gln Val Met Ser Lys Arg Ser Arg Ser
```

Leu Asn Ser Ala Ala Phe Tyr Tyr Arg Val
            340                 345

<210> SEQ ID NO 32
<211> LENGTH: 346
<212> TYPE: PRT
<213> ORGANISM: Human rotavirus

<400> SEQUENCE: 32

Met Tyr Gly Ile Glu Tyr Thr Thr Ile Leu Ile Phe Leu Ile Ser Ile
1               5                   10                  15

Ile Leu Leu Asn Tyr Ile Leu Lys Ser Val Thr Arg Ile Met Asp Tyr
            20                  25                  30

Ile Ile Tyr Arg Phe Leu Leu Ile Phe Val Ala Leu Phe Ala Leu Thr
        35                  40                  45

Lys Ala Gln Asn Tyr Gly Leu Asn Ile Pro Ile Thr Gly Ser Met Asp
50                  55                  60

Thr Val Tyr Ser Asn Ser Thr Arg Glu Glu Val Phe Leu Thr Ser Thr
65                  70                  75                  80

Leu Cys Leu Tyr Tyr Pro Thr Glu Ala Ser Thr Gln Ile Ser Asp Gly
                85                  90                  95

Glu Trp Lys Asp Ser Leu Ser Gln Met Phe Leu Ile Lys Gly Trp Pro
            100                 105                 110

Thr Gly Ser Val Tyr Phe Lys Glu Tyr Ser Asn Ile Val Asp Phe Ser
        115                 120                 125

Val Asp Pro Gln Leu Tyr Cys Asp Tyr Asn Leu Val Leu Met Lys Tyr
130                 135                 140

Asp Gln Ser Leu Glu Leu Asp Met Ser Glu Leu Ala Asp Leu Ile Leu
145                 150                 155                 160

Asn Glu Trp Leu Cys Asn Pro Met Asp Ile Thr Leu Tyr Tyr Tyr Gln
                165                 170                 175

Gln Ser Gly Glu Ser Asn Lys Trp Ile Ser Met Gly Ser Ser Cys Thr
            180                 185                 190

Val Lys Val Cys Pro Leu Asn Thr Gln Thr Leu Gly Ile Gly Cys Gln
        195                 200                 205

Thr Thr Asn Val Asp Ser Phe Glu Thr Val Ala Glu Asn Glu Lys Leu
210                 215                 220

Ala Ile Val Asp Val Val Asp Gly Ile Asn His Lys Ile Asn Leu Thr
225                 230                 235                 240

Thr Thr Thr Cys Thr Ile Arg Asn Cys Lys Lys Leu Gly Pro Arg Glu
                245                 250                 255

Asn Val Ala Val Ile Gln Val Gly Gly Ala Asn Ile Leu Asp Ile Thr
            260                 265                 270

Ala Asp Pro Thr Thr Asn Pro Gln Ile Glu Arg Met Met Arg Val Asn
        275                 280                 285

Trp Lys Arg Trp Trp Gln Val Phe Tyr Thr Ile Val Asp Tyr Ile Asn
290                 295                 300

Gln Ile Val Gln Val Met Ser Lys Arg Ser Arg Ser Leu Asn Ser Ala
305                 310                 315                 320

Asp Tyr Ile Asn Gln Ile Val Gln Val Met Ser Lys Arg Ser Arg Ser
                325                 330                 335

Leu Asn Ser Ala Ala Phe Tyr Tyr Arg Val
            340                 345

<210> SEQ ID NO 33
<211> LENGTH: 346
<212> TYPE: PRT
<213> ORGANISM: Human rotavirus

<400> SEQUENCE: 33

```
Met Tyr Gly Ile Glu Tyr Thr Thr Ile Leu Ile Phe Leu Ile Ser Ile
1               5                   10                  15

Ile Leu Leu Asn Tyr Ile Leu Lys Ser Val Thr Arg Ile Met Asp Tyr
            20                  25                  30

Ile Ile Tyr Arg Phe Leu Leu Ile Phe Val Ala Leu Phe Ala Leu Thr
        35                  40                  45

Lys Ala Gln Asn Tyr Gly Leu Asn Ile Pro Ile Thr Gly Ser Met Asp
    50                  55                  60

Thr Val Tyr Ser Asn Ser Thr Arg Glu Glu Val Phe Leu Thr Ser Thr
65                  70                  75                  80

Leu Cys Leu Tyr Tyr Pro Thr Glu Ala Ser Thr Gln Ile Ser Asp Gly
                85                  90                  95

Glu Trp Lys Asp Ser Leu Ser Gln Met Phe Leu Ile Lys Gly Trp Pro
            100                 105                 110

Thr Gly Ser Val Tyr Phe Lys Glu Tyr Ser Asn Ile Val Asp Phe Ser
        115                 120                 125

Val Asp Pro Gln Leu Tyr Cys Asp Tyr Asn Leu Val Leu Met Lys Tyr
    130                 135                 140

Asp Gln Ser Leu Glu Leu Asp Met Ser Glu Leu Ala Asp Leu Ile Leu
145                 150                 155                 160

Asn Glu Trp Leu Cys Asn Pro Met Asp Ile Thr Leu Tyr Tyr Tyr Gln
                165                 170                 175

Gln Ser Gly Glu Ser Asn Lys Trp Ile Ser Met Gly Ser Ser Cys Thr
            180                 185                 190

Val Lys Val Cys Pro Leu Asn Thr Gln Thr Leu Gly Ile Gly Cys Gln
        195                 200                 205

Thr Thr Asn Val Asp Ser Phe Glu Thr Val Ala Glu Asn Glu Lys Leu
210                 215                 220

Ala Ile Val Asp Val Val Asp Gly Ile Asn His Lys Ile Asn Leu Thr
225                 230                 235                 240

Thr Thr Thr Cys Thr Ile Arg Asn Cys Lys Lys Leu Gly Pro Arg Glu
                245                 250                 255

Asn Val Ala Val Ile Gln Val Gly Gly Ala Asn Ile Leu Asp Ile Thr
            260                 265                 270

Ala Asp Pro Thr Thr Asn Pro Gln Ile Glu Arg Met Met Arg Val Asn
        275                 280                 285

Trp Lys Arg Trp Trp Gln Val Phe Tyr Thr Ile Val Asp Tyr Ile Asn
    290                 295                 300

Gln Ile Val Gln Val Met Ser Lys Arg Ser Arg Ser Leu Asn Ser Ala
305                 310                 315                 320

Asp Tyr Ile Asn Gln Ile Val Gln Val Met Ser Lys Arg Ser Arg Ser
                325                 330                 335

Leu Asn Ser Ala Ala Phe Tyr Tyr Arg Val
            340                 345
```

<210> SEQ ID NO 34
<211> LENGTH: 1566
<212> TYPE: DNA
<213> ORGANISM: Human rotavirus

<400> SEQUENCE: 34

```
ggcttttttt atgaaaagtc ttgtggaagc catggctact ttcaaagatg cttgttatta      60
ttataagaga attaacaaat tgaatcatgc agtcttgaag ttaggagtta atgatacatg     120
gagaccatca cctccgacca aatataaagg atggtgtctg gactgttgcc aacacactga    180
cttaacttac tgtcgaggtt gtaccatgta tcatgtatgt cagtggtgta gtcaatatga    240
tagatgcttt cttgataatc aaccacatct attgagaatg agaactttca agaatgaagt    300
gacgaaaaat gatttaatga atttaattga catgtataat atattatttc ctataaatca    360
aagaatagta gataaattta ttagtagtac aagacaacat aaatgtagaa atgaatgtat    420
gacacagtgg tataatcacc tattgatgcc aataacatta caatctctat caattgaatt    480
agatggtgat gtttattacg tatttggata ttatgatagt atgcgtgaca ttaatcaaac    540
tccattctca tttacaaatt aatagatat gtatgataag ttgctacttg ataatgtaaa    600
ttttaatcga atgtcattct taccagtagc attacaacaa gaatatgcac tcagatattt    660
ttcaaaatca aggtttatta gtgaaaagag gaaatgtatt agtgatttac attttccac    720
taatgtaata gaaaatttac acaatccaag ttttaaaata caaattacac gtaattgtag    780
tgaattatct tctgattgga acggagcatg caaacttgtt aaagatatga gtacttattt    840
taatgtgcta aaacatcac atattgaatt ttatagtatt tcaaccagat gtagaatgtt    900
tacgcagcat aaacttaaaa tagcatccaa acatataaaa ccaaattatg taacatcaaa    960
tcatagaaca tcagcgactg aggtgcataa ctgtaaatgg tgctcaatta ataacggtta   1020
tactgtatgg aatgatttta gaattaagaa gatatatgat aacattttca attttctacg   1080
agctttagtc aaatcaaatt ctaatattgg acattgttcg tcgcaggaaa agatatatga   1140
acatattaaa gatgttctgg atgtatgtga tgatgaaaaa tggaaaatgg cggtagcgga   1200
aatatttaat tgtttagaac cagtagaact tgatactgtt aaatatgttc tgtttaatca   1260
tgaggtaaat tgggatgtta ttaatttatt agttcagagc gttggtaaag taccacaaat   1320
actgactttta aatgacatta tcataatcat gaaatctatc atatatgagt ggtttgatat   1380
cagatatatg aggaatacac caatgactac atttacagtt gacaaattaa gacagttatg   1440
tacaggagtg aagactgttg attatgattc cggcatatct gacgttgaat aatgaaatag   1500
agatcacatt tgccaccata agactccctg cactagagta gcgcctaggc agcataaaat   1560
gtgacc                                                                1566
```

<210> SEQ ID NO 35
<211> LENGTH: 1569
<212> TYPE: DNA
<213> ORGANISM: Human rotavirus

<400> SEQUENCE: 35

```
ggcttttttt ttgaaaagtc ttgtggaagc catggctact ttcaaagatg cttgttatta      60
ttataagaga attaacaaat tgaatcatgc agtcttgaag ttaggagtta atgatacatg     120
gagaccatca cctccgacca aatataaagg atggtgtctg gactgttgcc aacacactga    180
cttaacttac tgtcgaggtt gtaccatgta tcatgtatgt cagtggtgta gtcaatatga    240
tagatgcttt cttgatagtc aaccacatct attgagaatg agaactttca agaatgaagt    300
gacgaaaaat gatttaatga atttgattga catgtataat atattatttc ctataaatca    360
aagaatagta gacaaattta ttagtagtac aagacaacat aaatgtagaa atgaatgtat    420
```

```
gacacagtgg tataatcacc tattgatgcc aataacatta caatctctat caattgaatt    480
agatggtgat gtttattacg tatttggata ttatgatagt atgcgtgaca ttaatcaaac    540
tccattctca tttacaaatt taatagatat gtatgataag ttgctacttg ataatgtaaa    600
ttttaatcga atgtcattct taccagtagc attacaacaa gaatatgcac tcagatattt    660
ttcaaaatca aggtttatta gtgaaaagag gaaatgtatt agtgatttac attttttccac   720 taatgtaata gaaaatttac acaatccaag ttttaaaata caaattacac gtaattgtag    780
tgaattatct tctgattgga acggagcatg taaacttgtt aaagatatga gtacttattt    840
taatgtgcta aaaacatcac atattgaatt ttatagtatt tcaaccagat gtagaatgtt    900
tacgcagcat aaacttaaaa tagcatctaa acatataaaa ccaaattatg taacatcaaa    960
tcatagaaca tcagcgactg aggtgcataa ctgtaaatgg tgctcaatta ataacggtta   1020
tactgtatgg aatgatttta gaattaagaa gatatatgat aacattttca attttctacg   1080
agctttagtc aaatcaaatt ctaatattgg acattgttcg tcgcaggaaa agatatatga   1140
acatattaaa gatgttctgg atgtatgtga tgatgaaaaa tggaaaatgg cggtagcgga   1200
aatatttaat tgtttaggac cagtagaact tgatactgtt aaatatgtta tgtttaatca   1260
tgaggtaaat tgggatgtta ttaatttatt agttcagagc gttggtaaag taccacaaat   1320
actgacttta aatgacatta tcataatcat gaaatctatc atatatgagt ggtttgatat   1380
cagatatatg aggaatacac caatgactac atttacagtt gacaaattaa gacagttatg   1440
tacaggaatg aagactgttg attatgattc cggcatatct gacgttgaat aatgaaatag   1500
agatcacatt tgccaccata agactccctg cactagagta gcgcctaggc agcataaaaa   1560
agtgtgacc                                                           1569
```

<210> SEQ ID NO 36
<211> LENGTH: 1569
<212> TYPE: DNA
<213> ORGANISM: Human rotavirus

<400> SEQUENCE: 36

```
ggcttttttt ttgaaaagtc ttgtggaagc catggctact ttcaaagatg cttgttatta     60
ttataagaga attaacaaat tgaatcatgc agtcttgaag ttaggagtta atgatacatg    120
gagaccatca cctccgacca aatataaagg atggtgtctg gactgttgcc aacacactga    180
cttaacttac tgtcgaggtt gtaccatgta tcatgtatgt cagtggtgta gtcaatatga    240
tagatgcttt cttgatagtc aaccacatct attgagaatg agaactttca agaatgaagt    300
gacgaaaaat gatttaatga atttgattga catgtataat atattatttc ctataaatca    360
aagaatagta gacaaattta ttagtagtac aagacgacat aaatgtagaa atgaatgtat    420
gacacagtgg tataatcacc tattgatgcc aataacatta caatctctat caattgaatt    480
agatggtgat gtttattacg tatttggata ttatgatagt atgcgtgaca ttaatcaaac    540
tccattctca tttacaaatt taatagatat gtatgataag ttgctacttg ataatgtaaa    600
ttttaatcga atgtcattct taccagtagc attacaacaa gaatatgcac tcagatattt    660
ttcaaaatca aggtttatta gtgaaaagag gaaatgtatt agtgatttac attttttccac   720 taatgtaata gaaaatttac acaatccaag ttttaaaata caaattacac gtaattgtag    780
tgaattatct tctgattgga acggagcatg taaacttgtt aaagatatga gtacttattt    840
taatgtgcta aaaacatcac atattgaatt ttatagtatt tcaaccagat gtagaatgtt    900
tacgcagcat aaacttaaaa tagcatctaa acatataaaa ccaaattatg taacatcaaa    960
```

-continued

```
tcatagaaca tcagcgactg aggtgcataa ctgtaaatgg tgctcaatta ataacggtta    1020
tactgtatgg aatgatttta gaattaagaa gatatatgat aacatttttca attttctacg   1080 agctttagtc aaatcaaatt ctaatattgg acattgttcg tcgcaggaaa agatatatga    1140
acatattaaa gatgttctgg atgtatgtga tgatgaaaaa tggaaaatgg cggtagcgga    1200
aatatttaat tgtttaggac cagtagaact tgatactgtt aaatatgtta tgtttaatca    1260
tgaggtaaat tgggatgtta ttaatttatt agttcagagc gttggtaaag taccacaaat    1320
actgacttta aatgacatta tcataatcat gaaatctatc atatatgagt ggtttgatat    1380
cagatatatg aggaatacac caatgactac atttacagtt gacaaattaa gacagttatg    1440
tacaggaatg aagactgttg attatgattc cggcatatct gacgttgaat aatgaaatag    1500
agatcacatt tgccaccata agactccctg cactagagta gcgcctaggc agcataaaaa    1560
agtgtgacc                                                            1569

<210> SEQ ID NO 37
<211> LENGTH: 1058
<212> TYPE: DNA
<213> ORGANISM: Human rotavirus

<400> SEQUENCE: 37
ggcttttaaa gcgtctcagt cgccgtttga gcttacggtg tagccatggc tgagctagct     60
tgcttttgtt atcctcattt ggagaacgat agctataaat ttattccttt taataattta    120
gcaataaaat gtatgttgac agctaaagtg gacaaaaagg atcaagataa attttacaat    180
tctattattt atggaattgc gccgccgcca caatttaaaa aacgttataa tactaatgac    240
aattcaagag gtatgaatta tgaaacgcct atgttaatca aggtggccat attaattttgt   300 gaagcactta attcaattaa agttactcaa tctgatgttg ctaatgttct ttcaagagtg    360
gtttctgtta gacattgga aaatctggtt ttaagaaaag aaaaccatca ggatgtgctg     420
tttcattcaa aagaattatt attaaaatcc gttttaatag ctattggtca atcgaaagaa    480
attgaaacta ctgctactgc tgaaggagga gaaatagtat tcagaatgt agcttttact    540 atgtggaaat taacgtattt agatcataag ttgatgccta ttttggacca aaatttttatt  600 gaatacaaaa ttacaatgaa tgaagataaa ccaatttcag atgtgcatgt taaggaactt    660
atcgctgaat tgagatggca gtaatagaa tttgctgtaa taacacatgg taaaggtcac    720
tatagagttg ttaaatattc atcagttgct aaccatgcag atagagtgtt gctacatat    780 aaaaataatg ctaagagtgg taatgttatt gactttaact tattggacca agaatcatt    840 tggcaaaatt ggtatgcatt tacatcctca atgaaacaag gtttcacgct tgatgtatgt    900
aagaaactgc tatttcaaaa gatgaaacag gagagaaacc catttaaagg actgtcaact    960
gatagaaaga tggatgaagt ctcacgtatt ggaatttaat tcgctttcga tttgagaatg    1020
atgatgacgg agcaagaata gaaagcgctt atgtgacc                            1058

<210> SEQ ID NO 38
<211> LENGTH: 1059
<212> TYPE: DNA
<213> ORGANISM: Human rotavirus

<400> SEQUENCE: 38
ggcttttaaa gcgtctcagt cgccgtttga gccttgcggt gtagccatgg ctgagctagc     60
ttgcttttgt tatcctcatt tggagaacga tagctataaa tttattcctt ttaataattt    120
```

| | |
|---|---|
| agcaataaaa tgtatgttga cagcaaaagt agataaaaaa gatcaagata aattttataa | 180 |
| ttctattgtt tatgggattg ctccaccacc acaatttaga aaacgttata atactagtga | 240 |
| taattcgaga ggaatgaatt acgaaacaat tatgtttaat aaggtggcta tcttaatttg | 300 |
| tgaagcactt aattcgatta aagttacaca atctgaagtt gcaaatgttc tttcaagagt | 360 |
| agtttccgtt agacatttgg aaaatctagt attaaggaaa gaaaatcatc aagatgtact | 420 |
| tttccattcg aaagaactac tcttaaaatc tgtgttgata gctattggtc agtcaaaaga | 480 |
| aatcgaaact actgctactg ccgaaggagg agaaatagta tttcagaatg cagcttttac | 540 |
| tatgtggaaa ttgacgtatt tagatcataa attaatgcct attttggatc agaatttcat | 600 |
| tgaatataaa attacgttga atgaagataa accaatttca gatgtatgtg ttaaagaact | 660 |
| cgttgctgaa ttaagatggc agtataacag atttgctgta ataacacatg gtaaaggtca | 720 |
| ctatagagtt gttaaatatt catcagttgc taaccatgca gatagagtat ttgctacata | 780 |
| taagaataat gctaagagtg gtaatactac tgatttcaat ttgctagacc aaagaattat | 840 |
| ttggcaaaat tggtatgcat ttacatcttc aatgaaacaa ggtaatacaa ttgatgtatg | 900 |
| taagaaacta ctcttttcaaa agatgaaaca agagaaaaat ccgttcaaag gattgtcaac | 960 |
| tgatagaaaa atggatgaag tctcacatgt tggaatttaa ttcgctttcg attcaagaat | 1020 |
| gatgatgacg aagcaagaat agaaagcgct tatgtgacc | 1059 |

<210> SEQ ID NO 39
<211> LENGTH: 1059
<212> TYPE: DNA
<213> ORGANISM: Human rotavirus

<400> SEQUENCE: 39

| | |
|---|---|
| ggcttttaaa gcgtctcagt cgccgtttga gccttgcggt gtagccatgg ctgagctagc | 60 |
| ttgcttttgt tatcctcatt tggagaacga tagctataaa tttattcctt ttaataattt | 120 |
| agcaataaaa tgtatgttga cagcaaaagt agataaaaaa gatcaagata aattttataa | 180 |
| ttctattgtt tatgggattg ctccaccacc acaatttaga aaacgttata atactagtga | 240 |
| taattcgaga ggaatgaatt acgaaacaat tatgtttaat aaggtggcta tcttaatttg | 300 |
| tgaagcactt aattcgatta aagttacaca atctgaagtt gcaaatgttc tttcaagagt | 360 |
| agtttccgtt agacatttgg aaaatctagt attaaggaaa gaaaatcatc aagatgtact | 420 |
| tttccattcg aaagaactac tcttaaaatc tgtgttgata gctattggtc agtcaaaaga | 480 |
| aatcgaaact actgctactg ccgaaggagg agaaatagta tttcagaatg cagcttttac | 540 |
| tatgtggaaa ttgacgtatt tagatcataa attaatgcct attttggatc agaatttcat | 600 |
| tgaatataaa attacgttga atgaagataa accaatttca gatgtatgtg ttaaagaact | 660 |
| cgttgctgaa ttaagatggc agtataacag atttgctgta ataacacatg gtaaaggtca | 720 |
| ctatagagtt gttaaatatt catcagttgc taaccatgca gatagagtat ttgctacata | 780 |
| taagaataat gctaagagtg gtaatactac tgatttcaat ttgctagacc aaagaattat | 840 |
| ttggcaaaat tggtatgcat ttacatcttc aatgaaacaa ggtaatacaa ttgatgtatg | 900 |
| taagaaacta ctcttttcaaa agatgaaaca agagaaaaat ccgttcaaag gattgtcaac | 960 |
| tgatagaaaa atggatgaag tctcacatgt tggaatttaa ttcgctttcg attcaagaat | 1020 |
| gatgatgacg aagcaagaat agaaagcgct tatgtgacc | 1059 |

<210> SEQ ID NO 40
<211> LENGTH: 1075

```
<212> TYPE: DNA
<213> ORGANISM: Human rotavirus

<400> SEQUENCE: 40
ggcttttaat gcttttcagt ggttgctgct caagatggag tctactcagc agatggtaag      60
ttctattatt aatacttctt ttgaagctgc agttgttgct gccacttcaa cattagaatt     120
aatgggtatt caatatgatt acaatgaagt atttactaga gttaaaagta aatttgatta     180
tgtaatggat gattctggcg ttaaaaacaa ccttttgggt aaagctataa ctattgggcc     240
ggcgtgtaat gaaaagtttg gctcagcaat tagaaataga aattggatga ttgattccaa     300
aacagttgct aaattagatg aagacgtgaa taaacttaga atgacgttat cttctaaagg     360
aatcgatcaa aagatgagag tacttaatgc ttgttttagt gtaaaaagaa taccagggaa     420
atcatcatca ataatcaaat gcaccagact tatgaaggat aaactagaac gtggagaagt     480
tgaagttgat gattcatatg ttgatgagaa atggaaatt gatactattg attggaaatc      540
tcgttatgat cagttagaaa aaagatttga gtcactaaaa caaagagtta atgagaaata     600
caatgcttgg gtacaaaaag caaagaaagt aaatgaaaat atgtactctc ttcagaatgt     660
catttcacaa cagcaaaacc aaatagcaga tcttcaacaa tattgtaata aattggaagt     720
tgatttgcaa ggcaaattta gttcattagt gtcgtcagtt gagtggtatc taagatctat     780
ggaactacca gatgatgtaa agactgatgt tgaacagcag ttaaattcaa ttgatttaat     840
taatcccatt ggtgctatag atgatatcga atcattgatt agaaatttaa ttcaagatta     900
tgacagaaca tttttaatgt taaaaggact tttgaagcaa tgcaactatg aatatgcata     960
tgagtagtca cataatttaa aaatattaac catctacaca tgaccctcta tgagcacaat    1020
agttaaaagc taacactgtc aaaaacctaa atggctatag gggcgttatg tgacc         1075

<210> SEQ ID NO 41
<211> LENGTH: 1074
<212> TYPE: DNA
<213> ORGANISM: Human rotavirus

<400> SEQUENCE: 41
ggcttttaat gcttttcagt ggttgctgct caagatggag tctactcagc agatggtaag      60
ctctattatt aacacttctt ttgaagctgc agttgttgct gccacttcaa cattagaatt     120
aatgggtatt caatatgatt acaatgaagt atttactaga gttaaaagta aatttgatta     180
tgtaatggat gactctggtg ttaaaaataa tcttttgggt aaagctataa ctattgacca     240
ggcgttaat ggaaagtttg gctcagctat tagaaataga aattggatga ctgactctaa      300
aacggttgct aaattggatg aagacgtaaa taaacttaga atgacattgt cttctaaagg     360
aatcgaccaa aagatgagag tacttaatgc ttgttttagt gtgaaaagaa taccaggaaa     420
atcatcatca ataattaagt gcactaaact catgaaggat aaaatagaac gtggggaagt     480
tgaggttgat gattcatata ttgatgagaa atggaaatt gataccattg attggaaatc      540
tcgttatgac caattagaaa aaagatttga gtcactaaaa caaagagtta ctgagaaata     600
caatacttgg gtacaaaaag cgaagaaagt aaatgagaat atgtactctc ttcagaatgt     660
catttcacaa cagcagaatc aaatagcaga tcttcaacaa tattgtaata aattggaaac     720
tgacttgcaa ggcaaattca gttcattagt gtcatcagtt gagtggtatt taagatctat     780
ggaattacca gatgatgtaa agaatgatat tgaacagcag ttaaattcaa ttgatttaat     840
taatcccatt aatgctatag atgatatcga atcattggtt agaaatttag ttcaggatta     900
```

```
tgatagaaca ttttaatgc taaagggact gttgaagcaa tgcaactatg aatatgtata    960
tgaatagtca cataattaaa atcattaacc atctacacat gaccctctat gagcacaata   1020
gttaaaagct aacactgtca aaaacctaaa tggctatagg ggcgttatgt gacc         1074

<210> SEQ ID NO 42
<211> LENGTH: 1074
<212> TYPE: DNA
<213> ORGANISM: Human rotavirus

<400> SEQUENCE: 42
ggcttttaat gcttttcagt ggttgctgct caagatggag tctactcagc agatggtaag     60
ctctattatt aacacttctt ttgaagctgc agttgttgct gccacttcaa cattagaatt    120
aatgggtatt caatatgatt acaatgaagt atttactaga gttaaaagta aatttgatta    180
tgtaatggat gactctggtg ttaaaaataa tcttttgggt aaagctataa ctattgacca    240
ggcgttaaat ggaaagtttg gctcagctat tagaaataga aattggatga ctgactctaa    300
aacggttgct aaattggatg aagacgtaaa taaacttaga atgacattgt cttctaaagg    360
aatcgaccaa aagatgagag tacttaatgc ttgttttagt gtgaaaagaa taccaggaaa    420
atcatcatca ataattaagt gcactaaact catgaaggat aaaatagaac gtggggaagt    480
tgaggttgat gattcatata ttgatgagaa aatggaaatt gataccattg attggaaatc    540
tcgttatgac caattagaaa aaagatttga gtcactaaaa caaagagtta ctgagaaata    600
caatacttgg gtacaaaaag cgaagaaagt aaatgagaat atgtactctc ttcagaatgt    660
catttcacaa cagcagaatc aaatagcaga tcttcaacaa tattgtaata aattggaaac    720
tgacttgcaa ggcaaattca gttcattagt gtcatcagtt gagtggtatt aagatctat    780 ggaattacca gatgatgtaa agaatgatat tgaacagcag ttaaattcaa ttgatttaat    840
taatcccatt aatgctatag atgatatcga atcattggtt agaaatttag ttcaggatta    900
tgatagaaca ttttaatgc taaagggact gttgaagcaa tgcaactatg aatatgtata    960
tgaatagtca cataattaaa atcattaacc atctacacat gaccctctat gagcacaata   1020
gttaaaagct aacactgtca aaaacctaaa tggctatagg ggcgttatgt gacc         1074

<210> SEQ ID NO 43
<211> LENGTH: 750
<212> TYPE: DNA
<213> ORGANISM: Human rotavirus

<400> SEQUENCE: 43
ggcttttaaa agttctgttc cgagagagcg cgtgcggaaa gatggataag cttgccgacc     60
tcaactacac attgagtgta atcactctaa tgaatgacac attgcattct ataattcagg    120
atcctggaat ggcgtatttt acatatattg catctgttct aacagttttg ttcacattac    180
ataaagcttc aattccaacc atgaaaatag cattgaaaac atcaaaatgt tcatataaag    240 tgattaaaata ttgtatagtc acgatcatta atactctttt aagattggct ggatataaag    300
agcaggttac tactaaagac gaaattgagc aacagatgga tagaattgtt aaagagatga    360
gacgtcagct ggagatgatt gataaactaa ctactcgtga aattgaacag gttgaattgc    420
ttaaaagtat acatgacaac ttgataacta gatcagttga cgttatagat atgtcgaagg    480
aattcaatca gaaaaacatc aaaacgctag atgaatggga gagtggaagg aatccatatg    540
aaccgtcaga ggtgactgca tccatgtgag aggttgagtt accgtcgtct gtcttcggaa    600
gcggcggaac tcttcaccgc aagccccatt agacctgatg attgactgag aagccacagt    660
```

```
caatcatatc gcgtgtggct cagccttaat cccgtttaac caatccagcg agtgttggac    720
gttaatggaa ggaatggtct tagtgtgacc                                    750

<210> SEQ ID NO 44
<211> LENGTH: 750
<212> TYPE: DNA
<213> ORGANISM: Human rotavirus

<400> SEQUENCE: 44
ggcttttaaa agttctgttc cgagagagcg cgtgcggaaa gatggataag cttgccgacc     60
tcaactacac attgagtgta atcactttaa tgaatgacac attgcattct ataattcagg    120
accctggaat ggcgtatttt ccatatattg catctgttct aacagtgttg ttcacattac    180
ataaagcttc aattccaaca atgaaaatag cattaaaaac gtcaaaatgt tcatacaaag    240
tgatcaagta ttgtatagtc acaattatta atactctttt aaaattggca ggatataaag    300
aacaagttac cactaaagac gaaattgagc aacagatgga tagaattgta aaagagatga    360
gacgtcagct ggagatgatt gataaattaa ctactcgtga aattgaacaa gttgaattgc    420
ttaaacgtat atatgacaat ttaataacta gaccagttga cattgtagat atgacgaagg    480
aatttaatca gaagaatata aaaacgctag atgagtggga gagcggaaaa aatccatatg    540
aaccgataga ggtgactgca tctatgtgag aggttgagtt gccgtcgtct gtcctcggaa    600
gcggcggaac tcttcaccgc aagccccatt ggacctgatg attgactgag aagccacagt    660
caatcatatc gcgtgtggct cagccttaat cccgtttgac caatccagcg aatgttggac    720
gttaatggaa ggaaaggtct taatgtgacc                                    750

<210> SEQ ID NO 45
<211> LENGTH: 750
<212> TYPE: DNA
<213> ORGANISM: Human rotavirus

<400> SEQUENCE: 45
ggcttttaaa agttctgttc cgagagagcg cgtgcggaaa gatggataag cttgccgacc     60
tcaactacac attgagtgta atcactttaa tgaatgacac attgcattct ataattcagg    120
accctggaat ggcgtatttt ccatatattg catctgttct aacagtgttg ttcacattac    180
ataaagcttc aattccaaca atgaaaatag cattaaaaac gtcaaaatgt tcatacaaag    240
tgatcaagta ttgtatagtc acaattatta atactctttt aaaattggca ggatataaag    300
aacaagttac cactaaagac gaaattgagc aacagatgga tagaattgta aaagagatga    360
gacgtcagct ggagatgatt gataaattaa ctactcgtga aattgaacaa gttgaattgc    420
ttaaacgtat atatgacaat ttaataacta gaccagttga cattgtagat atgacgaagg    480
aatttaatca gaagaatata aaaacgctag atgagtggga gagcggaaaa aatccatatg    540
aaccgataga ggtgactgca tctatgtgag aggttgagtt gccgtcgtct gtcctcggaa    600
gcggcggaac tcttcaccgc aagccccatt ggacctgatg attgactgag aagccacagt    660
caatcatatc gcgtgtggct cagccttaat cccgtttgac caatccagcg aatgttggac    720
gttaatggaa ggaaaggtct taatgtgacc                                    750

<210> SEQ ID NO 46
<211> LENGTH: 664
<212> TYPE: DNA
<213> ORGANISM: Human rotavirus
```

<400> SEQUENCE: 46

```
ggcttttaaa gcgctacagt gatgtctctc agcattgacg tgacgagtct tccctcaatt      60
tcttctagca ttttaaaaa tgaatcgtct tctacaacgt caactctttc tggaaaatct     120
attggtagga acgaacagta tgtttcacca gatatcgatg cgttcaataa atacatgttg     180
tcgaagtctc cagaggatat tggaccatct gattctgctt caaacgatcc actcaccagc     240
ttttcgatta gatcgaatgc ggttaagaca aatgcagatg ctggcgtgtc tatggattca     300
tcaacacaat cacgacctta agcaacgtt gggtgcgatc aaatggattt ctccttaaat     360
aaaggtatta atgttagtgc tagtcttgat tcatgtgtat caatttcaac taatcaaaaa     420
aaggagaaat ctaagaagga taaaagtagg aaacactacc caagaattga agcagattct     480
gactctgagg attatgtttt ggatgattca gatagtgatg acggcaaatg taagaattgt     540
aaatataaaa agaaatattt tgcattaaga atgaggatga acaagtcgc aatgcaattg     600
atagaagact tgtaatgtcg acctgaggac acactaggga gctccccact cccgttttgt     660
gacc                                                                 664
```

<210> SEQ ID NO 47
<211> LENGTH: 664
<212> TYPE: DNA
<213> ORGANISM: Human rotavirus

<400> SEQUENCE: 47

```
ggcttttaaa gcgctacagt gatgtctctc agcattgacg taacaagtct tccctcaatt      60
tcttctagta tctttaaaaa tgaatcgtct tctacaacgt caactctttc tggaaaatct     120
attggtagga gtgaacagta catttcacca gatgcagaag cattcaataa gtacatgttg     180
tcgaagtctc cagaggatat tggaccatct gattctgctt caaacgatcc actcaccagc     240
ttttcgatta gatcgaatgc agttaagaca aatgcagacg ctggcgtgtc tatggattca     300
tcgacacaat cacgacctta agcaacgtt ggatgcgatc aattggattt ctccttgacc     360
aaaggtatta atgttagtgc taatcttgat tcatgtatat caatttcaac tgatcataag     420
aaggagaaat ccaagaaaga taaaagtagg aaacactacc cgagaattga agcagattct     480
gattctgaag attatgtttt ggatgattca gatagtgatg acggtaaatg caagaattgt     540
aaatataaga aaaatatttt cgcactaaga atgaggatga agcgagtcgc aatgcaattg     600
atcgaagatt tgtaatgtca acctgagagc acactaggga gctccccact cccgttttgt     660
gacc                                                                 664
```

<210> SEQ ID NO 48
<211> LENGTH: 664
<212> TYPE: DNA
<213> ORGANISM: Human rotavirus

<400> SEQUENCE: 48

```
ggcttttaaa gcgctacagt gatgtctctc agcattgacg taacaagtct tccctcaatt      60
tcttctagta tctttaaaaa tgaatcgtct tctacaacgt caactctttc tggaaaatct     120
attggtagga gtgaacagta catttcacca gatgtagaag cattcaataa gtacatgttg     180
tcgaagtctc cagaggatat tggaccatct gattctgctt caaacgatcc actcaccagc     240
ttttcgatta gatcgaatgc agttaagaca aatgcagacg ctggcgtgtc tatggattca     300
tcgacacaat cacgacctta agcaacgtt ggatgcgatc aattggattt ctccttgacc     360
aaaggtatta atgttagtgc taatcttgat tcatgtatat caatttcaac tgatcataag     420
```

| | |
|---|---|
| aaggagaaat ccaagaaaga taaaagtagg aaacactacc cgagaattga agcagattct | 480 |
| gattctgaag attatgtttt ggatgattca gatagtgatg acgtaaaatg caagaattgt | 540 |
| aaatataaga aaaaatattt cgcactaaga atgaggatga agcgagtcgc aatgcaattg | 600 |
| atcgaagatt tgtaatgtca acctgagagc acactaggga gctccccact cccgttttgt | 660 |
| gacc | 664 |

<210> SEQ ID NO 49
<211> LENGTH: 3302
<212> TYPE: DNA
<213> ORGANISM: Human rotavirus

<400> SEQUENCE: 49

| | |
|---|---|
| ggctattaaa gctgtacaat ggggaagtac aatctaattt tgtcagaata tttatcattc | 60 |
| gtttataatt cacaatctgc agttcaaata ccaatctatt attcttccaa ttctgaatta | 120 |
| gaaacgagat gcattgaatt tcatgccaaa tgtgttgata attcaaagaa agggttatca | 180 |
| ttaaaaccat tatttgagga atataaagat gtaacagata atgcgacttt attatcccata | 240 |
| ttatcatatt cgtatgataa atataatgct gtagagcgga aattagttag ttatgctaaa | 300 |
| ggtaaaccac ttgaagctga tttaacagca aacgaacttg attatgaaaa taataaaata | 360 |
| acttctgaac tatttcagtc agccgaagaa tacactgatt cattaatgga tcccgccata | 420 |
| ttgacttcac tatcttcaaa tttaaatgca gttatgtttt ggctagaacg acattcaaac | 480 |
| gatattgctg atgcaaataa aatttataaa cgcagattag atttatttac tatagtagca | 540 |
| tctacaataa ataaatatgg ggtaccgaga cataatgaga aatacagata cgaatatgaa | 600 |
| gtaatgaaag ataaaccata ctatttagtg acttgggcta attcgtccat agaaatgctt | 660 |
| atgtcagtat tttcacatga agattatcta atagcaaaag aattgattgt tttatcatat | 720 |
| tcaaataggt cgacattagc taaattggtt tcatctccaa tgtctatatt agttgcattg | 780 |
| atagatatta atggtacatt cattacgaat gaagagttag agcttgaatt ttcagataaa | 840 |
| tatgttaaag caattgtacc tgatcagact ttcgatgaat tgcaagagat gattaataat | 900 |
| atgaaaaaaa ttggtttagt agatattcct aggatgatcc aagaatggtt aatcgattgc | 960 |
| tcattagaga aattcacgct gatgtcaaaa atttactctt ggtcattcca tgttggattt | 1020 |
| agaaagcaga aaatgattga tgcggcgtta gaccaattga agacggaata tactaaggat | 1080 |
| gtggatgatg aaatgtacaa tgaatacact atgttaatta gagatgaaat agtgaaaatg | 1140 |
| ttagaaattc cagttaaaca tgatgatcat ctacttcgtg attcagaact agctggattg | 1200 |
| ttatcaatgt catcagcttc aaatggtgaa tcaagacaaa tcaaatttgg tcgcaaaaca | 1260 |
| atattttcaa ctaagaagaa tatgcatgtg atggatgata tagcacatgg aaagtatact | 1320 |
| ccaggtgtta ttcctccagt gaacgtagat aaaccaattc cactaggtcg tagagatgtt | 1380 |
| cctggaaggc gtacgagaat tatattcata cttccatatg agtatttttat tgcacaacat | 1440 |
| gctgtggtag aaaagatgct attgtatgca aaacatacta gagaatatgc ggaattctat | 1500 |
| tcacagtcaa atcaattgtt atcatacggt gatgttacga gattttttgtc cagtaactct | 1560 |
| atggttttat atacagacgt ttcacaatgg gactcgtcgc agcataacac acagccattc | 1620 |
| aggaagggaa taattatggg tctagacatg ctatctaata tgactaacga tccaaaggta | 1680 |
| gtacaagcat tgaatttata taagcaaaca caaattaacc ttatggattc atacgttcag | 1740 |
| ataccagatg gtaacgtaat caaaaagaac cagtacggag ctgtcgcttc aggagaaaaa | 1800 |

```
caaactaaag cagctaattc catagctaac ttagcccttaa ttaaaacagt actatcaagg    1860
attgcaaata atactctttt tataactaaa ataattagag taagtggtga tgacaattat    1920
gcagtattac aatttaatac tgacctcaca aaacagatga ttcaagatgt gtctaatgac    1980
gtgagatata tatattttag aatgaatgca aaagttaaag cactagtgtc gacagttggt    2040
attgaaatag caaaaagata cttagctgga ggaaaaatat tctttagagc tggcataaat    2100
ttattaaata atgaaaaacg tgggcagagt acgcaatggg atcaagcagc tattctatat    2160
tcaaattaca ttgttaacaa attacgagga tttgagactg atagagaatt tatattaact    2220
aaaattatac aaatgacttc cgtagccatc actggatcgc taaggttatt tccatcagaa    2280
cgagtattaa ctaccaattc aacgttcaaa gtatttgatt cagaagattt cattatagaa    2340
tatggaacaa ctgatgatga agtgtatata caaagagcat tcatgtcatt gtctagtcag    2400
aaatcgggaa tagctgatga aattgcctct tcgcaaacat ttaaaaatta tgttagtaaa    2460
ttatctgatc aattattagt atcaaaaaat gtaattgtat ctaaaggtat agcagtaacg    2520
gagaaggcta aattgaattc atacgcgcca atatatttag aaaaacgtcg tgcgcaaata    2580
tcagcgttat taaccatgtt gcagaaacca gtgtcattta aatcaaataa aaatactatt    2640
aatgaaattt tacgtgatat aaaaccattc tttgtcacta ctgaagataa tttaccaatt    2700
caatatagaa aatttatgcc tacattgcca gataatgttc aatacgtcat acaatgtata    2760
ggatcaagga catatcaaat agaagatagc ggatcgaaat cgtcaatttc aaagttaata    2820
tcaaaatatt cagtttataa accatcaatt gaagagttgt acaaagttat atctctaaga    2880
gaacaagaaa tacaattgta tttggtgtca ttaggagttc cattagttga tgcgagtgca    2940
tatgtagcat caaggatata ttcacaagat aaatataaaa tattagaatc ttatgtatat    3000
aacttactat caattaatta tggatgctat caattattcg atttcaactc tccagatcta    3060
gaaaagctta tacgaattcc ttttaaaggc aaaataccag ctgtaacgtt catattgcat    3120
ctttatgcta agttagaaat aataaattat gctataaaga atagagcttg gattagtgta    3180
ttctgtaatt atccaaaatc tgagatgatt aagttatgga agaaaatgtg gagcataaca    3240
gcactacgat cgccctatac tagtgcgaat ttcctttcaag attagaacgc ttagatgtga    3300
cc                                                                  3302

<210> SEQ ID NO 50
<211> LENGTH: 3302
<212> TYPE: DNA
<213> ORGANISM: Human rotavirus

<400> SEQUENCE: 50
ggctattaaa gctgtacaat ggggaagtac aatctaatct tgtcagaata tttatcattt      60
gtttataatt cacaatctgc agttcaaata ccaatttatt attcttccaa ttcagaatta     120
gaaaaaagat gtattgagtt tcatgctaaa tgtgttgaca gttctaaaaa aggtatgtca     180
ttaaaacctt tatttgaaga gtataaagat gtaatagata atgcaacgtt actatctata     240
ttatcatatt cttatgataa atacaacgct gtggaacgta aactagtcaa ttatgctaaa     300
ggtaaacctt tagaggctga tttaacggca aacgagcttg attatgaaaa taacaaaata     360
acttctgaac tgtttcagtc agccgaagaa tataccgatt cattaatgga tcctgctata     420
ttaacttcat tatcttcaaa tttaaatgca gttatgtttt ggttagaacg acactcaaat     480
gacgttgctg atgcaaataa aatttataag cgtagactag atttatttac catagtggca     540
tctacaataa ataaatacgg agtacccaga cataatgaaa aatacagata tgaatacgaa     600
```

-continued

```
gtgatgaagg ataaaccgta ttacttagta acttgggcta actcatctat agaaatgctt    660
atgtcagtgt tttcacatga ggattattta atagcaaaag aattaataat cttatcatac    720
tcaaatagat caacgttagc aaaactagtt tcatctccaa tgtcaatatt agttgcatta    780
atagatatca atggtacgtt tattacgaat gaagaattgg aacttgagtt ttcggataaa    840
tatgttaagg caattgtacc tgatcaaatt ttcgatgaat tacaggaaat gattgacaat    900
atgaagaaag ttggtttagt agacatacca agaatgattc aagaatggtt agttgattgt    960
tcattagaga aatttacact gatgtcaaaa atttattctt ggtcatttca tgttggtttt   1020
agaaaacaaa aaatgattga tgcagcatta gaccaattga agacagagta cactgaagat   1080
gtagatggtg agatgtacaa tgagtataca atgttaatta gagatgaaat agttaaaatg   1140
ctagaagtac cagttaaaca tgacgatcat ctacttcgtg attcagaatt agctggattg   1200
ttatcaatgt catcagcttc aaatggtgaa tcaaggcaac ttaaatttgg tctcaaaaca   1260
atattttcaa ctaagaaaaa tatgcatgtt atggatgata ttgcacatgg aaggtatact   1320
cctggtatca ttcctccagt aaacgtagat agaccaattc cattaggtcg tagagatgtt   1380
cctggacgaa gaacaagaat tatattcata ttaccatatg aatactttat tgcgcagcac   1440
gctgtcgtag aaaaaatgtt atcatacgca aagcatacta gagagtatgc ggaattttac   1500
tcacagtcaa atcaattgct atcatacggt gatgtgacaa gattcttatc cagtaattct   1560
atggtgctat acacagacgt ttcacaatgg gattcgtcac aacataacac acagccattt   1620
agaaaaggaa taattatggg tttagatatg ttatctaata tgactaatga tccaaaagta   1680
atacaaacgc taaatttata taaacaaaca caaattaatc tcatggattc atatgttcaa   1740
atacctgatg gtaatgtaat caaaaagatt cagtatggtg ctgttgcttc aggagaaaaa   1800
caaactaagg cagctaattc tatagctaat ttggcactca ttaaaacagt attgtcaagg   1860
attgcaaata atattctttt tataaccaaa ataatcagag ttgatggtga tgataattat   1920
gcagtactac aatttaacac cgatgtcact aaacaaatgg tccaagatgt gtcaaacgat   1980
gtgagacata tatattctag aatgaatgct aaagttaaag cattggtatc tacagtcggt   2040
attgaaatag caaaaagata tatagctgga ggaaaaatat ttttttagagc tggtataaac   2100 ttattaaata tgagaagcg tggacaaagt acacaatggg atcaagcagc tattttatat   2160
tcgaactaca ttgttaacaa attacgagga tttgagactg atagagaatt tatattaact   2220
aaaattatac aaatgacatc tgtagccatt actggatcac taaggctatt tccgtcagaa   2280
cgagtgttaa ctactaattc tacattcaaa gtatttgact cagaagattt cattatagag   2340
tatggaacaa ctgacgatga agtatatata cagagagcat ttatgtcatt gtctagtcaa   2400
aagtcaggaa tagctgatga aattgcctct tcacaaacat tcaaaaatta tgttaataaa   2460
ttatctgacc aactattaat atcaaaaaac gtaattgtat ccaaaggtat agctgtaaca   2520
gaaaaagcga aattgaattc atatgcacca gtttatttag aaaaacgtcg tgcgcaaata   2580
tcagcgctat taactatgtt acagaagcca gtgtcattta aatcaaataa aattactatt   2640
aatgacattt tgcgtgacat aaaaccattt tttgttactt ctgaagccaa tttgccaatt   2700
caatacagaa aatttatgcc aacactacct gataacgtcc aatatgttat acaatgtata   2760
ggatcaagga cgtatcagat agaagatagt gggtcgaaat catcgatttc aaagttaata   2820
tcaaaatact cagtttacaa accatcaatt gaggaactat ataagttat atctttacga   2880 gaacaagaaa tacagttgta tttagtttca ctaggagttc cgccagttga tgcaggcacg   2940
```

-continued

| | |
|---|---|
| tacgtcgggt caagaatata ttcgcaagac aagtataaaa tattagaatc ttacgtatat | 3000 |
| aatttattat caattaatta tggatgttat caattattcg attttaattc tccagattta | 3060 |
| gagaaactta tacgaattcc ttttaaaggt aagataccag ccgtaacatt tatattacat | 3120 |
| ctctatgcaa aacttgaaat aataaatcat gccattaaga atggagcatg gattagtttg | 3180 |
| ttctgtaatt acccaaaatc tgagatgatt aaactatgga agaaaatgtg gaacataaca | 3240 |
| gcattacggt ctccctatac tagtgcgaat ttctttcaag attagagtgc ttagatgtga | 3300 |
| cc | 3302 |

<210> SEQ ID NO 51
<211> LENGTH: 3302
<212> TYPE: DNA
<213> ORGANISM: Human rotavirus

<400> SEQUENCE: 51

| | |
|---|---|
| ggctattaaa gctgtacaat ggggaagtac aatctaatct tgtcagaata tttatcattt | 60 |
| gtttataatt cacaatctgc agttcaaata ccaattatt attcttccaa ttcagaatta | 120 |
| gaaaaaagat gtattgagtt tcatgctaaa tgtgttgaca gttctaaaaa aggtatgtca | 180 |
| ttaaaacctt tatttgaaga gtataaagat gtaatagata atgcaacgtt actatctata | 240 |
| ttatcatatt cttatgataa atacaacgct gtggaacgta aactagtcaa ttatgctaaa | 300 |
| ggtaaacctt tagaggctga tttaacggca aacgagcttg attatgaaaa taacaaaata | 360 |
| acttctgaac tgtttcagtc agccgaagaa tataccgatt cattaatgga tcctgctata | 420 |
| ttaacttcat tatcttcaaa tttaaatgca gttatgtttt ggttagaacg acactcaaat | 480 |
| gacgttgctg atgcaaataa aatttataag cgtagactag atttatttac catagtggca | 540 |
| tctacaataa ataaatacgg agtacccaga cataatgaaa aatacagata tgaatacgaa | 600 |
| gtgatgaagg ataaaccgta ttacttagta acttgggcta actcatctat agaaatgctt | 660 |
| atgtcagtgt tttcacatga ggattattta atagcaaaag aattaataat cttatcatac | 720 |
| tcaaatagat caacgttagc aaaactagtt tcatctccaa tgtcaatatt agttgcatta | 780 |
| atagatatca atggtacgtt tattacgaat gaagaattgg aacttgagtt ttcggataaa | 840 |
| tatgttaagg caattgtacc tgatcaaatt ttcgatgaat tacaggaaat gattgacaat | 900 |
| atgaagaaag ttggtttagt agacatacca agaatgattc aagaatggtt agttgattgt | 960 |
| tcattagaga aatttacact gatgtcaaaa atttattctt ggtcatttca tgttggtttt | 1020 |
| agaaaacaaa aaatgattga tgcagcatta gaccaattga agacagagta cactgaagat | 1080 |
| gtagatggtg agatgtacaa tgagtataca atgttaatta gagatgaaat agttaaaatg | 1140 |
| ctagaagtac cagttaaaca tgacgatcat ctacttcgtg attcagaatt agctggattg | 1200 |
| ttatcaatgt catcagcttc aaatggtgaa tcaaggcaac ttaaatttgg tctcaaaaca | 1260 |
| atattttcaa ctaagaaaaa tatgcatgtt atggatgata ttgcacatgg aagtatact | 1320 |
| cctggtatca ttcctccagt aaacgtagat agaccaattc cattaggtcg tagagatgtt | 1380 |
| cctggacgaa gaacaagaat tatattcata ttaccatatg aatactttat tgcgcagcac | 1440 |
| gctgtcgtag aaaaaatgtt atcatacgca aagcatacta gagagtatgc ggaattttac | 1500 |
| tcacagtcaa atcaattgct atcatacggt gatgtgacaa gattcttatc cagtaattct | 1560 |
| atggtgctat acacagacgt ttcacaatgg gattcgtcac aacataacac acagccattt | 1620 |
| agaaaaggaa taattatggg tttagatatg ttatctaata tgactaatga tccaaaagta | 1680 |
| atacaaacgc taaatttata taaacaaaca caaattaatc tcatggattc atatgttcaa | 1740 |

```
atacctgatg gtaatgtaat caaaaagatt cagtatggtg ctgttgcttc aggagaaaaa    1800
caaactaagg cagctaattc tatagctaat ttggcactca ttaaaacagt attgtcaagg    1860
attgcaaata aatattcttt tataaccaaa ataatcagag ttgatggtga tgataattat    1920
gcagtactac aatttaacac cgatgtcact aaacaaatgg tccaagatgt gtcaaacgat    1980
gtgagacata tatattctag aatgaatgct aaagttaaag cattggtatc tacagtcggt    2040
attgaaatag caaaaagata tatagctgga ggaaaaatat tttttagagc tggtataaac    2100
ttattaaata atgagaagcg tggacaaagt acacaatggg atcaagcagc tattttatat    2160
tcgaactaca ttgttaacaa attacgagga tttgagactg atagagaatt tatattaact    2220
aaaattatac aaatgacatc tgtagccatt actggatcac taaggctatt ccgtcagaa    2280 cgagtgttaa ctactaattc tacattcaaa gtatttgact cagaagattt cattatagag    2340
tatggaacaa ctgacgatga agtatatata cagagagcat ttatgtcatt gtctagtcaa    2400
aagtcaggaa tagctgatga aattgcctct tcacaaacat tcaaaaatta tgttaataaa    2460
ttatctgacc aactattaat atcaaaaaac gtaattgtat ccaaaggtat agctgtaaca    2520
gaaaaagcga aattgaattc atatgcacca gtttatttag aaaaacgtcg tgcgcaaata    2580
tcagcgctat taactatgtt acagaagcca gtgtcattta aatcaaataa aattactatt    2640
aatgacattt tgcgtgacat aaaccatttt tttgttactt ctgaagccaa tttgccaatt    2700
caatacagaa aatttatgcc aacactacct gataacgtcc aatatgttat acaatgtata    2760
ggatcaagga cgtatcagat agaagatagt gggtcgaaat catcgatttc aaagttaata    2820
tcaaaatact cagtttacaa accatcaatt gaggaactat ataaagttat atctttacga    2880
gaacaagaaa tacagttgta tttagtttca ctaggagttc cgccagttga tgcaggcacg    2940
tacgtcgggt caagaatata ttcgcaagac aagtataaaa tattagaatc ttacgtatat    3000
aatttattat caattaatta tggatgttat caattattcg atttttaatc tccagattta    3060
gagaaactta tacgaattcc ttttaaaggt aagataccag ccgtaacatt tatattacat    3120
ctctatgcaa aacttgaaat aataaatcat gccattaaga atggagcatg gattagtttg    3180
ttctgtaatt acccaaaatc tgagatgatt aaactatgga agaaaatgtg gaacataaca    3240
gcattacggt ctccctatac tagtgcgaat ttctttcaag attagagtgc ttagatgtga    3300
cc                                                                    3302
```

<210> SEQ ID NO 52
<211> LENGTH: 2747
<212> TYPE: DNA
<213> ORGANISM: Human rotavirus

<400> SEQUENCE: 52

```
ggctattaaa ggctcaatgg cgtacaggaa gcgcggaact aaacgtgaag acttaccaca      60 acaaatgaa cgtctgcaag aaaaagaaat tgaaaataat atagacgtaa ccatggaaaa     120
taaaaataaa aatattaata aaataataa taaaaataac aatagaaagc agcaattatc     180
tgacaaagtg ttattacaaa aagaggaaat aataactgat gtacaagatg acatcaaaat     240
aactgatgaa gttaaaaaat cgtcaaaaga agagtcgaaa cagttactcg aaatattaaa     300
aacgaaagaa gatcatcaga agaagtaca gtacgaaatt ctacaaaaaa caataccgac     360
ttttgaacca aaagaatcaa ttttgaaaaa attagaagat ataagaccag aacaagctaa     420
gaagcaaatg aaattgttta gaatatttga accaagacaa ttaccaatct accgagcaaa     480
```

-continued

```
tggtgagaaa gaattaagga atagatggta ttggaaattg aaaaaggata cgttgccaga      540
cggagattat gacgtacgcg aatattttt aaatttatat gatcaaatac tgatagaaat      600
gccagattat ttattactaa aagatatggc tgtagaaaat aaaaactcta gggatgctgg      660
taaagttgta gattctgaga ctgcaagtat ttgtgatgcc atatttcaag atgaagagac      720
agagggagtt attagaagat ttatcgcaga tatgagacaa caaattcaag ctgatagaaa      780
tattgtcaat tatccatcaa ttttacatcc aattgaccat gcatttaatg aatattttct      840
gaaccatcaa ttagttgaac cattgaataa cgacattatt tttaattata taccagaaag      900
aataagaaat gatgtcaact atattttgaa tatggatatg aatttaccat caacagcaag      960
atatattaga ccaaatctgt tgcaagatag actaaattta catgataatt ttgaatcatt     1020
atgggacaca ataactacat cgaattatat attagcaaga tcagtcgtgc ctgatttgaa     1080
ggaaaaagaa ttagtttcga ctgaagctca gatacagaaa atgtctcaag atttgcagct     1140
tgaagcttta acaatacaat ctgaaacgca atttctggcc ggcataaatt cacaagcagc     1200
aaatgattgt tttaaaacac tgatagcagc tatgttaagt caacgtacaa tgtcattaga     1260
ttttgtaact acgaattata tgtcacttat atctggcatg tggctattga ctgttatacc     1320
aaatgatatg tttcttcgtg agtcgctagt tgcatgcgaa ttggctataa taaacactat     1380
agtttaccca gcatttggaa tgcaaagaat gcattatagg aatggcgatc cccagactcc     1440
atttcaaata gcagagcaac aaatacaaaa ttttcaagta gctaattggt tacattttat     1500
taataataat agatttagac aagttgttat tgatggagtg ttaaatcaaa cacttaatga     1560
caacattagg aatggacaag ttattaatca attaatggaa gcattaatgc agttatctag     1620
acaacaattt ccgaccatgc cagttgatta caaaagatca atccaaagag gaatattgtt     1680
attgtctaac agattgggtc agttagttga tttaacgaga ttattatcat ataattatga     1740
aactctaatg gcttgtataa ctatgaatat gcagcatgtt caaactctca ctactgaaag     1800
attacagtta acttctgtca catctttatg tatgttaatt ggaaatacca cagtaattcc     1860
aagtccacaa acactatttc actattataa tataaatgta aattttcatt caaattataa     1920
tgaacgaatt aacgatgctg tggctatcat tacggctgct aatagactaa atttatatca     1980
gaaaaaaatg aaatcaatag ttgaggattt tttgaaaaga ttgcaaattt ttgatgtacc     2040
acgagtacca gatgatcaaa tgtacagatt gagagacaga cttagattat tgccagttga     2100
aagacgaaga cttgatatat ttaacttaat attaatgaat atggagcaga tcgaacgagc     2160
ttcagataaa attgctcaag gagtaataat tgcttataga gatatgcagc tagaaagaga     2220
tgagatgtat ggatttgtta acatcgctag gaacctcgat ggatatcaac aaatcaattt     2280
agaagagtta atgagaactg gagactatgg tcaaattact actatgctat taaacaatca     2340
gcctgtagct ttggtaggag cattaccatt tgtaacagat tcatcagtta tatcgcttat     2400
agcgaaattg gatgccacag tatttgctca aatagttaaa cttagaaaag tggacacttt     2460
aaaaccgata ttgtataaaa taaattctga ttctaatgat ttctacttag ttgcaaatta     2520
tgattggata ccgacttcaa ctacaaaagt ttataaacaa gtaccacaac cttttgattt     2580
cagagcatca atgcatatgt taacgtctaa cttaacttt accgtttatt ctgatttact     2640
atctttcgtt tctgcagaca cggttgaacc tattaacgca attgcttttg acaatatgcg     2700
cattatgaac gaactgtaaa cgccaacccc actgtggaga tatgacc                  2747
```

<210> SEQ ID NO 53
<211> LENGTH: 2747

<212> TYPE: DNA
<213> ORGANISM: Human rotavirus

<400> SEQUENCE: 53

```
ggctattaaa ggctcaatgg cgtacaggaa gcgcggaact aaacgtgaag acttaccaca      60
acaaaatgaa cgtctgcaag aaaaagaaat tgaaaataat atagacgtaa ccatggaaaa     120
taaaaataaa aatattaata aaaataataa tagaaataac aatagaaagc agcaattatc     180
tgacaaagtg ttatcacaaa aagaggaaat aataactgat gtacaagatg acatcaaaat     240
aactgatgaa gttaaaaaat cgtcaaaaga agagtcgaaa cagttactcg aaatattaaa     300
aacgaaagaa gatcatcaga aagaagtaca gtacgaaatt ctacaaaaaa caataccgac     360
ttttgaacca aaagaatcaa ttttgaaaaa attagaagat ataagaccag aacaagctaa     420
gaagcaaatg aaattgttta gaatatttga accaagacaa ttaccaatct accgagcaaa     480
tggtgagaaa gaattaagga atagatggta ttggaaattg aaaaaggata cgttgccaga     540
cggagattat gacgtacgcg aatattttt aaatttatat gatcaaatac tgatagaaat     600
gccagattat ttattactaa agatatggc tgtagaaaat aaaaactcta gggatgctgg     660
taaagttgta gattctgaga ctgcaagtat ttgtgatgcc atatttcaag atgaagagac     720
agagggagtt attagaagat ttatcgcaga tatgagacaa caaattcaag ctgatagaaa     780
tattgtcaat tatccatcaa ttttacatcc aattgaccat gcatttaatg aatattttct     840
gaaccatcaa ttagttgaac cattgaataa cgacattatt tttaattata taccagaaag     900
aataagaaat gatgtcaact atattttgaa tatggatatg aatttaccat caacagcaag     960
atatattaga ccaaatctgt tgcaagatag actaaattta catgataatt ttgaatcatt    1020
atgggacaca ataactacat cgaattatat attagcaaga tcagtcgtgc ctgatttgaa    1080
ggaaaaagaa ttagtttcaa ctgaagctca gatacagaaa atgtctcaag atttgcagct    1140
tgaagcttta acaatacaat ctgaaacgca atttctggcc ggcataaatt cacaagcagc    1200
aaatgattgt tttaaaacac tgatagcagc tatgttaagt caacgtacaa tgtcattaga    1260
ttttgtaact acgaattata tgtcacttat atctggcatg tggctattga ctgttatacc    1320
aaatgatatg tttcttcgtg agtcgctagt tgcatgcgaa ttggctataa taaacactat    1380
agtttacccca gcatttggaa tgcaaagaat gcattatagg aatggcgatc cccagactcc    1440
atttcaaata gcagagcaac aaatacaaaa ttttcaagta gctaattggt tacattttat    1500
taataataat agatttagac aagttgttat tgatggagtg ttaaatcaaa cacttaatga    1560
caacattagg aatggacaag ttattaatca attaatggaa gcattaatgc agttatctag    1620
acaacaattt ccgaccatgc cagttgatta caaaagatca atccaaagag gaatattgtt    1680
attgtctaac agattgggtc agttagttga tttaacgaga ttattatcat ataattatga    1740
aactctaatg gcttgtataa ctatgaatat gcaacatgtt caaactctca ctactgaaag    1800
attacagtta acttctgtca catctttatg tatgttaatt ggaaatacca cagtaattcc    1860
aagtccacaa acactatttc actattataa tgtaaatgta aattttcatt caaattataa    1920
tgaacgaatt aacgatgctg tggctatcat tacggccgct aatagactaa atttatatca    1980
gaaaaaaatg aaatcaatag ttgaggattt tttgaaaaga ttgcaaattt ttgatgtacc    2040
acgagtacca gatgatcaaa tgtacagatt gagagacaga cttagattat tgccagttga    2100
aagacgaaga cttgatatat ttaacttaat attaatgaat atggagcaga tcgaacgagc    2160
ttcagataaa attgctcaag gagtaataat tgcttataga gatatgcagc tagaaagaga    2220
```

```
tgagatgtat ggatttgtta acatcgctag gaacctcgat ggatatcaac aaatcaattt    2280
agaagagtta atgagaactg gagactatgg tcaaattact actatgctat aaacaatca     2340 gcctgtagct ttggtaggag cattaccatt tgtaacagat tcatcagtta tatcgcttat    2400
agcgaaattg gatgccacag tatttgctca aatagttaaa cttagaaaag tggacacttt    2460
aaaaccgata ttgtataaaa taaattctga ttctaatgat ttctacttag ttgcaaatta    2520
tgattggata ccgacttcaa ctacaaaagt ttataaacaa gtaccacaac cttttgattt    2580
cagagcatca atgcatatgt taacgtctaa cttaactttt accgtttatt ctgatttact    2640
atctttcgtt tctgcagaca cggttgaacc tattaacgca attgcttttg acaatatgcg    2700
cattatgaac gaactgtaaa cgccaacccc actgtggaga tatgacc                  2747
```

<210> SEQ ID NO 54
<211> LENGTH: 2747
<212> TYPE: DNA
<213> ORGANISM: Human rotavirus

<400> SEQUENCE: 54

```
ggctattaaa ggctcaatgg cgtacaggaa gcgcggaact aaacgtgaag acttaccaca      60
acaaaatgaa cgtctgcaag aaaaagaaat tgaaaataat atagacgtaa ccatggaaaa     120
taaaaataaa aatattaata aaaataataa tagaaataac aatagaaagc agcaattatc     180
tgacaaagtg ttatcacaaa aagaggaaat aataactgat gtacaagatg catcaaaat     240 aactgatgaa gttaaaaaat cgtcaaaaga gagtcgaaa cagttactcg aaatattaaa     300
aacgaaagaa gatcatcaga aagaagtaca gtacgaaatt ctacaaaaaa caataccgac     360
ttttgaacca aagaatcaa ttttgaaaaa attagaagat ataagaccag aacaagctaa     420
gaagcaaatg aaattgttta gaatatttga accaagacaa ttaccaatct accgagcaaa     480
tggtgagaaa gaattaagga atagatggta ttggaaattg aaaaaggata cgttgccaga     540
cggagattat gacgtacgcg aatattttt aaatttatat gatcaaatac tgatagaaat     600
gccagattat ttattactaa agatatggc tgtagaaaat aaaaactcta gggatgctgg     660
taaagttgta gattctgaga ctgcaagtat ttgtgatgcc atattcaag atgaagagac     720 agagggagtt attagaagat ttatcgcaga tatgagacaa caaattcaag ctgatagaaa     780
tattgtcaat tatccatcaa ttttacatcc aattgaccat gcatttaatg aatattttct    840
gaaccatcaa ttagttgaac cattgaataa cgacattatt tttaattata taccagaaag    900
aataagaaat gatgtcaact atattttgaa tatggatatg aatttaccat caacagcaag    960
atatattaga ccaaatctgt tgcaagatag actaaattta catgataatt ttgaatcatt   1020
atgggacaca ataactacat cgaattatat attagcaaga tcagtcgtgc ctgatttgaa   1080
ggaaaaagaa ttagtttcaa ctgaagctca gatacagaaa atgtctcaag atttgcagct   1140
tgaagcttta acaatacaat ctgaaacgca atttctggcc ggcataaatt cacaagcagc   1200
aaatgattgt tttaaaacac tgatagcagc tatgttaagt caacgtacaa tgtcattaga   1260
ttttgtaact acgaattata tgtcacttat atctggcatg tggctattga ctgttatacc   1320
aaatgatatg tttcttcgtg agtcgctagt tgcatgcgaa ttggctataa taaacactat   1380
agtttaccca gcatttggaa tgcaaagaat gcattatagg aatggcgatc cccagactcc   1440
atttcaaata gcagagcaac aaatacaaaa ttttcaagta gctaattggt tacatttat    1500 taataataat agatttagac aagttgttat tgatggagtg ttaaatcaaa cacttaatga   1560
caacattagg aatggacaag ttattaatca attaatggaa gcattaatgc agttatctag   1620
```

```
acaacaattt ccgaccatgc cagttgatta caaaagatca atccaaagag gaatattgtt      1680
attgtctaac agattgggtc agttagttga tttaacgaga ttattatcat ataattatga      1740
aactctaatg gcttgtataa ctatgaatat gcaacatgtt caaactctca ctactgaaag      1800
attacagtta acttctgtca catctttatg tatgttaatt ggaaatacca cagtaattcc      1860
aagtccacaa acactatttc actattataa tgtaaatgta aattttcatt caaattataa      1920
tgaacgaatt aacgatgctg tggctatcat tacggccgct aatagactaa atttatatca      1980
gaaaaaaatg aaatcaatag ttgaggattt tttgaaaaga ttgcaaattt ttgatgtacc      2040
acgagtacca gatgatcaaa tgtacagatt gagagacaga cttagattat tgccagttga      2100
aagacgaaga cttgatatat ttaacttaat attaatgaat atggagcaga tcgaacgagc      2160
ttcagataaa attgctcaag gagtaataat tgcttataga gatatgcagc tagaaagaga      2220
tgagatgtat ggatttgtta acatcgctag gaacctcgat ggatatcaac aaatcaattt      2280
agaagagtta atgagaactg gagactatgg tcaaattact actatgctat aaacaatca      2340 gcctgtagct ttggtaggag cattaccatt tgtaacagat tcatcagtta tatcgcttat      2400
agcgaaattg gatgccacag tatttgctca aatagttaaa cttagaaaag tggacacttt      2460
aaaaccgata ttgtataaaa taaattctga ttctaatgat ttctacttag ttgcaaatta      2520
tgattggata ccgacttcaa ctacaaaagt ttataaacaa gtaccacaac cttttgattt      2580
cagagcatca atgcatatgt taacgtctaa cttaactttt accgtttatt ctgatttact      2640
atctttcgtt tctgcagaca cggttgaacc tattaacgca attgcttttg acaatatgcg      2700
cattatgaac gaactgtaaa cgccaacccc actgtggaga tatgacc                   2747

<210> SEQ ID NO 55
<211> LENGTH: 2591
<212> TYPE: DNA
<213> ORGANISM: Human rotavirus

<400> SEQUENCE: 55
ggctattaaa gcagtactag tagtgtgttt tacctctgat ggtgtaaaca tgaaagtatt        60
agctttaaga catagtgtgg ctcagatata tgcagatact caggtgtaca cacatgatga       120
ctctaaagat gattatgaaa atgcgttctt aatttctaat ctcactacac ataatatatt       180
atatttaaat tatagtgtaa aaacactgca atattgaat aaatccggta tagctgcaat        240
agagatacag aagatagatg agttattcac gctaattaga tgtaattta catacgacta        300 tattgatgac gttgtctatt tacatgatta ttcatattt gctaataatg aaatacggac        360
tgaccaatat tgggtaacca agacaaatat agaagactat ctattaccag gatggaaatt       420
gacatatgtt ggatacaatg gaagtgatac gagaggacat tataatttt ctttttagatg       480 tcagaatgca gctacagatg atgatgtaat aatagagtat atctattcaa atgaattaga       540
cttccagaac tttatactca aaagattaa agaaaggatg acaacatcac taccaatagc        600
aagactttca aatcgcgtat ttagagataa attatttaaa acgttgtcag taaatcatga       660
taaagtagtt aatgttggac ctagaaatga atctatgttt acttttttag accatccatc       720
aataaaacaa ttctctaatg gaccatattt ggttaaagat acaattaaac tcaaacaaga       780
gagatggctt ggtaaaagat tatcacagtt tgacattggt caatataaga atatgttaaa       840
tgtattaacg actttatatc aatattacga tatgtatcat gaaaaaccaa ttatatat         900 gataggatca gcgccctcgt attggatata tgatgtcaaa cagtactctg acttgaaatt       960
```

```
tgagacatgg gatccactag atacaccata ttctaattta catcataagg aattatttta    1020
cataaatgac gtgcaaaaac ttaaagataa ttcgatacta tatatagata taagaacaga    1080
tagaggaaat atggactgga aggaatggcg aaaagtggtg aagggcaaa ctgctgacaa     1140 tttacatatt gcatataaat atctatctac aggaaaagct aagatatgtt gtgttaaaat    1200
gaccgctatg gatgtagaat taccaatatc tgcaaaactg cttcaccatc caactacaga    1260
aattagatca gagttttatt taatgatgga tatatgggac tccaaaaata ttaaaagatt    1320
cataccaaaa ggtgtattat actcatatat aaacaataca attactgaaa acgtatttat    1380
acaacaacct tttaagttga aaacattgaa aaatgaatat gtaatagcac tttatgcttt    1440
atcaaatgat cttaacaata gagaagatgt ggtaaaacta atcaataatc agaaaagagc    1500
gttaataacg gtgagaatta acaatacatt taaagatgaa ccgaaagtcg gatttaaaaa    1560
catttacgat tggacatttt tgccaacgga ttttgagatg aatggatcaa taattacctc    1620
atatgatgga tgtctaggta ttttggttt atcaatatca ctagcttcaa aaccaaccgg     1680
taataatcat ttattcattt taagtggtac ggacaagtat tttaaattgg atcaattcgc    1740
aaatcatatg agtatatcac gacgatcaca tcagatacga ttttctgagt cagccacttc    1800
atactcggga tacatttta gagatttgtc taataataat ttcaatttaa taggtacgaa     1860
tgtagagaat tcagtatccg gacacgtata taatgcattg atttattata gatataatta    1920
ctcatttgac cttaaacgat ggatatactt acattcaaca ggtaaagcta gcattgaagg    1980
tggtaagtat tatgaacatg ctccaataga attaatttat gcatgcaggt cagcaagaga    2040
attcgcgaaa ttgcaagatg atttaacagt attaagatat tcaaatgaga tagaaaacta    2100
tatcaataaa gtttatagta taacatacgc cgacgaccct aattacttta ttggaattaa    2160
gtttaaaaat attccttaca agtataacgt taaagtacca catctcacat ttggcgtgtt    2220
aaatatttct gaacagatgt taccagatgc aatagcaatt ttaaagaaat ttaagaatga    2280
actatttgga atggacataa caacgagtta tacatatatg ttatctgatg aggtgtatgt    2340
agcaaatata agtggtgtac tatcaacata tttcaaaatt tacaacgcgt tttataaaga    2400
acaaattaca tttggacagt caagaatgtt tattccccat gtaacgttga gttttagtaa    2460
tgagaaaaca gtgagaatag acactacaaa attgtacata gattccattt atctaagaaa    2520
aataaaaggt gacacagtgt ttgatatgac tgagtgagct aaaaacttaa cacactagtc    2580
atgatgtgac c                                                         2591

<210> SEQ ID NO 56
<211> LENGTH: 2591
<212> TYPE: DNA
<213> ORGANISM: Human rotavirus

<400> SEQUENCE: 56
ggctattaaa gcagtaccag tagtgtgttt tacctctgat ggtgtaaaca tgaaagtatt      60
agctttaaga catagtgtgg ctcaggtgta tgcagacact caggtgtaca cacatgatga     120
ttctaaagat gagtatgaga acgcattctt aatttctaat ctcactacac ataatatatt     180
atatttaaat tataatgtaa aaacgctaca gatattaaat aaatctggta tagctgcaat     240
agagatacag aagatagatg aattattcac gttaattaga tgtaactta catatgatta     300 cattgataat gttgtttact tacatgacta ttcatattat actaataatg aaatacggac     360
tgaccaacat tggataacca agacaaatat agaagattat ttattaccag gatggaagct    420
gacatacgtt ggatacaatg gaagtgatac gcgcggacat tataattttt catttagatg    480
```

```
tcaaaatgca gctacagatg atgatgcaat aatagagtat atctattcag atgaattaga      540
cttccagagt tttatactca agaagattaa agaaaggatg acaacatcac taccaatagc      600
aagactttca aatcgtgtat ttagagataa gttatttaaa acgttatcag taaatcatga      660
taaagtagtt aatattgggc ccagaaatga atctatgttt acttttttag actatccatc      720
aataaaacag ttctcgaatg gaccgtattt agttaaagat acaattaaac tcaaacaaga      780
gagatggctt ggtaaaagat tatcacagtt tgatattggt caatataaga atatgctaaa      840
tgtattaacg actttgtatc aatattacga tatatatcat gaaaaaccaa tcgtatatat      900
gataggatca gcgccttcgt attggatata tgacgtcaaa cagtattcta acttgaaatt      960
tgaaacgtgg gatccactag atacaccata ctctaattta catcataagg aattatttta     1020
catgaatgac gtgcaaaaac ttaaagataa ttcaatacta tatatagata taagaacaga     1080
tagaggaact gtagactgga aggaatggcg aaaaatagta gaaaggcaaa ctattgacaa     1140
tttgcatatt gcatacaaat atctatctac agggaaagct aaggtatgtt gcgttaaaat     1200
gaccgccatg gatttagaat taccaatatc tgcaaaattg cttcaccatc caactacaga     1260
gattagatca gagtttttatc tagtgatgga tatatgggac tctaaaaata ttaaaagatt     1320
cataccaaaa ggtgtattat actcatatat aaacaataca attactgaaa acgtattcat     1380
acaacaacct tttaagttga aaacattgaa aaatgaatat ataatagcac tttatgcttt     1440
atcaaatgat tttaacaaca gagaagatgt ggtgaaacta attaataatc agaaaaaagc     1500
gttaatgaca gtgagaatta ataatacgtt taaagacgaa ccaaaagtcg gatttaaaaa     1560
catttacgat tggacatttc taccaacgga ttttgaaact aatggatcaa taattacttc     1620
atatgatggg tgtctaggta tctttggttt atcaatatcg ctagcttcaa aaccaactgg     1680
taataatcat ttgttcattt taagtggaac agacaagtat tttaaattgg atcaatttgc     1740
aaatcatatg agcatatcac gacgatcaca tcagatacga ttttcggagt cagccacttc     1800
atattcggga tatattttta gggatttgtc taataataat ttcaatttaa taggtacgaa     1860
tgtagagaat tcagtatccg gacacgtgta taatgcattg atttattata gataataatta    1920 ttcatttgac cttaaacgat ggatatactt acattcaaca ggcaaagcta gtattgaagg     1980
tggtaagtat tatgaacacg ctccaattga attgatttat gcatgcagat cagcgagaga     2040
atttgcgaaa ctgcaagatg atttaacggt ttaagatat tcaaatgaga tagaaaaacta     2100 tatcaacaga gtttatagca taacatacgc cgacgatcct aattacttta ttggagttaa     2160
gtttaaaaat attccttata agtataacgt taaagtacca catctcacat ttggcgtgtt     2220
aaatatttct gaacaaatgc taccagatgt aataacgatt ttaaagagat ttaagaatga     2280
gttatttgga atgaagtaa caacgagtta tacgtacatg ttatctgatg aggtgtatgt     2340
agcaaatata agtggtgtac tatcaacata tttcaaaatt tataatgcgt tttataaaga     2400
gcaaatcaca tttggacagt caagaatgtt tattcctcat gtaacgttga gttttagtaa     2460
tgagaaaacg gtgagaatag acactacaaa actgtacata gattctattt acttaagaaa     2520
aataaaaggt aacacggtgt ttgatatgac tgggtgagct aaaaacttaa cacactagtc     2580
atgatgtgac c                                                          2591
```

<210> SEQ ID NO 57
<211> LENGTH: 2591
<212> TYPE: DNA
<213> ORGANISM: Human rotavirus

<400> SEQUENCE: 57

```
ggctattaaa gcagtaccag tagtgtgttt tacctctgat ggtgtaaaca tgaaagtatt        60
agctttaaga catagtgtgg ctcaggtgta tgcagacact caggtgtaca cacatgatga       120
ttctaaagat gagtatgaga acgcattctt aatttctaat ctcactacac ataatatatt       180
atatttaaat tataatgtaa aaacgctaca gatattaaat aaatctggta tagctgcaat       240
agagatacag aagatagatg aattattcac gttaattaga tgtaacttta catatgatta       300
cattgataat gttgtttact tacatgacta ttcatattat actaataatg aaatacggac       360
tgaccaacat tggataacca agacaaatat agaagattat ttattaccag gatggaagct       420
gacatacgtt ggatacaatg gaagtgatac gcgcggacat tataatttttt catttagatg       480
tcaaaatgca gctacagatg atgatgcaat aatagagtat atctattcag atgaattaga       540
cttccagagt tttatactca agaagattaa agaaaggatg acaacatcac taccaatagc       600
aagactttca aatcgtgtat ttagagataa gttatttaaa acgttatcag taaatcatga       660
taaagtagtt aatattgggc ccagaaatga atctatgttt acttttttag actatccatc       720
aataaaacag ttctcgaatg gaccgtattt agttaaagat acaattaaac tcaaacaaga       780
gagatggctt ggtaaaagat tatcacagtt tgatattggt caatataaga atatgctaaa       840
tgtattaacg actttgtatc aatattacga tatatcat gaaaaaccaa tcgtatatat         900
gataggatca gcgccttcgt attggatata tgacgtcaaa cagtattcta acttgaaatt       960
tgaaacgtgg gatccactag atacaccata ctctaattta catcataagg aattatttta      1020
catgaatgac gtgcaaaaac ttaaagataa ttcaatacta tatatagata taagaacaga      1080
tagaggaact gtagactgga aggaatggcg aaaaatagta gaaaggcaaa ctattgacaa      1140
tttgcatatt gcatacaaat atctatctac agggaaagct aaggtatgtt gcgttaaaat      1200
gaccgccatg gatttagaat taccaatatc tgcaaaattg cttcaccatc caactacaga      1260
gattagatca gagtttate tagtgatgga tatatgggac tctaaaaata ttaaaagatt       1320
cataccaaaa ggtgtattat actcatatat aaacaataca attactgaaa acgtattcat      1380
acaacaacct tttaagttga aaacattgaa aaatgaatat ataatagcac tttatgcttt      1440
atcaaatgat tttaacaaca gagaagatgt ggtgaaacta attaataatc agaaaaaagc      1500
gttaatgaca gtgagaatta ataatacgtt taaagacgaa ccaaaagtcg gatttaaaaa      1560
catttacgat tggacatttc taccaacgga ttttgaaact aatggatcaa taattacttc      1620
atatgatggg tgtctaggta tctttggttt atcaatatcg ctagcttcaa aaccaactgg      1680
taataatcat ttgttcattt taagtggaac agacaagtat tttaaattgg atcaatttgc      1740
aaatcatatg agcatatcac gacgatcaca tcagatacga ttttcggagt cagccacttc      1800
atattcggga tatattttta gggatttgtc taataataat ttcaatttaa taggtacgaa      1860
tgtagagaat tcagtatccg gacacgtgta taatgcattg atttattata gatataatta      1920
ttcatttgac cttaaacgat ggatatactt acattcaaca ggcaaagcta gtattgaagg      1980
tggtaagtat tatgaacacg ctccaattga attgatttat gcatgcagat cagcgagaga      2040
atttgcgaaa ctgcaagatg atttaacggt tattaagatat tcaaatgaga tagaaaaacta      2100
tatcaacaga gtttatagca taacatacgc cgacgatcct aattacttta ttggagttaa      2160
gtttaaaaat attccttata agtataacgt taaagtacca catctcacat ttggcgtgtt      2220
aaatatttct gaacaaatgc taccagagtg aataacgatt ttaaagagat ttaagaatga      2280
gttatttgga atggaagtaa caacgagtta tacgtacatg ttatctgatg aggtgtatgt      2340
```

-continued

```
agcaaatata agtggtgtac tatcaacata tttcaaaatt tataatgcgt tttataaaga    2400
gcaaatcaca tttggacagt caagaatgtt tattcctcat gtaacgttga gttttagtaa    2460
tgagaaaacg gtgagaatag acactacaaa actgtacata gattctattt acttaagaaa    2520
aataaaaggt aacacggtgt ttgatatgac tgggtgagct aaaaacttaa cacactagtc    2580
aagatgtgac c                                                        2591
```

<210> SEQ ID NO 58
<211> LENGTH: 2359
<212> TYPE: DNA
<213> ORGANISM: Human rotavirus

<400> SEQUENCE: 58

```
ggctataaaa tggcttcgct catttataga cagcttctca ctaattcata ttcagtagat      60
ttacatgatg aaatagagca aattgggtca gaaaaaactc aaaacgtaac tgtaaatcca     120
ggtccatttg cccaaactag atatgctcca gtaaattggg gtcatggaga gataaatgat     180
tcaaccacag tagaaccaat tttagatggt ccttatcagc ctactacatt taaaccactt     240
actgattatt ggatacttat taactcaaat acaaatggag tggtatacga gagtacgaat     300
aatagtgact tttggactgc agtcgttgct gttgaaccgc acgttaatcc agtagataga     360
caatatactg tatttggtga aaataaacaa tttaatgtaa gaaatgattc agataaatgg     420 aagttttag aaatgtttag aggcagtagt caaaatgaat tttataatag acgtacacta     480
acttctgata ctaaactcgt aggaatatta aaatatggtg aaggatatg gacatttcat     540 ggtgaaacac cgagagctac tactgatagc tcaaatactg caaatttaaa cgatatatca     600
attataatac attcagaatt ttatattatc ccaaggtccc aagaatctaa gtgtaatgaa     660
tatattaaca atggtttgcc accaattcaa aatactagaa atgtagtacc attatcatta     720
tcatctagat ccatacagta taaaagagca caagttaatg aagatattac aatttcaaaa     780
acctcattat ggaaagaaat gcaatgtaat agggatatta aattagatt taaatttggt     840 aatagtattg taaaactggg gggactaggt tataaatggt ccgaaatatc atataaagca     900
gcaaattatc aatataatta tctacgtgat ggcgaacaag taactgcaca tactacttgc     960
tcagtaaatg gagtaaataa ttttagctac aacggaggat ctttacctac tgattttagt    1020
gtctcaaggt atgaagttat taaagaaaat tcttatgtat atgtagatta ttgggatgat    1080
tcaaaagcat ttagaaatat ggtatatgtc agatcattag cagctaattt gaactcagtg    1140 aaaatgtacag gtgaagttaa actttagt ataccgtgtag gtgcatggcc agtcatgaat    1200
ggaggcgctg tttcgttgca ttttgctgga gttacattat ctacgcaatt cacagatttc    1260
gtatcattga attcactacg atttagattt agtttgacag tggatgagcc atctttttca    1320
atattgagaa cacgtacggt gaatttgtac ggattaccag ctgcaaatcc aaataatgga    1380
aatgaatact atgaaatatc aggaaggttt tcgctcattt ctttagttcc aactaatgat    1440
gattatcaga ctccaattat gaattcagta acagtaagac aagatttaga acgtcaactt    1500
actgatttac gagaggaatt taattcatta tcacaagaaa tagctatgtc acaattaatt    1560
gatttagcgt tataccttt agatatgttt tctatgttt caggaattaa aagtacaatt    1620
gatttgacta aatcaatggc aactagtgta atgaaaaaat ttagaaaatc aaaattagct    1680
acatcaattt cagaaatgac taattcattg tcagacgcag catcatcagc atcaagaagc    1740
gtttctatca gatcgaatat atccacaatt tcgaattgga ctaatgtttc aaatgatgta    1800
```

|  |  |
|---|---|
| tcaaatgtga ctaattcgtt gagtgatatt tcaacacaaa cgtctacaat cagtaagaac | 1860 |
| cttagattaa agaaatgat tactcaaact gaaggaatga gttttgatga tatttcagcg | 1920 |
| gcagtattaa aaacaaaaat agatatgtct actcaaattg gaaagaatac tttacccgat | 1980 |
| atagtcacag aggcatctga gaaatttatt ccaaaacgat cgtatcgaat attgaaagat | 2040 |
| gatgaagtaa tggaaattaa tactgaaggg aaagtctttg catataaaat cgacacactt | 2100 |
| aatgaagtgc catttgatgt aaataaattt gctgaacttg taacaaattc tccagttata | 2160 |
| tcagcaataa tcgattttaa aacattaaaa aatttgaatg ataattatgg aattactcga | 2220 |
| atagaagcat taaatttaat taaatcgaat ccaaatgtat tacgtaattt cattaaccaa | 2280 |
| aataatccaa ttataaggaa tagaattgaa cagctaattc tacaatgtaa attgtgagaa | 2340 |
| cgctattgag gatgtgacc | 2359 |

<210> SEQ ID NO 59
<211> LENGTH: 2359
<212> TYPE: DNA
<213> ORGANISM: Human rotavirus

<400> SEQUENCE: 59

|  |  |
|---|---|
| ggctataaaa tggcttcgct catttataga cagcttctca ctaattcata ttcagtagat | 60 |
| ttatatgatg aaatagagca aattggatca ggaaaaactc agaatgtaac cataaatccg | 120 |
| ggtccatttg cacagactag atatgctcca gtcaattggg gtcatggaga gataaatgat | 180 |
| tcgactacag tagaaccaat tttagacggt ccttatcagc caactacatt tactccacct | 240 |
| aacgattatt ggatacttat taattcaaat acaaatggag tggtatatga agtacaaat | 300 |
| aatagtgact tttggactgc agtcgttgct attgaaccgc atgtcacccc agtagataga | 360 |
| caatatatga tatttggtga aagtaaacaa tttaatgtga gtaacgattc aaataaatgg | 420 |
| aagttttag aaatgttcag aagcagtagt caaaatgaat tttataatag acgtacatta | 480 |
| acttctgaca ccagacttgt aggaatatta aaatatggtg gaagagtatg gacatttcat | 540 |
| ggtgaaacac caagagctac tactgacagt tcaagtactg caaatttaaa taatatatca | 600 |
| attacaattc attcagaatt ttacattatt ccaaggtccc aggaatctaa atgcaatgaa | 660 |
| tatattaata atggtctgcc accaattcaa aatactagaa atgtagttcc attaccatta | 720 |
| tcatctagat cgatacagta taagagagca caagttgatg aagacattat agtttcaaaa | 780 |
| acttcattat ggaaagaaat gcagtataat agggatatta taattagatt taaatttggt | 840 |
| aatagtattg taaagatggg aggactaggt tataaatggt ctgaaatatc atataaggca | 900 |
| gcaaattatc aatataatta tttacgtgac ggtgaacaag taaccgcaca caccacttgt | 960 |
| tcagtaaatg gagtgaacaa ttttagctat aatggagggt ccctacccac tgattttggt | 1020 |
| atttcaaggt atgaagttat taagaaaaat tcttatgtat atgtagacta ttgggatgat | 1080 |
| tcaaaagcat ttagaaatat ggtatatgtt agatcattag cagctaattt aaattcagtg | 1140 |
| agatgtacag gtggaagtta tgatttcagt ataccagtag gtgcatggcc agtaataaat | 1200 |
| ggtggcgctg tttcgttgca ttttgccgga gttacattat ccacgcaatt tactgatttt | 1260 |
| gtatcattga attcattacg atttagattt agtttgacag ttgatgaacc acctttctca | 1320 |
| atattgagaa cacgtacagt gaatttgtat ggattaccag ccgctaatcc gaataatgga | 1380 |
| aatgaatact acgaaatatc aggaaggttt tcactcattt ctttagttcc gactaatgat | 1440 |
| gattatcaga ctccaattat gaattcagtg acggtaagca aagatttaga gcgccaactt | 1500 |
| actgatttac gggaagaatt taactcattg tcacaagaaa tagctatggc acaattgatt | 1560 |

-continued

```
gatttagcac tgttgcctct agatatgttt tccatgtttt caggaattaa aagtacaatt 1620
gatttaacta aatcaatggc gactagtgta atgaagaaat ttagaaaatc aaaattagct 1680
acatcaattt cagaaatgac taattcattg tcagatgctg cttcatcagc atcaagaaac 1740
gtttctatta gatcgaattt atctgcgatt tcaaattgga ctaatgtttc aaatgatgtg 1800
tcaaacgtaa ctaattcatt aaatgatatt tcaacacaaa catctacaat tggtaagaaa 1860
cttagattaa aagaaatgat tactcaaact gaaggaatga gctttgatga catttcagca 1920
gctgtactaa aaacaaaaat agatatgtct actcaaattg gaaaaaatac tttacctgat 1980
atagttacag aagcatctga gaaatttatt ccaaaacgat catatcgaat attaaaggat 2040
gatgaagtaa tggaaattaa tactgaagga aaattctttg catacaaaat taatacattt 2100
gatgaagttc cattcgatgt aaacaaattc gctgaactag taacagattc tccagttata 2160
tcagcgataa tcgattttaa gacattgaaa aatttaaatg ataattatgg aatcactcgg 2220
acagaagcgt taaatttaat taagtcgaat ccaaatatgt tacgtaattt cattaatcaa 2280
aataatccaa ttataaggaa tagaattgaa cagttaatac tacaatgtaa attgtgagaa 2340
cgctattgag gatgtgacc 2359

<210> SEQ ID NO 60
<211> LENGTH: 2359
<212> TYPE: DNA
<213> ORGANISM: Human rotavirus
<400> SEQUENCE: 60
ggctataaaa tggcttcgct catttataga cagcttctca ctaattcata ttcagtagat 60
ttatatgatg aaatagagca aattggatca ggaaaaactc agaatgtaac cataaatccg 120
ggtccatttg cacagactag atatgctcca gtcaattggg atcatggaga gataaatgat 180
tcgactacag tagaaccaat tttagacggt ccttatcagc caactacatt tactccacct 240
aacgattatt ggatacttat taattcaaat acaaatggag tggtatatga aagtacaaat 300
aatagtgact tttggactgc agtcgttgct attgaaccgc atgtcacccc agtagataga 360
caatatatga tatttggtga aagtaaacaa tttaatgtga gtaacgattc aaataaatgg 420
aagtttttag aaatgttcag aagcagtagt caaaatgaat tttataatag acgtacatta 480
acttctgaca ccagacttgt aggaatatta aaatatggtg gaagagtatg gacatttcat 540
ggtgaaacac caagagctac tactgacagt tcaagtactg caaatttaaa taatatatca 600
attacaattc attcagaatt ttacattatt ccaaggtccc aggaatctaa atgcaatgaa 660
tatattaata atggtctgcc accaattcaa aatactagaa atgtagttcc attaccatta 720
tcatctagat cgatacagta taagagagca caagttgatg aagacattat agtttcaaaa 780
acttcattat ggaaagaaat gcagtataat agggatatta taattagatt taaatttggt 840
aatagtattg taaagatggg aggactaggt tataaatggt ctgaaatatc atataaggca 900
gcaaattatc aatataatta tttacgtgac ggtgaacaag taaccgcaca caccacttgt 960
tcagtaaatg gagtgaacaa ttttagctat aatggagggt tcctacccac tgattttggt 1020
atttcaaggt atgaagttat taaagaaaat tcttatgtat atgtagacta ttggggatgat 1080
tcaaaagcat ttagaaatat agtatatgtt agatcattag cagctaattt aaattcagtg 1140
agatgtacag gtggaagtta tcatttcagt ctaccagtag gtgcatggcc agtaataaat 1200
ggtggcgctg tttcgttgca ttttgccgga gttacattat ccacgcaatt tactgatttt 1260
```

```
gtatcattga attcattacg atttagattt agtttgacag ttgatgaacc acctttctca   1320
atattgagaa cacgtacagt gaatttgtat ggattaccag ccgctaatcc gaataatgga   1380
aatgaatact acgaaatatc aggaaggttt tcactcattt ctttagttcc gactaatgat   1440
gattatcaga ctccaattat gaattcagtg acggtaagac aagatttaga gcgccaactt   1500
actgatttac gggaagaatt taactcattg tcacaagaaa tagctatggc acaattgatt   1560
gatttagcac tgttgcctct agatatgttt tccatgtttt caggaattaa agtacaatt    1620 gatttaacta aatcaatggc gactagtgta atgaagaaat ttagaaaatc aaaattagct   1680
acatcaattt cagaaatgac taattcattg tcagatgctg cttcatcagc atcaagaaac   1740
gtttctatta gatcgaattt atctgcgatt tcaaattgga ctaatgtttc aaatgatgtg   1800
tcaaacgtaa ctaattcatt aaatgatatt tcaacacaaa catctacaat tggtaagaaa   1860
cttagattaa aagaaatgat tactcaaact gaaggaatga gctttgatga catttcagca   1920
gctgtactaa aaacaaaaat agatatgtct actcaaattg gaaaaaatac tttacctgat   1980
atagttacag aagcatctga gaatttatt ccaaaacgat cataccgaat attaaaggat    2040
gatgaagtaa tggaaattaa tactgaagga aaattctttg catacaaaat taatacattt   2100
gatgaagttc cattcgatgt aaacaaattc gctgaactag taacagattc tccagttata   2160
tcagcgataa tcgatttaa gacattgaaa aatttaaatg ataattatgg aatcactcgg    2220
acagaagcgt taaatttaat taagtcgaat ccaaatatgt tacgtaattt cattaatcaa   2280
aataatccaa ttataaggaa tagaattgaa cagttaatac tacaatgtaa attgtgagaa   2340
cgctattgag gatgtgacc                                                2359

<210> SEQ ID NO 61
<211> LENGTH: 1356
<212> TYPE: DNA
<213> ORGANISM: Human rotavirus

<400> SEQUENCE: 61
ggctttaaaa cgaagtcttc gacatggagg ttctgtactc actgtcaaaa actcttaaag     60
atgctaggga caaaattgtt gaaggtacat tatattctaa tgttagcgat ctcattcaac    120
aattcaatca aatgatagta actatgaatg gaaatgactt tcaaactgga ggaattggta    180
atttacctat taggaattgg acttcgatt ttggtctatt aggtacaaca cttttaaatt     240
tagacgctaa ttacgttgag aatgctagaa ctacaattga atattttatt gatttttattg   300 ataatgtatg tatggatgaa atggcaagag aagctcaaag aaatggagta gctccacaat    360
ccgaagcatt ggggaagtta gcaggtatta aattcaaaag aataaatttt gataattcat    420
ctgaatatat agaaaattgg aacttacaaa ataggaggca gcgtaccgga tttgtttttc    480
ataaacctaa tatatttcca tactcagctt cattcacttt aaatagatct caaccaatgc    540
atgacaattt gatgggaact atgtggctta atgctggatc agaaattcag gtagctggat    600
ttgattattc atgcgctata aatgcaccag caaacataca gcaatttgaa catattgtcc    660
agcttagacg tgcgctaact acagctacta aactttatt gcctgatgca gagagattca    720
gttttccaag agttattaat tcagctgatg gcgcgactac atggttttt aatccagtca    780 ttttaagacc gaataatgtt gaagtagaat ttttgttgaa tggacaaatt atcaatacat    840
atcaagctag atttggcact attattgcaa gaaatttcga tacgattcgg tcattattcc    900
agttaatgcg tccaccaaat atgacgccag ctgttaatgc actgttccg caagcacaac     960 cttttcaaca tcatgcaaca gttggactta cattacgtat tgaatctgca gtttgtgaat    1020
```

```
cagtgcttgc ggatgctaat gagactctat tggcgaatgt gaccgcagta cgtcaagagt   1080
atgctatacc agttggtcca gtatttccac caggcatgaa ttggactgaa ttaattacta   1140
actattcacc atctagagaa gataatttac aacgtgtttt tacggtagct tccattagaa   1200
gcatgttgat taagtgagga ccagactaag catctggtat ccaatcttag ttagcatgta   1260
gctacatcaa gtcattcaga ctcttcaagt aaggacatga tttcatgttc gctacgtaga   1320
gtaactgtct gaatgatgta gtgagaggat gtgacc                               1356
```

<210> SEQ ID NO 62
<211> LENGTH: 1356
<212> TYPE: DNA
<213> ORGANISM: Human rotavirus

<400> SEQUENCE: 62

```
ggctttaaaa cgaagtcttc gacatggagg ttctgtattc attgtcaaaa actcttaaag     60
atgctaggga taagattgtt gaaggtacat tatattctaa tgttagcgat cttattcagc    120
aatttaatca aatgatagta accatgaacg gaaatgactt tcaaactgga ggaattggca    180
atttacccat tagaaattgg acatttgact ttggcctact aggtactacg cttttaaatc    240
ttgatgctaa ttatgttgag actgctagaa ctacgatcga gtattttatt gatttcattg    300
ataatgtatg tatggatgaa atggcaagag agtctcaaag aaatggagta gctccacaat    360
ctgaggcatt gagaaagcta gccggtatta aatttaaaag aataaacttt aataattcat    420
cagaatatat agaaaattgg aatttacaaa atagaagaca acgtactgga tttgtttttc    480
ataaacctaa tatatttcca tactcagcgt catttacttt aaatagatct caaccaatgc    540
atgataattt aatgggaacc atgtggctta atgctggatc agaaattcaa gtagctggat    600
ttgactattc gtgtgctcta aatgctccag caaatattca gcaatttgaa catattgtcc    660
agctaaggcg tgcgctaact acagctacta taactttgtt acctgatgca gaaagattta    720
gttttccaag agttattaat tcagcagatg gcgcaactac atggttcttt aatccaatca    780
tcctaagacc aaacaatgta gaagtagaat tttactgaa tggacaaatt attaatacat    840
atcaagctag atttggcact attgtcgcaa gaaattttga tacaattcgc ctgtcattcc    900
aattaatgcg tccaccaaac atgacgccag ccgtaaatgc attatttccg caagcacaac    960
cttttcaaca tcatgcaaca gttggactta cgttacgtat tgagtctgca gtttgtgaat   1020
cagtgcttgc ggatgcaaat gaaactttat tggcgaatgt taccgcagta cgtcaagagt   1080
atgctatacc agttggacca gtatttccac caggcatgaa ttggactgag ctaattacta   1140
actattcacc atctagggaa gataatttgc aacgtgtctt tacagtagcc tctatcagaa   1200
gcatgttaat taagtgagga ccagactaac catctggtat ccaatcttag ttagcatgta   1260
gctatatcaa gtcattcaga ctctacaagt aaggacatgg ctccatgttc gctacgtaga   1320
gtaactgtat gaatgatgta gtgagaggat gtgacc                               1356
```

<210> SEQ ID NO 63
<211> LENGTH: 1356
<212> TYPE: DNA
<213> ORGANISM: Human rotavirus

<400> SEQUENCE: 63

```
ggctttaaaa cgaagtcttc gacatggagg ttctgtattc attgtcaaaa actcttaaag     60
atgctaggga taagattgtt gaaggtacat tatattctaa tgttagcgat cttattcagc    120
```

| | |
|---|---|
| aatttaatca aatgatagta accatgaacg gaaatgactt tcaaactgga ggaattggca | 180 |
| atttacccat tagaaattgg acatttgact ttggcctact aggtactacg cttttaaatc | 240 |
| ttgatgctaa ttatgttgag actgctagaa ctacgatcga gtatttatt gatttcattg | 300 |
| ataatgtatg tatggatgaa atggtaagag agtctcaaag aaatggagta gctccacaat | 360 |
| ctgaggcatt gagaaagcta gccggtatta aatttaaaag aataaacttt aataattcat | 420 |
| cagaatatat agaaaattgg aatttacaaa atagaagaca acgtactgga tttgtttttc | 480 |
| ataaacctaa tatatttcca tactcagcgt catttacttt aaatagatct caaccaatgc | 540 |
| atgataattt aatgggaacc atgtggctta atgctggatc agaaattcaa gtagctggat | 600 |
| ttgactattc gtgtgctcta aatgctccag caaatattca gcaatttgaa catattgtcc | 660 |
| agctaaggcg tgcgctaact acagctacta aactttgtt acctgatgca gaaagattta | 720 |
| gttttccaag agttattaat tcagcagatg gcgcaactac atggttcttt aatccaatca | 780 |
| tcctaagacc aaacaatgta gaagtagaat ttttactgaa tggacaaatt attaatacat | 840 |
| atcaagctag atttggcact attgtcgcaa gaaattttga tacaattcgc ctgtcattcc | 900 |
| aattaatgcg tccaccaaac atgacgccag ccgtaaatgc attatttccg caagcacaac | 960 |
| cttttcaaca tcatgcaaca gttggactta cgttacgtat tgagtctgca gtttgtgaat | 1020 |
| cagtgcttgc ggatgcaaat gaaactttat tggcgaatgt taccgcagta cgtcaagagt | 1080 |
| atgctatacc agttggacca gtatttccac caggcatgaa ttggactgag ctaattacta | 1140 |
| actattcacc atctagggaa gataaatttgc aacgtgtctt tacagtagcc tctatcagaa | 1200 |
| gcatgttaat taagtgagga ccagactaac catctggtat ccaatcttag ttagcatgta | 1260 |
| gctatatcaa gtcattcaga ctctacaagt aaggacatgg ctccatgttc gctacgtaga | 1320 |
| gtaactgtat gaatgatgta gtgagaggat gtgacc | 1356 |

<210> SEQ ID NO 64
<211> LENGTH: 1062
<212> TYPE: DNA
<213> ORGANISM: Human rotavirus

<400> SEQUENCE: 64

| | |
|---|---|
| ggctttaaaa gagagaattt ccgtttggct aacggttagc tccttttaat gtatggtatt | 60 |
| gaatatacca caattctaat cttttttgata tcaatcattc tactcaacta tatattaaaa | 120 |
| tcagtgactc gaataatgga ctacattata tacagatttt tgttgattac tgtagcatta | 180 |
| tttgccttga cgagagctca gaattatgga cttaacttac caataacagg atcaatggac | 240 |
| actgtatata ccaactctac tcaagaagaa gtgttcctaa cttctacatt atgtctatat | 300 |
| tatccaactg aagcaagtac tcaaatcaat gatggtgact ggaaagactc attgtcgcaa | 360 |
| atgtttctca caaaaggttg gccaacagga tctgtttact tcaaagagta ctcaagtatt | 420 |
| gttgattttt ctgttgaccc gcaactgtat gttgattttt ccgttgaccc acaattatat | 480 |
| gaccaaagtc ttgaattaga tatgtcagag ttagctgatt taatattgaa tgaatggtta | 540 |
| tgcaacccaa tggatataac attatactat tatcaacaat cgggagaatc aaataagtgg | 600 |
| atatcgatgg gatcatcatg tactgtgaaa gtgtgtccgc tgaatacaca aacgttaggg | 660 |
| ataggttgtc aaacaacaaa cgtagactca tttgaaatgg ttgctgagaa tgagaaatta | 720 |
| gctatagtgg atgtcgttga tgggataaat cataaaataa atttaacaac tacgacatgt | 780 |
| actattcgaa attgtaagaa attaggtcca agagaaaatg tagctgtaat acaagttggt | 840 |
| ggttctaatg tattagatat aacagcagat ccaacaacta atccacaaac tgagagaatg | 900 |

```
atgagagtga attggaaaaa atggtggcaa gtattttata ctatagtaga ttatattaac      960
caaattgtac aggtgatgtc caaaagatca agatcattaa attctgcggc ttttattat     1020 agagtataga tatatcttag attagaattg ttcgatgtga cc                       1062
```

<210> SEQ ID NO 65
<211> LENGTH: 1062
<212> TYPE: DNA
<213> ORGANISM: Human rotavirus

<400> SEQUENCE: 65

```
ggctttaaaa gagagaattt ccgtttggct aacggttagc tccttttaat gtatggtatt       60
gaatatacca caattctaat ctttctgata tcaatcattc tacttaacta tatattaaaa      120
tcagtgaccc gaataatgga ctacattata tatagatttt tgttaatttt tgtagcatta      180
tttgccttaa ctaaagctca gaattatgga cttaatatac caataacagg atcaatggat      240
actgtatatt ccaactctac tcgagaagaa gtatttctaa catccacatt atgtttgtac      300
tatccaactg aagcaagtac tcaaatcagt gatggtgaat ggaaagactc attatcgcaa      360
atgtttctta taaaaggttg gccaacagga tcagtctatt ttaaagagta ctcaaatatc      420
gttgattttt ccgttgaccc acaattatat tgtgattata acttagtact aatgaagtat      480
gatcaaagtc ttgaattaga tatgtcagaa ttagctgatt tgatattgaa tgaatggtta      540
tgtaatccaa tggatataac attatattat tatcagcaat cgggagaatc aaataagtgg      600
atatcaatgg gatcatcatg tactgtgaaa gtgtgtccac tgaatacaca acgttagga      660 ataggttgtc aaacaacgaa tgtagactca tttgaaacag ttgctgagaa tgaaaaatta      720
gctatagtgg atgtcgttga tgggataaat cataaaataa atttgacaac tacaacatgt      780
actattcgaa attgtaagaa gttaggtcca agagagaatg tggctgtaat acaagttggt      840
ggcgctaata tattagacat aacagcggat ccaacaacta atccacaaat tgagagaatg      900
atgagagtga attggaaaag atggtggcaa gtgttctata ctatagtaga ttatattaat      960
cagattgtac aggtaatgtc caaaagatca agatcattaa attccgctgc gttctattat     1020
agagtataga tatatcttag attagaattg tatgatgtga cc                       1062
```

<210> SEQ ID NO 66
<211> LENGTH: 1062
<212> TYPE: DNA
<213> ORGANISM: Human rotavirus

<400> SEQUENCE: 66

```
ggctttaaaa gagagaattt ccgtttggct aacggttagc tccttttaat gtatggtatt       60
gaatatacca caattctaat ctttctgata tcaatcattc tacttaacta tatattaaaa      120
tcagtgaccc gaataatgga ctacattata tatagatttt tgttaatttt tgtagcatta      180
tttgccttaa ctaaagctca gaattatgga cttaatatac caataacagg atcaatggat      240
actgtatatt ccaactctac tcgagaagaa gtatttctaa catccacatt atgtttgtac      300
tatccaactg aagcaagtac tcaaatcagt gatggtgaat ggaaagactc attatcgcaa      360
atgtttctta taaaaggttg gccaacagga tcagtctatt ttaaagagta ctcaaatatc      420
gttgattttt ccgttgaccc acaattatat tgtgattata acttagtact aatgaagtat      480
gatcaaagtc ttgaattaga tatgtcagaa ttagctgatt tgatattgaa tgaatggtta      540
tgtaatccaa tggatataac attatattat tatcagcaat cgggagaatc aaataagtgg      600
```

| | |
|---|---|
| atatcaatgg gatcatcatg tactgtgaaa gtgtgtccac tgaatacaca aacgttagga | 660 |
| ataggttgtc aaacaacaaa tgtagactca tttgaaacag ttgctgagaa tgaaaaatta | 720 |
| gctatagtgg atgtcgttga tgggataaat cataaaataa atttgacaac tacaacatgt | 780 |
| actattcgaa attgtaagaa gttaggtcca agagagaatg tggctgtaat acaagttggt | 840 |
| ggcgctaata tattagacat aacagcggat ccaacaacta atccacaaat tgagagaatg | 900 |
| atgagagtga attggaaaag atggtggcaa gtgttctata ctatagtaga ttatattaat | 960 |
| cagattgtac aggtaatgtc caaaagatca agatcattaa attccgctgc gttctattat | 1020 |
| agagtataga tatatcttag attagaattg tatgatgtga cc | 1062 |

<210> SEQ ID NO 67
<211> LENGTH: 1564
<212> TYPE: DNA
<213> ORGANISM: Human rotavirus

<400> SEQUENCE: 67

| | |
|---|---|
| ggctttttt tgaaaagtct tgtggaagcc atggctactt ttaaagatgc ttgctatcaa | 60 |
| tataaaaaat taaacaaatt aaataatgca gttttaaagt taggagctaa tgatgtctgg | 120 |
| agaccttcta ctctaacaaa acgtaaagga tggtgcttag attgttgtca acacacggat | 180 |
| ttaacttact gccaaggatg tctaatatat cacgtttgtg aatggtgtag tcaatataac | 240 |
| agatgttttc ttgatgatga tcctcattta ctaagaatgc gaacttttag aaatgaaatc | 300 |
| acaaagagtg atttagaaaa cttaattaat atgtataata cattatttcc tataaataaa | 360 |
| aaaatagttc ataaatttgc aaacacaatt aaacagcata atgcagaaaa tgagtattca | 420 |
| acacaatggt ataatcattt cttgatgcct attacattac agtctttatc aatagaatta | 480 |
| gatggagata tatattatat atttggttat tatgacgata tgcataaaat taatcagact | 540 |
| cccttctcat tcacgaattt aattagtaaa tacgatatgt tactacttga tagtataaat | 600 |
| tttgacagaa tggcattttt accattaaca ttacaacaag agtatgcact tagatatttt | 660 |
| tcaaaatcaa gatttattac tgaaagaaga aaatgtattg aaattttaca ttttttcagat | 720 |
| aatatattag ataatttaca taacccaaat tttacattac aagtgattag gaattgtagt | 780 |
| aatatgtcag ttgaatggaa taaggcgtgt aatattatta gaaatataag tgattatttc | 840 |
| gatatactaa aatcgtcaca cactgagttc tataatatat ctcctagatg tagaatgttc | 900 |
| acacaatata aattaaaaat agcatctaaa ttaattaaac caaattatgt agcatcaaat | 960 |
| cataattcct tggctactga agtacataat tgtaaatggt gttcaattaa taataactct | 1020 |
| attgtatgga atgattttag aattaaaaat gtttataatg atatatttaa ttttattaga | 1080 |
| gctttagtaa atcaaatct ttatgtggga cattgctctt cagaagaaaa gatatatgaa | 1140 |
| tctattaaag aagttctaaa cgtgtgtaaa gaaaacgaat ggaacatgtt ggtaacggaa | 1200 |
| atgttcaatc aattagaacc aataaaatta atgagaata attacatttt attaaattat | 1260 |
| gaaataaatt ggaatgtcat gaatgtatta attaatagta tcggtaaaat accaaaaata | 1320 |
| ttaactttga gtgatgttat tttaatttta cgtataataa tatatgattg gtttgatata | 1380 |
| aggtttatga gaaacacgcc aatgactacg ttcacagtta taaaattaaa acaattatat | 1440 |
| gaaaaggata gaactgcaga acatgattcc aggatatccg atattgaatg attttaaaga | 1500 |
| aattctcgcc accatgagac tctctgcact agagtagcgc ctaggcagca ttaaaagtgt | 1560 |
| gacc | 1564 |

<210> SEQ ID NO 68
<211> LENGTH: 1569
<212> TYPE: DNA
<213> ORGANISM: Human rotavirus

<400> SEQUENCE: 68

```
ggcttttttt ttgaaaagtc ttgtggaagc catggctact tttaaagatg cttgctatca     60
atataaaaaa ttaaacaaat taaataatgc agttttaaag ttaggagcta atgatgtttg    120
gagaccttct actctaacaa aacgtaaagg atggtgctta gattgttgtc aacacacgga    180
tttgacttac tgccaaggat gcttaatata tcacgtttgt gaatggtgta gtcaatatag    240
cagatgcttt cttgataatg atccgcattt actaagaatg cgaactttta gaaatgaaat    300
cacaaagagt gacttagaaa acttaattaa tatgtatgat acattatttc ctataaatca    360
aaaaatagtt aataagtttg caaacacaat taaacaacat aaatgtagaa atgagtattt    420
gatacaatgg tataatcatt ttttaatgcc aattacacta cagtctttat caatagaatt    480
agatggagat atatattata tatttggtta ctatgacgat atgcataaaa ttaatcagac    540
tcccttctca ttcacgaatt taattagtaa atatgatgta ttacttctag atagcataaa    600
ttttgacaga atggcatttt taccattaac attacagcaa gaatatgcac ttagatattt    660
ttcaaaatca agatttatta ctgaaagaag gaaatgtatt gaactttcac atttttcaga    720
taatatatta aatgatttac ataatccgaa ttttacatta caagtgatta gaaattgcag    780
caatatgtca gttgaatgga ataaagcatg taatcttatt aaaaatataa gtaattattt    840
cgatatactc aaatcgtcac atactgagtc ttataatgta tctcctagat gtagagtatt    900
cacacaatat aaattaaaaa tagcatctaa attaattaaa ccaaattatg tagcatcaaa    960
tcataattcc ttggctactg aagtacacaa ttgcaaatgg tgttcaatta ataataattc   1020
tattgtatgg actgatttca ggattaaaaa tgtttataac gatatattta attttattag   1080
ggctttagtg aaatcaaatc tttacgtggg acattgttct tcagaagaaa agatatatga   1140
atctattaag gatattttaa atgtatgtaa agaaaacgaa tggaacatgt tggtaacgga   1200
aatattcaat caattagatc caataaagct aaatgatgat agctatgttt tgttgaatta   1260
tgaaataaat tggaatgtta tgaatgtatt aattaatagt atcggtaaag taccaaaaat   1320
attaactttg agtgacgtta tttcgatttt acgtataaata atatatgatt ggtttgacat   1380
aaggtttatg agaaatactc caatgactac gttcacagtt aataaattga agcaattata   1440
tgaaaaggat agaactgcag aatatgattc aggtatatcc gatgttgact aatttcagag   1500
aaattatgtt cgccaccata agactctctg cactagagta gcgcctaggc agcataaaaa   1560
agtgtgacc                                                           1569
```

<210> SEQ ID NO 69
<211> LENGTH: 1569
<212> TYPE: DNA
<213> ORGANISM: Human rotavirus

<400> SEQUENCE: 69

```
ggcttttttt ttgaaaagtc ttgtggaagc catggctact tttaaagatg cttgctatca     60
atataaaaaa ttaaacaaat taaataatgc agttttaaag ttaggagcta atgatgtttg    120
gagaccttct actctaacaa aacgtaaagg atggtgctta gattgttgtc aacacacgga    180
tttgacttac tgccaaggat gcttaatata tcacgtttgt gaatggtgta gtcaatatag    240
cagatgcttt cttgataatg atccgcattt actaagaatg cgaactttta gaaatgaaat    300
```

-continued

```
cacaaagagt gacttagaaa acttaattaa tatgtatgat acattatttc ctataaatca      360
aaaaatagtt aataagtttg caaacacaat taaacaacat aaatgtagaa atgagtattt      420
gatacaatgg tataatcatt ttttaatgcc aattacacta cagtctttat caatagaatt      480
agatggagat atatattata tatttggtta ctatgacgat atgcataaaa ttaatcagac      540
tcccttctca ttcacgaatt taattagtaa atatgatgta ttacttctag atagcataaa      600
ttttgacaga atggcatttt taccattaac attacagcaa gaatatgcac ttagatattt      660
ttcaaaatca agatttatta ctgaaagaag gaaatgtatt gaactttcac attttttcaga     720 taatatatta aatgatttac ataatccgaa ttttacatta caagtgatta gaaattgcag      780
caatatgtca gttgaatgga ataaagcatg taatcttatt aaaaatataa gtaattattt      840
cgatatactc aaatcgtcac atactgagtc ttataatgta tctcctagat gtagagtatt      900
cacacaatat aaattaaaaa tagcatctaa attaattaaa ccaaattatg tagcatcaaa      960
tcataattcc ttggctactg aagtacacaa ttgcaaatgg tgttcaatta ataataattc     1020
tattgtatgg actgatttca ggattaaaaa tgtttataac gatatattta attttattag     1080
ggctttagtg aaatcaaatc tttacgtggg acattgttct tcagaagaaa agatatatga     1140
atctattaag gatattttaa atgtatgtaa agaaaacgaa tggaacatgt tggtaacgga     1200
aatattcaat caattagatc caataaagct aaatgatgat agctatgttt tgttgaatta     1260
tgaaataaat tggaatgtta tgaatgtatt aattaatagt atcggtaaag taccaaaaat     1320
attaactttg agtgacgtta tttcgatttt acgtataata atatatgatt ggtttgacat     1380
aaggtttatg agaaatactc caatgactac gttcacagtt aataaattga agcaattata     1440
tgaaaaggat agaactgcag aatatgattc aggtatatcc gatgttgact aatttcagag     1500
aaattatgtt cgccaccata agactctctg cactagagta gcgcctaggc agcataaaaa     1560
agtgtgacc                                                             1569
```

<210> SEQ ID NO 70
<211> LENGTH: 486
<212> TYPE: PRT
<213> ORGANISM: Human rotavirus

<400> SEQUENCE: 70

```
Met Ala Thr Phe Lys Asp Ala Cys Tyr Gln Tyr Lys Lys Leu Asn Lys
1               5                   10                  15

Leu Asn Asn Ala Val Leu Lys Leu Gly Ala Asn Asp Val Trp Arg Pro
            20                  25                  30

Ser Thr Leu Thr Lys Arg Lys Gly Trp Cys Leu Asp Cys Cys Gln His
        35                  40                  45

Thr Asp Leu Thr Tyr Cys Gln Gly Cys Leu Ile Tyr His Val Cys Glu
    50                  55                  60

Trp Cys Ser Gln Tyr Asn Arg Cys Phe Leu Asp Asp Pro His Leu
65                  70                  75                  80

Leu Arg Met Arg Thr Phe Arg Asn Glu Ile Thr Lys Ser Asp Leu Glu
                85                  90                  95

Asn Leu Ile Asn Met Tyr Asn Thr Leu Phe Pro Ile Asn Lys Lys Ile
            100                 105                 110

Val His Lys Phe Ala Asn Thr Ile Lys Gln His Lys Cys Arg Asn Glu
        115                 120                 125

Tyr Ser Thr Gln Trp Tyr Asn His Phe Leu Met Pro Ile Thr Leu Gln
    130                 135                 140
```

```
Ser Leu Ser Ile Glu Leu Asp Gly Asp Ile Tyr Tyr Ile Phe Gly Tyr
145                 150                 155                 160

Tyr Asp Asp Met His Lys Ile Asn Gln Thr Pro Phe Ser Phe Thr Asn
                165                 170                 175

Leu Ile Ser Lys Tyr Asp Met Leu Leu Leu Asp Ser Ile Asn Phe Asp
            180                 185                 190

Arg Met Ala Phe Leu Pro Leu Thr Leu Gln Gln Glu Tyr Ala Leu Arg
        195                 200                 205

Tyr Phe Ser Lys Ser Arg Phe Ile Thr Glu Arg Arg Lys Cys Ile Glu
    210                 215                 220

Ile Leu His Phe Ser Asp Asn Ile Leu Asp Asn Leu His Asn Pro Asn
225                 230                 235                 240

Phe Thr Leu Gln Val Ile Arg Asn Cys Ser Asn Met Ser Val Glu Trp
                245                 250                 255

Asn Lys Ala Cys Asn Ile Ile Arg Asn Ile Ser Asp Tyr Phe Asp Ile
                260                 265                 270

Leu Lys Ser Ser His Thr Glu Phe Tyr Asn Ile Ser Pro Arg Cys Arg
            275                 280                 285

Met Phe Thr Gln Tyr Lys Leu Lys Ile Ala Ser Lys Leu Ile Lys Pro
        290                 295                 300

Asn Tyr Val Ala Ser Asn His Asn Ser Leu Ala Thr Glu Val His Asn
305                 310                 315                 320

Cys Lys Trp Cys Ser Ile Asn Asn Asn Ser Ile Val Trp Asn Asp Phe
                325                 330                 335

Arg Ile Lys Asn Val Tyr Asn Asp Ile Phe Asn Phe Ile Arg Ala Leu
                340                 345                 350

Val Lys Ser Asn Leu Tyr Val Gly His Cys Ser Ser Glu Glu Lys Ile
            355                 360                 365

Tyr Glu Ser Ile Lys Glu Val Leu Asn Val Cys Lys Glu Asn Glu Trp
        370                 375                 380

Asn Met Leu Val Thr Glu Met Phe Asn Gln Leu Glu Pro Ile Lys Leu
385                 390                 395                 400

Asn Glu Asn Asn Tyr Ile Leu Leu Asn Tyr Glu Ile Asn Trp Asn Val
                405                 410                 415

Met Asn Val Leu Ile Asn Ser Ile Gly Lys Ile Pro Lys Ile Leu Thr
                420                 425                 430

Leu Ser Asp Val Ile Leu Ile Leu Arg Ile Ile Ile Tyr Asp Trp Phe
            435                 440                 445

Asp Ile Arg Phe Met Arg Asn Thr Pro Met Thr Thr Phe Thr Val Asn
        450                 455                 460

Lys Leu Lys Gln Leu Tyr Glu Lys Asp Arg Thr Ala Glu His Asp Ser
465                 470                 475                 480

Arg Ile Ser Asp Ile Glu
            485

<210> SEQ ID NO 71
<211> LENGTH: 486
<212> TYPE: PRT
<213> ORGANISM: Human rotavirus

<400> SEQUENCE: 71

Met Ala Thr Phe Lys Asp Ala Cys Tyr Gln Tyr Lys Lys Leu Asn Lys
1               5                   10                  15

Leu Asn Asn Ala Val Leu Lys Leu Gly Ala Asn Asp Val Trp Arg Pro
            20                  25                  30
```

-continued

```
Ser Thr Leu Thr Lys Arg Lys Gly Trp Cys Leu Asp Cys Cys Gln His
             35                  40                  45

Thr Asp Leu Thr Tyr Cys Gln Gly Cys Leu Ile Tyr His Val Cys Glu
 50                  55                  60

Trp Cys Ser Gln Tyr Ser Arg Cys Phe Leu Asp Asn Asp Pro His Leu
 65                  70                  75                  80

Leu Arg Met Arg Thr Phe Arg Asn Glu Ile Thr Lys Ser Asp Leu Glu
                 85                  90                  95

Asn Leu Ile Asn Met Tyr Asp Thr Leu Phe Pro Ile Asn Gln Lys Ile
            100                 105                 110

Val Asn Lys Phe Ala Asn Thr Ile Lys Gln His Lys Cys Arg Asn Glu
            115                 120                 125

Tyr Leu Ile Gln Trp Tyr Asn His Phe Leu Met Pro Ile Thr Leu Gln
        130                 135                 140

Ser Leu Ser Ile Glu Leu Asp Gly Asp Ile Tyr Tyr Ile Phe Gly Tyr
145                 150                 155                 160

Tyr Asp Asp Met His Lys Ile Asn Gln Thr Pro Phe Ser Phe Thr Asn
                165                 170                 175

Leu Ile Ser Lys Tyr Asp Val Leu Leu Leu Asp Ser Ile Asn Phe Asp
            180                 185                 190

Arg Met Ala Phe Leu Pro Leu Thr Leu Gln Gln Glu Tyr Ala Leu Arg
        195                 200                 205

Tyr Phe Ser Lys Ser Arg Phe Ile Thr Glu Arg Arg Lys Cys Ile Glu
    210                 215                 220

Leu Ser His Phe Ser Asp Asn Ile Leu Asn Asp Leu His Asn Pro Asn
225                 230                 235                 240

Phe Thr Leu Gln Val Ile Arg Asn Cys Ser Asn Met Ser Val Glu Trp
                245                 250                 255

Asn Lys Ala Cys Asn Leu Ile Lys Asn Ile Ser Asn Tyr Phe Asp Ile
            260                 265                 270

Leu Lys Ser Ser His Thr Glu Ser Tyr Asn Val Ser Pro Arg Cys Arg
        275                 280                 285

Val Phe Thr Gln Tyr Lys Leu Lys Ile Ala Ser Lys Leu Ile Lys Pro
    290                 295                 300

Asn Tyr Val Ala Ser Asn His Asn Ser Leu Ala Thr Glu Val His Asn
305                 310                 315                 320

Cys Lys Trp Cys Ser Ile Asn Asn Ser Ile Val Trp Thr Asp Phe
                325                 330                 335

Arg Ile Lys Asn Val Tyr Asn Asp Ile Phe Asn Phe Ile Arg Ala Leu
            340                 345                 350

Val Lys Ser Asn Leu Tyr Val Gly His Cys Ser Ser Glu Glu Lys Ile
        355                 360                 365

Tyr Glu Ser Ile Lys Asp Ile Leu Asn Val Cys Lys Glu Asn Glu Trp
    370                 375                 380

Asn Met Leu Val Thr Glu Ile Phe Asn Gln Leu Asp Pro Ile Lys Leu
385                 390                 395                 400

Asn Asp Asp Ser Tyr Val Leu Leu Asn Tyr Glu Ile Asn Trp Asn Val
                405                 410                 415

Met Asn Val Leu Ile Asn Ser Ile Gly Lys Val Pro Lys Ile Leu Thr
            420                 425                 430

Leu Ser Asp Val Ile Ser Ile Leu Arg Ile Ile Ile Tyr Asp Trp Phe
        435                 440                 445
```

```
Asp Ile Arg Phe Met Arg Asn Thr Pro Met Thr Thr Phe Thr Val Asn
    450                 455                 460

Lys Leu Lys Gln Leu Tyr Glu Lys Asp Arg Thr Ala Glu Tyr Asp Ser
465                 470                 475                 480

Gly Ile Ser Asp Val Asp
                485

<210> SEQ ID NO 72
<211> LENGTH: 486
<212> TYPE: PRT
<213> ORGANISM: Human rotavirus

<400> SEQUENCE: 72

Met Ala Thr Phe Lys Asp Ala Cys Tyr Gln Tyr Lys Lys Leu Asn Lys
1               5                   10                  15

Leu Asn Asn Ala Val Leu Lys Leu Gly Ala Asn Asp Val Trp Arg Pro
                20                  25                  30

Ser Thr Leu Thr Lys Arg Lys Gly Trp Cys Leu Asp Cys Cys Gln His
            35                  40                  45

Thr Asp Leu Thr Tyr Cys Gln Gly Cys Leu Ile Tyr His Val Cys Glu
    50                  55                  60

Trp Cys Ser Gln Tyr Ser Arg Cys Phe Leu Asp Asn Asp Pro His Leu
65                  70                  75                  80

Leu Arg Met Arg Thr Phe Arg Asn Glu Ile Thr Lys Ser Asp Leu Glu
                85                  90                  95

Asn Leu Ile Asn Met Tyr Asp Thr Leu Phe Pro Ile Asn Gln Lys Ile
            100                 105                 110

Val Asn Lys Phe Ala Asn Thr Ile Lys Gln His Lys Cys Arg Asn Glu
    115                 120                 125

Tyr Leu Ile Gln Trp Tyr Asn His Phe Leu Met Pro Ile Thr Leu Gln
130                 135                 140

Ser Leu Ser Ile Glu Leu Asp Gly Asp Ile Tyr Tyr Ile Phe Gly Tyr
145                 150                 155                 160

Tyr Asp Asp Met His Lys Ile Asn Gln Thr Pro Phe Ser Phe Thr Asn
                165                 170                 175

Leu Ile Ser Lys Tyr Asp Val Leu Leu Leu Asp Ser Ile Asn Phe Asp
            180                 185                 190

Arg Met Ala Phe Leu Pro Leu Thr Leu Gln Gln Glu Tyr Ala Leu Arg
    195                 200                 205

Tyr Phe Ser Lys Ser Arg Phe Ile Thr Glu Arg Arg Lys Cys Ile Glu
210                 215                 220

Leu Ser His Phe Ser Asp Asn Ile Leu Asn Asp Leu His Asn Pro Asn
225                 230                 235                 240

Phe Thr Leu Gln Val Ile Arg Asn Cys Ser Asn Met Ser Val Glu Trp
                245                 250                 255

Asn Lys Ala Cys Asn Leu Ile Lys Asn Ile Ser Asn Tyr Phe Asp Ile
            260                 265                 270

Leu Lys Ser Ser His Thr Glu Ser Tyr Asn Val Ser Pro Arg Cys Arg
    275                 280                 285

Val Phe Thr Gln Tyr Lys Leu Lys Ile Ala Ser Lys Leu Ile Lys Pro
290                 295                 300

Asn Tyr Val Ala Ser Asn His Asn Ser Leu Ala Thr Glu Val His Asn
305                 310                 315                 320

Cys Lys Trp Cys Ser Ile Asn Asn Asn Ser Ile Val Trp Thr Asp Phe
                325                 330                 335
```

-continued

```
Arg Ile Lys Asn Val Tyr Asn Asp Ile Phe Asn Phe Ile Arg Ala Leu
            340                 345                 350

Val Lys Ser Asn Leu Tyr Val Gly His Cys Ser Ser Glu Glu Lys Ile
            355                 360                 365

Tyr Glu Ser Ile Lys Asp Ile Leu Asn Val Cys Lys Glu Asn Glu Trp
            370                 375                 380

Asn Met Leu Val Thr Glu Ile Phe Asn Gln Leu Asp Pro Ile Lys Leu
385                 390                 395                 400

Asn Asp Asp Ser Tyr Val Leu Leu Asn Tyr Glu Ile Asn Trp Asn Val
                405                 410                 415

Met Asn Val Leu Ile Asn Ser Ile Gly Lys Val Pro Lys Ile Leu Thr
            420                 425                 430

Leu Ser Asp Val Ile Ser Ile Leu Arg Ile Ile Ile Tyr Asp Trp Phe
            435                 440                 445

Asp Ile Arg Phe Met Arg Asn Thr Pro Met Thr Thr Phe Thr Val Asn
            450                 455                 460

Lys Leu Lys Gln Leu Tyr Glu Lys Asp Arg Thr Ala Glu Tyr Asp Ser
465                 470                 475                 480

Gly Ile Ser Asp Val Asp
                485

<210> SEQ ID NO 73
<211> LENGTH: 1059
<212> TYPE: DNA
<213> ORGANISM: Human rotavirus

<400> SEQUENCE: 73
ggcttttaaa gcgtctcagt cgccgtttga gccttgcggt gtagccatgg ctgagctagc      60
ttgcttttgt tatccccatt tggagaatga tagctataaa tttattccat ttaataattt     120
agccataaaa tgtatgttga cagcaaaagt ggataaaaaa gatcaggata aattttacaa     180
ttcaataatt tatggtattg cgccaccacc gcaatttaaa aaacgttata atacaaatga     240
caattccaga ggaatgaatt acgaaacttc aatgtttaat aaggtggcag cattaatttg     300
tgaagcatta aattcaacca aagttactca atctgatatt gctagtgtgc tctcaagagt     360
agtttctgta agacatttgg aaaacttagt attaagaaga gaaaatcatc aagacgtgtt     420
atttcattca aaagagctac tattaaaatc agtactaata gctattggtc attcgaaaga     480
aattgaaacg accgctactg ctgagggagg ggaaattgtt ttccaaaata cagcatttac     540
aatgtggaga ttgacgtatt tggagcataa attaatgcca attcttgatc aaatttcat      600 tgagtacaaa attacagtta acgaaggtaa accaatctca gaatctcata taaaagaact     660
tattgctgaa ttgcggtggc aatataataa atttgcggtg attactcatg gtaaaggtca     720
ctacagagtt gtaaagtatt catcagttgc aaatcatgcg gacagagttt acgctactta     780
caagagtaac aataagaatg gaaatatgtt ggaatttaac ctactggatc aaagaataat     840
atggcaaaat tggtatgcgt ttacgtcctc gatgaaacaa ggtaatactc tcgatacatg     900
caagaaacta ctctttcaaa aaattaagcg agaaagtaat ccgttcaagg gactgtcaac     960
tgataggaag atggatgaag tttctcaaat ggaatttaa ttcgttatcg attcaagaat    1020
gggtataacg aagtaagaat agaaagcgct tatgtgacc                          1059

<210> SEQ ID NO 74
<211> LENGTH: 1059
<212> TYPE: DNA
```

<213> ORGANISM: Human rotavirus

<400> SEQUENCE: 74

```
ggcttttaaa gcgtctcagt cgccgtttga gccttgcggt gtagccatgg ctgagctagc      60
ttgcttttgc tatccccatt tggagaacga tagctataaa tttattcctt ttaacaattt     120
ggctataaaa tgtatgttga cagcaaaagt agagaaaaaa gatcaggaca aattttacaa     180
ttcgataatc tatggtattg cgccgccacc acaatttaaa aaacgctata atacaaatga     240
taactcaaga ggaatgaatt atgagactgt aatgtttaac aaggtggcgg tgctaatttg     300
tgaagcattg aattcaatta agtcacgca gtctgatgtt gcaagtgtac tttcaagagt      360
agtttctgtg agacatcttg agaatttagt attgagaaga gaaaatcatc aggatgttct     420
ttttcactca aaagagctac tactcaaatc agttttaata gctattggtc attcaaagga     480
gattgaaacg actgccactg ctgaaggggg agaaattgtt tttcaaaatg cagcatttac     540
aatgtggaaa ttgacatatt tggaacataa actaatgcca attcttgatc aaaactttat     600
tgaatataaa attacagtaa atgaagataa accaatttca gagtcacacg taaaagaact     660
tattgctgaa ttcggtggc aatacaataa atttgcagta attacgcatg gtaaaggtca      720
ctatagagtt ataaaatact cgtcagttgc aaatcacgca gaccgagttt acgctacttt     780
taagagtaat aacaaaaacg gaggtccact agagtttaat ttgcttgacc aaagaataat     840
atggcaaaat tggtacgcat ttacgtcctc aatgaaacaa ggtaatactc ttgatgtatg     900
caaaaaacta ctcttcaaaa aaatgaaacg agaaagtaat ccatttaagg ggctgtcaac     960
tgatagaaaa atggatgaag tttctcaagt aggaatctaa ttcgttatct gtttgaaggt    1020
gggtatggca gagtaagaat agaaagcgct tatgtgacc                           1059
```

<210> SEQ ID NO 75
<211> LENGTH: 1059
<212> TYPE: DNA
<213> ORGANISM: Human rotavirus

<400> SEQUENCE: 75

```
ggcttttaaa gcgtctcagt cgccgtttga gccttgcggt gtagccatgg ctgagctagc      60
ttgcttttgc tatccccatt tggagaacga tagctataaa tttattcctt ttaacaattt     120
ggctataaaa tgtatgttga cagcaaaagt agagaaaaaa gatcaggaca aattttacaa     180
ttcgataatc tatggtattg cgccgccacc acaatttaaa aaacgctata atacaaatga     240
taactcaaga ggaatgaatt atgagactgt aatgtttaac aaggtggcgg tgctaatttg     300
tgaagcattg aattcaatta agtcacgca gtctgatgtt gcaagtgtac tttcaagagt      360
agtttctgtg agacatcttg agaatttagt attgagaaga gaaaatcatc aggatgttct     420
ttttcactca aaagagctac tactcaaatc agttttaata gctattggtt attcaaagga     480
gattgaaacg actgccactg ctgaaggggg agaaattgtt tttcaaaatg cagcatttac     540
aatgtggaaa ttgacatatt tggaacataa actaatgcca attcttgatc aaaactttat     600
tgaatataaa attacagtaa atgaagataa accaatttca gagtcacacg taaaagaact     660
tattgctgaa ttcggtggc aatacaataa atttgcagta attacgcatg gtaaaggtca      720
ctatagagtt ataaaatact cgtcagttgc aaatcacgca gaccgagttt acgctacttt     780
taagagtaat aacaaaaacg gaggtccact agagtttaat ttgcttgacc aaagaataat     840
atggcaaaat tggtacgcat ttacgtcctc aatgaaacaa ggtaatactc ttgatgtatg     900
caaaaaacta ctcttcaaaa aaatgaaacg agaaagtaat ccatttaagg ggctgtcaac     960
```

```
tgatagaaaa atggatgaag tttctcaagt aggaatctaa ttcgttatct gtttgaaggt    1020
gggtatggca gagtaagaat agaaagcgct tatgtgacc                           1059
```

<210> SEQ ID NO 76
<211> LENGTH: 316
<212> TYPE: PRT
<213> ORGANISM: Human rotavirus

<400> SEQUENCE: 76

```
Met Ala Glu Leu Ala Cys Phe Cys Tyr Pro His Leu Glu Asn Asp Ser
1               5                   10                  15

Tyr Lys Phe Ile Pro Phe Asn Asn Leu Ala Ile Lys Cys Met Leu Thr
            20                  25                  30

Ala Lys Val Asp Lys Lys Asp Gln Asp Lys Phe Tyr Asn Ser Ile Ile
        35                  40                  45

Tyr Gly Ile Ala Pro Pro Gln Phe Lys Lys Arg Tyr Asn Thr Asn
    50                  55                  60

Asp Asn Ser Arg Gly Met Asn Tyr Glu Thr Ser Met Phe Asn Lys Val
65                  70                  75                  80

Ala Ala Leu Ile Cys Glu Ala Leu Asn Ser Thr Lys Val Thr Gln Ser
                85                  90                  95

Asp Ile Ala Ser Val Leu Ser Arg Val Ser Val Arg His Leu Glu
            100                 105                 110

Asn Leu Val Leu Arg Arg Glu Asn His Gln Asp Val Leu Phe His Ser
        115                 120                 125

Lys Glu Leu Leu Leu Lys Ser Val Leu Ile Ala Ile Gly His Ser Lys
    130                 135                 140

Glu Ile Glu Thr Thr Ala Thr Ala Glu Gly Gly Glu Ile Val Phe Gln
145                 150                 155                 160

Asn Thr Ala Phe Thr Met Trp Arg Leu Thr Tyr Leu Glu His Lys Leu
                165                 170                 175

Met Pro Ile Leu Asp Pro Asn Phe Ile Glu Tyr Lys Ile Thr Val Asn
            180                 185                 190

Glu Gly Lys Pro Ile Ser Glu Ser His Ile Lys Glu Leu Ile Ala Glu
        195                 200                 205

Leu Arg Trp Gln Tyr Asn Lys Phe Ala Val Ile Thr His Gly Lys Gly
    210                 215                 220

His Tyr Arg Val Val Lys Tyr Ser Ser Val Ala Asn His Ala Asp Arg
225                 230                 235                 240

Val Tyr Ala Thr Tyr Lys Ser Asn Asn Lys Asn Gly Asn Met Leu Glu
                245                 250                 255

Phe Asn Leu Leu Asp Gln Arg Ile Ile Trp Gln Asn Trp Tyr Ala Phe
            260                 265                 270

Thr Ser Ser Met Lys Gln Gly Asn Thr Leu Asp Thr Cys Lys Lys Leu
        275                 280                 285

Leu Phe Gln Lys Ile Lys Arg Glu Ser Asn Pro Phe Lys Gly Leu Ser
    290                 295                 300

Thr Asp Arg Lys Met Asp Glu Val Ser Gln Ile Gly
305                 310                 315
```

<210> SEQ ID NO 77
<211> LENGTH: 316
<212> TYPE: PRT
<213> ORGANISM: Human rotavirus

```
<400> SEQUENCE: 77

Met Ala Glu Leu Ala Cys Phe Cys Tyr Pro His Leu Glu Asn Asp Ser
1               5                   10                  15

Tyr Lys Phe Ile Pro Phe Asn Asn Leu Ala Ile Lys Cys Met Leu Thr
                20                  25                  30

Ala Lys Val Glu Lys Lys Asp Gln Asp Lys Phe Tyr Asn Ser Ile Ile
            35                  40                  45

Tyr Gly Ile Ala Pro Pro Gln Phe Lys Lys Arg Tyr Asn Thr Asn
    50                  55                  60

Asp Asn Ser Arg Gly Met Asn Tyr Glu Thr Val Met Phe Asn Lys Val
65                  70                  75                  80

Ala Val Leu Ile Cys Glu Ala Leu Asn Ser Ile Lys Val Thr Gln Ser
                85                  90                  95

Asp Val Ala Ser Val Leu Ser Arg Val Val Ser Val Arg His Leu Glu
            100                 105                 110

Asn Leu Val Leu Arg Arg Glu Asn His Gln Asp Val Leu Phe His Ser
        115                 120                 125

Lys Glu Leu Leu Leu Lys Ser Val Leu Ile Ala Ile Gly His Ser Lys
130                 135                 140

Glu Ile Glu Thr Thr Ala Thr Ala Glu Gly Gly Glu Ile Val Phe Gln
145                 150                 155                 160

Asn Ala Ala Phe Thr Met Trp Lys Leu Thr Tyr Leu Glu His Lys Leu
                165                 170                 175

Met Pro Ile Leu Asp Gln Asn Phe Ile Glu Tyr Lys Ile Thr Val Asn
            180                 185                 190

Glu Asp Lys Pro Ile Ser Glu Ser His Val Lys Glu Leu Ile Ala Glu
        195                 200                 205

Leu Arg Trp Gln Tyr Asn Lys Phe Ala Val Ile Thr His Gly Lys Gly
210                 215                 220

His Tyr Arg Val Ile Lys Tyr Ser Ser Val Ala Asn His Ala Asp Arg
225                 230                 235                 240

Val Tyr Ala Thr Phe Lys Ser Asn Asn Lys Asn Gly Gly Pro Leu Glu
                245                 250                 255

Phe Asn Leu Leu Asp Gln Arg Ile Ile Trp Gln Asn Trp Tyr Ala Phe
            260                 265                 270

Thr Ser Ser Met Lys Gln Gly Asn Thr Leu Asp Val Cys Lys Lys Leu
        275                 280                 285

Leu Phe Lys Lys Met Lys Arg Glu Ser Asn Pro Phe Lys Gly Leu Ser
290                 295                 300

Thr Asp Arg Lys Met Asp Glu Val Ser Gln Val Gly
305                 310                 315

<210> SEQ ID NO 78
<211> LENGTH: 316
<212> TYPE: PRT
<213> ORGANISM: Human rotavirus

<400> SEQUENCE: 78

Met Ala Glu Leu Ala Cys Phe Cys Tyr Pro His Leu Glu Asn Asp Ser
1               5                   10                  15

Tyr Lys Phe Ile Pro Phe Asn Asn Leu Ala Ile Lys Cys Met Leu Thr
                20                  25                  30

Ala Lys Val Glu Lys Lys Asp Gln Asp Lys Phe Tyr Asn Ser Ile Ile
            35                  40                  45
```

```
Tyr Gly Ile Ala Pro Pro Gln Phe Lys Lys Arg Tyr Asn Thr Asn
     50              55                  60

Asp Asn Ser Arg Gly Met Asn Tyr Glu Thr Val Met Phe Asn Lys Val
65              70                  75                  80

Ala Val Leu Ile Cys Glu Ala Leu Asn Ser Ile Lys Val Thr Gln Ser
                 85                  90                  95

Asp Val Ala Ser Val Leu Ser Arg Val Val Ser Val Arg His Leu Glu
            100                 105                 110

Asn Leu Val Leu Arg Arg Glu Asn His Gln Asp Val Leu Phe His Ser
            115                 120                 125

Lys Glu Leu Leu Leu Lys Ser Val Leu Ile Ala Ile Gly Tyr Ser Lys
        130                 135                 140

Glu Ile Glu Thr Thr Ala Thr Ala Glu Gly Gly Ile Val Phe Gln
145                 150                 155                 160

Asn Ala Ala Phe Thr Met Trp Lys Leu Thr Tyr Leu Glu His Lys Leu
                165                 170                 175

Met Pro Ile Leu Asp Gln Asn Phe Ile Glu Tyr Lys Ile Thr Val Asn
            180                 185                 190

Glu Asp Lys Pro Ile Ser Glu Ser His Val Lys Glu Leu Ile Ala Glu
        195                 200                 205

Leu Arg Trp Gln Tyr Asn Lys Phe Ala Val Ile Thr His Gly Lys Gly
    210                 215                 220

His Tyr Arg Val Ile Lys Tyr Ser Ser Val Ala Asn His Ala Asp Arg
225                 230                 235                 240

Val Tyr Ala Thr Phe Lys Ser Asn Asn Lys Asn Gly Gly Pro Leu Glu
                245                 250                 255

Phe Asn Leu Leu Asp Gln Arg Ile Ile Trp Gln Asn Trp Tyr Ala Phe
            260                 265                 270

Thr Ser Ser Met Lys Gln Gly Asn Thr Leu Asp Val Cys Lys Lys Leu
        275                 280                 285

Leu Phe Lys Lys Met Lys Arg Glu Ser Asn Pro Phe Lys Gly Leu Ser
    290                 295                 300

Thr Asp Arg Lys Met Asp Glu Val Ser Gln Val Gly
305                 310                 315

<210> SEQ ID NO 79
<211> LENGTH: 1064
<212> TYPE: DNA
<213> ORGANISM: Human rotavirus

<400> SEQUENCE: 79
ggcttttaat gcttttcagt ggttgatgct caagatggag tctactcaac agatggcatc      60
ttctattatt aactcttctt ttgaagctgc agttgtcgct gcaacttcta cgttggagtt     120
aatgggtatt caatatgatt ataatgaagt atacactaga gttaaaagta agtttgattt     180
tgtaatggat gattctggtg ttaaaaataa tttaatgggt aaagcagcta caattgatca     240
ggctttgaat ggtaagtttta gttcatctat tagaaataga aattggatga ctgattctaa     300
aactgtatca agattggatg aagatgtgaa caaacttagg ttattattat catcgaaggg     360
aattgatcaa aaaatgagag ttcttaatgc gtgctttagt gttaagagag tgcctggaaa     420
atcatcatct gtcattaaat gtactagact aatgaaagag aagatagaac gcggagaagt     480
cgaagtggat gatacattcg ttgaagagag aatggaaatt gacactatag attggaaatc     540
cagatatgac caacttgaaa gacgatttga gtcattaaag cagcgagtta atgaaaagta     600
```

```
caataattgg gttattaagg caaggaaagt aaatgaaaat atgaactctc ttcaaaacgt    660
tatttcgcaa cagcaagctc atatcaatga attacaaata tataataaca aactagagcg    720
tgatttacaa tcaaaaatag gatcagttat ttcatccatt gaatggtact tacggtccat    780
ggagctatca gatgacatta aatcagatat tgaacaacaa ctcaattcaa tagatcatat    840
taatccagtt aatgctttcg atgattttga gtccattctt cgtaatttaa tatctgatta    900
tgatagaatt tttattatgt ttaaaggatt gttgcagcaa agtaattaca cttatactta    960
tgagtaaaca tggtataacc atcttcacgt aaccctctat gagcacaata gttaaaagct   1020
aacactgtca aaaacctaaa tggctatagg ggcgttatgt gacc                    1064
```

<210> SEQ ID NO 80
<211> LENGTH: 1066
<212> TYPE: DNA
<213> ORGANISM: Human rotavirus

<400> SEQUENCE: 80

```
ggcttttaat gcttttcagt ggttgatgct caagatggag tctactcaac agatggtatc     60
ttctattatt aactcttctt ttgaagctgc agttgtcgct gcaacttcta cattagaatt    120
aatgggtatt caatatgatt ataatgaagt atatactaga gttaaaagta agtttgattt    180
tgtaatggat gattctggcg ttaagaataa tctaataggt aaagcagcta caattgatca    240
ggctttgaat ggtaagttta gttcatctat cagaaataga aattggatga ctgattcaaa    300
aactgtagca agattagatg aagatgtgaa caaacttaga ttattattgt catcgaaagg    360
aattgatcaa aaaatgagag ttcttaatgc atgctttagt gttaagagaa tacctggaaa    420
atcgtcatcc atcattaaat gtactaggtt aatgaaagag aaaatagaac gtggagaagt    480
cgaagtggat gatgcattca ttgaagaaaa aatggaaatt gacactatag attggaaatc    540
cagatatgat caacttgaaa gacgatttga gtcgttaaaa cagcgagtta atgaaaagta    600
caataattgg gttattaagg caaggaaagt aaacgaaaac atgaactctc ttcagaatgt    660
tatttcgcaa cagcaagctc atattaatga attacaagta tataataata aactagagcg    720
tgatttacaa tcaaaaatag gatcagttat ttcatccatt gaatggtact tacggtctat    780
ggaactatca gatgacatta aatcagatat tgaacaacaa cttaattcaa tagatcatat    840
taatccagtt aatgcttttg atgattttga gtctattctt cgtaatttaa tatctgatta    900
tgatagaatt tttattatgt ttaaaggatt gttgcagcaa agtaattaca cttataccta    960
tgaataaaca tggcatatta ccatcttcac gtaaccctct atgagcacaa tagttaaaag   1020
ctaacactgt caaaaaccta atggctata ggggcgttat gtgacc                   1066
```

<210> SEQ ID NO 81
<211> LENGTH: 1066
<212> TYPE: DNA
<213> ORGANISM: Human rotavirus

<400> SEQUENCE: 81

```
ggcttttaat gcttttcagt ggttgatgct caagatggag tctactcaac agatggtatc     60
ttctattatt aactcttctt ttgaagctgc agttgtcgct gcaacttcta cattagaatt    120
aatgggtatt caatatgatt ataatgaagt atatactaga gttaaaagta agtttgattt    180
tgtaatggat gattctggcg ttaagaataa tctaataggt aaagcagcta caattgatca    240
ggctttgaat ggtaagttta gttcatctat cagaaataga aattggatga ctgattcaaa    300
aactgtagca agattagatg aagatgtgaa caaacttaga ttattattgt catcgaaagg    360
```

```
aattgatcaa aaaatgagag ttcttaatgc atgctttagt gttaagagaa tacctggaaa    420
atcgtcatcc atcattaaat gtactaggtt aatgaaagag aaaatagaac gtggagaagt    480
cgaagtggat gatgcattca ttgaagaaaa aatggaaatt gacactatag attggaaatc    540
cagatatgat caacttgaaa gacgatttga gtcgttaaaa cagcgagtta atgaaaagta    600
caataattgg gttattaagg caaggaaagt aaacgaaaac atgaactctc ttcagaatgt    660
tatttcgcaa cagcaagctc atattaatga attacaagta tataataata aactagagcg    720
tgatttacaa tcaaaaatag gatcagttat ttcatccatt gaatggtact acggtctat     780 ggaactatca gatgacatta aatcagatat tgaacaacaa cttaattcaa tagatcatat    840
taatccagtt aatgcttttg atgattttga gtctattctt cgtaatttaa tatctgatta    900
tgatagaatt tttattatgt ttaaaggatt gttgcagcaa agtaattaca cttatacctc    960
tgaataaaca tggcatatta ccatcttcac gtaaccctct atgagcacaa tagttaaaag   1020
ctaacactgt caaaaaccta aatggctata ggggcgttat gtgacc                  1066
```

<210> SEQ ID NO 82
<211> LENGTH: 313
<212> TYPE: PRT
<213> ORGANISM: Human rotavirus

<400> SEQUENCE: 82

```
Met Leu Lys Met Glu Ser Thr Gln Gln Met Ala Ser Ser Ile Ile Asn
1               5                   10                  15

Ser Ser Phe Glu Ala Ala Val Val Ala Ala Thr Ser Thr Leu Glu Leu
            20                  25                  30

Met Gly Ile Gln Tyr Asp Tyr Asn Glu Val Tyr Thr Arg Val Lys Ser
        35                  40                  45

Lys Phe Asp Phe Val Met Asp Asp Ser Gly Val Lys Asn Asn Leu Met
    50                  55                  60

Gly Lys Ala Ala Thr Ile Asp Gln Ala Leu Asn Gly Lys Phe Ser Ser
65                  70                  75                  80

Ser Ile Arg Asn Arg Asn Trp Met Thr Asp Ser Lys Thr Val Ser Arg
                85                  90                  95

Leu Asp Glu Asp Val Asn Lys Leu Arg Leu Leu Ser Ser Lys Gly
            100                 105                 110

Ile Asp Gln Lys Met Arg Val Leu Asn Ala Cys Phe Ser Val Lys Arg
        115                 120                 125

Val Pro Gly Lys Ser Ser Val Ile Lys Cys Thr Arg Leu Met Lys
    130                 135                 140

Glu Lys Ile Glu Arg Gly Glu Val Glu Val Asp Asp Thr Phe Val Glu
145                 150                 155                 160

Glu Arg Met Glu Ile Asp Thr Ile Asp Trp Lys Ser Arg Tyr Asp Gln
                165                 170                 175

Leu Glu Arg Arg Phe Glu Ser Leu Lys Gln Arg Val Asn Glu Lys Tyr
            180                 185                 190

Asn Asn Trp Val Ile Lys Ala Arg Lys Val Asn Glu Asn Met Asn Ser
        195                 200                 205

Leu Gln Asn Val Ile Ser Gln Gln Ala His Ile Asn Glu Leu Gln
    210                 215                 220

Ile Tyr Asn Asn Lys Leu Glu Arg Asp Leu Gln Ser Lys Ile Gly Ser
225                 230                 235                 240

Val Ile Ser Ser Ile Glu Trp Tyr Leu Arg Ser Met Glu Leu Ser Asp
```

245                 250                 255
Asp Ile Lys Ser Asp Ile Glu Gln Gln Leu Asn Ser Ile Asp His Ile
                260                 265                 270

Asn Pro Val Asn Ala Phe Asp Asp Phe Glu Ser Ile Leu Arg Asn Leu
            275                 280                 285

Ile Ser Asp Tyr Asp Arg Ile Phe Ile Met Phe Lys Gly Leu Leu Gln
        290                 295                 300

Gln Ser Asn Tyr Thr Tyr Thr Tyr Glu
305                 310

<210> SEQ ID NO 83
<211> LENGTH: 313
<212> TYPE: PRT
<213> ORGANISM: Human rotavirus

<400> SEQUENCE: 83

Met Leu Lys Met Glu Ser Thr Gln Gln Met Val Ser Ile Ile Asn
1               5                   10                  15

Ser Ser Phe Glu Ala Ala Val Val Ala Ala Thr Ser Thr Leu Glu Leu
                20                  25                  30

Met Gly Ile Gln Tyr Asp Tyr Asn Glu Val Tyr Thr Arg Val Lys Ser
            35                  40                  45

Lys Phe Asp Phe Val Met Asp Asp Ser Gly Val Lys Asn Asn Leu Ile
50                  55                  60

Gly Lys Ala Ala Thr Ile Asp Gln Ala Leu Asn Gly Lys Phe Ser Ser
65                  70                  75                  80

Ser Ile Arg Asn Arg Asn Trp Met Thr Asp Ser Lys Thr Val Ala Arg
                85                  90                  95

Leu Asp Glu Asp Val Asn Lys Leu Arg Leu Leu Leu Ser Ser Lys Gly
            100                 105                 110

Ile Asp Gln Lys Met Arg Val Leu Asn Ala Cys Phe Ser Val Lys Arg
        115                 120                 125

Ile Pro Gly Lys Ser Ser Ser Ile Ile Lys Cys Thr Arg Leu Met Lys
    130                 135                 140

Glu Lys Ile Glu Arg Gly Glu Val Glu Val Asp Asp Ala Phe Ile Glu
145                 150                 155                 160

Glu Lys Met Glu Ile Asp Thr Ile Asp Trp Lys Ser Arg Tyr Asp Gln
                165                 170                 175

Leu Glu Arg Arg Phe Glu Ser Leu Lys Gln Arg Val Asn Glu Lys Tyr
            180                 185                 190

Asn Asn Trp Val Ile Lys Ala Arg Lys Val Asn Glu Asn Met Asn Ser
        195                 200                 205

Leu Gln Asn Val Ile Ser Gln Gln Gln Ala His Ile Asn Glu Leu Gln
    210                 215                 220

Val Tyr Asn Asn Lys Leu Glu Arg Asp Leu Gln Ser Lys Ile Gly Ser
225                 230                 235                 240

Val Ile Ser Ser Ile Glu Trp Tyr Leu Arg Ser Met Glu Leu Ser Asp
                245                 250                 255

Asp Ile Lys Ser Asp Ile Glu Gln Gln Leu Asn Ser Ile Asp His Ile
            260                 265                 270

Asn Pro Val Asn Ala Phe Asp Asp Phe Glu Ser Ile Leu Arg Asn Leu
        275                 280                 285

Ile Ser Asp Tyr Asp Arg Ile Phe Ile Met Phe Lys Gly Leu Leu Gln
    290                 295                 300

```
Gln Ser Asn Tyr Thr Tyr Thr Tyr Glu
305                 310
```

```
<210> SEQ ID NO 84
<211> LENGTH: 313
<212> TYPE: PRT
<213> ORGANISM: Human rotavirus

<400> SEQUENCE: 84
```

```
Met Leu Lys Met Glu Ser Thr Gln Gln Met Val Ser Ser Ile Ile Asn
1               5                   10                  15

Ser Ser Phe Glu Ala Ala Val Val Ala Ala Thr Ser Thr Leu Glu Leu
            20                  25                  30

Met Gly Ile Gln Tyr Asp Tyr Asn Glu Val Tyr Thr Arg Val Lys Ser
        35                  40                  45

Lys Phe Asp Phe Val Met Asp Asp Ser Gly Val Lys Asn Asn Leu Ile
50                  55                  60

Gly Lys Ala Ala Thr Ile Asp Gln Ala Leu Asn Gly Lys Phe Ser Ser
65                  70                  75                  80

Ser Ile Arg Asn Arg Asn Trp Met Thr Asp Ser Lys Thr Val Ala Arg
                85                  90                  95

Leu Asp Glu Asp Val Asn Lys Leu Arg Leu Leu Leu Ser Ser Lys Gly
            100                 105                 110

Ile Asp Gln Lys Met Arg Val Leu Asn Ala Cys Phe Ser Val Lys Arg
        115                 120                 125

Ile Pro Gly Lys Ser Ser Ile Ile Lys Cys Thr Arg Leu Met Lys
130                 135                 140

Glu Lys Ile Glu Arg Gly Glu Val Glu Val Asp Asp Ala Phe Ile Glu
145                 150                 155                 160

Glu Lys Met Glu Ile Asp Thr Ile Asp Trp Lys Ser Arg Tyr Asp Gln
                165                 170                 175

Leu Glu Arg Arg Phe Glu Ser Leu Lys Gln Arg Val Asn Glu Lys Tyr
            180                 185                 190

Asn Asn Trp Val Ile Lys Ala Arg Lys Val Asn Glu Asn Met Asn Ser
        195                 200                 205

Leu Gln Asn Val Ile Ser Gln Gln Ala His Ile Asn Glu Leu Gln
210                 215                 220

Val Tyr Asn Asn Lys Leu Glu Arg Asp Leu Gln Ser Lys Ile Gly Ser
225                 230                 235                 240

Val Ile Ser Ser Ile Glu Trp Tyr Leu Arg Ser Met Glu Leu Ser Asp
                245                 250                 255

Asp Ile Lys Ser Asp Ile Glu Gln Gln Leu Asn Ser Ile Asp His Ile
            260                 265                 270

Asn Pro Val Asn Ala Phe Asp Asp Phe Glu Ser Ile Leu Arg Asn Leu
        275                 280                 285

Ile Ser Asp Tyr Asp Arg Ile Phe Ile Met Phe Lys Gly Leu Leu Gln
    290                 295                 300

Gln Ser Asn Tyr Thr Tyr Thr Tyr Glu
305                 310
```

```
<210> SEQ ID NO 85
<211> LENGTH: 687
<212> TYPE: DNA
<213> ORGANISM: Human rotavirus

<400> SEQUENCE: 85
```

| | |
|---|---|
| cggaaagatg gaaaagctta ccgacctcaa ttacacattg agtgtaatca ctttaatgaa | 60 |
| taatacatta cacacaatac tagaggatcc aggaatggcg tattttcctt atattgcatc | 120 |
| tgtcctgaca gttttattcg cattacacaa agcgtcaatt ccaacaatga aaatagcatt | 180 |
| gaagacgtca aaatgttcat ataaagtagt aaagtattgt attgtaacga tctttaatac | 240 |
| attactaaaa ctagcaggtt acaagaaaca aattactact aaagatgaaa tagaaaagca | 300 |
| aatggacaga gttgttaaag aaatgagacg tcaattagag atgattgata aactaactac | 360 |
| gcgtgaaatt gagcaagttg aattacttaa acgtatctac gataaattga tggtgcgatc | 420 |
| gactgacgag atagatatga caaagaaat taatcaaaag aacgtgagaa cgctagaaga | 480 |
| gtgggagaat ggaaaaaatc cttatgaacc aaaagaagtg actgcagcaa tgtgagaggt | 540 |
| tgagctgccg tcgactgtct tcggaagcgg cggagttctt tacagtaagc tccatcagac | 600 |
| ctgatggctg gctaagaagc catagtcagc catatcgcgt gtggcttaag ccttaatccc | 660 |
| gtttaaccaa tccggtcagc accggac | 687 |

<210> SEQ ID NO 86
<211> LENGTH: 751
<212> TYPE: DNA
<213> ORGANISM: Human rotavirus

<400> SEQUENCE: 86

| | |
|---|---|
| ggcttttaaa agttctgttc cgagagagcg cgtgcggaaa gatggaaaag tttaccgacc | 60 |
| tcaactacac attgagtgta atcactttaa tgaatagtac attacataca atattagagg | 120 |
| atccaggaat ggcgtatttt ccttatattg catctgtcat gacagttttg tttacattac | 180 |
| acaaagcgtc aattccaaca atgaaaatag cattgaagac gtcaaaatgt tcgtataaag | 240 |
| tagtaaagta ttgtattgta acggttctta atacattatt aaagttagca ggttacaaag | 300 |
| aacaaattac tactaaagat gaaatagaaa acaaatggga cagagtcgtt aaagaaatga | 360 |
| gacgtcagtt agagatgatt gataaactaa ctacacgtga aattgaacaa gttgaattac | 420 |
| ttaaacgcat ctacgataaa ttaatagtgc gatcgactga tgaaatagat atgacaaaag | 480 |
| aaattaatca aaagaacgta agaacgctag aagagtggga gagcgggaaa atccttatg | 540 |
| aaccaaaaga agtgactgca gcgatgtgag aggttgagct gccgtcgact gtcttcggaa | 600 |
| gcggcggagt tctttacagt aaactccatt ggacccgatg gctggctaag aagccatagt | 660 |
| cagccatatc gcgtgtggct taagccttaa tcccgtttaa ctaatccggt cagcaccgga | 720 |
| cgttaatgga aggaaaggtc ttaatgtgac c | 751 |

<210> SEQ ID NO 87
<211> LENGTH: 751
<212> TYPE: DNA
<213> ORGANISM: Human rotavirus

<400> SEQUENCE: 87

| | |
|---|---|
| ggcttttaaa agttctgttc cgagagagcg cgtgcggaaa gatggaaaag tttaccgacc | 60 |
| tcaactacac attgagtgta atcactttaa tgaatagtac attacataca atattagagg | 120 |
| atccaggaat ggcgtatttt ccttatattg catctgtcat gacagttttg tttacattac | 180 |
| acaaagcgtc aattccaaca atgaaaatag cattgaagac gtcaaaatgt tcgtataaag | 240 |
| tagtaaagta ttgtattgta acggttctta atacattatt aaagttagca ggttacaaag | 300 |
| aacaaattac tactaaagat gaaatagaaa acaaatggga cagagtcgtt aaagaaatga | 360 |
| gacgtcagtt agagatgatt gataaactaa ctacacgtga aattgaacaa gttgaattac | 420 |

```
ttaaacgcat ctacgataaa ttaatagtgc gatcgactga tgaaatagat atgacaaaag    480
aaattaatca aaagaacgta agaacgctag aagagtggga gagcgggaaa aatccttatg    540
aaccaaaaga agtgactgca gcgatgtgag aggttgagct gccgtcgact gtcttcggaa    600
gcggcggagt tctttacagt aaactccatt ggacccgatg gctggctaag aagccatagt    660
cagccatatc gcgtgtggct taagccttaa tcccgtttaa ctaatccggt cagcaccgga    720
cgttaatgga aggaaaggtc ttaatgtgac c                                   751
```

<210> SEQ ID NO 88
<211> LENGTH: 175
<212> TYPE: PRT
<213> ORGANISM: Human rotavirus

<400> SEQUENCE: 88

```
Met Glu Lys Leu Thr Asp Leu Asn Tyr Thr Leu Ser Val Ile Thr Leu
1               5                   10                  15

Met Asn Asn Thr Leu His Thr Ile Leu Glu Asp Pro Gly Met Ala Tyr
            20                  25                  30

Phe Pro Tyr Ile Ala Ser Val Leu Thr Val Leu Phe Ala Leu His Lys
        35                  40                  45

Ala Ser Ile Pro Thr Met Lys Ile Ala Leu Lys Thr Ser Lys Cys Ser
    50                  55                  60

Tyr Lys Val Val Lys Tyr Cys Ile Val Thr Ile Phe Asn Thr Leu Leu
65                  70                  75                  80

Lys Leu Ala Gly Tyr Lys Glu Gln Ile Thr Thr Lys Asp Glu Ile Glu
                85                  90                  95

Lys Gln Met Asp Arg Val Val Lys Glu Met Arg Gln Leu Glu Met
            100                 105                 110

Ile Asp Lys Leu Thr Thr Arg Glu Ile Glu Gln Val Glu Leu Leu Lys
            115                 120                 125

Arg Ile Tyr Asp Lys Leu Met Val Arg Ser Thr Asp Glu Ile Asp Met
        130                 135                 140

Thr Lys Glu Ile Asn Gln Lys Asn Val Arg Thr Leu Glu Glu Trp Glu
145                 150                 155                 160

Asn Gly Lys Asn Pro Tyr Glu Pro Lys Glu Val Thr Ala Ala Met
                165                 170                 175
```

<210> SEQ ID NO 89
<211> LENGTH: 175
<212> TYPE: PRT
<213> ORGANISM: Human rotavirus

<400> SEQUENCE: 89

```
Met Glu Lys Phe Thr Asp Leu Asn Tyr Thr Leu Ser Val Ile Thr Leu
1               5                   10                  15

Met Asn Ser Thr Leu His Thr Ile Leu Glu Asp Pro Gly Met Ala Tyr
            20                  25                  30

Phe Pro Tyr Ile Ala Ser Val Met Thr Val Leu Phe Thr Leu His Lys
        35                  40                  45

Ala Ser Ile Pro Thr Met Lys Ile Ala Leu Lys Thr Ser Lys Cys Ser
    50                  55                  60

Tyr Lys Val Val Lys Tyr Cys Ile Val Thr Val Leu Asn Thr Leu Leu
65                  70                  75                  80

Lys Leu Ala Gly Tyr Lys Glu Gln Ile Thr Thr Lys Asp Glu Ile Glu
                85                  90                  95
```

```
Lys Gln Met Asp Arg Val Val Lys Glu Met Arg Arg Gln Leu Glu Met
            100                 105                 110

Ile Asp Lys Leu Thr Thr Arg Glu Ile Glu Gln Val Glu Leu Leu Lys
            115                 120                 125

Arg Ile Tyr Asp Lys Leu Ile Val Arg Ser Thr Asp Glu Ile Asp Met
130                 135                 140

Thr Lys Glu Ile Asn Gln Lys Asn Val Arg Thr Leu Glu Glu Trp Glu
145                 150                 155                 160

Ser Gly Lys Asn Pro Tyr Glu Pro Lys Glu Val Thr Ala Ala Met
            165                 170                 175

<210> SEQ ID NO 90
<211> LENGTH: 175
<212> TYPE: PRT
<213> ORGANISM: Human rotavirus

<400> SEQUENCE: 90

Met Glu Lys Phe Thr Asp Leu Asn Tyr Thr Leu Ser Val Ile Thr Leu
1               5                   10                  15

Met Asn Ser Thr Leu His Thr Ile Leu Glu Asp Pro Gly Met Ala Tyr
            20                  25                  30

Phe Pro Tyr Ile Ala Ser Val Met Thr Val Leu Phe Thr Leu His Lys
            35                  40                  45

Ala Ser Ile Pro Thr Met Lys Ile Ala Leu Lys Thr Ser Lys Cys Ser
        50                  55                  60

Tyr Lys Val Val Lys Tyr Cys Ile Val Thr Val Leu Asn Thr Leu Leu
65                  70                  75                  80

Lys Leu Ala Gly Tyr Lys Glu Gln Ile Thr Thr Lys Asp Glu Ile Glu
                85                  90                  95

Lys Gln Met Asp Arg Val Val Lys Glu Met Arg Arg Gln Leu Glu Met
            100                 105                 110

Ile Asp Lys Leu Thr Thr Arg Glu Ile Glu Gln Val Glu Leu Leu Lys
            115                 120                 125

Arg Ile Tyr Asp Lys Leu Ile Val Arg Ser Thr Asp Glu Ile Asp Met
130                 135                 140

Thr Lys Glu Ile Asn Gln Lys Asn Val Arg Thr Leu Glu Glu Trp Glu
145                 150                 155                 160

Ser Gly Lys Asn Pro Tyr Glu Pro Lys Glu Val Thr Ala Ala Met
            165                 170                 175

<210> SEQ ID NO 91
<211> LENGTH: 740
<212> TYPE: DNA
<213> ORGANISM: Human rotavirus

<400> SEQUENCE: 91
atgtctctca gtattgatgt gactagtctt ccttcaattt cttcaagtgt ttataaaaat    60
gaatcgtctt caacaacgtc aactatttct ggaaaatcta ttggtaggag tgaacagtac   120
atttcaccag atgcagaagc tttcaataaa tacatgttgt caaaatctcc agaagatatt   180
ggaccttctg attctgcatc gaacgatcca ctcaccagct tttcgattag atcgaatgca   240
gttaagacaa atgcagatgc tggcgtgtct atggattcat cagcgcaatc acgaccatct   300
agcgacattg atacgatca atggatttc tccttgaata aagtattaa atttgatgct   360 acagtggact cttcaatatc aatatctacc acatcaaaga aggagaaatc taaacaagaa   420
```

```
aacaaaaata agtataaaaa atgttaccca aaaatcgaag cagagtctga ttccgatgat    480
tacatattag atgattcaga tagcgatgat ggaaaatgta aaaattgcaa atataaaaag    540
aaatattttg cacttcgttt aagaatgaaa caagttgcaa tgcaattaat taaagattta    600
tgaaaatttt ctgattactc ttgtcattaa ttactaaata ttcactcaat gcacggataa    660
taaatgctat ctaattatat tgtatgataa ttattacaat atatactgtg ttattgaatt    720
taatgatatc ctaatgatag                                                740
```

```
<210> SEQ ID NO 92
<211> LENGTH: 816
<212> TYPE: DNA
<213> ORGANISM: Human rotavirus

<400> SEQUENCE: 92
ggcttttaaa gcgctacagt gatgtctctt agtattgacg tgactagtct tccttcaatt     60
tcttctagtg tttataaaaa tgaatcgttt tcaacaacgt caactatttc tggaaaatct    120
attggtagga gtgaacagta catttcacca gatgcagaag ccttcaataa gtacatgttg    180
tcaaaatctc cagaagatat tggaccttct gattctgcat cgaacgatcc actcaccagc    240
ttttcgatta gatcgaatgc agttaagaca aatgcagatg ctggcgtgtc tatggattca    300
tcagcacaat cacgaccatc tagcgacatt ggatacgatc aaatggattt ctccttaaat    360
aaaggtatta aaattgatgc tacaatggat tcttcaatat caatatctac cacatcaaag    420
aaggagaaat ctaaacaaga gaacaaaaat aaatataaaa aatattatcc aaaaattgaa    480
gcagaatctg attctgatga atacgtatta gatgattcag atagtgatga tggaaaatgt    540
aaaaattgca agtataaaaa gaaatattttg gcacttcgtt taagaatgaa acaagttgca    600
atgcaattga ttaagatttt gtgaaaattt tcttattact cttatcatta actgttaaat    660
atttacttaa tatacagata gtgaatgttg tttaattata ttatatgata gtattattat    720
atcgcgttat tgaatttaat aactttctaa tgagagaaga ttgatgcgtc taccctaaga    780
gatcactagg gagctcccca ctcccgtttt gtgacc                              816
```

```
<210> SEQ ID NO 93
<211> LENGTH: 816
<212> TYPE: DNA
<213> ORGANISM: Human rotavirus

<400> SEQUENCE: 93
ggcttttaaa gcgctacagt gatgtctctt agtattgacg tgactagtct tccttcaatt     60
tcttctagtg tttataaaaa tgaatcgttt tcaacaacgt caactatttc tggaaaatct    120
attggcagga gtgaacagta catttcacca gatgcagaag ccttcaataa gtacatgttg    180
tcaaaatctc cagaagatgt tggaccttct gattctgcat cgaacgatcc actcaccagc    240
ttttcgatta gatcgaatgc agttaagaca aatgcagatg ctggcgtgtc tatggattca    300
tcagcacaat cacgaccatc tagcgacatt ggatacgatc aaatggattt ctccttaaat    360
aaaggtatta aaattgatgc tacaatggat tcttcaatat caatatctac cacatcaaag    420
aaggagaaat ctaaacaaga gaacaaaaat aaatataaaa aatattatcc aaaaattgaa    480
gcagaatctg attctgatga atacgtatta gatgattcag atagtgatga tggaaaatgt    540
aaaaattgca agtataaaaa gaaatattttg gcacttcgtt taagaatgaa acaagttgca    600
atgcaattga ttaagatttt gtgaaaattt tcttattact cttatcatta actgttaaat    660
atttacttaa tatacagata gtgaatgttg tttaattata ttatatgata gtattattat    720
```

```
atcgcgttat tgaatttaat aactttctaa tgagagaaga ttgatgcgtc taccctaaga    780
gatcactagg gagctcccca ctcccgtttt gtgacc                              816
```

<210> SEQ ID NO 94
<211> LENGTH: 200
<212> TYPE: PRT
<213> ORGANISM: Human rotavirus

<400> SEQUENCE: 94

```
Met Ser Leu Ser Ile Asp Val Thr Ser Leu Pro Ser Ile Ser Ser
1               5                   10                  15

Val Tyr Lys Asn Glu Ser Ser Thr Thr Ser Thr Ile Ser Gly Lys
                20                  25                  30

Ser Ile Gly Arg Ser Glu Gln Tyr Ile Ser Pro Asp Ala Glu Ala Phe
            35                  40                  45

Asn Lys Tyr Met Leu Ser Lys Ser Pro Glu Asp Ile Gly Pro Ser Asp
        50                  55                  60

Ser Ala Ser Asn Asp Pro Leu Thr Ser Phe Ser Ile Arg Ser Asn Ala
65                  70                  75                  80

Val Lys Thr Asn Ala Asp Ala Gly Val Ser Met Asp Ser Ser Ala Gln
                85                  90                  95

Ser Arg Pro Ser Ser Asp Ile Gly Tyr Asp Gln Met Asp Phe Ser Leu
            100                 105                 110

Asn Lys Gly Ile Lys Phe Asp Ala Thr Val Asp Ser Ser Ile Ser Ile
        115                 120                 125

Ser Thr Thr Ser Lys Lys Glu Lys Ser Lys Gln Glu Asn Lys Asn Lys
130                 135                 140

Tyr Lys Lys Cys Tyr Pro Lys Ile Glu Ala Glu Ser Asp Ser Asp Asp
145                 150                 155                 160

Tyr Ile Leu Asp Asp Ser Asp Ser Asp Gly Lys Cys Lys Asn Cys
                165                 170                 175

Lys Tyr Lys Lys Lys Tyr Phe Ala Leu Arg Leu Arg Met Lys Gln Val
            180                 185                 190

Ala Met Gln Leu Ile Lys Asp Leu
        195                 200
```

<210> SEQ ID NO 95
<211> LENGTH: 200
<212> TYPE: PRT
<213> ORGANISM: Human rotavirus

<400> SEQUENCE: 95

```
Met Ser Leu Ser Ile Asp Val Thr Ser Leu Pro Ser Ile Ser Ser
1               5                   10                  15

Val Tyr Lys Asn Glu Ser Phe Ser Thr Thr Ser Thr Ile Ser Gly Lys
                20                  25                  30

Ser Ile Gly Arg Ser Glu Gln Tyr Ile Ser Pro Asp Ala Glu Ala Phe
            35                  40                  45

Asn Lys Tyr Met Leu Ser Lys Ser Pro Glu Asp Ile Gly Pro Ser Asp
        50                  55                  60

Ser Ala Ser Asn Asp Pro Leu Thr Ser Phe Ser Ile Arg Ser Asn Ala
65                  70                  75                  80

Val Lys Thr Asn Ala Asp Ala Gly Val Ser Met Asp Ser Ser Ala Gln
                85                  90                  95

Ser Arg Pro Ser Ser Asp Ile Gly Tyr Asp Gln Met Asp Phe Ser Leu
```

100                 105                 110
Asn Lys Gly Ile Lys Ile Asp Ala Thr Met Asp Ser Ser Ile Ser Ile
            115                 120                 125
Ser Thr Thr Ser Lys Lys Glu Lys Ser Lys Gln Glu Asn Lys Asn Lys
            130                 135                 140
Tyr Lys Lys Tyr Tyr Pro Lys Ile Glu Ala Glu Ser Asp Ser Asp Glu
145                 150                 155                 160
Tyr Val Leu Asp Asp Ser Asp Ser Asp Gly Lys Cys Lys Asn Cys
                165                 170                 175
Lys Tyr Lys Lys Tyr Phe Ala Leu Arg Leu Arg Met Lys Gln Val
                180                 185                 190
Ala Met Gln Leu Ile Lys Asp Leu
            195                 200

<210> SEQ ID NO 96
<211> LENGTH: 200
<212> TYPE: PRT
<213> ORGANISM: Human rotavirus

<400> SEQUENCE: 96

Met Ser Leu Ser Ile Asp Val Thr Ser Leu Pro Ser Ile Ser Ser
1               5                   10                  15
Val Tyr Lys Asn Glu Ser Phe Ser Thr Thr Ser Thr Ile Ser Gly Lys
            20                  25                  30
Ser Ile Gly Arg Ser Glu Gln Tyr Ile Ser Pro Asp Ala Glu Ala Phe
            35                  40                  45
Asn Lys Tyr Met Leu Ser Lys Ser Pro Glu Asp Val Gly Pro Ser Asp
50                  55                  60
Ser Ala Ser Asn Asp Pro Leu Thr Ser Phe Ser Ile Arg Ser Asn Ala
65                  70                  75                  80
Val Lys Thr Asn Ala Asp Ala Gly Val Ser Met Asp Ser Ser Ala Gln
            85                  90                  95
Ser Arg Pro Ser Ser Asp Ile Gly Tyr Asp Gln Met Asp Phe Ser Leu
            100                 105                 110
Asn Lys Gly Ile Lys Ile Asp Ala Thr Met Asp Ser Ser Ile Ser Ile
            115                 120                 125
Ser Thr Thr Ser Lys Lys Glu Lys Ser Lys Gln Glu Asn Lys Asn Lys
            130                 135                 140
Tyr Lys Lys Tyr Tyr Pro Lys Ile Glu Ala Glu Ser Asp Ser Asp Glu
145                 150                 155                 160
Tyr Val Leu Asp Asp Ser Asp Ser Asp Gly Lys Cys Lys Asn Cys
                165                 170                 175
Lys Tyr Lys Lys Tyr Phe Ala Leu Arg Leu Arg Met Lys Gln Val
                180                 185                 190
Ala Met Gln Leu Ile Lys Asp Leu
            195                 200

<210> SEQ ID NO 97
<211> LENGTH: 3302
<212> TYPE: DNA
<213> ORGANISM: Human rotavirus

<400> SEQUENCE: 97
ggctattaaa gctatacaat ggggaagtat aatctaatct tgtcagaata tttgtcattt        60
atatataatt cacaatctgc agttcaaatt ccaatttatt attcttccaa tagtgaatta      120

-continued

| | |
|---|---|
| gagagtagat gcatagaatt tcattccaaa tgtttagaaa attcgaaaaa tggtttatca | 180 |
| ctgaagaaat tatttagtga atacagtgat gttattgaga atgctacatt attatcaata | 240 |
| ttatcgtact cctatgacaa gtacaacgcc gttgaacgga aattagttaa atatgcaaaa | 300 |
| agtaaaccgt tagaggcaga tttaacattg aatgaactag actatgaaaa taataaaata | 360 |
| acatctgagt tatttccaac agaagaagaa tatactgatt cattgatgga tccagcaatt | 420 |
| ctgacttcct tatcatctaa tttgaacgca gtcatgtttt ggttggaaaa acacgaaaat | 480 |
| gatactgctg aaaagcttaa aatttataag agaagattgg atttatttag tatagtagct | 540 |
| tcaactataa acaaatatgg tgtgccaaga cacaatgcaa aatatagata tgagtatgat | 600 |
| gtgatgaaag ataaaccata ttacttagta acatgggcga attcttcgat cgaaatgtta | 660 |
| atgtcagtct tttctcatga agattactta attgcaaaag aattgatagt attatcatat | 720 |
| tctaatagat caactttagc aaagttggtg tcatctccaa tgtcaatttt agtcgcttta | 780 |
| gtggatatta atggaacgtt tattacgaat gaggagttag aattagaatt ttcaaataaa | 840 |
| tatgtacgag ccatagtgcc cgatcaaaca tttgatgaac taaaacaaat gctcgataat | 900 |
| atgaggaaag ctggattggt tgacatacct aagatgatac aagactggtt agttgattgt | 960 |
| tcaattgaaa gatttccatt aatggctaaa atatactcat ggtcatttca cgttggattc | 1020 |
| agaaagcaaa aaatgttaga tgctgctcta gaccaattaa aaactgagta tacagaaaat | 1080 |
| gtagatgatg aaatgtatcg tgaatatact atgttgataa gagatgaagt tgttaagatg | 1140 |
| cttgaagaat cagtaaaaca tgacgaccat ttgttacaag attctgaatt agctggattg | 1200 |
| ctatcaatgt cgtcggcatc aaatggagaa tctagacagc ttaaatttgg cagaaagacg | 1260 |
| atttttttcaa ctaaaaagaa catgcatgta atggatgata tggctaatgg aagatacact | 1320 |
| ccaggcataa ttccacctgt gaatgctgat aagccaaatac cgttaggaag aagagatgta | 1380 |
| ccaggaagaa gaactaggat aatatttata ttaccatatg agtatttttat agcacagcat | 1440 |
| gctgtggttg agaaaatgtt aatttatgcg aaacatacta gagaatatgc tgaattttat | 1500 |
| tcacaatcaa accagctctt atcatatggt gatgtcacac gtttcctttc caacaattct | 1560 |
| atggtattgt acacagacgt atctcaatgg gattcatctc aacataatac gcaaccatttt | 1620 |
| agaaaaggaa taataatggg gttagatata ttagctaaca tgactaatga tgctagagtc | 1680 |
| atccagacac taaatctata taaacaaacg caaattaatt tgatggactc atatgttcaa | 1740 |
| ataccagatg gcaatgttat taagaaaata cagtatggag ccgtagcatc aggagaaaaa | 1800 |
| caaactaaag cagctaactc tatagcaaat ctagcattaa ttaagactgt cttatcacgt | 1860 |
| atctctaaca aatactcatt catcacaaaa ataataagag ttgacggcga tgataactat | 1920 |
| gctgtactac agtttaacac agaagtgacc aaacaaatgg ttcaagatgt atcaaatgac | 1980 |
| gtgagagaaa cttacgcacg aatgaacgct aaagtcaaag ctctagtatc cacagtagga | 2040 |
| atagaaatag ccaaaaggta tattgcagga ggaaaaatat ttttttagagc cggaataaat | 2100 |
| ttacttaata atgaaaaaag aggacaaagt acgcaatggg atcaagcagc agttctttat | 2160 |
| tctaactata ttgtaaatag acttaggggt tttgagactg atagagaatt tattctaact | 2220 |
| aaaataatgc aaatgacgtc agttgctatt actggatcgt taagacttttt tccctctgaa | 2280 |
| cgcgtattaa ccacaaactc tacgtttaaa gtattcgatt cagaagattt tatcatagag | 2340 |
| tatggaacaa ctgatgatga agtgtatata caaagagcat ttatgtcttt atcaagtcag | 2400 |
| aaatcaggaa tagctgatga atatctgcg tcatcaacgt ttaaaaatta cgtgtctaaa | 2460 |
| ttatcagaac aattacttttt ttcaaaaaat aatatagtat ctagaggaat agctttaact | 2520 |

-continued

```
gaaaaagcga aattgaattc gtatgcacca atatcactcg agaagagacg tgcgcaaata    2580
tcagctttat taacaatgct acaaaaacca gtcacttttta aatcgagcaa aataacgata   2640
aacgatatac ttaaagatat aaaaccgttt ttcacattga gtgaagcaca tttaccaatg   2700
cagtatcaaa agttcatgcc aaacttgccg gaaaacgtac aatacataat tcagtgtata   2760
gggtcaagaa cttatcagat tgaagatgat ggttcaaaat cagcaatctc ccggcttata   2820
tcaaagtatt cagtttataa accatcaatt gaggagctgt ataaagtaat ttcactacat   2880
gaaaatgaaa tacaattgta tttaatttca ctaggcatac caaaaataga tgctgataca   2940
tatgtcgggt caaagattta ttctcaagat aaatatagga tactggaatc atatgtatat   3000
aatctgttat ctatcaatta tggatgttat caattatttg actttaattc accggactta   3060
gaaaagctga ttagaatacc gttcaaagga aagataccag ctgtcacatt tatattacat   3120
ttatacgcta aattagaagt tataaactac gcgattaaga atggttcatg gataagtcta   3180
ttttgtaact acccaaaatc agaaatgata aagttatgga agaaaatgtg gaatattacg   3240
tcgttacgtt cgccatacac taatgcaaac ttctttcaag attagaacgc ttagatgtga   3300
cc                                                                  3302
```

<210> SEQ ID NO 98
<211> LENGTH: 3302
<212> TYPE: DNA
<213> ORGANISM: Human rotavirus

<400> SEQUENCE: 98

```
ggctattaaa gctgtacaat ggggaagtat aatctaatct tgtcagaata tttatcattt     60
atatataatt cacaatctgc agttcaaatt ccaatttatt attcttccaa tagtgagctg    120
gaaagtagat gtatagaatt tcattctaaa tgtctagaaa attcgaaaaa tggtctatca    180
ctgaaaaaac tattcaatga atatagcgat gtcattgaga atgctacgtt attatcaata    240
ttatcatatt cctacgacaa atataacgcc gttgaacgga aattagtaaa aatgcgaaa    300 ggtaaaccgc ttgaggcaga cctaacggtg aatgaactgg attatgaaaa taataaaata    360
acatctgagt tgtttccgac agcggaagaa tacaccgact cattgatgga tccagcaatt    420
ctaacttcct tgtcatcaaa tttaaacgca gtcatgtttt ggttagaaaa acacgaaaat    480
gatactgctg aaagatttaa gatttataaa agaagattag acttattcat tatagtagcc    540
tcaaccgtaa acaaatatgg tgtaccaaga cacaatgcaa aatatagata tgagtatgat    600
gtgatgaaag ataaaccata ttacttagtg acatgggcaa actcttctat tgaaatgcta    660
atgtcagttt tttctcatga agattattta attgcaagag aattgatagt actgtcatat    720
tctaatagat caactttggc aaaattagta tcatctccaa tgtcaatttt agttgcttta    780
gtggatatta atggaacgtt tattacgaat gaggagttag aattagagtt ttcaaataaa    840
tacgtgcgag ccgtagtacc agatcaaaca tttgatgaat aaaacagat gctagacagt    900 atgaggaaag ctggattggt tgatatacct aaaatgatac aagactggtt agttgattgt    960
tccatcgaga aatttccact aatggctaaa atatactcat ggtcgtttca tgttgggttc   1020
aggaagcaaa aaatgttaga cgctgcctta gaccaattga aaactgagta tatagaagat   1080
gtagatgacg aaatgtatcg tgaatataca atgttaataa agatgaagt tgttaaaatg   1140 cttgaagaat cagtaaaaca tgatgaccac ctattacaag attctgaatt agctggcttg   1200
ttatcaatgt cttcagcatc gaatggagaa tcaagacagc ttaaatttgg tagaaagaca   1260
```

```
gtttttttcaa ctaaaaagaa catgcatgtt atggatgata tggctaatgg aagatataca    1320
ccaggtataa ttccacctgt aaatgctgat aaaccaatac cgttaggaag aagagatgta    1380
ccaggaagaa gaactagaat aatattcata ttgccgtatg aatattttat agcacagcat    1440
gctgtggttg agaaaatgtt aatctatgca aagcatacca gagaatacgc tgaattctat    1500
tcgcaatcaa atcaactctt atcatacggt gatgttacac gtttcctttc taataatgcg    1560
atggtgttat atacagacgt atctcaatgg gattcatctc aacataatac gcaaccgttt    1620
agaaaaggaa taataatggg attggatata ttagctaaca tgactaatga tgctaaagtt    1680
attcagacac taaatttata taaacaaaca caaattaact tgatggactc atatgttcaa    1740
ataccagatg gtaatgttat taagaaaata cagtatggag ctgtagcatc aggagagaaa    1800
caaacgaagg cagctaactc tatagcgaat ctagcactaa ttaaaacggt tttatcacgt    1860
atttctaata atattcatt tgccacaaaa ataataagag ttgacggtga tgataactac    1920
gctgtactac aatttaatac ggaagtgact aaacaaatgg ttcaagatgt ttcgaacgat    1980
gtgagagaaa tttacgcacg aatgaatgct aaagtcaaag ctctagtatc cacggtagga    2040
atagaaatag ctaaaagata cattgcagga ggaaaaatat tctttagagc aggaataaat    2100
ttgcttaata atgaaaaaag aggacaaagt acgcaatggg atcaggcagc agttttatac    2160
tctaattaca ttgtaaatag acttagaggg tttgagactg atagaagaat tatttttaact    2220 aaaataatgc aaatgacgtc tgttgctatt actgggtcgc taagactttt tccttctgaa    2280
cgtgtgttaa ctacgaattc tacatttaag gtatttgatt cagaagattt tatcatagag    2340
tatggaacaa ctgatgatga agtatatata cagagagcat ttatgtcttt gtcaagtcag    2400
agatcaggaa tagctgatga aatagctgca tcgccaacat ttaaaaatta cgtgtctaga    2460
ctatcagaac agctactttt ttcaaaaaat aatatagtat ctaaaggaat agctttgact    2520
gaaaaagcaa agttgaattc gtatgcacca atatcacttg aaaaaagacg tgcacagata    2580 tcagcttttgt tgacaatgct acaaaaacca gttactttca aatcaaacaa aataacaata    2640
aatgacatac ttaaagacat taaaccattt tttacagtga gtgaagcaca tttaccaata    2700
cagtatcaaa agtttatgcc aaccttacca gaaaacgtac aatatataat tcaatgtata    2760
gggtcaagaa cttaccagat tgaagatgat ggttcaaaat cagcaatatc ccggcttata    2820
tcaaagtact cagtttataa accatcgatc gaggaactac ataaagtaat ttcattacat    2880
gagaatgaaa tacaattata tttaatttca ttaggcatac caaaaataga tgctgataca    2940
tatgttggtt caaagattta ttctcaagac aaatacagga tattggaatc atatgtatat    3000
aacctgttat ccatcaatta tggatgctat caattattcg actttaattc accggacttg    3060
gaaaaattaa ttagaatacc atttaaaggg aagataccag ctgtcacatt tatattgcat    3120
ttatatgcta aattagaagt tataaaccat gcgattaaaa atggttcatg gataagtcta    3180
ttctgtaact atccgaaatc agaaatgata aagttatgga agaaaatgtg gaacattaca    3240
tcgttacgtt caccatatac caatgcaaat ttctttcaag attagaacgc ttagatgtga    3300
cc                                                                  3302
```

<210> SEQ ID NO 99
<211> LENGTH: 3302
<212> TYPE: DNA
<213> ORGANISM: Human rotavirus

<400> SEQUENCE: 99

```
ggctattaaa gctgtacaat ggggaagtat aatctaatct tgtcagaata tttatcattt      60
```

| | |
|---|---|
| atatataatt cacaatctgc agttcaaatt ccaatttatt attcttccaa tagtgagctg | 120 |
| gaaagtagat gtatagaatt tcattctaaa tgtctagaaa attcgaaaaa tggtctatca | 180 |
| ctgaaaaaac tattcaatga atatagcgat gtcattgaga atgctacgtt attatcaata | 240 |
| ttatcatatt cctacgacaa atataacgcc gttgaacgga aattagtaaa atatgcgaaa | 300 |
| ggtaaaccgc ttgaggcaga cctaacggtg aatgaactgg attatgaaaa taataaaata | 360 |
| acatctgagt tgtttccgac agcggaagaa tacaccgact cattgatgga tccagcaatt | 420 |
| ctaacttcct tgtcatcaag tttaaacgca gtcatgtttt ggttagaaaa acacgaaaat | 480 |
| gatactgctg aaagatttaa gatttataaa agaagattag acttattcat tatagtagcc | 540 |
| tcaaccgtaa acaaatatgg tgtaccaaga cataatgcaa atatagata cgaatatgat | 600 |
| gtgatgaaag ataaaccata ttacttagtg acatgggcaa actcttctat tgaaatgcta | 660 |
| atgtcagttt tttctcatga agattattta attgcaagag aattgatagt actgtcatat | 720 |
| tctaatagat caactttggc aaaattagta tcatctccaa tgtcaatttt agttgcttta | 780 |
| gtggatatta atggaacgtt tattacgaat gaggagttag aattagagtt ttcaaataaa | 840 |
| tacgtgcgag ccgtagtacc agatcaaaca tttgatgaat taaaacagat gctagacagt | 900 |
| atgaggaaag ctggattggt tgatatacct aaaatgatac aagactggtt agttgattgt | 960 |
| tccatcgaga aatttccact aatggctaaa atatactcat ggtcgtttca tgttgggttc | 1020 |
| aggaagcaaa aaatgttaga cgctgcctta gaccaattga aaactgagta tatagaagat | 1080 |
| gtagatgacg aaatgtatcg tgaatataca atgttaataa gagatgaagt tgttaaaatg | 1140 |
| cttgaagaat cagtaaaaca tgatgaccac ctattacaag attctgaatt agctggcttg | 1200 |
| ttatcaatgt cttcagcatc gaatggagaa tcaagacagc ttaaatttgg tagaaagaca | 1260 |
| gttttttcaa ctaaaaagaa catgcatgtt atggatgata tggctaatgg aagatataca | 1320 |
| ccaggtataa ttccacctgt aaatgctgat aaaccaatac cgttaggaag aagagatgta | 1380 |
| ccaggaagaa gaactagaat aatattcata ttgccgtatg aatatttat agcacagcat | 1440 |
| gctgtggttg agaaaatgtt aatctatgca aagcatacca gagaatacgc tgaattctat | 1500 |
| tcgcaatcaa atcaactctt atcatacggt gatgttacac gtttcctttc taataatgcg | 1560 |
| atggtgttat atacagacgt atctcaatgg gattcatctc aacataatac gcaaccgttt | 1620 |
| agaaaaggaa taataatggg attggatata ttagctaaca tgactaatga tgctaaagtt | 1680 |
| attcagacac taaatttata taaacaaaca caattaact tgatggactc atatgttcaa | 1740 |
| ataccagatg gtaatgttat taagaaaata cagtatggag ctgtagcatc aggagagaaa | 1800 |
| caaacgaagg cagctaactc tatagcgaat ctagcactaa ttaaaacggt tttatcacgt | 1860 |
| atttctaata aatattcatt tgccacaaaa ataataagag ttgacggtga tgataactac | 1920 |
| gctgtactac aatttaatac ggaagtgact aaacaaatgg ttcaagatgt ttcgaacgat | 1980 |
| gtgagagaaa tttacgcacg aatgaatgct aaagtcaaag ctctagtatc cacggtagga | 2040 |
| atagaaatag ctaaaagata cattgcagga ggaaaaatat tctttagagc aggaataaat | 2100 |
| ttgcttaata tgaaaaaag aggacaaagt acgcaatggg atcaggcagc agtttttatac | 2160 |
| tctaattaca ttgtaaatag acttagaggg tttgagactg atagagaatt tattttaact | 2220 |
| aaaataatgc aaatgacgtc tgttgctatt actgggtcgc taagacttttt tccttctgaa | 2280 |
| cgtgtgttaa ctacgaattc tacatttaag gtatttgatt cagaagattt tatcatagag | 2340 |
| tatgaaacaa ctgatgatga agtatatata cagagagcat ttatgtcttt gtcaagtcag | 2400 |

```
agatcaggaa tagctgatga aatagctgca tcgccaacat ttaaaaatta cgtgtctaga    2460
ctatcagaac agctactttt ttcaaaaaat aatatagtat ctaaaggaat agctttgact    2520
gaaaaagcaa agttgaattc gtatgcacca atatcacttg aaaaaagacg tgcacagata    2580
tcagctttgt tgacaatgct acaaaaacca gttactttca aatcaaacaa ataacaata     2640 aatgacatac ttaaagacat taaaccatttt tttacagtga gtgaagcaca tttaccaata   2700
cagtatcaaa agtttatgcc aaccttacca gaaaacgtac aatatataat tcaatgtata    2760
gggtcaagaa cttaccagat tgaagatgat ggttcaaaat cagcaatatc ccggcttata    2820
tcaaagtact cagtttataa accatcgatc gaggaactat ataagtaat ttcattacat     2880 gagaatgaaa tacaattata tttaatttca ttaggcatac caaaaataga tgctgataca    2940
tatgttggtt caaagattta ttctcaagac aaatacagga tattggaatc atatgtatat    3000
aacctgttat ccatcaatta tggatgctat caattattcg actttaattc accggacttg    3060
gaaaaattaa ttagaatacc atttaaaggg aagataccag ctgtcacatt tatattgcat    3120
ttatatgcta aattagaagt tataaaccat gcgattaaaa atggttcatg ataagtcta     3180 ttctgtaact atccgaaatc agaaatgata aagttatgga agaaaatgtg gaacattaca    3240
tcgttacgtt caccatatac caatgcaaat ttctttcaag attagaacgc ttagatgtga    3300
cc                                                                    3302

<210> SEQ ID NO 100
<211> LENGTH: 1088
<212> TYPE: PRT
<213> ORGANISM: Human rotavirus

<400> SEQUENCE: 100

Met Gly Lys Tyr Asn Leu Ile Leu Ser Glu Tyr Leu Ser Phe Ile Tyr
1               5                   10                  15

Asn Ser Gln Ser Ala Val Gln Ile Pro Ile Tyr Tyr Ser Ser Asn Ser
            20                  25                  30

Glu Leu Glu Ser Arg Cys Ile Glu Phe His Ser Lys Cys Leu Glu Asn
        35                  40                  45

Ser Lys Asn Gly Leu Ser Leu Lys Lys Leu Phe Ser Glu Tyr Ser Asp
    50                  55                  60

Val Ile Glu Asn Ala Thr Leu Leu Ser Ile Leu Ser Tyr Ser Tyr Asp
65                  70                  75                  80

Lys Tyr Asn Ala Val Glu Arg Lys Leu Val Lys Tyr Ala Lys Ser Lys
                85                  90                  95

Pro Leu Glu Ala Asp Leu Thr Leu Asn Glu Leu Asp Tyr Glu Asn Asn
            100                 105                 110

Lys Ile Thr Ser Glu Leu Phe Pro Thr Glu Glu Tyr Thr Asp Ser
        115                 120                 125

Leu Met Asp Pro Ala Ile Leu Thr Ser Leu Ser Ser Asn Leu Asn Ala
    130                 135                 140

Val Met Phe Trp Leu Glu Lys His Glu Asn Asp Thr Ala Glu Lys Leu
145                 150                 155                 160

Lys Ile Tyr Lys Arg Arg Leu Asp Leu Phe Ser Ile Val Ala Ser Thr
                165                 170                 175

Ile Asn Lys Tyr Gly Val Pro Arg His Asn Ala Lys Tyr Arg Tyr Glu
            180                 185                 190

Tyr Asp Val Met Lys Asp Lys Pro Tyr Tyr Leu Val Thr Trp Ala Asn
        195                 200                 205
```

```
Ser Ser Ile Glu Met Leu Met Ser Val Phe Ser His Glu Asp Tyr Leu
    210                 215                 220
Ile Ala Lys Glu Leu Ile Val Leu Ser Tyr Ser Asn Arg Ser Thr Leu
225                 230                 235                 240
Ala Lys Leu Val Ser Ser Pro Met Ser Ile Leu Val Ala Leu Val Asp
                245                 250                 255
Ile Asn Gly Thr Phe Ile Thr Asn Glu Glu Leu Glu Leu Glu Phe Ser
                260                 265                 270
Asn Lys Tyr Val Arg Ala Ile Val Pro Asp Gln Thr Phe Asp Glu Leu
            275                 280                 285
Lys Gln Met Leu Asp Asn Met Arg Lys Ala Gly Leu Val Asp Ile Pro
290                 295                 300
Lys Met Ile Gln Asp Trp Leu Val Asp Cys Ser Ile Glu Arg Phe Pro
305                 310                 315                 320
Leu Met Ala Lys Ile Tyr Ser Trp Ser Phe His Val Gly Phe Arg Lys
                325                 330                 335
Gln Lys Met Leu Asp Ala Ala Leu Asp Gln Leu Lys Thr Glu Tyr Thr
                340                 345                 350
Glu Asn Val Asp Asp Glu Met Tyr Arg Glu Tyr Thr Met Leu Ile Arg
            355                 360                 365
Asp Glu Val Val Lys Met Leu Glu Glu Ser Val Lys His Asp Asp His
        370                 375                 380
Leu Leu Gln Asp Ser Glu Leu Ala Gly Leu Leu Ser Met Ser Ser Ala
385                 390                 395                 400
Ser Asn Gly Glu Ser Arg Gln Leu Lys Phe Gly Arg Lys Thr Ile Phe
                405                 410                 415
Ser Thr Lys Lys Asn Met His Val Met Asp Asp Met Ala Asn Gly Arg
                420                 425                 430
Tyr Thr Pro Gly Ile Ile Pro Pro Val Asn Ala Asp Lys Pro Ile Pro
            435                 440                 445
Leu Gly Arg Arg Asp Val Pro Gly Arg Arg Thr Arg Ile Ile Phe Ile
450                 455                 460
Leu Pro Tyr Glu Tyr Phe Ile Ala Gln His Ala Val Val Glu Lys Met
465                 470                 475                 480
Leu Ile Tyr Ala Lys His Thr Arg Glu Tyr Ala Glu Phe Tyr Ser Gln
                485                 490                 495
Ser Asn Gln Leu Leu Ser Tyr Gly Asp Val Thr Arg Phe Leu Ser Asn
                500                 505                 510
Asn Ser Met Val Leu Tyr Thr Asp Val Ser Gln Trp Asp Ser Ser Gln
            515                 520                 525
His Asn Thr Gln Pro Phe Arg Lys Gly Ile Ile Met Gly Leu Asp Ile
        530                 535                 540
Leu Ala Asn Met Thr Asn Asp Ala Arg Val Ile Gln Thr Leu Asn Leu
545                 550                 555                 560
Tyr Lys Gln Thr Gln Ile Asn Leu Met Asp Ser Tyr Val Gln Ile Pro
                565                 570                 575
Asp Gly Asn Val Ile Lys Lys Ile Gln Tyr Gly Ala Val Ala Ser Gly
            580                 585                 590
Glu Lys Gln Thr Lys Ala Ala Asn Ser Ile Ala Asn Leu Ala Leu Ile
        595                 600                 605
Lys Thr Val Leu Ser Arg Ile Ser Asn Lys Tyr Ser Phe Ile Thr Lys
    610                 615                 620
Ile Ile Arg Val Asp Gly Asp Asp Asn Tyr Ala Val Leu Gln Phe Asn
```

```
            625                 630                 635                 640
        Thr Glu Val Thr Lys Gln Met Val Gln Asp Val Ser Asn Asp Val Arg
                        645                 650                 655
        Glu Thr Tyr Ala Arg Met Asn Ala Lys Val Lys Ala Leu Val Ser Thr
                        660                 665                 670
        Val Gly Ile Glu Ile Ala Lys Arg Tyr Ile Ala Gly Lys Ile Phe
                        675                 680                 685
        Phe Arg Ala Gly Ile Asn Leu Leu Asn Glu Lys Arg Gly Gln Ser
                        690                 695                 700
        Thr Gln Trp Asp Gln Ala Ala Val Leu Tyr Ser Asn Tyr Ile Val Asn
        705                 710                 715                 720
        Arg Leu Arg Gly Phe Glu Thr Asp Arg Glu Phe Ile Leu Thr Lys Ile
                        725                 730                 735
        Met Gln Met Thr Ser Val Ala Ile Thr Gly Ser Leu Arg Leu Phe Pro
                        740                 745                 750
        Ser Glu Arg Val Leu Thr Thr Asn Ser Thr Phe Lys Val Phe Asp Ser
                        755                 760                 765
        Glu Asp Phe Ile Ile Glu Tyr Gly Thr Thr Asp Glu Val Tyr Ile
                        770                 775                 780
        Gln Arg Ala Phe Met Ser Leu Ser Ser Gln Lys Ser Gly Ile Ala Asp
        785                 790                 795                 800
        Glu Ile Ser Ala Ser Thr Phe Lys Asn Tyr Val Ser Lys Leu Ser
                        805                 810                 815
        Glu Gln Leu Leu Phe Ser Lys Asn Asn Ile Val Ser Arg Gly Ile Ala
                        820                 825                 830
        Leu Thr Glu Lys Ala Lys Leu Asn Ser Tyr Ala Pro Ile Ser Leu Glu
                        835                 840                 845
        Lys Arg Arg Ala Gln Ile Ser Ala Leu Leu Thr Met Leu Gln Lys Pro
        850                 855                 860
        Val Thr Phe Lys Ser Ser Lys Ile Thr Ile Asn Asp Ile Leu Lys Asp
        865                 870                 875                 880
        Ile Lys Pro Phe Phe Thr Leu Ser Glu Ala His Leu Pro Met Gln Tyr
                        885                 890                 895
        Gln Lys Phe Met Pro Asn Leu Pro Glu Asn Val Gln Tyr Ile Ile Gln
                        900                 905                 910
        Cys Ile Gly Ser Arg Thr Tyr Gln Ile Glu Asp Gly Ser Lys Ser
                        915                 920                 925
        Ala Ile Ser Arg Leu Ile Ser Lys Tyr Ser Val Tyr Lys Pro Ser Ile
                        930                 935                 940
        Glu Glu Leu Tyr Lys Val Ile Ser Leu His Glu Asn Glu Ile Gln Leu
        945                 950                 955                 960
        Tyr Leu Ile Ser Leu Gly Ile Pro Lys Ile Asp Ala Asp Thr Tyr Val
                        965                 970                 975
        Gly Ser Lys Ile Tyr Ser Gln Asp Lys Tyr Arg Ile Leu Glu Ser Tyr
                        980                 985                 990
        Val Tyr Asn Leu Leu Ser Ile Asn Tyr Gly Cys Tyr Gln Leu Phe Asp
                        995                1000                1005
        Phe Asn Ser Pro Asp Leu Glu Lys Leu Ile Arg Ile Pro Phe Lys
                       1010                1015                1020
        Gly Lys Ile Pro Ala Val Thr Phe Ile Leu His Leu Tyr Ala Lys
                       1025                1030                1035
        Leu Glu Val Ile Asn Tyr Ala Ile Lys Asn Gly Ser Trp Ile Ser
                       1040                1045                1050
```

-continued

```
Leu Phe Cys Asn Tyr Pro Lys Ser Glu Met Ile Lys Leu Trp Lys
    1055                1060                1065

Lys Met Trp Asn Ile Thr Ser Leu Arg Ser Pro Tyr Thr Asn Ala
1070                1075                1080

Asn Phe Phe Gln Asp
    1085

<210> SEQ ID NO 101
<211> LENGTH: 1088
<212> TYPE: PRT
<213> ORGANISM: Human rotavirus

<400> SEQUENCE: 101

Met Gly Lys Tyr Asn Leu Ile Leu Ser Glu Tyr Leu Ser Phe Ile Tyr
1               5                   10                  15

Asn Ser Gln Ser Ala Val Gln Ile Pro Ile Tyr Tyr Ser Ser Asn Ser
            20                  25                  30

Glu Leu Glu Ser Arg Cys Ile Glu Phe His Ser Lys Cys Leu Glu Asn
        35                  40                  45

Ser Lys Asn Gly Leu Ser Leu Lys Lys Leu Phe Asn Glu Tyr Ser Asp
    50                  55                  60

Val Ile Glu Asn Ala Thr Leu Leu Ser Ile Leu Ser Tyr Ser Tyr Asp
65                  70                  75                  80

Lys Tyr Asn Ala Val Glu Arg Lys Leu Val Lys Tyr Ala Lys Gly Lys
                85                  90                  95

Pro Leu Glu Ala Asp Leu Thr Val Asn Glu Leu Asp Tyr Glu Asn Asn
            100                 105                 110

Lys Ile Thr Ser Glu Leu Phe Pro Thr Ala Glu Glu Tyr Thr Asp Ser
        115                 120                 125

Leu Met Asp Pro Ala Ile Leu Thr Ser Leu Ser Ser Asn Leu Asn Ala
    130                 135                 140

Val Met Phe Trp Leu Glu Lys His Glu Asn Asp Thr Ala Glu Arg Phe
145                 150                 155                 160

Lys Ile Tyr Lys Arg Arg Leu Asp Leu Phe Ile Ile Val Ala Ser Thr
                165                 170                 175

Val Asn Lys Tyr Gly Val Pro Arg His Asn Ala Lys Tyr Arg Tyr Glu
            180                 185                 190

Tyr Asp Val Met Lys Asp Lys Pro Tyr Tyr Leu Val Thr Trp Ala Asn
        195                 200                 205

Ser Ser Ile Glu Met Leu Met Ser Val Phe Ser His Glu Asp Tyr Leu
    210                 215                 220

Ile Ala Arg Glu Leu Ile Val Leu Ser Tyr Ser Asn Arg Ser Thr Leu
225                 230                 235                 240

Ala Lys Leu Val Ser Ser Pro Met Ser Ile Leu Val Ala Leu Val Asp
                245                 250                 255

Ile Asn Gly Thr Phe Ile Thr Asn Glu Glu Leu Glu Leu Glu Phe Ser
            260                 265                 270

Asn Lys Tyr Val Arg Ala Val Val Pro Asp Gln Thr Phe Asp Glu Leu
        275                 280                 285

Lys Gln Met Leu Asp Ser Met Arg Lys Ala Gly Leu Val Asp Ile Pro
    290                 295                 300

Lys Met Ile Gln Asp Trp Leu Val Asp Cys Ser Ile Glu Lys Phe Pro
305                 310                 315                 320

Leu Met Ala Lys Ile Tyr Ser Trp Ser Phe His Val Gly Phe Arg Lys
```

```
                    325                 330                 335
Gln Lys Met Leu Asp Ala Ala Leu Asp Gln Leu Lys Thr Glu Tyr Ile
                340                 345                 350
Glu Asp Val Asp Glu Met Tyr Arg Glu Tyr Thr Met Leu Ile Arg
            355                 360                 365
Asp Glu Val Val Lys Met Leu Glu Glu Ser Val Lys His Asp His
        370                 375                 380
Leu Leu Gln Asp Ser Glu Leu Ala Gly Leu Leu Ser Met Ser Ser Ala
385                 390                 395                 400
Ser Asn Gly Glu Ser Arg Gln Leu Lys Phe Gly Arg Lys Thr Val Phe
                405                 410                 415
Ser Thr Lys Lys Asn Met His Val Met Asp Asp Met Ala Asn Gly Arg
                420                 425                 430
Tyr Thr Pro Gly Ile Ile Pro Pro Val Asn Ala Asp Lys Pro Ile Pro
                435                 440                 445
Leu Gly Arg Arg Asp Val Pro Gly Arg Arg Thr Arg Ile Ile Phe Ile
            450                 455                 460
Leu Pro Tyr Glu Tyr Phe Ile Ala Gln His Ala Val Val Glu Lys Met
465                 470                 475                 480
Leu Ile Tyr Ala Lys His Thr Arg Glu Tyr Ala Glu Phe Tyr Ser Gln
                485                 490                 495
Ser Asn Gln Leu Leu Ser Tyr Gly Asp Val Thr Arg Phe Leu Ser Asn
                500                 505                 510
Asn Ala Met Val Leu Tyr Thr Asp Val Ser Gln Trp Asp Ser Ser Gln
                515                 520                 525
His Asn Thr Gln Pro Phe Arg Lys Gly Ile Ile Met Gly Leu Asp Ile
            530                 535                 540
Leu Ala Asn Met Thr Asn Asp Ala Lys Val Ile Gln Thr Leu Asn Leu
545                 550                 555                 560
Tyr Lys Gln Thr Gln Ile Asn Leu Met Asp Ser Tyr Val Gln Ile Pro
                565                 570                 575
Asp Gly Asn Val Ile Lys Lys Ile Gln Tyr Gly Ala Val Ala Ser Gly
            580                 585                 590
Glu Lys Gln Thr Lys Ala Ala Asn Ser Ile Ala Asn Leu Ala Leu Ile
        595                 600                 605
Lys Thr Val Leu Ser Arg Ile Ser Asn Lys Tyr Ser Phe Ala Thr Lys
        610                 615                 620
Ile Ile Arg Val Asp Gly Asp Asp Asn Tyr Ala Val Leu Gln Phe Asn
625                 630                 635                 640
Thr Glu Val Thr Lys Gln Met Val Gln Asp Val Ser Asn Asp Val Arg
                645                 650                 655
Glu Ile Tyr Ala Arg Met Asn Ala Lys Val Lys Ala Leu Val Ser Thr
            660                 665                 670
Val Gly Ile Glu Ile Ala Lys Arg Tyr Ile Ala Gly Lys Ile Phe
        675                 680                 685
Phe Arg Ala Gly Ile Asn Leu Leu Asn Asn Glu Lys Arg Gly Gln Ser
        690                 695                 700
Thr Gln Trp Asp Gln Ala Ala Val Leu Tyr Ser Asn Tyr Ile Val Asn
705                 710                 715                 720
Arg Leu Arg Gly Phe Glu Thr Asp Arg Glu Phe Ile Leu Thr Lys Ile
                725                 730                 735
Met Gln Met Thr Ser Val Ala Ile Thr Gly Ser Leu Arg Leu Phe Pro
                740                 745                 750
```

Ser Glu Arg Val Leu Thr Thr Asn Ser Thr Phe Lys Val Phe Asp Ser
         755                 760                 765

Glu Asp Phe Ile Ile Glu Tyr Gly Thr Thr Asp Asp Glu Val Tyr Ile
    770                 775                 780

Gln Arg Ala Phe Met Ser Leu Ser Ser Gln Arg Ser Gly Ile Ala Asp
785                 790                 795                 800

Glu Ile Ala Ala Ser Pro Thr Phe Lys Asn Tyr Val Ser Arg Leu Ser
                805                 810                 815

Glu Gln Leu Leu Phe Ser Lys Asn Asn Ile Val Ser Lys Gly Ile Ala
            820                 825                 830

Leu Thr Glu Lys Ala Lys Leu Asn Ser Tyr Ala Pro Ile Ser Leu Glu
        835                 840                 845

Lys Arg Arg Ala Gln Ile Ser Ala Leu Leu Thr Met Leu Gln Lys Pro
850                 855                 860

Val Thr Phe Lys Ser Asn Lys Ile Thr Ile Asn Asp Ile Leu Lys Asp
865                 870                 875                 880

Ile Lys Pro Phe Phe Thr Val Ser Glu Ala His Leu Pro Ile Gln Tyr
                885                 890                 895

Gln Lys Phe Met Pro Thr Leu Pro Glu Asn Val Gln Tyr Ile Ile Gln
            900                 905                 910

Cys Ile Gly Ser Arg Thr Tyr Gln Ile Glu Asp Asp Gly Ser Lys Ser
        915                 920                 925

Ala Ile Ser Arg Leu Ile Ser Lys Tyr Ser Val Tyr Lys Pro Ser Ile
930                 935                 940

Glu Glu Leu Tyr Lys Val Ile Ser Leu His Glu Asn Glu Ile Gln Leu
945                 950                 955                 960

Tyr Leu Ile Ser Leu Gly Ile Pro Lys Ile Asp Ala Asp Thr Tyr Val
                965                 970                 975

Gly Ser Lys Ile Tyr Ser Gln Asp Lys Tyr Arg Ile Leu Glu Ser Tyr
            980                 985                 990

Val Tyr Asn Leu Leu Ser Ile Asn Tyr Gly Cys Tyr Gln Leu Phe Asp
        995                 1000                1005

Phe Asn Ser Pro Asp Leu Glu Lys Leu Ile Arg Ile Pro Phe Lys
    1010                1015                1020

Gly Lys Ile Pro Ala Val Thr Phe Ile Leu His Leu Tyr Ala Lys
    1025                1030                1035

Leu Glu Val Ile Asn His Ala Ile Lys Asn Gly Ser Trp Ile Ser
    1040                1045                1050

Leu Phe Cys Asn Tyr Pro Lys Ser Glu Met Ile Lys Leu Trp Lys
    1055                1060                1065

Lys Met Trp Asn Ile Thr Ser Leu Arg Ser Pro Tyr Thr Asn Ala
    1070                1075                1080

Asn Phe Phe Gln Asp
    1085

<210> SEQ ID NO 102
<211> LENGTH: 1088
<212> TYPE: PRT
<213> ORGANISM: Human rotavirus

<400> SEQUENCE: 102

Met Gly Lys Tyr Asn Leu Ile Leu Ser Glu Tyr Leu Ser Phe Ile Tyr
1               5                   10                  15

Asn Ser Gln Ser Ala Val Gln Ile Pro Ile Tyr Tyr Ser Ser Asn Ser

```
                20              25              30
Glu Leu Glu Ser Arg Cys Ile Glu Phe His Ser Lys Cys Leu Glu Asn
            35              40              45

Ser Lys Asn Gly Leu Ser Leu Lys Lys Leu Phe Asn Glu Tyr Ser Asp
        50              55              60

Val Ile Glu Asn Ala Thr Leu Leu Ser Ile Leu Ser Tyr Ser Tyr Asp
65              70              75              80

Lys Tyr Asn Ala Val Glu Arg Lys Leu Val Lys Tyr Ala Lys Gly Lys
                85              90              95

Pro Leu Glu Ala Asp Leu Thr Val Asn Glu Leu Asp Tyr Glu Asn Asn
            100             105             110

Lys Ile Thr Ser Glu Leu Phe Pro Thr Ala Glu Glu Tyr Thr Asp Ser
        115             120             125

Leu Met Asp Pro Ala Ile Leu Thr Ser Leu Ser Ser Leu Asn Ala
        130             135             140

Val Met Phe Trp Leu Glu Lys His Glu Asn Asp Thr Ala Glu Arg Phe
145             150             155             160

Lys Ile Tyr Lys Arg Arg Leu Asp Leu Phe Ile Ile Val Ala Ser Thr
                165             170             175

Val Asn Lys Tyr Gly Val Pro Arg His Asn Ala Lys Tyr Arg Tyr Glu
            180             185             190

Tyr Asp Val Met Lys Asp Lys Pro Tyr Tyr Leu Val Thr Trp Ala Asn
            195             200             205

Ser Ser Ile Glu Met Leu Met Ser Val Phe Ser His Glu Asp Tyr Leu
        210             215             220

Ile Ala Arg Glu Leu Ile Val Leu Ser Tyr Ser Asn Arg Ser Thr Leu
225             230             235             240

Ala Lys Leu Val Ser Ser Pro Met Ser Ile Leu Val Ala Leu Val Asp
                245             250             255

Ile Asn Gly Thr Phe Ile Thr Asn Glu Glu Leu Glu Leu Glu Phe Ser
            260             265             270

Asn Lys Tyr Val Arg Ala Val Val Pro Asp Gln Thr Phe Asp Glu Leu
        275             280             285

Lys Gln Met Leu Asp Ser Met Arg Lys Ala Gly Leu Val Asp Ile Pro
    290             295             300

Lys Met Ile Gln Asp Trp Leu Val Asp Cys Ser Ile Glu Lys Phe Pro
305             310             315             320

Leu Met Ala Lys Ile Tyr Ser Trp Ser Phe His Val Gly Phe Arg Lys
                325             330             335

Gln Lys Met Leu Asp Ala Ala Leu Asp Gln Leu Lys Thr Glu Tyr Ile
            340             345             350

Glu Asp Val Asp Asp Glu Met Tyr Arg Glu Tyr Thr Met Leu Ile Arg
            355             360             365

Asp Glu Val Val Lys Met Leu Glu Glu Ser Val Lys His Asp His
        370             375             380

Leu Leu Gln Asp Ser Glu Leu Ala Gly Leu Leu Ser Met Ser Ser Ala
385             390             395             400

Ser Asn Gly Glu Ser Arg Gln Leu Lys Phe Gly Arg Lys Thr Val Phe
                405             410             415

Ser Thr Lys Lys Asn Met His Val Met Asp Asp Met Ala Asn Gly Arg
            420             425             430

Tyr Thr Pro Gly Ile Ile Pro Pro Val Asn Ala Asp Lys Pro Ile Pro
        435             440             445
```

```
Leu Gly Arg Arg Asp Val Pro Gly Arg Arg Thr Arg Ile Ile Phe Ile
    450                 455                 460
Leu Pro Tyr Glu Tyr Phe Ile Ala Gln His Ala Val Val Glu Lys Met
465                 470                 475                 480
Leu Ile Tyr Ala Lys His Thr Arg Glu Tyr Ala Glu Phe Tyr Ser Gln
                485                 490                 495
Ser Asn Gln Leu Leu Ser Tyr Gly Asp Val Thr Arg Phe Leu Ser Asn
            500                 505                 510
Asn Ala Met Val Leu Tyr Thr Asp Val Ser Gln Trp Asp Ser Ser Gln
            515                 520                 525
His Asn Thr Gln Pro Phe Arg Lys Gly Ile Ile Met Gly Leu Asp Ile
    530                 535                 540
Leu Ala Asn Met Thr Asn Asp Ala Lys Val Ile Gln Thr Leu Asn Leu
545                 550                 555                 560
Tyr Lys Gln Thr Gln Ile Asn Leu Met Asp Ser Tyr Val Gln Ile Pro
                565                 570                 575
Asp Gly Asn Val Ile Lys Lys Ile Gln Tyr Gly Ala Val Ala Ser Gly
            580                 585                 590
Glu Lys Gln Thr Lys Ala Ala Asn Ser Ile Ala Asn Leu Ala Leu Ile
    595                 600                 605
Lys Thr Val Leu Ser Arg Ile Ser Asn Lys Tyr Ser Phe Ala Thr Lys
    610                 615                 620
Ile Ile Arg Val Asp Gly Asp Asp Asn Tyr Ala Val Leu Gln Phe Asn
625                 630                 635                 640
Thr Glu Val Thr Lys Gln Met Val Gln Asp Val Ser Asn Asp Val Arg
                645                 650                 655
Glu Ile Tyr Ala Arg Met Asn Ala Lys Val Lys Ala Leu Val Ser Thr
            660                 665                 670
Val Gly Ile Glu Ile Ala Lys Arg Tyr Ile Ala Gly Gly Lys Ile Phe
    675                 680                 685
Phe Arg Ala Gly Ile Asn Leu Leu Asn Asn Glu Lys Arg Gly Gln Ser
690                 695                 700
Thr Gln Trp Asp Gln Ala Ala Val Leu Tyr Ser Asn Tyr Ile Val Asn
705                 710                 715                 720
Arg Leu Arg Gly Phe Glu Thr Asp Arg Glu Phe Ile Leu Thr Lys Ile
                725                 730                 735
Met Gln Met Thr Ser Val Ala Ile Thr Gly Ser Leu Arg Leu Phe Pro
            740                 745                 750
Ser Glu Arg Val Leu Thr Thr Asn Ser Thr Phe Lys Val Phe Asp Ser
    755                 760                 765
Glu Asp Phe Ile Ile Glu Tyr Gly Thr Thr Asp Asp Glu Val Tyr Ile
    770                 775                 780
Gln Arg Ala Phe Met Ser Leu Ser Ser Gln Arg Ser Gly Ile Ala Asp
785                 790                 795                 800
Glu Ile Ala Ala Ser Pro Thr Phe Lys Asn Tyr Val Ser Arg Leu Ser
                805                 810                 815
Glu Gln Leu Leu Phe Ser Lys Asn Asn Ile Val Ser Lys Gly Ile Ala
            820                 825                 830
Leu Thr Glu Lys Ala Lys Leu Asn Ser Tyr Ala Pro Ile Ser Leu Glu
    835                 840                 845
Lys Arg Arg Ala Gln Ile Ser Ala Leu Leu Thr Met Leu Gln Lys Pro
850                 855                 860
```

-continued

```
Val Thr Phe Lys Ser Asn Lys Ile Thr Ile Asn Asp Ile Leu Lys Asp
865                 870                 875                 880

Ile Lys Pro Phe Phe Thr Val Ser Glu Ala His Leu Pro Ile Gln Tyr
                885                 890                 895

Gln Lys Phe Met Pro Thr Leu Pro Glu Asn Val Gln Tyr Ile Ile Gln
            900                 905                 910

Cys Ile Gly Ser Arg Thr Tyr Gln Ile Glu Asp Asp Gly Ser Lys Ser
        915                 920                 925

Ala Ile Ser Arg Leu Ile Ser Lys Tyr Ser Val Tyr Lys Pro Ser Ile
    930                 935                 940

Glu Glu Leu Tyr Lys Val Ile Ser Leu His Glu Asn Glu Ile Gln Leu
945                 950                 955                 960

Tyr Leu Ile Ser Leu Gly Ile Pro Lys Ile Asp Ala Asp Thr Tyr Val
                965                 970                 975

Gly Ser Lys Ile Tyr Ser Gln Asp Lys Tyr Arg Ile Leu Glu Ser Tyr
            980                 985                 990

Val Tyr Asn Leu Leu Ser Ile Asn  Tyr Gly Cys Tyr Gln  Leu Phe Asp
        995                 1000                1005

Phe Asn  Ser Pro Asp Leu Glu  Lys Leu Ile Arg Ile  Pro Phe Lys
    1010                1015                1020

Gly Lys  Ile Pro Ala Val Thr  Phe Ile Leu His Leu  Tyr Ala Lys
    1025                1030                1035

Leu Glu  Val Ile Asn His Ala  Ile Lys Asn Gly Ser  Trp Ile Ser
    1040                1045                1050

Leu Phe  Cys Asn Tyr Pro Lys  Ser Glu Met Ile Lys  Leu Trp Lys
    1055                1060                1065

Lys Met  Trp Asn Ile Thr Ser  Leu Arg Ser Pro Tyr  Thr Asn Ala
    1070                1075                1080

Asn Phe  Phe Gln Asp
    1085
```

<210> SEQ ID NO 103
<211> LENGTH: 2684
<212> TYPE: DNA
<213> ORGANISM: Human rotavirus

<400> SEQUENCE: 103

```
ggctattaaa ggctcaatgg cgtacaggaa acgtggagcg cgccgtgagg caaacttaaa      60
taataatgat cgaatgcagg agaaaaatga tgaaaagcaa gattcaaata aaatacaatt     120
atctgataag gtactttcga agaaagaaga aattgtaaca gatagtcatg aagaagttaa     180
aattactgat gaggtgaaaa aatcaacaaa agaagaatca aagcagttgc ttgaagtgtt     240
aaaaacaaag gaagaacatc agaaagagat acagtatgaa atattgcaga aaactatacc     300
aacatttgaa cctaaagaaa caatattgaa aaaactagag gatattaaac cagaactagc     360
gaaaaaacag actaagctat ttagaatatt tgaaccgaaa caactaccga tttatagagc     420
aaatggagaa agagagttgc gtaatagatg gtgttggaaa ttaaaaaaag ataccttacc     480
agatggagat tacgatgtga gagaatattt tctgaatctg tatgatcaag tgcttactga     540
gatgccagac tatctattat taaaagatat ggcagtcgaa aataagaact ccagagatgc     600
aggtaaggtt gttgattcag aaacggctag catatgcgac gccatttttc aagatgaaga     660
aacagaaggt gctgtcagaa gattcattgc agagatgaga cagcgtgtgc aagctgatag     720
aaatgttgtc aactatccat caatattgca tccaatagat tatgcattta atgaatactt     780
```

-continued

| | |
|---|---|
| tttgcaacat caattagttg aaccattgaa taatgatata atatttaatt atataccaga | 840 |
| aaggataaga aatgatgtta attacattct caatatggat agaaatctac catcaactgc | 900 |
| cagatatata agacctaact tacttcaaga tagattaaat ttacacgata attttgaatc | 960 |
| gctatgggat acaataacca catcaaatta tatcttggca agatcaatag taccagattt | 1020 |
| aaaagaacta gtatcaactg aagcacaaat tcagaaaatg tcgcaagatt tgcaattaga | 1080 |
| agcgttaaca attcaatcag aaacacagtt tctaacgggt ataaattcac aagcagccaa | 1140 |
| cgattgcttt aaaactttaa ttgcagcaat gttaagtcaa cgtactatgt cattggactt | 1200 |
| tgtaactact aattatatgt cattaatttc aggtatgtgg ctattgacag tcataccaaa | 1260 |
| tgatatgttt ataagggagt cgttagtagc gtgccagcta gctatagtaa atacaataat | 1320 |
| ctatccagca tttggaatgc aacgcatgca ttatagaaac ggggatccac aaacaccgtt | 1380 |
| tcagatagca gaacagcaaa ttcaaaattt ccaagttgca aattggttgc attttgttaa | 1440 |
| taataatcaa tttagacagg cagttattga tggtgtattg aaccaggtat aaatgacaa | 1500 |
| tattagaagt ggtcatgtta ttaatcaact aatggaagct ttaatgcagt tgtcgcgaca | 1560 |
| acaatttcca accatgccag ttgattataa gaggtcaatt caacgtggaa tattactgtt | 1620 |
| atctaacaga cttggtcagt tagttgattt aactagatta ttagcttaca attacgagac | 1680 |
| attaatggca tgtattacaa tgaacatgca acatgttcaa actttaacaa cagaaaaatt | 1740 |
| acaattaacg tcagtcacat cattatgtat gcttattgga aacgcgactg ttataccaag | 1800 |
| tccacaaaca ttatttcatt attataacgt taatgttaat tttcattcaa attataatga | 1860 |
| gagaattaat gatgcagtag ctataataac tgctgctaat agactaaacc tatatcagaa | 1920 |
| aaaaatgaag gcaattgttg aggatttttt aaagagatta tatattttg atgtatctag | 1980 |
| agttccggac gaccaaatgt atagattaag ggacagatta cgcttattgc cagtagaaat | 2040 |
| cagaagattg gatatcttta acctaatatt aatgaatatg gatcaaattg aacgtgcctc | 2100 |
| agataaaatt gctcaaggtg taatcattgc ttatcgtgac atgcatcttg aaagagatga | 2160 |
| gatgtacgga tatgtaaata tagctagaaa tttagacgga ttccaacaga taaatttaga | 2220 |
| ggagctaatg agatcaggtg attatgcgca ataactaac atgcttttaa ataatcaacc | 2280 |
| ggtagcattg gttggagcac ttccatttat tactgattca tcagtcatat cactaatagc | 2340 |
| aaaacttgac gctacagtgt tcgctcaaat agtcaaatta cgaaaagttg atactttaaa | 2400 |
| accaatatta tacaaaataa attcagattc aaatgacttt tatttggtag ctaactatga | 2460 |
| ttgggtgcca acttcgacta cgaaagtata caaacaggtc ccgcaacaat ttgattttag | 2520 |
| aaattcaatg catatgttaa cttcgaatct cactttaca gtttattcag accttctcgc | 2580 |
| attcgtgtca gctgatacag tagaacctat aaatgcggtt gcgtttgaca acatgcgcat | 2640 |
| catgaacgaa ttgtagacgc caaccccact gtggagatat gacc | 2684 |

<210> SEQ ID NO 104
<211> LENGTH: 2684
<212> TYPE: DNA
<213> ORGANISM: Human rotavirus

<400> SEQUENCE: 104

| | |
|---|---|
| ggctattaaa ggctcaatgg cgtacaggaa acgtggagcg cgccgtgagg cgaacttaaa | 60 |
| taataatgat cgaatgcagg agaaaattga tgaaaaacaa gattcaaata aaatacaatt | 120 |
| atctgataag gtactttcga agaaagaaga agttgtaacg gatagtcatg aggaagttaa | 180 |
| agttactgat gaggtaaaaa aatcaacgaa agaagaatcg aaacaattgc ttgaagtatt | 240 |

```
gaaaacaaag gaagaacatc agaaagaaat acagtatgaa atattacaaa aaactatacc    300
aacattcgaa cctaaagaga cgatattgag aaaattagag gatattaaac cagaactagc    360
gaaaaaacag actaagctat ttagaatatt tgaaccgaaa caattaccga tttatagagc    420
aaatggagag agagaattac gtaatagatg gtattggaaa ttaaaaaaag atacactacc    480
agacggagac tatgatgtga gagagtattt tctgaatttg tatgatcaag tgcttactga    540
aatgccagac tacttattat tgaaagatat ggcagtagaa aataagaact ctagggatgc    600
aggtaaagtc gttgattcag aaacggctaa tatatgcgat gccatatttc aagatgaaga    660 aacgaaggt  gccgttagaa gattcattgc agaaatgaga cagcgtgtgc aagctgatag    720
aaatgttgtc aattatccat caatattaca tccaatagat tatgcattta atgaatactt    780
tttacaacat caattggttg aaccattgaa taatgatata atatttaatt atataccaga    840
aaggataaga aatgatgtta attatattct caatatggac agaaatttac catcaactgc    900
cagatatata agacctaatt tacttcaaga tagattgaat ttgcacgata attttgaatc    960
actatgggat acaataacta catcaaatta tattttggcg agatcggtag taccagattt    1020
aaaagaatta gtttcaacgg aagcacaaat tcagaaaatg tcacaagatt tgcaattaga    1080
agcattaaca attcagtcag aaacacagtt tctaacaggt ataaattcac aagcagctaa    1140
cgattgtttt aaaaccttaa ttgcagcaat gttaagtcaa cgtactatgt cattagattt    1200
tgtaactact aattatatgt cattgatttc aggtatgtgg ctattgacgg tcgtgccaaa    1260
tgatatgttt ataagggaat cattagtcgc gtgtcaacta gctatagtaa atacgataat    1320
ctatccagca tttggaatgc aacgaatgca ttatagaaac ggagatccac aaacaccgtt    1380
tcagatagca gaacagcaaa ttcaaaattt ccaagtcgca aattggttac attttgttaa    1440
taataatcaa tttagacagg cagttattga tggtgtattg aatcaggtac tgaatgacaa    1500
tattagaaat ggtcatgtta ttaatcaact gatggaagct ctaatgcagc tgtcgcgaca    1560
acaatttcca accatgccaa ttgattataa agatcaatt  caacgtggaa tattactgtt    1620
atctaacaga cttggtcagt tagttgattt aactagatta ttagcttaca attatgagac    1680
attaatggca tgcattacaa tgaacatgca acatgttcaa accttaacaa cagaaaaatt    1740
acaactaaca tcagttacat cattatgtat gcttattgga aatgcgactg ttattccaag    1800
tccacaaaca ttatttcatt attataacgt taacgttaat tttcattcaa attacaatga    1860
gagaattaat gatgcagtag ctataataac tgctgccaac agattgaatc tatatcagaa    1920
aaagatgaag gctattgttg aggatttctt aaaaagatta tacattttg atgtatctag    1980 agttcctgac gaccaaatgt atagattaag ggatagatta cgtttattgc cagtagaaat    2040
cagaagatta gatatcttca atctaatact aatgaacatg gatcaaattg aacgtgcctc    2100
agataaaatt gctcaaggtg tgatcattgc ttatcgtgac atgcatcttg aaagagatga    2160
gatgtacgga tatgtaaata tagctagaaa tttagtggaa tttcaacaga taaatctaga    2220
ggagctgatg agatcaggtg actatgcgca aataactaac atgctttgga ataatcaacc    2280
agtagcattg gttggagcac ttccatttat tactgattca tcagttatat cgctgatagc    2340
aaaacttgac gctacagtgt tcgctcaaat agttaaatta cgaaaagttg atactttaaa    2400
accaatatta tacaaaataa attcagactc aaatgacttt tatttagtag ccaattatga    2460
ttgggtgcca acttcgacta caaaagtata caaacaggtt ccgcaacagt ttgattttag    2520
aaattcaatg catatgttaa cttcgaatct tacttttacg gttattcag  atcttctcgc    2580
```

-continued

| | |
|---|---|
| gttcgtatca gctgacacag tagaacctat aaatgcagtt gcatttgaca atatgcgcat | 2640 |
| catgaacgaa ttgtagacgc caaccccact gtggagatat gacc | 2684 |

<210> SEQ ID NO 105
<211> LENGTH: 2684
<212> TYPE: DNA
<213> ORGANISM: Human rotavirus

<400> SEQUENCE: 105

| | |
|---|---|
| ggctattaaa ggctcaatgg cgtacaggaa acgtggagcg cgccgtgagg cgaacttaaa | 60 |
| taataatgat cgaatgcagg agaaaattga tgaaaaacaa gattcaaata aaatacaatt | 120 |
| atctgataag gtactttcga agaaagaaga agttgtaacg gatagtcatg aggaagttaa | 180 |
| agttactgat gaggtaaaaa aatcaacgaa agaagaatcg aaacaattgc ttgaagtatt | 240 |
| gaaaacaaag gaagaacatc agaaagaaat acagtatgaa atattacaaa aaactatacc | 300 |
| aacattcgaa cctaaagaga cgatattgag aaaattagag gatattaaac cagaactagc | 360 |
| gaaaaaacag actaagctat ttagaatatt tgaaccgaaa caattaccga tttatagagc | 420 |
| aaatggagag agagaattac gtaatagatg gtattggaaa ttaaaaaaag atacactacc | 480 |
| agacggagac tatgatgtga gagagtattt tctgaatttg tatgatcaag tgcttactga | 540 |
| aatgccagac tacttattat tgaaagatat ggcagtagaa aataagaact ctagggatgc | 600 |
| aggtaaagtc gttgattcag aaacggctaa tatatgcgat gccatatttc aagatgaaga | 660 |
| aacggaaggt gccgttagaa gattcattgc agaaatgaga cagcgtgtgc aagctgatag | 720 |
| aaatgttgtc aattatccat caatattaca tccaatagat tatgcattta atgaatactt | 780 |
| tttacaacat caattggttg aaccattgaa taatgatata atatttaatt atataccaga | 840 |
| aaggataaga aatgatgtta attatattct caatatggac agaaatttac catcaactgc | 900 |
| cagatatata agacctaatt tacttcaaga tagattgaat ttgcacgata attttgaatc | 960 |
| actatgggat acaataacta catcaaatta tattttggcg agatcggtag taccagattt | 1020 |
| aaaagaatta gtttcaacgg aagcacaaat tcagaaaatg tcacaagatt tgcaattaga | 1080 |
| agcattaaca attcagtcag aaacacagtt tctaacaggt ataaattcac aagcagctaa | 1140 |
| cgattgtttt aaaaccttaa ttgcagcaat gttaagtcaa cgtactatgt cattagattt | 1200 |
| tgtaactact aattatatgt cattgatttc aggtatgtgg ctattgacgg tcgtgccaaa | 1260 |
| tgatatgttt ataagggaat cattagtcgc gtgtcaacta gctatagtaa atacgataat | 1320 |
| ctatccagca tttggaatgc aacgaatgca ttatagaaac ggagatccac aaacaccgtt | 1380 |
| tcagatagca gaacagcaaa ttcaaaattt ccaagtcgca aattggttac attttgttaa | 1440 |
| taataatcaa tttagacagg cagttattga tggtgtattg aatcaggtac tgaatgacaa | 1500 |
| tattagaaat ggtcatgtta ttaatcaact gatggaagct ctaatgcagc tgtcgcgaca | 1560 |
| acaatttcca accatgccaa ttgattataa gagatcaatt caacgtggaa tattactgtt | 1620 |
| atctaacaga cttggtcagt tagttgattt aactagatta ttagcttaca attatgagac | 1680 |
| attaatggca tgcattacaa tgaacatgca acatgttcaa accttaacaa cagaaaaatt | 1740 |
| acaactaaca tcagttacat cattatgtat gctattggga aatgcgactg ttattccaag | 1800 |
| tccacaaaca ttatttcatt attataacgt taacgttaat tttcattcaa attacaatga | 1860 |
| gagaattaat gatgcagtag ctataataac tgctgccaac agattgaatc tatatcagaa | 1920 |
| aaagatgaag gctattgttg aggatttctt aaaaagatta tacatttttg atgtatctag | 1980 |
| agttcctgac gaccaaatgt atagattaag ggatagatta cgtttattgc cagtagaaat | 2040 |

-continued

```
cagaagatta gatatcttca atctaatact aatgaacatg gatcaaattg aacgtgcctc    2100
agataaaatt gctcaaggtg tgatcattgc ttatcgtgac atgcatcttg aaagagatga    2160
gatgtacgga tatgtaaata tagctagaaa tttagatgga tttcaacaga taaatctaga    2220
ggagctgatg agatcaggtg actatgcgca ataactaac atgcttttga ataatcaacc     2280
agtagcattg gttggagcac ttccatttat tactgattca tcagttatat cgctgatagc    2340
aaaacttgac gctacagtgt tcgctcaaat agttaaatta cgaaaagttg atactttaaa    2400
accaatatta tacaaaataa attcagactc aaatgacttt tatttagtag ccaattatga    2460
ttgggtgcca acttcgacta caaaagtata caaacaggtt ccgcaacagt ttgattttag    2520
aaattcaatg catatgttaa cttcgaatct tacttttacg gtttattcag atcttctcgc    2580
gttcgtatca gctgacacag tagaacctat aaatgcagtt gcatttgaca atatgcgcat    2640
catgaacgaa ttgtagacgc caaccccact gtggagatat gacc                    2684
```

<210> SEQ ID NO 106
<211> LENGTH: 879
<212> TYPE: PRT
<213> ORGANISM: Human rotavirus

<400> SEQUENCE: 106

```
Met Ala Tyr Arg Lys Arg Gly Ala Arg Arg Glu Ala Asn Leu Asn Asn
1               5                   10                  15

Asn Asp Arg Met Gln Glu Lys Asn Asp Glu Lys Gln Asp Ser Asn Lys
            20                  25                  30

Ile Gln Leu Ser Asp Lys Val Leu Ser Lys Lys Glu Ile Val Thr
        35                  40                  45

Asp Ser His Glu Glu Val Lys Ile Thr Asp Val Lys Lys Ser Thr
    50                  55                  60

Lys Glu Glu Ser Lys Gln Leu Leu Glu Val Leu Lys Thr Lys Glu Glu
65                  70                  75                  80

His Gln Lys Glu Ile Gln Tyr Glu Ile Leu Gln Lys Thr Ile Pro Thr
                85                  90                  95

Phe Glu Pro Lys Glu Thr Ile Leu Lys Lys Leu Glu Asp Ile Lys Pro
            100                 105                 110

Glu Leu Ala Lys Lys Gln Thr Lys Leu Phe Arg Ile Phe Glu Pro Lys
        115                 120                 125

Gln Leu Pro Ile Tyr Arg Ala Asn Gly Glu Arg Glu Leu Arg Asn Arg
    130                 135                 140

Trp Cys Trp Lys Leu Lys Lys Asp Thr Leu Pro Asp Gly Asp Tyr Asp
145                 150                 155                 160

Val Arg Glu Tyr Phe Leu Asn Leu Tyr Asp Gln Val Leu Thr Glu Met
                165                 170                 175

Pro Asp Tyr Leu Leu Leu Lys Asp Met Ala Val Glu Asn Lys Asn Ser
            180                 185                 190

Arg Asp Ala Gly Lys Val Val Asp Ser Glu Thr Ala Ser Ile Cys Asp
        195                 200                 205

Ala Ile Phe Gln Asp Glu Glu Thr Glu Gly Ala Val Arg Arg Phe Ile
    210                 215                 220

Ala Glu Met Arg Gln Arg Val Gln Ala Asp Arg Asn Val Val Asn Tyr
225                 230                 235                 240

Pro Ser Ile Leu His Pro Ile Asp Tyr Ala Phe Asn Glu Tyr Phe Leu
                245                 250                 255
```

```
Gln His Gln Leu Val Glu Pro Leu Asn Asn Asp Ile Ile Phe Asn Tyr
            260                 265                 270

Ile Pro Glu Arg Ile Arg Asn Asp Val Asn Tyr Ile Leu Asn Met Asp
        275                 280                 285

Arg Asn Leu Pro Ser Thr Ala Arg Tyr Ile Arg Pro Asn Leu Leu Gln
    290                 295                 300

Asp Arg Leu Asn Leu His Asp Asn Phe Glu Ser Leu Trp Asp Thr Ile
305                 310                 315                 320

Thr Thr Ser Asn Tyr Ile Leu Ala Arg Ser Ile Val Pro Asp Leu Lys
                325                 330                 335

Glu Leu Val Ser Thr Glu Ala Gln Ile Gln Lys Met Ser Gln Asp Leu
            340                 345                 350

Gln Leu Glu Ala Leu Thr Ile Gln Ser Glu Thr Gln Phe Leu Thr Gly
        355                 360                 365

Ile Asn Ser Gln Ala Ala Asn Asp Cys Phe Lys Thr Leu Ile Ala Ala
    370                 375                 380

Met Leu Ser Gln Arg Thr Met Ser Leu Asp Phe Val Thr Thr Asn Tyr
385                 390                 395                 400

Met Ser Leu Ile Ser Gly Met Trp Leu Leu Thr Val Ile Pro Asn Asp
                405                 410                 415

Met Phe Ile Arg Glu Ser Leu Val Ala Cys Gln Leu Ala Ile Val Asn
            420                 425                 430

Thr Ile Ile Tyr Pro Ala Phe Gly Met Gln Arg Met His Tyr Arg Asn
        435                 440                 445

Gly Asp Pro Gln Thr Pro Phe Gln Ile Ala Glu Gln Gln Ile Gln Asn
450                 455                 460

Phe Gln Val Ala Asn Trp Leu His Phe Val Asn Asn Asn Gln Phe Arg
465                 470                 475                 480

Gln Ala Val Ile Asp Gly Val Leu Asn Gln Val Leu Asn Asp Asn Ile
                485                 490                 495

Arg Ser Gly His Val Ile Asn Gln Leu Met Glu Ala Leu Met Gln Leu
            500                 505                 510

Ser Arg Gln Gln Phe Pro Thr Met Pro Val Asp Tyr Lys Arg Ser Ile
        515                 520                 525

Gln Arg Gly Ile Leu Leu Ser Asn Arg Leu Gly Gln Leu Val Asp
    530                 535                 540

Leu Thr Arg Leu Leu Ala Tyr Asn Tyr Glu Thr Leu Met Ala Cys Ile
545                 550                 555                 560

Thr Met Asn Met Gln His Val Gln Thr Leu Thr Thr Glu Lys Leu Gln
                565                 570                 575

Leu Thr Ser Val Thr Ser Leu Cys Met Leu Ile Gly Asn Ala Thr Val
            580                 585                 590

Ile Pro Ser Pro Gln Thr Leu Phe His Tyr Tyr Asn Val Asn Val Asn
        595                 600                 605

Phe His Ser Asn Tyr Asn Glu Arg Ile Asn Asp Ala Val Ala Ile Ile
    610                 615                 620

Thr Ala Ala Asn Arg Leu Asn Leu Tyr Gln Lys Lys Met Lys Ala Ile
625                 630                 635                 640

Val Glu Asp Phe Leu Lys Arg Leu Tyr Ile Phe Asp Val Ser Arg Val
                645                 650                 655

Pro Asp Asp Gln Met Tyr Arg Leu Arg Asp Arg Leu Arg Leu Leu Pro
            660                 665                 670

Val Glu Ile Arg Arg Leu Asp Ile Phe Asn Leu Ile Leu Met Asn Met
```

```
              675                 680                 685
Asp Gln Ile Glu Arg Ala Ser Asp Lys Ile Ala Gln Gly Val Ile Ile
690                 695                 700

Ala Tyr Arg Asp Met His Leu Glu Arg Asp Glu Met Tyr Gly Tyr Val
705                 710                 715                 720

Asn Ile Ala Arg Asn Leu Asp Gly Phe Gln Gln Ile Asn Leu Glu Glu
                725                 730                 735

Leu Met Arg Ser Gly Asp Tyr Ala Gln Ile Thr Asn Met Leu Leu Asn
                740                 745                 750

Asn Gln Pro Val Ala Leu Val Gly Ala Leu Pro Phe Ile Thr Asp Ser
                755                 760                 765

Ser Val Ile Ser Leu Ile Ala Lys Leu Asp Ala Thr Val Phe Ala Gln
                770                 775                 780

Ile Val Lys Leu Arg Lys Val Asp Thr Leu Lys Pro Ile Leu Tyr Lys
785                 790                 795                 800

Ile Asn Ser Asp Ser Asn Asp Phe Tyr Leu Val Ala Asn Tyr Asp Trp
                805                 810                 815

Val Pro Thr Ser Thr Thr Lys Val Tyr Lys Gln Val Pro Gln Gln Phe
                820                 825                 830

Asp Phe Arg Asn Ser Met His Met Leu Thr Ser Asn Leu Thr Phe Thr
                835                 840                 845

Val Tyr Ser Asp Leu Leu Ala Phe Val Ser Ala Asp Thr Val Glu Pro
                850                 855                 860

Ile Asn Ala Val Ala Phe Asp Asn Met Arg Ile Met Asn Glu Leu
865                 870                 875

<210> SEQ ID NO 107
<211> LENGTH: 879
<212> TYPE: PRT
<213> ORGANISM: Human rotavirus

<400> SEQUENCE: 107

Met Ala Tyr Arg Lys Arg Gly Ala Arg Arg Glu Ala Asn Leu Asn Asn
1               5                   10                  15

Asn Asp Arg Met Gln Glu Lys Ile Asp Glu Lys Gln Asp Ser Asn Lys
                20                  25                  30

Ile Gln Leu Ser Asp Lys Val Leu Ser Lys Lys Glu Glu Val Val Thr
                35                  40                  45

Asp Ser His Glu Glu Val Lys Val Thr Asp Glu Val Lys Lys Ser Thr
50                  55                  60

Lys Glu Glu Ser Lys Gln Leu Leu Glu Val Leu Lys Thr Lys Glu Glu
65                  70                  75                  80

His Gln Lys Glu Ile Gln Tyr Glu Ile Leu Gln Lys Thr Ile Pro Thr
                85                  90                  95

Phe Glu Pro Lys Glu Thr Ile Leu Arg Lys Leu Glu Asp Ile Lys Pro
                100                 105                 110

Glu Leu Ala Lys Lys Gln Thr Lys Leu Phe Arg Ile Phe Glu Pro Lys
                115                 120                 125

Gln Leu Pro Ile Tyr Arg Ala Asn Gly Glu Arg Glu Leu Arg Asn Arg
                130                 135                 140

Trp Tyr Trp Lys Leu Lys Lys Asp Thr Leu Pro Asp Gly Asp Tyr Asp
145                 150                 155                 160

Val Arg Glu Tyr Phe Leu Asn Leu Tyr Asp Gln Val Leu Thr Glu Met
                165                 170                 175
```

```
Pro Asp Tyr Leu Leu Lys Asp Met Ala Val Glu Asn Lys Asn Ser
            180                 185                 190

Arg Asp Ala Gly Lys Val Val Asp Ser Glu Thr Ala Asn Ile Cys Asp
        195                 200                 205

Ala Ile Phe Gln Asp Glu Glu Thr Glu Gly Ala Val Arg Arg Phe Ile
210                 215                 220

Ala Glu Met Arg Gln Arg Val Gln Ala Asp Arg Asn Val Val Asn Tyr
225                 230                 235                 240

Pro Ser Ile Leu His Pro Ile Asp Tyr Ala Phe Asn Glu Tyr Phe Leu
            245                 250                 255

Gln His Gln Leu Val Glu Pro Leu Asn Asn Asp Ile Ile Phe Asn Tyr
            260                 265                 270

Ile Pro Glu Arg Ile Arg Asn Asp Val Asn Tyr Ile Leu Asn Met Asp
        275                 280                 285

Arg Asn Leu Pro Ser Thr Ala Arg Tyr Ile Arg Pro Asn Leu Leu Gln
290                 295                 300

Asp Arg Leu Asn Leu His Asp Asn Phe Glu Ser Leu Trp Asp Thr Ile
305                 310                 315                 320

Thr Thr Ser Asn Tyr Ile Leu Ala Arg Ser Val Val Pro Asp Leu Lys
            325                 330                 335

Glu Leu Val Ser Thr Glu Ala Gln Ile Gln Lys Met Ser Gln Asp Leu
            340                 345                 350

Gln Leu Glu Ala Leu Thr Ile Gln Ser Glu Thr Gln Phe Leu Thr Gly
        355                 360                 365

Ile Asn Ser Gln Ala Ala Asn Asp Cys Phe Lys Thr Leu Ile Ala Ala
370                 375                 380

Met Leu Ser Gln Arg Thr Met Ser Leu Asp Phe Val Thr Thr Asn Tyr
385                 390                 395                 400

Met Ser Leu Ile Ser Gly Met Trp Leu Leu Thr Val Pro Asn Asp
            405                 410                 415

Met Phe Ile Arg Glu Ser Leu Val Ala Cys Gln Leu Ala Ile Val Asn
            420                 425                 430

Thr Ile Ile Tyr Pro Ala Phe Gly Met Gln Arg Met His Tyr Arg Asn
        435                 440                 445

Gly Asp Pro Gln Thr Pro Phe Gln Ile Ala Glu Gln Ile Gln Asn
450                 455                 460

Phe Gln Val Ala Asn Trp Leu His Phe Val Asn Asn Gln Phe Arg
465                 470                 475                 480

Gln Ala Val Ile Asp Gly Val Leu Asn Gln Val Leu Asn Asp Asn Ile
            485                 490                 495

Arg Asn Gly His Val Ile Asn Gln Leu Met Glu Ala Leu Met Gln Leu
            500                 505                 510

Ser Arg Gln Gln Phe Pro Thr Met Pro Ile Asp Tyr Lys Arg Ser Ile
        515                 520                 525

Gln Arg Gly Ile Leu Leu Ser Asn Arg Leu Gly Gln Leu Val Asp
530                 535                 540

Leu Thr Arg Leu Leu Ala Tyr Asn Tyr Glu Thr Leu Met Ala Cys Ile
545                 550                 555                 560

Thr Met Asn Met Gln His Val Gln Thr Thr Glu Lys Leu Gln
            565                 570                 575

Leu Thr Ser Val Thr Ser Leu Cys Met Leu Ile Gly Asn Ala Thr Val
            580                 585                 590

Ile Pro Ser Pro Gln Thr Leu Phe His Tyr Tyr Asn Val Asn Val Asn
```

```
                    595                 600                 605
            Phe His Ser Asn Tyr Asn Glu Arg Ile Asn Asp Ala Val Ala Ile Ile
                610                 615                 620

Thr Ala Ala Asn Arg Leu Asn Leu Tyr Gln Lys Lys Met Lys Ala Ile
            625                 630                 635                 640

Val Glu Asp Phe Leu Lys Arg Leu Tyr Ile Phe Asp Val Ser Arg Val
                                645                 650                 655

Pro Asp Asp Gln Met Tyr Arg Leu Arg Asp Arg Leu Arg Leu Leu Pro
                            660                 665                 670

Val Glu Ile Arg Arg Leu Asp Ile Phe Asn Leu Ile Leu Met Asn Met
                        675                 680                 685

Asp Gln Ile Glu Arg Ala Ser Asp Lys Ile Ala Gln Gly Val Ile Ile
                    690                 695                 700

Ala Tyr Arg Asp Met His Leu Glu Arg Asp Glu Met Tyr Gly Tyr Val
            705                 710                 715                 720

Asn Ile Ala Arg Asn Leu Asp Gly Phe Gln Gln Ile Asn Leu Glu Glu
                                725                 730                 735

Leu Met Arg Ser Gly Asp Tyr Ala Gln Ile Thr Asn Met Leu Leu Asn
                            740                 745                 750

Asn Gln Pro Val Ala Leu Val Gly Ala Leu Pro Phe Ile Thr Asp Ser
                        755                 760                 765

Ser Val Ile Ser Leu Ile Ala Lys Leu Asp Ala Thr Val Phe Ala Gln
                    770                 775                 780

Ile Val Lys Leu Arg Lys Val Asp Thr Leu Lys Pro Ile Leu Tyr Lys
            785                 790                 795                 800

Ile Asn Ser Asp Ser Asn Asp Phe Tyr Leu Val Ala Asn Tyr Asp Trp
                                805                 810                 815

Val Pro Thr Ser Thr Thr Lys Val Tyr Lys Gln Val Pro Gln Gln Phe
                            820                 825                 830

Asp Phe Arg Asn Ser Met His Met Leu Thr Ser Asn Leu Thr Phe Thr
                        835                 840                 845

Val Tyr Ser Asp Leu Leu Ala Phe Val Ser Ala Asp Thr Val Glu Pro
                    850                 855                 860

Ile Asn Ala Val Ala Phe Asp Asn Met Arg Ile Met Asn Glu Leu
            865                 870                 875

<210> SEQ ID NO 108
<211> LENGTH: 879
<212> TYPE: PRT
<213> ORGANISM: Human rotavirus

<400> SEQUENCE: 108

Met Ala Tyr Arg Lys Arg Gly Ala Arg Arg Glu Ala Asn Leu Asn Asn
1               5                   10                  15

Asn Asp Arg Met Gln Glu Lys Ile Asp Glu Lys Gln Asp Ser Asn Lys
                20                  25                  30

Ile Gln Leu Ser Asp Lys Val Leu Ser Lys Lys Glu Glu Val Val Thr
            35                  40                  45

Asp Ser His Glu Glu Val Lys Val Thr Asp Glu Val Lys Lys Ser Thr
        50                  55                  60

Lys Glu Glu Ser Lys Gln Leu Leu Glu Val Leu Lys Thr Lys Glu Glu
    65                  70                  75                  80

His Gln Lys Glu Ile Gln Tyr Glu Ile Leu Gln Lys Thr Ile Pro Thr
                85                  90                  95
```

```
Phe Glu Pro Lys Glu Thr Ile Leu Arg Lys Leu Glu Asp Ile Lys Pro
                100                 105                 110

Glu Leu Ala Lys Lys Gln Thr Lys Leu Phe Arg Ile Phe Glu Pro Lys
            115                 120                 125

Gln Leu Pro Ile Tyr Arg Ala Asn Gly Glu Arg Glu Leu Arg Asn Arg
        130                 135                 140

Trp Tyr Trp Lys Leu Lys Lys Asp Thr Leu Pro Asp Gly Asp Tyr Asp
145                 150                 155                 160

Val Arg Glu Tyr Phe Leu Asn Leu Tyr Asp Gln Val Leu Thr Glu Met
                165                 170                 175

Pro Asp Tyr Leu Leu Leu Lys Asp Met Ala Val Glu Asn Lys Asn Ser
            180                 185                 190

Arg Asp Ala Gly Lys Val Val Asp Ser Glu Thr Ala Asn Ile Cys Asp
        195                 200                 205

Ala Ile Phe Gln Asp Glu Glu Thr Glu Gly Ala Val Arg Arg Phe Ile
210                 215                 220

Ala Glu Met Arg Gln Arg Val Gln Ala Asp Arg Asn Val Val Asn Tyr
225                 230                 235                 240

Pro Ser Ile Leu His Pro Ile Asp Tyr Ala Phe Asn Glu Tyr Phe Leu
                245                 250                 255

Gln His Gln Leu Val Glu Pro Leu Asn Asn Asp Ile Ile Phe Asn Tyr
            260                 265                 270

Ile Pro Glu Arg Ile Arg Asn Asp Val Asn Tyr Ile Leu Asn Met Asp
        275                 280                 285

Arg Asn Leu Pro Ser Thr Ala Arg Tyr Ile Arg Pro Asn Leu Leu Gln
290                 295                 300

Asp Arg Leu Asn Leu His Asp Asn Phe Glu Ser Leu Trp Asp Thr Ile
305                 310                 315                 320

Thr Thr Ser Asn Tyr Ile Leu Ala Arg Ser Val Pro Asp Leu Lys
                325                 330                 335

Glu Leu Val Ser Thr Glu Ala Gln Ile Gln Lys Met Ser Gln Asp Leu
            340                 345                 350

Gln Leu Glu Ala Leu Thr Ile Gln Ser Glu Thr Gln Phe Leu Thr Gly
        355                 360                 365

Ile Asn Ser Gln Ala Ala Asn Asp Cys Phe Lys Thr Leu Ile Ala Ala
370                 375                 380

Met Leu Ser Gln Arg Thr Met Ser Leu Asp Phe Val Thr Thr Asn Tyr
385                 390                 395                 400

Met Ser Leu Ile Ser Gly Met Trp Leu Leu Thr Val Pro Asn Asp
                405                 410                 415

Met Phe Ile Arg Glu Ser Leu Val Ala Cys Gln Leu Ala Ile Val Asn
            420                 425                 430

Thr Ile Ile Tyr Pro Ala Phe Gly Met Gln Arg Met His Tyr Arg Asn
        435                 440                 445

Gly Asp Pro Gln Thr Pro Phe Gln Ile Ala Glu Gln Ile Gln Asn
450                 455                 460

Phe Gln Val Ala Asn Trp Leu His Phe Val Asn Asn Gln Phe Arg
465                 470                 475                 480

Gln Ala Val Ile Asp Gly Val Leu Asn Gln Val Leu Asn Asp Asn Ile
                485                 490                 495

Arg Asn Gly His Val Ile Asn Gln Leu Met Glu Ala Leu Met Gln Leu
            500                 505                 510

Ser Arg Gln Gln Phe Pro Thr Met Pro Ile Asp Tyr Lys Arg Ser Ile
```

```
                515                 520                 525
Gln Arg Gly Ile Leu Leu Ser Asn Arg Leu Gly Gln Leu Val Asp
    530                 535                 540

Leu Thr Arg Leu Leu Ala Tyr Asn Tyr Glu Thr Leu Met Ala Cys Ile
545                 550                 555                 560

Thr Met Asn Met Gln His Val Gln Thr Leu Thr Thr Glu Lys Leu Gln
                565                 570                 575

Leu Thr Ser Val Thr Ser Leu Cys Met Leu Ile Gly Asn Ala Thr Val
            580                 585                 590

Ile Pro Ser Pro Gln Thr Leu Phe His Tyr Tyr Asn Val Asn Val Asn
        595                 600                 605

Phe His Ser Asn Tyr Asn Glu Arg Ile Asn Asp Ala Val Ala Ile Ile
    610                 615                 620

Thr Ala Ala Asn Arg Leu Asn Leu Tyr Gln Lys Lys Met Lys Ala Ile
625                 630                 635                 640

Val Glu Asp Phe Leu Lys Arg Leu Tyr Ile Phe Asp Val Ser Arg Val
                645                 650                 655

Pro Asp Asp Gln Met Tyr Arg Leu Arg Asp Arg Leu Arg Leu Leu Pro
            660                 665                 670

Val Glu Ile Arg Arg Leu Asp Ile Phe Asn Leu Ile Leu Met Asn Met
        675                 680                 685

Asp Gln Ile Glu Arg Ala Ser Asp Lys Ile Ala Gln Gly Val Ile Ile
    690                 695                 700

Ala Tyr Arg Asp Met His Leu Glu Arg Asp Glu Met Tyr Gly Tyr Val
705                 710                 715                 720

Asn Ile Ala Arg Asn Leu Asp Gly Phe Gln Gln Ile Asn Leu Glu Glu
                725                 730                 735

Leu Met Arg Ser Gly Asp Tyr Ala Gln Ile Thr Asn Met Leu Leu Asn
            740                 745                 750

Asn Gln Pro Val Ala Leu Val Gly Ala Leu Pro Phe Ile Thr Asp Ser
        755                 760                 765

Ser Val Ile Ser Leu Ile Ala Lys Leu Asp Ala Thr Val Phe Ala Gln
    770                 775                 780

Ile Val Lys Leu Arg Lys Val Asp Thr Leu Lys Pro Ile Leu Tyr Lys
785                 790                 795                 800

Ile Asn Ser Asp Ser Asn Asp Phe Tyr Leu Val Ala Asn Tyr Asp Trp
                805                 810                 815

Val Pro Thr Ser Thr Thr Lys Val Tyr Lys Gln Val Pro Gln Gln Phe
            820                 825                 830

Asp Phe Arg Asn Ser Met His Met Leu Thr Ser Asn Leu Thr Phe Thr
        835                 840                 845

Val Tyr Ser Asp Leu Leu Ala Phe Val Ser Ala Asp Thr Val Glu Pro
    850                 855                 860

Ile Asn Ala Val Ala Phe Asp Asn Met Arg Ile Met Asn Glu Leu
865                 870                 875

<210> SEQ ID NO 109
<211> LENGTH: 2591
<212> TYPE: DNA
<213> ORGANISM: Human rotavirus

<400> SEQUENCE: 109
ggctattaaa gcagtactag tagtgtgttt tacctctgat ggtgtaaaca tgaaagtatt     60
agctttaaga catagtgtgg ctcagatata tgcagatact caggtgtaca cacatgatga    120
```

```
ctctaaagat gattatgaaa atgcgttctt aatttctaat ctcactacac ataatatatt      180
atatttaaat tatagtgtaa aaacactgca aatattgaat aaatccggta tagctgcaat      240
agagatacag aagatagatg agttattcac gctaattaga tgtaatttta catacgacta      300
tattgatgac gttgtctatt tacatgatta ttcatatatt gctaataatg aaatacggac      360
tgaccaatat tgggtaacca agacaaatat agaagactat ctattaccag gatggaaatt      420
gacatatgtt ggatacaatg gaagtgatac gagaggacat tataattttt cttttagatg      480
tcagaatgca gctacagatg atgatgtaat aatagagtat atctattcaa atgaattaga      540
cttccagaac tttatactca aaaagattaa agaaaggatg acaacatcac taccaatagc      600
aagactttca aatcgcgtat ttagagataa attatttaaa acgttgtcag taaatcatga      660
taaagtagtt aatgttggac ctagaaatga atctatgttt acttttttag accatccatc      720
aataaaacaa ttctctaatg gaccatattt ggttaaagat acaattaaac tcaaacaaga      780
gagatggctt ggtaaaagat tatcacagtt tgacattggt caatataaga atatgttaaa      840
tgtattaacg actttatatc aatattacga tatgtatcat gaaaaaccaa ttatatatat      900
gataggatca gcgccctcgt attggatata tgatgtcaaa cagtactctg acttgaaatt      960
tgagacatgg gatccactag atacaccata ttctaattta catcataagg aattatttta     1020
cataaatgac gtgcaaaaac ttaaagataa ttcgatacta tatatagata taagaacaga     1080
tagaggaaat atggactgga aggaatggcg aaaagtggtg aagggcaaa ctgctgacaa      1140 tttacatatt gcatataaat atctatctac aggaaaagct aagatatgtt gtgttaaaat     1200
gaccgctatg gatgtagaat taccaatatc tgcaaaactg cttcaccatc caactacaga     1260
aattagatca gagtttttatt taatgatgga tatatgggac tccaaaaata ttaaaagatt     1320
cataccaaaa ggtgtattat actcatatat aaacaataca attactgaaa acgtatttat     1380
acaacaacct tttaagttga aaacattgaa aaatgaatat gtaatagcac tttatgcttt     1440
atcaaatgat cttaacaata gagaagatgt ggtaaaacta atcaataatc agaaaagagc     1500
gttaataacg gtgagaatta acaatacatt taaagatgaa ccgaaagtcg gatttaaaaa     1560
catttacgat tggacatttt tgccaacgga ttttgagatg aatggatcaa taattacctc     1620
atatgatgga tgtctaggta tttttggttt atcaatatca ctagcttcaa aaccaaccgg     1680
taataatcat ttattcattt taagtggtac ggacaagtat tttaaattgg atcaattcgc     1740
aaatcatatg agtatatcac gacgatcaca tcagatacga ttttctgagt cagccacttc     1800
atactcggga tacattttta gagatttgtc taataataat ttcaatttaa taggtacgaa     1860
tgtagagaat tcagtatccg gacacgtata taatgcattg atttattata gatataatta     1920
ctcatttgac cttaaacgat ggatatactt acattcaaca ggtaaagcta gcattgaagg     1980
tggtaagtat tatgaacatg ctccaataga attaatttat gcatgcaggt cagcaagaga     2040
attcgcgaaa ttgcaagatg atttaacagt attaagatat tcaaatgaga tagaaaacta     2100
tatcaataaa gttatagta taacatacgc cgacgaccct aattacttta ttggaattaa      2160
gtttaaaaat attccttaca agtataacgt taaagtacca catctcacat ttggcgtgtt     2220
aaatatttct gaacagatgt taccagatgc aatagcaatt ttaaagaaat taagaatga     2280 actatttgga atggacataa caacgagtta tacatatatg ttatctgatg aggtgtatgt     2340
agcaaatata agtggtgtac tatcaacata tttcaaaatt tacaacgcgt tttataaaga     2400
acaaattaca tttggacagt caagaatgtt tattccccat gtaacgttga gttttagtaa     2460
```

```
tgagaaaaca gtgagaatag acactacaaa attgtacata gattccattt atctaagaaa    2520
aataaaaggt gacacagtgt ttgatatgac tgagtgagct aaaaacttaa cacactagtc    2580
atgatgtgac c                                                         2591

<210> SEQ ID NO 110
<211> LENGTH: 2591
<212> TYPE: DNA
<213> ORGANISM: Human rotavirus

<400> SEQUENCE: 110
ggctattaaa gcagtaccag tagtgtgttt tacctctgat ggtgtaaaca tgaaagtatt      60
agctttaaga catagtgtgg ctcaggtgta tgcagacact caggtgtaca cacatgatga     120
ttctaaagat gagtatgaga acgcattctt aatttctaat ctcaccacac ataatatatt     180
atatttaaat tataatgtaa aaacgttaca aatattaaat aaatctggta tagctgcaat     240
agagatacag aagatagatg aattattcac gttaattaga tgtaacttta catatgatta     300
cattgatgat gttgtttact tacatgacta ctcatattat actaataatg aaatacgaac     360
tgaccaacat tggataacca agacaaatat agaagattat ttattaccag gatggaagct     420
gacatacgtt ggatataatg aagtgatac gcgcggacat tataattttt catttagatg      480
tcaaaatgcg gctacagatg atgatgcaat aatagagtat atctattcag atgaattaga     540
cttccagagt tttatactca agaagattaa agaaggatg acaacatcac taccaatagc      600
aagactctca aatcgcgtat ttagagataa gttatttaaa acgttatcag taaatcatga     660
taaagtagtt aatattgggc ccagaaatga atctatgttt acttttttag actatccatc     720
aataaaacag ttctcaaatg gaccgtattt agttaaagat acaattaaac tcaaacaaga     780
gagatggctt ggtaaaagat tatcgcagtt tgatattggt caatataaga atatgctaaa     840
tgtattaacc actttgtatc aatattatga tatatatcat gaaaaaccaa tcatatatat     900
gataggatca gcgccttcgt attggatata tgacgtcaaa cagtattcta acttgaaatt     960
tgaaacgtgg gatccactag atacaccata ctctaattta catcataagg aattattttta    1020 cataaatgac gtgcaaaaac ttaaagataa ttcaatacta tatatagata tacgaacaga    1080
tagaggaact gtagactgga aggaatggcg aaaaatagtg gaaaggcaaa ctattgacaa    1140
cttgcgtatt gcatacaaat atctatctac agggaaagct aaagtatgtt gcgttaaaat    1200
gaccgctatg gatttagaat taccgatatc tgcaaagttg cttcaccatc caactacaga    1260
gattagatca gagtttttatc tagtgatgga tatatgggac tctaaaaata ttaaaagatt    1320
cataccaaaa ggtgtattat actcgtatat aaacaataca attactgaaa acgtattcat    1380
acaacaacct tttaagttaa aaacattgaa aaacgaatat ataatagcac tttatgcttt    1440
atcaaatgat tttaacaaca gagaagatgt ggtgaaacta attaataatc agaaaaaagc    1500
gttaatgaca gtgagaatta ataatacgtt taaagatgaa ccaaaagtcg gatttaaaaa    1560
catttacgat tggacatttc taccaacgga ttttgagact aatggatcaa taattacttc    1620
atatgatggg tgtctaggta tctttggttt atcaatatcg ctagcttcaa aaccaactgg    1680
taataatcat ttgttcattt taagtggaac agacaagtat tttaaactgg atcaatttgc    1740
aaatcatatg agcatatcac gacgatcaca tcaaataaga ttttcggagt cagccacttc    1800
atattcggga tatattttta gggatttgtc taataataat ttcaatttaa taggtacgaa    1860
tgtagagaat tcagtatccg gacacgtata taatgcattg atttattata gatataatta    1920
ttcatttgac cttaaacgat ggatatactt acattcaaca ggtaaagcta gtattgaagg    1980
```

| | |
|---|---|
| tggtaagtat tatgaacatg ctccaattga attgatttat gcatgcagat cagcgagaga | 2040 |
| atttgcgaaa ctgcaagatg atttaacggt attaagatat tcaaatgaga tagaaaacta | 2100 |
| tattaacaaa gtttatagca taacatacgc cgatgatcct aattacttta ttggagttaa | 2160 |
| gtttaaaaat attccttata agtacaacgt taaaatacca catctcacat ttggcgtgtt | 2220 |
| aaatatttct gaacaaatgc taccagatgt aataacgatt ttaaagagat ttaaaaatga | 2280 |
| gttatttgga atggaaataa caacgagtta tacgtacatg ttatctgatg aggtgtatgt | 2340 |
| agcaaatata agtggtgtac tgtcaacata tttcaaaatt tataatgcgt tttataaaga | 2400 |
| gcaaatcaca tttggacaat caagaatgtt tattcctcat gtaacgttga gttttagtaa | 2460 |
| tgagaaaacg gtgagaatag acatcacaaa actgtacata gattctattt acttaagaaa | 2520 |
| aataaaaggt gacacggtgt ttgatatgac tgggtgagct aaaaacttaa cacactagtc | 2580 |
| atgatgtgac c | 2591 |

<210> SEQ ID NO 111
<211> LENGTH: 2591
<212> TYPE: DNA
<213> ORGANISM: Human rotavirus

<400> SEQUENCE: 111

| | |
|---|---|
| ggctattaaa gcagtaccag tagtgtgttt tacctctgat ggtgtaaaca tgaaagtatt | 60 |
| agctttaaga catagtgtgg ctcaggtgta tgcagacact caggtgtaca cacatgatga | 120 |
| ttctaaagat gagtatgaga acgcattctt aatttctaat ctcaccacac ataatatatt | 180 |
| atatttaaat tataatgtaa aaacgttaca aatattaaat aaatctggta tagctgcaat | 240 |
| agagatacag aagatagatg aattattcac gttaattaga tgtaacttta catatgatta | 300 |
| cattgatgat gttgtttact tacatgacta ctcatattat actaataatg aaatacgaac | 360 |
| tgaccaacat tggataacca agacaaatat agaagattat ttattaccag gatggaagct | 420 |
| gacatacgtt ggatataatg gaagtgatac gcgcggacat tataattttt catttagatg | 480 |
| tcaaaatgcg gctacagatg atgatgcaat aatagagtat atctattcag atgaattaga | 540 |
| cttccagagt tttatactca agaagattaa agaaggatg acaacatcac taccaatagc | 600 |
| aagactctca aatcgcgtat ttagagataa gttatttaaa acgttatcag taaatcatga | 660 |
| taaagtagtt aatattgggc ccagaaatga atctatgttt acttttttag actatccatc | 720 |
| aataaaacag ttctcaaatg gaccgtattt agttaaagac acaattaaac tcaaacaaga | 780 |
| gagatggctt ggtaaaagat tatcgcagtt tgatattggt caatataaga atatgctaaa | 840 |
| tgtattaacc actttgtatc aatattatga tatatcat gaaaaaccaa tcatatatat | 900 |
| gataggatca gcgccttcgt attggatata tgacgtcaaa cagtattcta acttgaaatt | 960 |
| tgaaacgtgg gatccactag atacaccata ctctaattta catcataagg aattattta | 1020 |
| cataaatgac gtgcaaaaac ttaaagataa ttcaatacta tatatagata tacgaacaga | 1080 |
| tagaggaact gtagactgga aggaatggcg aaaaatagtg gaaaggcaaa ctattgacaa | 1140 |
| ctcgcgtatt gcatacaaat atctatctac agggaaagct aaagtatgtt gcgttaaaat | 1200 |
| gaccgctatg gatttagaat taccgatatc tgcaaagttg cttcaccatc caactacaga | 1260 |
| gattagatca gagttttatc tagtgatgga tatatgggac tctaaaaata ttaaaagatt | 1320 |
| cataccaaaa ggtgtattat actcgtatat aaacaataca attactgaaa acgtattcat | 1380 |
| acaacaacct tttaagttaa aaacattgaa aaacgaatat ataatagcac tttatgcttt | 1440 |

-continued

```
atcaaatgat tttaacaaca gagaagatgt ggtgaaacta attaataatc agaaaaaagc    1500
gttaatgaca gtgagaatta ataatacgtt taaagatgaa ccaaaagtcg gatttaaaaa    1560
catttacgat tggacatttc taccaacgga ttttgagact aatggatcaa taattacttc    1620
atatgatggg tgtctaggta tctttggttt atcaatatcg ctagcttcaa aaccaactgg    1680
taataatcat ttgttcattt taagtggaac agacaagtat tttaaactgg atcaatttgc    1740
aaatcatatg agcatatcac gacgatcaca tcaaataaga ttttcggagt cagccacttc    1800
atattcggga tatatttta gggatttgtc taataataat ttcaatttaa taggtacgaa    1860
tgtagagaat tcagtatccg ggcacgtata taatgcattg atttattata gatataatta    1920
ttcatttgac cttaaacgat ggatatactt acattcaaca ggtaaagcta gtattgaagg    1980
tggtaagtat tatgaacatg ctccaattga attgatttat gcatgcagat cagcgagaga    2040
atttgcgaaa ctgcaagatg atttaacggt attaagatat tcaaatgaga tagaaaacta    2100
tattaacaaa gtttatagca taacatacgc cgatgatcct aattacttta ttggagttaa    2160
gtttaaaaat attccttata agtacaacgt taaaatacca catctcacat ttggcgtgtt    2220
aaatatttct gaacaaatgc taccagatgt aataacgatt ttaaagagat ttaaaaatga    2280
gttatttgga atggaaataa caacgagtta tacgtacatg ttatctgatg aggtgtatgt    2340
agcaaatata agtggtgtac tgtcaacata tttcaaaatt tataatgcgt tttataaaga    2400
gcaaatcaca tttggacaat caagaatgtt tattcctcat gtaacgttga gttttagtaa    2460
tgagaaaacg gtgagaatag acatcacaaa actgtacata gattctattt acttaagaaa    2520
aataaaaggt gacacggtgt ttgatatgac tgggtgagct aaaaacttaa cacactagtc    2580
atgatgtgac c                                                        2591
```

<210> SEQ ID NO 112
<211> LENGTH: 835
<212> TYPE: PRT
<213> ORGANISM: Human rotavirus

<400> SEQUENCE: 112

```
Met Lys Val Leu Ala Leu Arg His Ser Val Ala Gln Ile Tyr Ala Asp
1               5                  10                  15

Thr Gln Val Tyr Thr His Asp Asp Ser Lys Asp Asp Tyr Glu Asn Ala
            20                  25                  30

Phe Leu Ile Ser Asn Leu Thr Thr His Asn Ile Leu Tyr Leu Asn Tyr
        35                  40                  45

Ser Val Lys Thr Leu Gln Ile Leu Asn Lys Ser Gly Ile Ala Ala Ile
    50                  55                  60

Glu Ile Gln Lys Ile Asp Glu Leu Phe Thr Leu Ile Arg Cys Asn Phe
65                  70                  75                  80

Thr Tyr Asp Tyr Ile Asp Asp Val Val Tyr Leu His Asp Tyr Ser Tyr
                85                  90                  95

Tyr Ala Asn Asn Glu Ile Arg Thr Asp Gln Tyr Trp Val Thr Lys Thr
            100                 105                 110

Asn Ile Glu Asp Tyr Leu Leu Pro Gly Trp Lys Leu Thr Tyr Val Gly
        115                 120                 125

Tyr Asn Gly Ser Asp Thr Arg Gly His Tyr Asn Phe Ser Phe Arg Cys
    130                 135                 140

Gln Asn Ala Ala Thr Asp Asp Val Ile Ile Glu Tyr Ile Tyr Ser
145                 150                 155                 160

Asn Glu Leu Asp Phe Gln Asn Phe Ile Leu Lys Lys Ile Lys Glu Arg
```

```
                165                 170                 175
Met Thr Thr Ser Leu Pro Ile Ala Arg Leu Ser Asn Arg Val Phe Arg
            180                 185                 190
Asp Lys Leu Phe Lys Thr Leu Ser Val Asn His Asp Lys Val Val Asn
        195                 200                 205
Val Gly Pro Arg Asn Glu Ser Met Phe Thr Phe Leu Asp His Pro Ser
    210                 215                 220
Ile Lys Gln Phe Ser Asn Gly Pro Tyr Leu Val Lys Asp Thr Ile Lys
225                 230                 235                 240
Leu Lys Gln Glu Arg Trp Leu Gly Lys Arg Leu Ser Gln Phe Asp Ile
                245                 250                 255
Gly Gln Tyr Lys Asn Met Leu Asn Val Leu Thr Thr Leu Tyr Gln Tyr
            260                 265                 270
Tyr Asp Met Tyr His Glu Lys Pro Ile Ile Tyr Met Ile Gly Ser Ala
        275                 280                 285
Pro Ser Tyr Trp Ile Tyr Asp Val Lys Gln Tyr Ser Asp Leu Lys Phe
    290                 295                 300
Glu Thr Trp Asp Pro Leu Asp Thr Pro Tyr Ser Asn Leu His His Lys
305                 310                 315                 320
Glu Leu Phe Tyr Ile Asn Asp Val Gln Lys Leu Lys Asp Asn Ser Ile
                325                 330                 335
Leu Tyr Ile Asp Ile Arg Thr Asp Arg Gly Asn Met Asp Trp Lys Glu
            340                 345                 350
Trp Arg Lys Val Val Glu Gly Gln Thr Ala Asp Asn Leu His Ile Ala
        355                 360                 365
Tyr Lys Tyr Leu Ser Thr Gly Lys Ala Lys Ile Cys Cys Val Lys Met
    370                 375                 380
Thr Ala Met Asp Val Glu Leu Pro Ile Ser Ala Lys Leu Leu His His
385                 390                 395                 400
Pro Thr Thr Glu Ile Arg Ser Glu Phe Tyr Leu Met Met Asp Ile Trp
                405                 410                 415
Asp Ser Lys Asn Ile Lys Arg Phe Ile Pro Lys Gly Val Leu Tyr Ser
            420                 425                 430
Tyr Ile Asn Asn Thr Ile Thr Glu Asn Val Phe Ile Gln Gln Pro Phe
        435                 440                 445
Lys Leu Lys Thr Leu Lys Asn Glu Tyr Val Ile Ala Leu Tyr Ala Leu
    450                 455                 460
Ser Asn Asp Leu Asn Asn Arg Glu Asp Val Val Lys Leu Ile Asn Asn
465                 470                 475                 480
Gln Lys Arg Ala Leu Ile Thr Val Arg Ile Asn Asn Thr Phe Lys Asp
                485                 490                 495
Glu Pro Lys Val Gly Phe Lys Asn Ile Tyr Asp Trp Thr Phe Leu Pro
            500                 505                 510
Thr Asp Phe Glu Met Asn Gly Ser Ile Thr Ser Tyr Asp Gly Cys
        515                 520                 525
Leu Gly Ile Phe Gly Leu Ser Ile Ser Leu Ala Ser Lys Pro Thr Gly
    530                 535                 540
Asn Asn His Leu Phe Ile Leu Ser Gly Thr Asp Lys Tyr Phe Lys Leu
545                 550                 555                 560
Asp Gln Phe Ala Asn His Met Ser Ile Ser Arg Arg Ser His Gln Ile
                565                 570                 575
Arg Phe Ser Glu Ser Ala Thr Ser Tyr Ser Gly Tyr Ile Phe Arg Asp
            580                 585                 590
```

```
Leu Ser Asn Asn Asn Phe Asn Leu Ile Gly Thr Asn Val Glu Asn Ser
            595                 600                 605

Val Ser Gly His Val Tyr Asn Ala Leu Ile Tyr Tyr Arg Tyr Asn Tyr
610                 615                 620

Ser Phe Asp Leu Lys Arg Trp Ile Tyr Leu His Ser Thr Gly Lys Ala
625                 630                 635                 640

Ser Ile Glu Gly Gly Lys Tyr Tyr Glu His Ala Pro Ile Glu Leu Ile
                645                 650                 655

Tyr Ala Cys Arg Ser Ala Arg Glu Phe Ala Lys Leu Gln Asp Asp Leu
            660                 665                 670

Thr Val Leu Arg Tyr Ser Asn Glu Ile Glu Asn Tyr Ile Asn Lys Val
            675                 680                 685

Tyr Ser Ile Thr Tyr Ala Asp Asp Pro Asn Tyr Phe Ile Gly Ile Lys
        690                 695                 700

Phe Lys Asn Ile Pro Tyr Lys Tyr Asn Val Lys Val Pro His Leu Thr
705                 710                 715                 720

Phe Gly Val Leu Asn Ile Ser Glu Gln Met Leu Pro Asp Ala Ile Ala
                725                 730                 735

Ile Leu Lys Lys Phe Lys Asn Glu Leu Phe Gly Met Asp Ile Thr Thr
            740                 745                 750

Ser Tyr Thr Tyr Met Leu Ser Asp Glu Val Tyr Val Ala Asn Ile Ser
        755                 760                 765

Gly Val Leu Ser Thr Tyr Phe Lys Ile Tyr Asn Ala Phe Tyr Lys Glu
    770                 775                 780

Gln Ile Thr Phe Gly Gln Ser Arg Met Phe Ile Pro His Val Thr Leu
785                 790                 795                 800

Ser Phe Ser Asn Glu Lys Thr Val Arg Ile Asp Thr Thr Lys Leu Tyr
                805                 810                 815

Ile Asp Ser Ile Tyr Leu Arg Lys Ile Lys Gly Asp Thr Val Phe Asp
            820                 825                 830

Met Thr Glu
        835

<210> SEQ ID NO 113
<211> LENGTH: 835
<212> TYPE: PRT
<213> ORGANISM: Human rotavirus

<400> SEQUENCE: 113

Met Lys Val Leu Ala Leu Arg His Ser Val Ala Gln Val Tyr Ala Asp
1               5                   10                  15

Thr Gln Val Tyr Thr His Asp Asp Ser Lys Asp Glu Tyr Glu Asn Ala
            20                  25                  30

Phe Leu Ile Ser Asn Leu Thr Thr His Asn Ile Leu Tyr Leu Asn Tyr
        35                  40                  45

Asn Val Lys Thr Leu Gln Ile Leu Asn Lys Ser Gly Ile Ala Ala Ile
    50                  55                  60

Glu Ile Gln Lys Ile Asp Glu Leu Phe Thr Leu Ile Arg Cys Asn Phe
65                  70                  75                  80

Thr Tyr Asp Tyr Ile Asp Asp Val Val Tyr Leu His Tyr Ser Tyr
                85                  90                  95

Tyr Thr Asn Asn Glu Ile Arg Thr Asp Gln His Trp Ile Thr Lys Thr
            100                 105                 110

Asn Ile Glu Asp Tyr Leu Leu Pro Gly Trp Lys Leu Thr Tyr Val Gly
```

-continued

```
                115                 120                 125
Tyr Asn Gly Ser Asp Thr Arg Gly His Tyr Asn Phe Ser Phe Arg Cys
    130                 135                 140
Gln Asn Ala Ala Thr Asp Asp Ala Ile Ile Glu Tyr Ile Tyr Ser
145                 150                 155                 160
Asp Glu Leu Asp Phe Gln Ser Phe Ile Leu Lys Lys Ile Lys Glu Arg
                165                 170                 175
Met Thr Thr Ser Leu Pro Ile Ala Arg Leu Ser Asn Arg Val Phe Arg
                180                 185                 190
Asp Lys Leu Phe Lys Thr Leu Ser Val Asn His Asp Lys Val Val Asn
                195                 200                 205
Ile Gly Pro Arg Asn Glu Ser Met Phe Thr Phe Leu Asp Tyr Pro Ser
                210                 215                 220
Ile Lys Gln Phe Ser Asn Gly Pro Tyr Leu Val Lys Asp Thr Ile Lys
225                 230                 235                 240
Leu Lys Gln Glu Arg Trp Leu Gly Lys Arg Leu Ser Gln Phe Asp Ile
                245                 250                 255
Gly Gln Tyr Lys Asn Met Leu Asn Val Leu Thr Thr Leu Tyr Gln Tyr
                260                 265                 270
Tyr Asp Ile Tyr His Glu Lys Pro Ile Ile Tyr Met Ile Gly Ser Ala
                275                 280                 285
Pro Ser Tyr Trp Ile Tyr Asp Val Lys Gln Tyr Ser Asn Leu Lys Phe
                290                 295                 300
Glu Thr Trp Asp Pro Leu Asp Thr Pro Tyr Ser Asn Leu His His Lys
305                 310                 315                 320
Glu Leu Phe Tyr Ile Asn Asp Val Gln Lys Leu Lys Asp Asn Ser Ile
                325                 330                 335
Leu Tyr Ile Asp Ile Arg Thr Asp Arg Gly Thr Val Asp Trp Lys Glu
                340                 345                 350
Trp Arg Lys Ile Val Glu Arg Gln Thr Ile Asp Asn Leu Arg Ile Ala
                355                 360                 365
Tyr Lys Tyr Leu Ser Thr Gly Lys Ala Lys Val Cys Cys Val Lys Met
                370                 375                 380
Thr Ala Met Asp Leu Glu Leu Pro Ile Ser Ala Lys Leu Leu His His
385                 390                 395                 400
Pro Thr Thr Glu Ile Arg Ser Glu Phe Tyr Leu Val Met Asp Ile Trp
                405                 410                 415
Asp Ser Lys Asn Ile Lys Arg Phe Ile Pro Lys Gly Val Leu Tyr Ser
                420                 425                 430
Tyr Ile Asn Asn Thr Ile Thr Glu Asn Val Phe Ile Gln Gln Pro Phe
                435                 440                 445
Lys Leu Lys Thr Leu Lys Asn Glu Tyr Ile Ile Ala Leu Tyr Ala Leu
                450                 455                 460
Ser Asn Asp Phe Asn Asn Arg Glu Asp Val Val Lys Leu Ile Asn Asn
465                 470                 475                 480
Gln Lys Lys Ala Leu Met Thr Val Arg Ile Asn Asn Thr Phe Lys Asp
                485                 490                 495
Glu Pro Lys Val Gly Phe Lys Asn Ile Tyr Asp Trp Thr Phe Leu Pro
                500                 505                 510
Thr Asp Phe Glu Thr Asn Gly Ser Ile Ile Ser Tyr Asp Gly Cys
                515                 520                 525
Leu Gly Ile Phe Gly Leu Ser Ile Ser Leu Ala Ser Lys Pro Thr Gly
                530                 535                 540
```

```
Asn Asn His Leu Phe Ile Leu Ser Gly Thr Asp Lys Tyr Phe Lys Leu
545                 550                 555                 560

Asp Gln Phe Ala Asn His Met Ser Ile Ser Arg Arg Ser His Gln Ile
                565                 570                 575

Arg Phe Ser Glu Ser Ala Thr Ser Tyr Ser Gly Tyr Ile Phe Arg Asp
                580                 585                 590

Leu Ser Asn Asn Phe Asn Leu Ile Gly Thr Asn Val Glu Asn Ser
                595                 600                 605

Val Ser Gly His Val Tyr Asn Ala Leu Ile Tyr Tyr Arg Tyr Asn Tyr
610                 615                 620

Ser Phe Asp Leu Lys Arg Trp Ile Tyr Leu His Ser Thr Gly Lys Ala
625                 630                 635                 640

Ser Ile Glu Gly Gly Lys Tyr Tyr Glu His Ala Pro Ile Glu Leu Ile
                645                 650                 655

Tyr Ala Cys Arg Ser Ala Arg Glu Phe Ala Lys Leu Gln Asp Asp Leu
                660                 665                 670

Thr Val Leu Arg Tyr Ser Asn Glu Ile Glu Asn Tyr Ile Asn Lys Val
                675                 680                 685

Tyr Ser Ile Thr Tyr Ala Asp Asp Pro Asn Tyr Phe Ile Gly Val Lys
690                 695                 700

Phe Lys Asn Ile Pro Tyr Lys Tyr Asn Val Lys Ile Pro His Leu Thr
705                 710                 715                 720

Phe Gly Val Leu Asn Ile Ser Glu Gln Met Leu Pro Asp Val Ile Thr
                725                 730                 735

Ile Leu Lys Arg Phe Lys Asn Glu Leu Phe Gly Met Glu Ile Thr Thr
                740                 745                 750

Ser Tyr Thr Tyr Met Leu Ser Asp Glu Val Tyr Val Ala Asn Ile Ser
                755                 760                 765

Gly Val Leu Ser Thr Tyr Phe Lys Ile Tyr Asn Ala Phe Tyr Lys Glu
                770                 775                 780

Gln Ile Thr Phe Gly Gln Ser Arg Met Phe Ile Pro His Val Thr Leu
785                 790                 795                 800

Ser Phe Ser Asn Glu Lys Thr Val Arg Ile Asp Ile Thr Lys Leu Tyr
                805                 810                 815

Ile Asp Ser Ile Tyr Leu Arg Lys Ile Lys Gly Asp Thr Val Phe Asp
                820                 825                 830

Met Thr Gly
        835

<210> SEQ ID NO 114
<211> LENGTH: 835
<212> TYPE: PRT
<213> ORGANISM: Human rotavirus

<400> SEQUENCE: 114

Met Lys Val Leu Ala Leu Arg His Ser Val Ala Gln Val Tyr Ala Asp
1               5                   10                  15

Thr Gln Val Tyr Thr His Asp Asp Ser Lys Asp Glu Tyr Glu Asn Ala
                20                  25                  30

Phe Leu Ile Ser Asn Leu Thr His Asn Ile Leu Tyr Leu Asn Tyr
                35                  40                  45

Asn Val Lys Thr Leu Gln Ile Leu Asn Lys Ser Gly Ile Ala Ala Ile
                50                  55                  60

Glu Ile Gln Lys Ile Asp Glu Leu Phe Thr Leu Ile Arg Cys Asn Phe
```

```
              65                  70                  75                  80
Thr Tyr Asp Tyr Ile Asp Asp Val Val Tyr Leu His Asp Tyr Ser Tyr
                    85                  90                  95

Tyr Thr Asn Asn Glu Ile Arg Thr Asp Gln His Trp Ile Thr Lys Thr
            100                 105                 110

Asn Ile Glu Asp Tyr Leu Leu Pro Gly Trp Lys Leu Thr Tyr Val Gly
            115                 120                 125

Tyr Asn Gly Ser Asp Thr Arg Gly His Tyr Asn Phe Ser Phe Arg Cys
        130                 135                 140

Gln Asn Ala Ala Thr Asp Asp Ala Ile Ile Glu Tyr Ile Tyr Ser
145                 150                 155                 160

Asp Glu Leu Asp Phe Gln Ser Phe Ile Leu Lys Ile Lys Glu Arg
                165                 170                 175

Met Thr Thr Ser Leu Pro Ile Ala Arg Leu Ser Asn Arg Val Phe Arg
            180                 185                 190

Asp Lys Leu Phe Lys Thr Leu Ser Val Asn His Asp Lys Val Val Asn
        195                 200                 205

Ile Gly Pro Arg Asn Glu Ser Met Phe Thr Phe Leu Asp Tyr Pro Ser
    210                 215                 220

Ile Lys Gln Phe Ser Asn Gly Pro Tyr Leu Val Lys Asp Thr Ile Lys
225                 230                 235                 240

Leu Lys Gln Glu Arg Trp Leu Gly Lys Arg Leu Ser Gln Phe Asp Ile
                245                 250                 255

Gly Gln Tyr Lys Asn Met Leu Asn Val Leu Thr Thr Leu Tyr Gln Tyr
            260                 265                 270

Tyr Asp Ile Tyr His Glu Lys Pro Ile Ile Tyr Met Ile Gly Ser Ala
        275                 280                 285

Pro Ser Tyr Trp Ile Tyr Asp Val Lys Gln Tyr Ser Asn Leu Lys Phe
    290                 295                 300

Glu Thr Trp Asp Pro Leu Asp Thr Pro Tyr Ser Asn Leu His His Lys
305                 310                 315                 320

Glu Leu Phe Tyr Ile Asn Asp Val Gln Lys Leu Lys Asp Asn Ser Ile
                325                 330                 335

Leu Tyr Ile Asp Ile Arg Thr Asp Arg Gly Thr Val Asp Trp Lys Glu
            340                 345                 350

Trp Arg Lys Ile Val Glu Arg Gln Thr Ile Asp Asn Ser Arg Ile Ala
        355                 360                 365

Tyr Lys Tyr Leu Ser Thr Gly Lys Ala Lys Val Cys Cys Val Lys Met
    370                 375                 380

Thr Ala Met Asp Leu Glu Leu Pro Ile Ser Ala Lys Leu Leu His His
385                 390                 395                 400

Pro Thr Thr Glu Ile Arg Ser Glu Phe Tyr Leu Val Met Asp Ile Trp
                405                 410                 415

Asp Ser Lys Asn Ile Lys Arg Phe Ile Pro Lys Gly Val Leu Tyr Ser
            420                 425                 430

Tyr Ile Asn Asn Thr Ile Thr Glu Asn Val Phe Ile Gln Gln Pro Phe
        435                 440                 445

Lys Leu Lys Thr Leu Lys Asn Glu Tyr Ile Ile Ala Leu Tyr Ala Leu
    450                 455                 460

Ser Asn Asp Phe Asn Asn Arg Glu Asp Val Val Lys Leu Ile Asn Asn
465                 470                 475                 480

Gln Lys Lys Ala Leu Met Thr Val Arg Ile Asn Asn Thr Phe Lys Asp
                485                 490                 495
```

| | | | | | | | | | | | |
|---|---|---|---|---|---|---|---|---|---|---|---|
|Glu|Pro|Lys|Val|Gly|Phe|Lys|Asn|Ile|Tyr|Asp|Trp|Thr|Phe|Leu|Pro|
| | |500| | | |505| | | |510| |

Thr Asp Phe Glu Thr Asn Gly Ser Ile Ile Thr Ser Tyr Asp Gly Cys
         515                 520              525

Leu Gly Ile Phe Gly Leu Ser Ile Ser Leu Ala Ser Lys Pro Thr Gly
     530               535              540

Asn Asn His Leu Phe Ile Leu Ser Gly Thr Asp Lys Tyr Phe Lys Leu
545                550              555              560

Asp Gln Phe Ala Asn His Met Ser Ile Ser Arg Arg Ser His Gln Ile
           565               570            575

Arg Phe Ser Glu Ser Ala Thr Ser Tyr Ser Gly Tyr Ile Phe Arg Asp
     580               585              590

Leu Ser Asn Asn Phe Asn Leu Ile Gly Thr Asn Val Glu Asn Ser
        595              600            605

Val Ser Gly His Val Tyr Asn Ala Leu Ile Tyr Tyr Arg Tyr Asn Tyr
     610               615              620

Ser Phe Asp Leu Lys Arg Trp Ile Tyr Leu His Ser Thr Gly Lys Ala
625                630              635              640

Ser Ile Glu Gly Gly Lys Tyr Tyr Glu His Ala Pro Ile Glu Leu Ile
           645               650            655

Tyr Ala Cys Arg Ser Ala Arg Glu Phe Ala Lys Leu Gln Asp Asp Leu
           660               665            670

Thr Val Leu Arg Tyr Ser Asn Glu Ile Glu Asn Tyr Ile Asn Lys Val
        675              680            685

Tyr Ser Ile Thr Tyr Ala Asp Asp Pro Asn Tyr Phe Ile Gly Val Lys
     690               695              700

Phe Lys Asn Ile Pro Tyr Lys Tyr Asn Val Lys Ile Pro His Leu Thr
705                710              715              720

Phe Gly Val Leu Asn Ile Ser Glu Gln Met Leu Pro Asp Val Ile Thr
           725               730            735

Ile Leu Lys Arg Phe Lys Asn Glu Leu Phe Gly Met Glu Ile Thr Thr
           740               745            750

Ser Tyr Thr Tyr Met Leu Ser Asp Glu Val Tyr Val Ala Asn Ile Ser
     755               760              765

Gly Val Leu Ser Thr Tyr Phe Lys Ile Tyr Asn Ala Phe Tyr Lys Glu
     770               775            780

Gln Ile Thr Phe Gly Gln Ser Arg Met Phe Ile Pro His Val Thr Leu
785                790              795              800

Ser Phe Ser Asn Glu Lys Thr Val Arg Ile Asp Ile Thr Lys Leu Tyr
           805               810            815

Ile Asp Ser Ile Tyr Leu Arg Lys Ile Lys Gly Asp Thr Val Phe Asp
           820               825            830

Met Thr Gly
        835

<210> SEQ ID NO 115
<211> LENGTH: 2359
<212> TYPE: DNA
<213> ORGANISM: Human rotavirus

<400> SEQUENCE: 115
ggctataaaa tggcttcact catttataga caacttctca ctaattcata ttcggtagac    60
ttacatgatg aaatagaaca gattggatcg gagaaaactc aaagtgtaac agtaaatcca   120

```
ggtccatttg cacaaaccag atacgctcca gttaattggg gtcatgggga gattaatgat      180
tcaactacag tggaaccagt tttagatggt ccttatcaac ccactacatt caaaccaccc      240
aatgattatt ggttgcttat tagttcaaat acaaatggag tagtctacga aagtacaaat      300 ataatgact tttggacagc agttatcgca gttgaaccac atgttagtca aacaaatagg      360
caatatattt tatttggtga aaataagcag tttaacgtag aaaacaattc agataaatgg      420
aaatttttcg aaatgtttaa aggtagtagt cagggtaatt tttctaatag acggactcta      480
acttctagta atagacttgt agggatgcta aaatatggtg gaagagtatg gacatttcat      540
ggtgaaacac caagagctac tactgatagt tcaaatactg cggatttaaa taatatatca      600
attataattc attcagagtt ttatattatt ccaagatccc aagaatctaa atgtaacgag      660
tatatcaata atggtttacc accaattcag aatactagaa atgtagttcc attatcttta      720
tcatccagat ctattcaata taggagagca caagttaatg aagatattac aatttcaaaa      780
acttcattat ggaaggaaat gcaatataat agagatatta taataagatt taaatttggt      840
aatagtgtta taaaactagg aggattggga tataaatggt ctgaaatatc atataaagca      900
gcgaattatc agtatagtta ttcacgtgat ggtgaacaag ttactgcaca taccacttgt      960
tcagtaaatg gagtaaacaa ttttagctat aatggaggct cactacctac tgatttcagt     1020
atttcgaggt atgaagttat taaagaaaat tcttatgtgt acatagacta ctgggatgat     1080
tcaaaagcat ttagaaatat ggtgtatgtt agatcgctag cagcaaattt aaattcagtg     1140
aaatgtacag gtgggagtta aatttaga ttgcccgtag gtaaatggcc tattatgaat     1200
ggtggtgctg tatcattaca ttttgctgga gttacattat ctacacagtt cactgatttt     1260
gtatcattaa attcactgcg atttagattc agtttaacag tagatgaacc atctttctca     1320
ataatacgaa cacgtacaat aaacttgtac ggattaccag cagctaatcc aaacaatgga     1380
aatgaatact atgaaatgtc aggaaggttt tcacttattt ctttagttca aaccaatgat     1440
gattatcaaa ctccaattat gaattcagta acagtaaggc aggatttaga acgccagctt     1500
aatgatttgc gagaagagtt taattcattg tcacaagaaa tagctatgtc acaattaatt     1560
gatttagcat tactacccttt agatatgttc tctatgtttt cgggaataaa aagcacaatt     1620
gatctaacca aatcaatggc aactagtgta atgaaaaaat ttagaaaatc gaaattagct     1680
acatcaattt cagaaatgac taattcattg tcagatgcgg cttcatcagc atcaagaagt     1740
gcttctatta gatcaaattt atctacgatt tcaaattgga ctaatacttc aaaaagtgtt     1800
tcaaatgtaa ctgactcagt aaatgatgtt tcaacacaaa catctacaat tagtaagaaa     1860
cttagattaa gagagatgat tactcaaact gaaggattga gttttgatga tatttcagca     1920
gctgtactga aaacgaaaat agatatgtcc acacaaattg gaaaaaacac tttacctgat     1980
atagttactg aagcgtctga aaaatttatt ccaaaacgat catatcgagt attaaaagat     2040
gatgaagtaa tggaaattaa tactgaagga aagttttttg catataaagt ggatacactc     2100
aatgagatac catttgatat aaataaattc gccgaacttg tcacggattc tccagttata     2160
tcagcaataa tagactttaa gacgttaaaa aatttaaacg acaattatgg aattactcgt     2220
attgaagcgt ttaatttaat taaatcgaat ccaaatgtgc tacgtaattt cattaatcaa     2280
aataatccaa ttataagaaa tagaattgag cagttaattc tacaatgtaa gttgtgagaa     2340
tgtcatccag gatgtgacc                                                  2359

<210> SEQ ID NO 116
<211> LENGTH: 2359
```

```
<212> TYPE: DNA
<213> ORGANISM: Human rotavirus

<400> SEQUENCE: 116
ggctataaaa tggcttcact catttataga caacttctca ctaattcata ttcggtagac      60
ttgcatgacg aaatagaaca gattggatcg gagaaaactc aaaatgtgac ggtaaatcca     120
ggcccatttg cacagactag atacgctcca gttaattggg gacacggaga gattaatgat     180
tcaactacag tagaaccagt tttagatggt ccttatcaac caactacatt caaaccaccc     240
aatgattatt ggctgcttat tagttcaaat acagatggag tagtctatga gagtacaaat     300
aatagtgact tttggacagc agttatcgct gttgaaccac atgtcagtca aacaaatagg     360
caatatgttt tatttggtga aaataagcag tttaacgtag aaaatagttc agataaatgg     420
aaatttttcg aaatgtttaa aggtagtagt cagagtgatt tttctaatag acggacttta     480
acctctaata ataaacttgt aggaatgcta aaatatggtg aagagtatg gacatttcat      540
ggtgaaacac caagagctac tactgatagt tcgaatactg cggatttaaa taatatatca     600
attataattc attcagagtt ttatattatt ccaagatccc aagaatctaa atgtaatgaa     660
tatattaata atggtttacc accaattcaa aatactagaa atgtagttcc attatctcta     720
tcatccagat ctattcaata tagaagagca caagttaatg aagatattac aatttcaaaa     780
acttcattat ggaaagaaat gcaatataat agagatatta ataagatt  taaatttggt     840
aatagtatca taaaattagg aggattggga tataaatggt ctgaaatatc atacaaagct     900
gcgaattatc aatatagcta ttcgcgtgat ggtgaacaag ttactgcaca taccacttgt     960
tcagtaaatg gagtaaataa ttttagctat aatggaggtt cactacctac tgatttcagt    1020
atttcgagat atgaggttat taagaaaaat tcttatgtat atatagatta ctgggatgat    1080
tcaaaagcat ttagaaatat ggtatatgtt agatcgttag cagcaaattt aaattcagtg    1140
aaatgcgtag gtggaagcta tgattttaga ttacctgtag gtgaatggcc tattatgaat    1200
ggcggtgctg tatcattaca ttttgccgga gttacattat ctacacagtt cactgatttt    1260
gtatcattga attcgctacg atttagattc agtttaacag tagatgaacc atctttctca    1320
ataatacgaa cacgtacaat gaacttatac ggattaccag cagctaatcc aaacaatgga    1380
aatgaatact atgaagtgtc aggaaggttc tcacttattt ctttagttcc aactaatgat    1440
gattatcaaa ttccaattat gaattcagta acagtaaggc aagatttaga acgtcagctt    1500
aatgatttac gagaagagtt taattcattg tcacaagaaa tagctatgtc acaattgatt    1560
gatttggcat tattaccttt agatatgttt tctatgtttt cggggataaa aagtactatt    1620
gatctgacca agtcaatggc aactagcgta atgaaaaaat ttagaaaatc aaaattagct    1680
acatcgattt cagaaatgac taattcattg tcagatgcgg cttcgtcggc atcaagaagt    1740
gcttctatta gatcaaattt atcgacaatt tcaaattggt ctgacgcttc aaaaagtgta    1800
ttaaatgtaa ctgactcagt aaatgatatt tcaacacaaa catctacaat tagtaaaaaa    1860
cttagattaa agaaatgat tactcaaact gaaggaatta gttttgacga tatttcagca    1920
gccgtattga aaacgaaaat agatatgtcc acacaaattg gaaaaaatac cttacctgat    1980
atagttactg aagcatctga aaagtttatt ccaaaacgat catatcgagt attaaaagat    2040
gatgaagtga tggaagttaa cactgaagga aagttttttg cttataaagt ggatacactt    2100
aatgagatcc catttgatat aaataaattc gctgaacttg tgacggattc tccagttata    2160
tcagcaataa tagattttaa aacgttaaag aatttaaacg ataattatgg aattacccgc    2220
```

| | |
|---|---|
| atagaagcgc ttaatttaat taaatcgaat ccgaatgtac tacgtaattt tattaatcaa | 2280 |
| aataatccaa ttataagaaa tagaattgag cagttaattc tacaatgtaa attgtgagaa | 2340 |
| cgctattgag gatgtgacc | 2359 |

<210> SEQ ID NO 117
<211> LENGTH: 2359
<212> TYPE: DNA
<213> ORGANISM: Human rotavirus

<400> SEQUENCE: 117

| | |
|---|---|
| ggctataaaa tggcttcact catttataga caacttctca ctaattcata ttcggtagac | 60 |
| ttgcatgacg aaatagaaca gattggatcg gagaaaactc aaaatgtgac ggtaaatcca | 120 |
| ggcccatttg cacagactag atacgctcca gttaattggg gacacggaga gattaatgat | 180 |
| tcaactacag tagaaccagt tttagatggt ccttatcaac caactacatt caaaccaccc | 240 |
| aatgattatt ggctgcttat tagttcaaat acagatggag tagtctatga gagtacaaat | 300 |
| aatagtgact tttggacagc agttatcgct gttgaaccac atgtcagtca aacaaatagg | 360 |
| caatatgttt tatttggtga aaataagcag tttaacgtag aaaatagttc agataaatgg | 420 |
| aaattttcg aaatgtttaa aggtagtagt cagagtgatt tttctaatag acggacttta | 480 |
| acctctaata taaacttgt aggaatgcta aaatatggtg aagagtatg gacatttcat | 540 |
| ggtgaaacac caagagctac tactgatagt tcgaatactg cggatttaaa taatatatca | 600 |
| attataattc attcagagtt ttatattatt ccaagatccc aagaatctaa atgtaatgaa | 660 |
| tatattaata atggtttacc accaattcaa aatactagaa atgtagttcc attatctcta | 720 |
| tcatccagat ctattcaata tagaagagca caagttaatg aagatattaa aatttcaaaa | 780 |
| acttcattat ggaaagaaat gcaatataat agagatatta taataagatt taaatttggt | 840 |
| aatagtatca taaaattagg aggattggga tataaatggt ctgaaatatc atacaaagct | 900 |
| gcgaattatc aatatagcta ttcgcgtgat ggtgaacaag ttactgcaca taccacttgt | 960 |
| tcagtaaatg gagtaaataa ttttagctat aatggaggtt cactacctac tgatttcagt | 1020 |
| atttcgagat atgaggttat taagaaaaat tcttatgtat atatagatta ctgggatgat | 1080 |
| tcaaaagcat ttagaaatat ggtatatgct agatcgttag cagcaaattt aaattcagtg | 1140 |
| aaatgcgtag gtgaagcta taattttaga ttacctgtag gtggatggcc tattatgaat | 1200 |
| ggcggtgctg tatcattaca ttttgccgga gttacattat ctacacagtt cactgatttt | 1260 |
| gtatcattga attcgctacg atttagattc agtttaacag tagatgaacc atctttctca | 1320 |
| ataatacgaa cacgtacaat gaacttatac ggattaccag cagctaatcc aaacaatgga | 1380 |
| aatgaatact atgaagtgtc aggaaggttc tcacttattt ctttagttcc aactaatgat | 1440 |
| gattatcaaa ttccaattat gaattcagta acagtaaggc aagatttaga acgtcagctt | 1500 |
| aatgatttac gagaagagtt taattcattg tcacaagaaa tagctatgtc acaattgatt | 1560 |
| gatttggcat tattaccttt agatatgttt tctatgtttt cggggataaa aagtactatt | 1620 |
| gatctgacca agtcaatggc aactagcgta atgaaaaaat ttagaaaatc aaaattagct | 1680 |
| acatcgattt cagaaatgac taattcattg tcagatgcgg cttcgtcggc atcaagaagt | 1740 |
| gcttctatta gatcaaattt atcgacaatt tcaaattggt ctgacgcttc aaaaagtgta | 1800 |
| ttaaatgtaa ctgactcagt aaatgatatt tcaacacaaa catctacaat tagtaaaaaa | 1860 |
| cttagattaa aagaaatgat tactcaaact gaaggaatta gttttgacga tatttcagca | 1920 |
| gccgtattga aaacgaaaat agatatgtcc acacaaattg gaaaaaatac cttacctgat | 1980 |

```
atagttactg aagcatctga aaagtttatt ccaaaacgat catatcgagt attaaaagat    2040
gatgaagtga tggaagttaa cactgaagga aagtttttg cttataaagt ggatacactt    2100
aatgagatcc catttgatat aaataaattc gctgaacttg tgacggattc tccagttata    2160
tcagcaataa tagattttaa aacgttaaag aatttaaacg ataattatgg aattacccgc    2220
atagaagcgc ttaatttaat taaatcgaat ccgaatgtac tacgtaattt tattaatcaa    2280
aataatccaa ttataagaaa tagaattgag cagttaattc tacaatgtaa attgtgagaa    2340
cgctattgag gatgtgacc                                                 2359
```

<210> SEQ ID NO 118
<211> LENGTH: 775
<212> TYPE: PRT
<213> ORGANISM: Human rotavirus

<400> SEQUENCE: 118

```
Met Ala Ser Leu Ile Tyr Arg Gln Leu Leu Thr Asn Ser Tyr Ser Val
1               5                   10                  15

Asp Leu His Asp Glu Ile Glu Gln Ile Gly Ser Glu Lys Thr Gln Ser
                20                  25                  30

Val Thr Val Asn Pro Gly Pro Phe Ala Gln Thr Arg Tyr Ala Pro Val
            35                  40                  45

Asn Trp Gly His Gly Glu Ile Asn Asp Ser Thr Thr Val Glu Pro Val
        50                  55                  60

Leu Asp Gly Pro Tyr Gln Pro Thr Thr Phe Lys Pro Pro Asn Asp Tyr
65                  70                  75                  80

Trp Leu Leu Ile Ser Ser Asn Thr Asn Gly Val Val Tyr Glu Ser Thr
                85                  90                  95

Asn Asn Asn Asp Phe Trp Thr Ala Val Ile Ala Val Glu Pro His Val
                100                 105                 110

Ser Gln Thr Asn Arg Gln Tyr Ile Leu Phe Gly Glu Asn Lys Gln Phe
            115                 120                 125

Asn Val Glu Asn Asn Ser Asp Lys Trp Lys Phe Phe Glu Met Phe Lys
        130                 135                 140

Gly Ser Ser Gln Gly Asn Phe Ser Asn Arg Arg Thr Leu Thr Ser Ser
145                 150                 155                 160

Asn Arg Leu Val Gly Met Leu Lys Tyr Gly Gly Arg Val Trp Thr Phe
                165                 170                 175

His Gly Glu Thr Pro Arg Ala Thr Thr Asp Ser Ser Asn Thr Ala Asp
                180                 185                 190

Leu Asn Asn Ile Ser Ile Ile His Ser Glu Phe Tyr Ile Ile Pro
            195                 200                 205

Arg Ser Gln Glu Ser Lys Cys Asn Glu Tyr Ile Asn Asn Gly Leu Pro
        210                 215                 220

Pro Ile Gln Asn Thr Arg Asn Val Val Pro Leu Ser Leu Ser Ser Arg
225                 230                 235                 240

Ser Ile Gln Tyr Arg Arg Ala Gln Val Asn Glu Asp Ile Thr Ile Ser
                245                 250                 255

Lys Thr Ser Leu Trp Lys Glu Met Gln Tyr Asn Arg Asp Ile Ile Ile
            260                 265                 270

Arg Phe Lys Phe Gly Asn Ser Val Ile Lys Leu Gly Gly Leu Gly Tyr
        275                 280                 285

Lys Trp Ser Glu Ile Ser Tyr Lys Ala Ala Asn Tyr Gln Tyr Ser Tyr
        290                 295                 300
```

```
Ser Arg Asp Gly Glu Gln Val Thr Ala His Thr Thr Cys Ser Val Asn
305                 310                 315                 320

Gly Val Asn Asn Phe Ser Tyr Asn Gly Gly Ser Leu Pro Thr Asp Phe
                325                 330                 335

Ser Ile Ser Arg Tyr Glu Val Ile Lys Glu Asn Ser Tyr Val Tyr Ile
            340                 345                 350

Asp Tyr Trp Asp Asp Ser Lys Ala Phe Arg Asn Met Val Tyr Val Arg
        355                 360                 365

Ser Leu Ala Ala Asn Leu Asn Ser Val Lys Cys Thr Gly Gly Ser Tyr
370                 375                 380

Asn Phe Arg Leu Pro Val Gly Lys Trp Pro Ile Met Asn Gly Gly Ala
385                 390                 395                 400

Val Ser Leu His Phe Ala Gly Val Thr Leu Ser Thr Gln Phe Thr Asp
                405                 410                 415

Phe Val Ser Leu Asn Ser Leu Arg Phe Arg Phe Ser Leu Thr Val Asp
            420                 425                 430

Glu Pro Ser Phe Ser Ile Ile Arg Thr Arg Thr Ile Asn Leu Tyr Gly
        435                 440                 445

Leu Pro Ala Ala Asn Pro Asn Gly Asn Glu Tyr Tyr Glu Met Ser
450                 455                 460

Gly Arg Phe Ser Leu Ile Ser Leu Val Gln Thr Asn Asp Asp Tyr Gln
465                 470                 475                 480

Thr Pro Ile Met Asn Ser Val Thr Val Arg Gln Asp Leu Glu Arg Gln
                485                 490                 495

Leu Asn Asp Leu Arg Glu Glu Phe Asn Ser Leu Ser Gln Glu Ile Ala
            500                 505                 510

Met Ser Gln Leu Ile Asp Leu Ala Leu Leu Pro Leu Asp Met Phe Ser
        515                 520                 525

Met Phe Ser Gly Ile Lys Ser Thr Ile Asp Leu Thr Lys Ser Met Ala
530                 535                 540

Thr Ser Val Met Lys Lys Phe Arg Lys Ser Lys Leu Ala Thr Ser Ile
545                 550                 555                 560

Ser Glu Met Thr Asn Ser Leu Ser Asp Ala Ala Ser Ser Ala Ser Arg
                565                 570                 575

Ser Ala Ser Ile Arg Ser Asn Leu Ser Thr Ile Ser Asn Trp Thr Asn
            580                 585                 590

Thr Ser Lys Ser Val Ser Asn Val Thr Asp Ser Val Asn Asp Val Ser
        595                 600                 605

Thr Gln Thr Ser Thr Ile Ser Lys Lys Leu Arg Leu Arg Glu Met Ile
610                 615                 620

Thr Gln Thr Glu Gly Leu Ser Phe Asp Asp Ile Ser Ala Ala Val Leu
625                 630                 635                 640

Lys Thr Lys Ile Asp Met Ser Thr Gln Ile Gly Lys Asn Thr Leu Pro
                645                 650                 655

Asp Ile Val Thr Glu Ala Ser Glu Lys Phe Ile Pro Lys Arg Ser Tyr
            660                 665                 670

Arg Val Leu Lys Asp Asp Glu Val Met Glu Ile Asn Thr Glu Gly Lys
        675                 680                 685

Phe Phe Ala Tyr Lys Val Asp Thr Leu Asn Glu Ile Pro Phe Asp Ile
690                 695                 700

Asn Lys Phe Ala Glu Leu Val Thr Asp Ser Pro Val Ile Ser Ala Ile
705                 710                 715                 720
```

```
Ile Asp Phe Lys Thr Leu Lys Asn Leu Asn Asp Asn Tyr Gly Ile Thr
                725                 730                 735

Arg Ile Glu Ala Phe Asn Leu Ile Lys Ser Pro Asn Val Leu Arg
        740                 745                 750

Asn Phe Ile Asn Gln Asn Asn Pro Ile Ile Arg Asn Arg Ile Glu Gln
            755                 760                 765

Leu Ile Leu Gln Cys Lys Leu
    770                 775

<210> SEQ ID NO 119
<211> LENGTH: 775
<212> TYPE: PRT
<213> ORGANISM: Human rotavirus

<400> SEQUENCE: 119

Met Ala Ser Leu Ile Tyr Arg Gln Leu Leu Thr Asn Ser Tyr Ser Val
1               5                   10                  15

Asp Leu His Asp Glu Ile Glu Gln Ile Gly Ser Glu Lys Thr Gln Asn
                20                  25                  30

Val Thr Val Asn Pro Gly Pro Phe Ala Gln Thr Arg Tyr Ala Pro Val
            35                  40                  45

Asn Trp Gly His Gly Glu Ile Asn Asp Ser Thr Thr Val Glu Pro Val
    50                  55                  60

Leu Asp Gly Pro Tyr Gln Pro Thr Thr Phe Lys Pro Pro Asn Asp Tyr
65                  70                  75                  80

Trp Leu Leu Ile Ser Ser Asn Thr Asp Gly Val Val Tyr Glu Ser Thr
                85                  90                  95

Asn Asn Ser Asp Phe Trp Thr Ala Val Ile Ala Val Glu Pro His Val
                100                 105                 110

Ser Gln Thr Asn Arg Gln Tyr Val Leu Phe Gly Glu Asn Lys Gln Phe
            115                 120                 125

Asn Val Glu Asn Ser Ser Asp Lys Trp Lys Phe Phe Glu Met Phe Lys
    130                 135                 140

Gly Ser Ser Gln Ser Asp Phe Ser Asn Arg Arg Thr Leu Thr Ser Asn
145                 150                 155                 160

Asn Lys Leu Val Gly Met Leu Lys Tyr Gly Gly Arg Val Trp Thr Phe
                165                 170                 175

His Gly Glu Thr Pro Arg Ala Thr Thr Asp Ser Ser Asn Thr Ala Asp
                180                 185                 190

Leu Asn Asn Ile Ser Ile Ile Ile His Ser Glu Phe Tyr Ile Ile Pro
            195                 200                 205

Arg Ser Gln Glu Ser Lys Cys Asn Glu Tyr Ile Asn Asn Gly Leu Pro
    210                 215                 220

Pro Ile Gln Asn Thr Arg Asn Val Val Pro Leu Ser Leu Ser Ser Arg
225                 230                 235                 240

Ser Ile Gln Tyr Arg Arg Ala Gln Val Asn Glu Asp Ile Thr Ile Ser
                245                 250                 255

Lys Thr Ser Leu Trp Lys Glu Met Gln Tyr Asn Arg Asp Ile Ile Ile
                260                 265                 270

Arg Phe Lys Phe Gly Asn Ser Ile Ile Lys Leu Gly Gly Leu Gly Tyr
            275                 280                 285

Lys Trp Ser Glu Ile Ser Tyr Lys Ala Ala Asn Tyr Gln Tyr Ser Tyr
    290                 295                 300

Ser Arg Asp Gly Glu Gln Val Thr Ala His Thr Thr Cys Ser Val Asn
305                 310                 315                 320
```

```
Gly Val Asn Asn Phe Ser Tyr Asn Gly Gly Ser Leu Pro Thr Asp Phe
                325                 330                 335

Ser Ile Ser Arg Tyr Glu Val Ile Lys Glu Asn Ser Tyr Val Tyr Ile
            340                 345                 350

Asp Tyr Trp Asp Asp Ser Lys Ala Phe Arg Asn Met Val Tyr Val Arg
        355                 360                 365

Ser Leu Ala Ala Asn Leu Asn Ser Val Lys Cys Val Gly Gly Ser Tyr
    370                 375                 380

Asp Phe Arg Leu Pro Val Gly Glu Trp Pro Ile Met Asn Gly Gly Ala
385                 390                 395                 400

Val Ser Leu His Phe Ala Gly Val Thr Leu Ser Gln Phe Thr Asp
                405                 410                 415

Phe Val Ser Leu Asn Ser Leu Arg Phe Arg Phe Ser Leu Thr Val Asp
                420                 425                 430

Glu Pro Ser Phe Ser Ile Ile Arg Thr Arg Thr Met Asn Leu Tyr Gly
                435                 440                 445

Leu Pro Ala Ala Asn Pro Asn Asn Gly Asn Glu Tyr Tyr Glu Val Ser
    450                 455                 460

Gly Arg Phe Ser Leu Ile Ser Leu Val Pro Thr Asn Asp Asp Tyr Gln
465                 470                 475                 480

Ile Pro Ile Met Asn Ser Val Thr Val Arg Gln Asp Leu Glu Arg Gln
                485                 490                 495

Leu Asn Asp Leu Arg Glu Glu Phe Asn Ser Leu Ser Gln Glu Ile Ala
                500                 505                 510

Met Ser Gln Leu Ile Asp Leu Ala Leu Leu Pro Leu Asp Met Phe Ser
            515                 520                 525

Met Phe Ser Gly Ile Lys Ser Thr Ile Asp Leu Thr Lys Ser Met Ala
            530                 535                 540

Thr Ser Val Met Lys Lys Phe Arg Lys Ser Lys Leu Ala Thr Ser Ile
545                 550                 555                 560

Ser Glu Met Thr Asn Ser Leu Ser Asp Ala Ala Ser Ser Ala Ser Arg
                565                 570                 575

Ser Ala Ser Ile Arg Ser Asn Leu Ser Thr Ile Ser Asn Trp Ser Asp
            580                 585                 590

Ala Ser Lys Ser Val Leu Asn Val Thr Asp Ser Val Asn Asp Ile Ser
        595                 600                 605

Thr Gln Thr Ser Thr Ile Ser Lys Lys Leu Arg Leu Lys Glu Met Ile
            610                 615                 620

Thr Gln Thr Glu Gly Ile Ser Phe Asp Asp Ile Ser Ala Ala Val Leu
625                 630                 635                 640

Lys Thr Lys Ile Asp Met Ser Thr Gln Ile Gly Lys Asn Thr Leu Pro
                645                 650                 655

Asp Ile Val Thr Glu Ala Ser Glu Lys Phe Ile Pro Lys Arg Ser Tyr
            660                 665                 670

Arg Val Leu Lys Asp Asp Glu Val Met Glu Val Asn Thr Glu Gly Lys
        675                 680                 685

Phe Phe Ala Tyr Lys Val Asp Thr Leu Asn Glu Ile Pro Phe Asp Ile
    690                 695                 700

Asn Lys Phe Ala Glu Leu Val Thr Asp Ser Pro Val Ile Ser Ala Ile
705                 710                 715                 720

Ile Asp Phe Lys Thr Leu Lys Asn Leu Asn Asp Asn Tyr Gly Ile Thr
                725                 730                 735
```

```
Arg Ile Glu Ala Leu Asn Leu Ile Lys Ser Asn Pro Asn Val Leu Arg
                740                 745                 750

Asn Phe Ile Asn Gln Asn Asn Pro Ile Ile Arg Asn Arg Ile Glu Gln
            755                 760                 765

Leu Ile Leu Gln Cys Lys Leu
        770             775

<210> SEQ ID NO 120
<211> LENGTH: 775
<212> TYPE: PRT
<213> ORGANISM: Human rotavirus

<400> SEQUENCE: 120

Met Ala Ser Leu Ile Tyr Arg Gln Leu Leu Thr Asn Ser Tyr Ser Val
1               5                   10                  15

Asp Leu His Asp Glu Ile Glu Gln Ile Gly Ser Glu Lys Thr Gln Asn
            20                  25                  30

Val Thr Val Asn Pro Gly Pro Phe Ala Gln Thr Arg Tyr Ala Pro Val
        35                  40                  45

Asn Trp Gly His Gly Glu Ile Asn Asp Ser Thr Thr Val Glu Pro Val
    50                  55                  60

Leu Asp Gly Pro Tyr Gln Pro Thr Thr Phe Lys Pro Pro Asn Asp Tyr
65                  70                  75                  80

Trp Leu Leu Ile Ser Ser Asn Thr Asp Gly Val Val Tyr Glu Ser Thr
                85                  90                  95

Asn Asn Ser Asp Phe Trp Thr Ala Val Ile Ala Val Glu Pro His Val
            100                 105                 110

Ser Gln Thr Asn Arg Gln Tyr Val Leu Phe Gly Glu Asn Lys Gln Phe
        115                 120                 125

Asn Val Glu Asn Ser Ser Asp Lys Trp Lys Phe Phe Glu Met Phe Lys
    130                 135                 140

Gly Ser Ser Gln Ser Asp Phe Ser Asn Arg Arg Thr Leu Thr Ser Asn
145                 150                 155                 160

Asn Lys Leu Val Gly Met Leu Lys Tyr Gly Gly Arg Val Trp Thr Phe
                165                 170                 175

His Gly Glu Thr Pro Arg Ala Thr Thr Asp Ser Ser Asn Thr Ala Asp
            180                 185                 190

Leu Asn Asn Ile Ser Ile Ile His Ser Glu Phe Tyr Ile Ile Pro
        195                 200                 205

Arg Ser Gln Glu Ser Lys Cys Asn Glu Tyr Ile Asn Asn Gly Leu Pro
    210                 215                 220

Pro Ile Gln Asn Thr Arg Asn Val Val Pro Leu Ser Leu Ser Ser Arg
225                 230                 235                 240

Ser Ile Gln Tyr Arg Arg Ala Gln Val Asn Glu Asp Ile Lys Ile Ser
                245                 250                 255

Lys Thr Ser Leu Trp Lys Glu Met Gln Tyr Asn Arg Asp Ile Ile Ile
            260                 265                 270

Arg Phe Lys Phe Gly Asn Ser Ile Ile Lys Leu Gly Gly Leu Gly Tyr
        275                 280                 285

Lys Trp Ser Glu Ile Ser Tyr Lys Ala Ala Asn Tyr Gln Tyr Ser Tyr
    290                 295                 300

Ser Arg Asp Gly Glu Gln Val Thr Ala His Thr Thr Cys Ser Val Asn
305                 310                 315                 320

Gly Val Asn Asn Phe Ser Tyr Asn Gly Gly Ser Leu Pro Thr Asp Phe
                325                 330                 335
```

```
Ser Ile Ser Arg Tyr Glu Val Ile Lys Glu Asn Ser Tyr Val Tyr Ile
            340                 345                 350

Asp Tyr Trp Asp Asp Ser Lys Ala Phe Arg Asn Met Val Tyr Ala Arg
        355                 360                 365

Ser Leu Ala Ala Asn Leu Asn Ser Val Lys Cys Val Gly Gly Ser Tyr
    370                 375                 380

Asn Phe Arg Leu Pro Val Gly Gly Trp Pro Ile Met Asn Gly Gly Ala
385                 390                 395                 400

Val Ser Leu His Phe Ala Gly Val Thr Leu Ser Thr Gln Phe Thr Asp
            405                 410                 415

Phe Val Ser Leu Asn Ser Leu Arg Phe Arg Phe Ser Leu Thr Val Asp
            420                 425                 430

Glu Pro Ser Phe Ser Ile Ile Arg Thr Arg Thr Met Asn Leu Tyr Gly
            435                 440                 445

Leu Pro Ala Ala Asn Pro Asn Asn Gly Asn Glu Tyr Tyr Glu Val Ser
            450                 455                 460

Gly Arg Phe Ser Leu Ile Ser Leu Val Pro Thr Asn Asp Asp Tyr Gln
465                 470                 475                 480

Ile Pro Ile Met Asn Ser Val Thr Val Arg Gln Asp Leu Glu Arg Gln
            485                 490                 495

Leu Asn Asp Leu Arg Glu Glu Phe Asn Ser Leu Ser Gln Glu Ile Ala
            500                 505                 510

Met Ser Gln Leu Ile Asp Leu Ala Leu Leu Pro Leu Asp Met Phe Ser
            515                 520                 525

Met Phe Ser Gly Ile Lys Ser Thr Ile Asp Leu Thr Lys Ser Met Ala
            530                 535                 540

Thr Ser Val Met Lys Lys Phe Arg Lys Ser Lys Leu Ala Thr Ser Ile
545                 550                 555                 560

Ser Glu Met Thr Asn Ser Leu Ser Asp Ala Ala Ser Ser Ala Ser Arg
                565                 570                 575

Ser Ala Ser Ile Arg Ser Asn Leu Ser Thr Ile Ser Asn Trp Ser Asp
            580                 585                 590

Ala Ser Lys Ser Val Leu Asn Val Thr Asp Ser Val Asn Asp Ile Ser
            595                 600                 605

Thr Gln Thr Ser Thr Ile Ser Lys Lys Leu Arg Leu Lys Glu Met Ile
            610                 615                 620

Thr Gln Thr Glu Gly Ile Ser Phe Asp Asp Ile Ser Ala Ala Val Leu
625                 630                 635                 640

Lys Thr Lys Ile Asp Met Ser Thr Gln Ile Gly Lys Asn Thr Leu Pro
                645                 650                 655

Asp Ile Val Thr Glu Ala Ser Glu Lys Phe Ile Pro Lys Arg Ser Tyr
            660                 665                 670

Arg Val Leu Lys Asp Asp Glu Val Met Glu Val Asn Thr Glu Gly Lys
            675                 680                 685

Phe Phe Ala Tyr Lys Val Asp Thr Leu Asn Glu Ile Pro Phe Asp Ile
            690                 695                 700

Asn Lys Phe Ala Glu Leu Val Thr Asp Ser Pro Val Ile Ser Ala Ile
705                 710                 715                 720

Ile Asp Phe Lys Thr Leu Lys Asn Leu Asn Asp Asn Tyr Gly Ile Thr
                725                 730                 735

Arg Ile Glu Ala Leu Asn Leu Ile Lys Ser Asn Pro Asn Val Leu Arg
            740                 745                 750
```

```
Asn Phe Ile Asn Gln Asn Asn Pro Ile Ile Arg Asn Arg Ile Glu Gln
            755                 760                 765

Leu Ile Leu Gln Cys Lys Leu
        770                 775

<210> SEQ ID NO 121
<211> LENGTH: 1356
<212> TYPE: DNA
<213> ORGANISM: Human rotavirus

<400> SEQUENCE: 121
ggcttttaaa cgaagtcttc aacatggatg ttttatattc attatcaaaa actcttaagg      60
atgctagaga caaaattgtc gaaggcactt tatactctaa tgttagtgat ctaattcaac     120
aatttaatca atgataatt actatgaatg gaatgaatt tcagactgga ggaattggta      180
atctaccaac cagaaattgg agttttgatt ttggtttact tggaactacg cttttgaact     240
tagacgctaa ctatgttgaa actgcgcgta acacaattga ttattttgtt gattttgtag     300
ataacgtatg tatggatgag atggttagag aatcacaaag aaacggaatt gcaccgcagt     360
cagaatcact tagaaaacta tcaggaatta aatttaaaag aataattttt gataattcgt     420
cggaatatat agaaaactgg aatttgcaaa atagaagaca agaactggt tttacatttc      480 ataaaccaaa catctttcca tattcagctt catttacgtt aaatagatca caacccgcgc     540
atgataattt aatgggtacg atgtggttga atgcaggttc agagattcaa gtcgctggat     600
ttgattattc ttgcgccatc aatgcaccag ccaacataca gcaatttgaa catatagttc     660
agctccgcag agtattaacg acggctacaa taactctctt accagatgct gaaagattta     720
gttttcctag agtaattaat tcagctgatg gagcaactac atggtatttt aatccagtaa     780
tacttagacc gaataatgtc gaagtagaat ttctattgaa tggacagata ataaatactt     840
atcaggcaag atttggtaca attgtagcta gaaattttga tacaattaga ttatcatttc     900
aattaatgag accaccaaat atgacccat cagtcgcagc acttttccct aacgcgcagc     960
catttgaaca tcatgctact gtaggcctaa cattacgaat tgaatctgca gtttgtgagt    1020
cagtgcttgc tgatgctagt gaaacaatgt tagctaatgt aacatctgtt agacaagaat    1080
atgcaatacc agttggacca gttttttccac caggtatgaa ttggactgat ttaattacta    1140
actattcacc atctagagag gataatttac aacgtgtatt tacagtagct tccattagaa    1200
gcatgcttgt taaatgagga ccgagctaat tacttggtat ccaactttga caagtatgta    1260
gctacgttaa gctgtttgaa ctctacaagt aagggtacgt ttacgtattc gctacgtaga    1320
gtaatcactc agatgacgta gtgagaggat gtgacc                              1356

<210> SEQ ID NO 122
<211> LENGTH: 1356
<212> TYPE: DNA
<213> ORGANISM: Human rotavirus

<400> SEQUENCE: 122
ggctttaaaa cgaagtcttc aacatggatg tcctgtactc c

```
cagattcact tagaaaattg tcaggcatta agttcaaaag ataaattttt gataattcat      420
cggaatatat agagaactgg aatctgcaaa atagaagaca cgaacaggt tttacatttc       480 ataaaccaaa tattttccct tattcagcgt cattcacact aaatagatca caaccagctc      540
atgataactt gatgggtacg atgtggctga acgcaggatc agaaattcag gtcgctggat      600
ttgactattc gtgtgcaatt aatgcgccag ctaatacaca acatttgag cacattgtac       660 agctccgaag agttttaact acagctacaa taacactttt accggatgca gaaagattca     720
gttttccaag agtaattaat tcagctgatg gagcaactac atggtacttt aatccagtaa     780
ttcttagacc aaacaacgtt gaagtggagt ttctactaaa cggtcagata taaacactt       840 accaggctag atttggaaca atcgtagcta gaaattttga tacaatcaga ttgtcgttcc     900
agttgatgag accaccaaat atgacaccag cagtagcagc attatttcca aatgcgcagc     960
catttgaaca tcatgctaca gtaggactga cactgagaat tgaatctgca gtttgtgaat    1020
ctgtacttgc cgacgcaagc gagacaatgc tagcaaatgt gacatctgtt agacaagaat     1080
acgcaatacc agttggacca gttttccac caggcatgaa ttggactgat ttgatcacta      1140
attattcacc atctagagag gataatttgc agcgtgtatt tacagtggct tccattagaa    1200
gcatgcttgt caaataaggg ccaagctaac cacttggtat ccgactttga tgagtatgta   1260
gctacgtcaa gctgtttgaa ctctgtaagt aaggatgcgt ctacgtattc gctacacaga    1320
gtaatcactc agatgatgta gtgagaggat gtgacc                             1356

<210> SEQ ID NO 123
<211> LENGTH: 1356
<212> TYPE: DNA
<213> ORGANISM: Human rotavirus

<400> SEQUENCE: 123
ggctttaaaa cgaagtcttc aacatggatg tcctgtactc cttgtcaaaa actcttaaag     60
atgctagaga caaaattgtc gaaggcacat tatactctaa tgtgagtgat ctaattcaac    120 aatttaaccaa atgataatt actatgaatg gaaatgagtt ccaaactgga ggaattggta    180
atctaccaat tagaaattgg aattttgatt ttggattact tggaacaact ctactaaatt    240
tagacgctaa ctacgtcgaa acagcccgca acacaattga ctattttgta gattttgtag    300
acaacgtatg tatggatgaa atggttagag aatcacaaag aaatggaatt gcaccacaat    360
cagattcact tagaaaattg tcaggcatta agttcaaaag ataaattttt gataattcat      420
cggaatatat agagaactgg aatctgcaaa atagaagaca cgaacaggt tttacatttc       480 ataaaccaaa tattttccct tattcagcgt cattcacact aaatagatca caaccagctc      540
atgataactt gatgggtacg atgtggctga acgcaggatc agaaattcag gtcgctggat      600
ttgactattc gtgtgcaatt aatgcgccag ctaatacaca acatttgag cacattgtac       660 agctccgaag agttttaact acagctacaa taacactttt accggatgca gaaagattca     720
gttttccaag agtaattaat tcagctgatg gagcaactac atggtacttt aatccagtaa     780
ttcttagacc aaacaacgtt gaagtggagt ttctactaaa cggtcagata taaacactt       840 accaggctag atttggaaca atcgtagcta gaaattttga tacaatcaga ttgtcgttcc     900
agttgatgag accaccaaat atgacaccag cagtagcagc attatttcca aatgcgcagc     960
catttgaaca tcatgctaca gtaggactga cactgagaat tgaatctgca gtttgtgaat    1020
ctgtacttgc cgacgcaagc gagacaatgc tagcaaatgt gacatctgtt agacaagaat     1080
```

-continued

```
acgcaatacc agttggacca gttttccac caggcatgaa ttggactgat ttgatcacta    1140
attattcacc atctagagag gataatttgc agcgtgtatt tacagtggct tccattagaa    1200
gcatgcttgt caaataaggg ccaagctaac cacttggtat ccgactttga tgagtatgta    1260
gctacgtcaa gctgtttgaa ctctgtaagt aaggatgcgt ctacgtattc gctacacaga    1320
gtaatcactc agatgatgta gtgagaggat gtgacc                              1356
```

<210> SEQ ID NO 124
<211> LENGTH: 397
<212> TYPE: PRT
<213> ORGANISM: Human rotavirus

<400> SEQUENCE: 124

```
Met Asp Val Leu Tyr Ser Leu Ser Lys Thr Leu Lys Asp Ala Arg Asp
1               5                   10                  15

Lys Ile Val Glu Gly Thr Leu Tyr Ser Asn Val Ser Asp Leu Ile Gln
            20                  25                  30

Gln Phe Asn Gln Met Ile Ile Thr Met Asn Gly Asn Glu Phe Gln Thr
        35                  40                  45

Gly Gly Ile Gly Asn Leu Pro Thr Arg Asn Trp Ser Phe Asp Phe Gly
    50                  55                  60

Leu Leu Gly Thr Thr Leu Leu Asn Leu Asp Ala Asn Tyr Val Glu Thr
65                  70                  75                  80

Ala Arg Asn Thr Ile Asp Tyr Phe Val Asp Phe Val Asp Asn Val Cys
                85                  90                  95

Met Asp Glu Met Val Arg Glu Ser Gln Arg Asn Gly Ile Ala Pro Gln
            100                 105                 110

Ser Glu Ser Leu Arg Lys Leu Ser Gly Ile Lys Phe Lys Arg Ile Asn
        115                 120                 125

Phe Asp Asn Ser Ser Glu Tyr Ile Glu Asn Trp Asn Leu Gln Asn Arg
130                 135                 140

Arg Gln Arg Thr Gly Phe Thr Phe His Lys Pro Asn Ile Phe Pro Tyr
145                 150                 155                 160

Ser Ala Ser Phe Thr Leu Asn Arg Ser Gln Pro Ala His Asp Asn Leu
                165                 170                 175

Met Gly Thr Met Trp Leu Asn Ala Gly Ser Glu Ile Gln Val Ala Gly
            180                 185                 190

Phe Asp Tyr Ser Cys Ala Ile Asn Ala Pro Ala Asn Ile Gln Gln Phe
        195                 200                 205

Glu His Ile Val Gln Leu Arg Arg Val Leu Thr Thr Ala Thr Ile Thr
    210                 215                 220

Leu Leu Pro Asp Ala Glu Arg Phe Ser Phe Pro Arg Val Ile Asn Ser
225                 230                 235                 240

Ala Asp Gly Ala Thr Thr Trp Tyr Phe Asn Pro Val Ile Leu Arg Pro
                245                 250                 255

Asn Asn Val Glu Val Glu Phe Leu Leu Asn Gly Gln Ile Ile Asn Thr
            260                 265                 270

Tyr Gln Ala Arg Phe Gly Thr Ile Val Ala Arg Asn Phe Asp Thr Ile
        275                 280                 285

Arg Leu Ser Phe Gln Leu Met Arg Pro Pro Asn Met Thr Pro Ser Val
    290                 295                 300

Ala Ala Leu Phe Pro Asn Ala Gln Pro Phe Glu His His Ala Thr Val
305                 310                 315                 320

Gly Leu Thr Leu Arg Ile Glu Ser Ala Val Cys Glu Ser Val Leu Ala
```

```
                        325                 330                 335
Asp Ala Ser Glu Thr Met Leu Ala Asn Val Thr Ser Val Arg Gln Glu
                340                 345                 350

Tyr Ala Ile Pro Val Gly Pro Val Phe Pro Pro Gly Met Asn Trp Thr
                355                 360                 365

Asp Leu Ile Thr Asn Tyr Ser Pro Ser Arg Glu Asp Asn Leu Gln Arg
            370                 375                 380

Val Phe Thr Val Ala Ser Ile Arg Ser Met Leu Val Lys
385                 390                 395

<210> SEQ ID NO 125
<211> LENGTH: 397
<212> TYPE: PRT
<213> ORGANISM: Human rotavirus

<400> SEQUENCE: 125

Met Asp Val Leu Tyr Ser Leu Ser Lys Thr Leu Lys Asp Ala Arg Asp
1               5                   10                  15

Lys Ile Val Glu Gly Thr Leu Tyr Ser Asn Val Ser Asp Leu Ile Gln
                20                  25                  30

Gln Phe Asn Gln Met Ile Ile Thr Met Asn Gly Asn Glu Phe Gln Thr
            35                  40                  45

Gly Gly Ile Gly Asn Leu Pro Ile Arg Asn Trp Asn Phe Asp Phe Gly
        50                  55                  60

Leu Leu Gly Thr Thr Leu Leu Asn Leu Asp Ala Asn Tyr Val Glu Thr
65                  70                  75                  80

Ala Arg Asn Thr Ile Asp Tyr Phe Val Asp Phe Val Asp Asn Val Cys
                85                  90                  95

Met Asp Glu Met Val Arg Glu Ser Gln Arg Asn Gly Ile Ala Pro Gln
            100                 105                 110

Ser Asp Ser Leu Arg Lys Leu Ser Gly Ile Lys Phe Lys Arg Ile Asn
        115                 120                 125

Phe Asp Asn Ser Ser Glu Tyr Ile Glu Asn Trp Asn Leu Gln Asn Arg
130                 135                 140

Arg Gln Arg Thr Gly Phe Thr Phe His Lys Pro Asn Ile Phe Pro Tyr
145                 150                 155                 160

Ser Ala Ser Phe Thr Leu Asn Arg Ser Gln Pro Ala His Asp Asn Leu
                165                 170                 175

Met Gly Thr Met Trp Leu Asn Ala Gly Ser Glu Ile Gln Val Ala Gly
            180                 185                 190

Phe Asp Tyr Ser Cys Ala Ile Asn Ala Pro Ala Asn Thr Gln Gln Phe
        195                 200                 205

Glu His Ile Val Gln Leu Arg Arg Val Leu Thr Thr Ala Thr Ile Thr
    210                 215                 220

Leu Leu Pro Asp Ala Glu Arg Phe Ser Phe Pro Arg Val Ile Asn Ser
225                 230                 235                 240

Ala Asp Gly Ala Thr Thr Trp Tyr Phe Asn Pro Val Ile Leu Arg Pro
                245                 250                 255

Asn Asn Val Glu Val Glu Phe Leu Leu Asn Gly Gln Ile Ile Asn Thr
            260                 265                 270

Tyr Gln Ala Arg Phe Gly Thr Ile Val Ala Arg Asn Phe Asp Thr Ile
        275                 280                 285

Arg Leu Ser Phe Gln Leu Met Arg Pro Pro Asn Met Thr Pro Ala Val
    290                 295                 300
```

```
Ala Ala Leu Phe Pro Asn Ala Gln Pro Phe Glu His His Ala Thr Val
305                 310                 315                 320

Gly Leu Thr Leu Arg Ile Glu Ser Ala Val Cys Glu Ser Val Leu Ala
            325                 330                 335

Asp Ala Ser Glu Thr Met Leu Ala Asn Val Thr Ser Val Arg Gln Glu
            340                 345                 350

Tyr Ala Ile Pro Val Gly Pro Val Phe Pro Pro Gly Met Asn Trp Thr
        355                 360                 365

Asp Leu Ile Thr Asn Tyr Ser Pro Ser Arg Glu Asp Asn Leu Gln Arg
        370                 375                 380

Val Phe Thr Val Ala Ser Ile Arg Ser Met Leu Val Lys
385                 390                 395

<210> SEQ ID NO 126
<211> LENGTH: 397
<212> TYPE: PRT
<213> ORGANISM: Human rotavirus

<400> SEQUENCE: 126

Met Asp Val Leu Tyr Ser Leu Ser Lys Thr Leu Lys Asp Ala Arg Asp
1               5                   10                  15

Lys Ile Val Glu Gly Thr Leu Tyr Ser Asn Val Ser Asp Leu Ile Gln
            20                  25                  30

Gln Phe Asn Gln Met Ile Ile Thr Met Asn Gly Asn Glu Phe Gln Thr
        35                  40                  45

Gly Gly Ile Gly Asn Leu Pro Ile Arg Asn Trp Asn Phe Asp Phe Gly
    50                  55                  60

Leu Leu Gly Thr Thr Leu Leu Asn Leu Asp Ala Asn Tyr Val Glu Thr
65                  70                  75                  80

Ala Arg Asn Thr Ile Asp Tyr Phe Val Asp Phe Val Asp Asn Val Cys
                85                  90                  95

Met Asp Glu Met Val Arg Glu Ser Gln Arg Asn Gly Ile Ala Pro Gln
            100                 105                 110

Ser Asp Ser Leu Arg Lys Leu Ser Gly Ile Lys Phe Lys Arg Ile Asn
        115                 120                 125

Phe Asp Asn Ser Ser Glu Tyr Ile Glu Asn Trp Asn Leu Gln Asn Arg
130                 135                 140

Arg Gln Arg Thr Gly Phe Thr Phe His Lys Pro Asn Ile Phe Pro Tyr
145                 150                 155                 160

Ser Ala Ser Phe Thr Leu Asn Arg Ser Gln Pro Ala His Asp Asn Leu
                165                 170                 175

Met Gly Thr Met Trp Leu Asn Ala Gly Ser Glu Ile Gln Val Ala Gly
            180                 185                 190

Phe Asp Tyr Ser Cys Ala Ile Asn Ala Pro Ala Asn Thr Gln Gln Phe
        195                 200                 205

Glu His Ile Val Gln Leu Arg Arg Val Leu Thr Thr Ala Thr Ile Thr
    210                 215                 220

Leu Leu Pro Asp Ala Glu Arg Phe Ser Phe Pro Arg Val Ile Asn Ser
225                 230                 235                 240

Ala Asp Gly Ala Thr Thr Trp Tyr Phe Asn Pro Val Ile Leu Arg Pro
                245                 250                 255

Asn Asn Val Glu Val Glu Phe Leu Leu Asn Gly Gln Ile Ile Asn Thr
            260                 265                 270

Tyr Gln Ala Arg Phe Gly Thr Ile Val Ala Arg Asn Phe Asp Thr Ile
        275                 280                 285
```

```
Arg Leu Ser Phe Gln Leu Met Arg Pro Pro Asn Met Thr Pro Ala Val
    290                 295                 300

Ala Ala Leu Phe Pro Asn Ala Gln Pro Phe Glu His His Ala Thr Val
305                 310                 315                 320

Gly Leu Thr Leu Arg Ile Glu Ser Ala Val Cys Glu Ser Val Leu Ala
                325                 330                 335

Asp Ala Ser Glu Thr Met Leu Ala Asn Val Thr Ser Val Arg Gln Glu
                340                 345                 350

Tyr Ala Ile Pro Val Gly Pro Val Phe Pro Pro Gly Met Asn Trp Thr
            355                 360                 365

Asp Leu Ile Thr Asn Tyr Ser Pro Ser Arg Glu Asp Asn Leu Gln Arg
370                 375                 380

Val Phe Thr Val Ala Ser Ile Arg Ser Met Leu Val Lys
385                 390                 395

<210> SEQ ID NO 127
<211> LENGTH: 1062
<212> TYPE: DNA
<213> ORGANISM: Human rotavirus

<400> SEQUENCE: 127
ggctttaaaa acgagaattt ccgtctggct agcggttagc tcttttttaat gtatggtatt    60
gaatatacca caattctgac catttttaata tctatcatat tattgaatta tatattaaaa   120
actataacta atacgatgga ctacataatt ttcaggtttt tactactcat tgctttaata   180
tcaccatttg taaggacaca tgctttaata tcaccatttg taaggacaca aaattacggc   240
atgtatttac caataacggg atcactagac gctgtataca caaattcaac tagtggagaa   300
tatccagcag aagctaaaaa tgagatttca gatgatgaat gggaaaatac tctatcacaa   360
ttatttttaa ctaaaggatg gccaattgga tcagtttatt ttaaagacta caatgatatt   420
aacacatttt ctgtgaatcc acaactgtat tgtgattata atgtagtatt gatgagatat   480
gacaatacat ctgaattaga tgcatcagag ttagcagatc ttatattgaa tgaatggctg   540
tgcaatccta tggacatatc actttactat tatcaacaaa gtagcgaatc aaataaatgg   600
atatcgatgg gaacagactg cacggtaaaa gtttgtccac tcaatacaca aaccttaggc   660
attggatgca aaactacgga cgtaaacaca tttgagattg ttgcgtcgtc tgaaaaatta   720
gtaattactg acgttgtaaa tggtgttaat cataagataa atatttcaat aaatacgtgc   780
actatacgta actgtaataa attaggacca cgagaaaatg ttgctataat tcaagttggt   840
ggaccgaacg cattagatat cactgctgat ccaacaacag tcccacaagt tcaaagaatc   900
atgcgaataa attggaaaaa atggtggcaa gtattttata cagtagttga ctatattaac   960
caagttatac aagtcatgtc caaacgatca agatcattag acgcagctgc attttattat  1020
agaatttaga tatagattag attagagttg tatgatgtga cc                     1062

<210> SEQ ID NO 128
<211> LENGTH: 1062
<212> TYPE: DNA
<213> ORGANISM: Human rotavirus

<400> SEQUENCE: 128
ggctttaaaa gagagaattt ccgtctggct agcggttagc tcttttttaat gtatggtatt    60
gaatatacca caattctgac catttttaata tctatcatat tattgaatta tatactaaaa   120
actataacta atacaatgga ctacataat

```
tcaccatttg tgaggacaca aaattacggc atgtatttac caataacggg atcactagac      240
gctgtataca caaattcaac tagtggagaa tcatttctaa cttcaacgtt atgtttatat      300
tatccaacag aagctaaaaa tgagatttca gataatgaat gggaaaatac tctatcacaa      360
ttatttttaa ctaaaggatg gccgactggg tcagtttatt ttaaagacta caatgatatt      420
actacatttt ctatgaatcc acaactgtat tgtgattata atgtagtatt gatgcgatat      480
gataatacat ctgaattaga tgcatcggaa ttagcagatc ttatattgaa cgaatggctg      540
tgcaatccta tggatatatc actttactat tatcaacaaa atagcgaatc aaataaatgg      600
atatcgatgg aacagactg cacggtaaaa gtttgtccac tcaatacgca aactttagga       660
attggatgca aaactacgga cgtggataca tttgagattg ttgcgtcgtc tgaaaaattg      720
gtaattactg atgttgtaaa tggtgttaat cataaaataa atatttcaat aaatacgtgc      780
actatacgta attgtaataa actaggacca cgagaaaatg ttgctataat tcaagttggt      840
ggaccgaacg cactagatat cactgctgat ccaacaacag ttccacaggt tcaaagaatt      900
atgcgagtaa attggaaaaa atggtggcaa gtgtttttata cagtagttga ttatattaac      960
caaattatac aagttatgtc caaacggtca agatcattag acacggctgc ttttattat      1020 agaatttaga tataacttag attagaattg tatgatgtga cc                         1062

<210> SEQ ID NO 129
<211> LENGTH: 1062
<212> TYPE: DNA
<213> ORGANISM: Human rotavirus

<400> SEQUENCE: 129
ggctttaaaa gagagaattt ccgtctggct agcggttagc tcttttttaat gtatggtatt       60 gaatatacca caattctgac catttttaata tctatcatat tattgaatta tatactaaaa     120
actataacta atacaatgga ctacataatt tttagatttt tactactcat cgctctgatg      180
tcaccatttg tgaggacaca aaattacggc atgtatttac caataacggg atcactagac      240
gctgtataca caaattcaac tagtggagaa tcatttctaa cttcaacgtt atgtttatat      300
tatccaacag aagctaaaaa tgagatttca gataatgaat gggaaaatac tctatcacaa      360
ttatttttaa ctaaaggatg gccgactggg tcagtttatt ttaaagacta caatgatatt      420
actacatttt ctatgaatcc acaactgtat tgtgattata atgtagtatt gatgcgatat      480
gataatacat ctgaattaga tgcatcggaa ttagcagatc ttatattgaa cgaatggctg      540
tgcaatccta tggatatatc actttactat tatcaacaaa atagcgaatc aaataaatgg      600
atatcgatgg aacagactg cacggtaaaa gtttgtccac tcaatacgca aactttagga       660
attggatgca aaactacgga cgtggataca tttgagattg ttgcgtcgtc tgaaaaattg      720
gtaattactg atgttgtaaa tggtgttaat cataaaataa atatttcaat aaatacgtgc      780
actatacgta attgtaataa actaggacca cgagaaaatg ttgctataat tcaagttggt      840
ggaccgaacg cactagatat cactgctgat ccaacaacag ttccacaggt tcaaagaatt      900
atgcgagtaa attggaaaaa atggtggcaa gtgtttttata cagtagttga ttatattaac      960
caaattatac aagttatgtc caaacggtca agatcattag acacggctgc ttttattat      1020 agaatttaga tataacttag attagaattg tatgatgtga cc                         1062

<210> SEQ ID NO 130
<211> LENGTH: 326
<212> TYPE: PRT
```

<213> ORGANISM: Human rotavirus

<400> SEQUENCE: 130

Met Tyr Gly Ile Glu Tyr Thr Thr Ile Leu Thr Ile Leu Ile Ser Ile
1               5                   10                  15

Ile Leu Leu Asn Tyr Ile Leu Lys Thr Ile Thr Asn Thr Met Asp Tyr
            20                  25                  30

Ile Ile Phe Arg Phe Leu Leu Leu Ile Ala Leu Ile Ser Pro Phe Val
        35                  40                  45

Arg Thr Gln Asn Tyr Gly Met Tyr Leu Pro Ile Thr Gly Ser Leu Asp
    50                  55                  60

Ala Val Tyr Thr Asn Ser Thr Ser Gly Glu Pro Phe Leu Thr Ser Thr
65                  70                  75                  80

Leu Cys Leu Tyr Tyr Pro Ala Glu Ala Lys Asn Glu Ile Ser Asp Asp
                85                  90                  95

Glu Trp Glu Asn Thr Leu Ser Gln Leu Phe Leu Thr Lys Gly Trp Pro
            100                 105                 110

Ile Gly Ser Val Tyr Phe Lys Asp Tyr Asn Asp Ile Asn Thr Phe Ser
        115                 120                 125

Val Asn Pro Gln Leu Tyr Cys Asp Tyr Asn Val Val Leu Met Arg Tyr
    130                 135                 140

Asp Asn Thr Ser Glu Leu Asp Ala Ser Glu Leu Ala Asp Leu Ile Leu
145                 150                 155                 160

Asn Glu Trp Leu Cys Asn Pro Met Asp Ile Ser Leu Tyr Tyr Tyr Gln
                165                 170                 175

Gln Ser Ser Glu Ser Asn Lys Trp Ile Ser Met Gly Thr Asp Cys Thr
            180                 185                 190

Val Lys Val Cys Pro Leu Asn Thr Gln Thr Leu Gly Ile Gly Cys Lys
        195                 200                 205

Thr Thr Asp Val Asn Thr Phe Glu Ile Val Ala Ser Ser Glu Lys Leu
210                 215                 220

Val Ile Thr Asp Val Val Asn Gly Val Asn His Lys Ile Asn Ile Ser
225                 230                 235                 240

Ile Asn Thr Cys Thr Ile Arg Asn Cys Asn Lys Leu Gly Pro Arg Glu
                245                 250                 255

Asn Val Ala Ile Ile Gln Val Gly Gly Pro Asn Ala Leu Asp Ile Thr
            260                 265                 270

Ala Asp Pro Thr Thr Val Pro Gln Val Gln Arg Ile Met Arg Ile Asn
        275                 280                 285

Trp Lys Lys Trp Trp Gln Val Phe Tyr Thr Val Val Asp Tyr Ile Asn
    290                 295                 300

Gln Val Ile Gln Val Met Ser Lys Arg Ser Arg Ser Leu Asp Ala Ala
305                 310                 315                 320

Ala Phe Tyr Tyr Arg Ile
                325

<210> SEQ ID NO 131
<211> LENGTH: 326
<212> TYPE: PRT
<213> ORGANISM: Human rotavirus

<400> SEQUENCE: 131

Met Tyr Gly Ile Glu Tyr Thr Thr Ile Leu Thr Ile Leu Ile Ser Ile
1               5                   10                  15

Ile Leu Leu Asn Tyr Ile Leu Lys Thr Ile Thr Asn Thr Met Asp Tyr 20                  25                  30
Ile Ile Phe Arg Phe Leu Leu Leu Ile Ala Leu Met Ser Pro Phe Val
            35                  40                  45

Arg Thr Gln Asn Tyr Gly Met Tyr Leu Pro Ile Thr Gly Ser Leu Asp
 50                  55                  60

Ala Val Tyr Thr Asn Ser Thr Ser Gly Glu Ser Phe Leu Thr Ser Thr
 65                  70                  75                  80

Leu Cys Leu Tyr Tyr Pro Thr Glu Ala Lys Asn Glu Ile Ser Asp Asn
                 85                  90                  95

Glu Trp Glu Asn Thr Leu Ser Gln Leu Phe Leu Thr Lys Gly Trp Pro
                100                 105                 110

Thr Gly Ser Val Tyr Phe Lys Asp Tyr Asn Asp Ile Thr Thr Phe Ser
                115                 120                 125

Met Asn Pro Gln Leu Tyr Cys Asp Tyr Asn Val Val Leu Met Arg Tyr
            130                 135                 140

Asp Asn Thr Ser Glu Leu Asp Ala Ser Glu Leu Ala Asp Leu Ile Leu
145                 150                 155                 160

Asn Glu Trp Leu Cys Asn Pro Met Asp Ile Ser Leu Tyr Tyr Tyr Gln
                165                 170                 175

Gln Asn Ser Glu Ser Asn Lys Trp Ile Ser Met Gly Thr Asp Cys Thr
                180                 185                 190

Val Lys Val Cys Pro Leu Asn Thr Gln Thr Leu Gly Ile Gly Cys Lys
            195                 200                 205

Thr Thr Asp Val Asp Thr Phe Glu Ile Val Ala Ser Ser Glu Lys Leu
            210                 215                 220

Val Ile Thr Asp Val Val Asn Gly Val Asn His Lys Ile Asn Ile Ser
225                 230                 235                 240

Ile Asn Thr Cys Thr Ile Arg Asn Cys Asn Lys Leu Gly Pro Arg Glu
                245                 250                 255

Asn Val Ala Ile Ile Gln Val Gly Gly Pro Asn Ala Leu Asp Ile Thr
            260                 265                 270

Ala Asp Pro Thr Thr Val Pro Gln Val Gln Arg Ile Met Arg Val Asn
            275                 280                 285

Trp Lys Lys Trp Trp Gln Val Phe Tyr Thr Val Val Asp Tyr Ile Asn
            290                 295                 300

Gln Ile Ile Gln Val Met Ser Lys Arg Ser Arg Ser Leu Asp Thr Ala
305                 310                 315                 320

Ala Phe Tyr Tyr Arg Ile
                325

<210> SEQ ID NO 132
<211> LENGTH: 326
<212> TYPE: PRT
<213> ORGANISM: Human rotavirus

<400> SEQUENCE: 132

Met Tyr Gly Ile Glu Tyr Thr Thr Ile Leu Thr Ile Leu Ile Ser Ile
 1                   5                  10                  15

Ile Leu Leu Asn Tyr Ile Leu Lys Thr Ile Thr Asn Thr Met Asp Tyr
            20                  25                  30

Ile Ile Phe Arg Phe Leu Leu Leu Ile Ala Leu Met Ser Pro Phe Val
            35                  40                  45

Arg Thr Gln Asn Tyr Gly Met Tyr Leu Pro Ile Thr Gly Ser Leu Asp
 50                  55                  60

```
Ala Val Tyr Thr Asn Ser Thr Ser Gly Glu Ser Phe Leu Thr Ser Thr
 65              70                  75                  80
Leu Cys Leu Tyr Tyr Pro Thr Glu Ala Lys Asn Glu Ile Ser Asp Asn
             85                  90                  95
Glu Trp Glu Asn Thr Leu Ser Gln Leu Phe Leu Thr Lys Gly Trp Pro
            100                 105                 110
Thr Gly Ser Val Tyr Phe Lys Asp Tyr Asn Asp Ile Thr Thr Phe Ser
            115                 120                 125
Met Asn Pro Gln Leu Tyr Cys Asp Tyr Asn Val Val Leu Met Arg Tyr
            130                 135                 140
Asp Asn Thr Ser Glu Leu Asp Ala Ser Glu Leu Ala Asp Leu Ile Leu
145                 150                 155                 160
Asn Glu Trp Leu Cys Asn Pro Met Asp Ile Ser Leu Tyr Tyr Tyr Gln
                165                 170                 175
Gln Asn Ser Glu Ser Asn Lys Trp Ile Ser Met Gly Thr Asp Cys Thr
                180                 185                 190
Val Lys Val Cys Pro Leu Asn Thr Gln Thr Leu Gly Ile Gly Cys Lys
            195                 200                 205
Thr Thr Asp Val Asp Thr Phe Glu Ile Val Ala Ser Ser Glu Lys Leu
            210                 215                 220
Val Ile Thr Asp Val Val Asn Gly Val Asn His Lys Ile Asn Ile Ser
225                 230                 235                 240
Ile Asn Thr Cys Thr Ile Arg Asn Cys Asn Lys Leu Gly Pro Arg Glu
                245                 250                 255
Asn Val Ala Ile Ile Gln Val Gly Gly Pro Asn Ala Leu Asp Ile Thr
            260                 265                 270
Ala Asp Pro Thr Thr Val Pro Gln Val Gln Arg Ile Met Arg Val Asn
            275                 280                 285
Trp Lys Lys Trp Trp Gln Val Phe Tyr Thr Val Val Asp Tyr Ile Asn
            290                 295                 300
Gln Ile Ile Gln Val Met Ser Lys Arg Ser Arg Ser Leu Asp Thr Ala
305                 310                 315                 320
Ala Phe Tyr Tyr Arg Ile
                325
```

HUMAN ROTAVIRUS STRAINS AND VACCINES

CROSS REFERENCE TO RELATED APPLICATIONS

This application is a divisional of U.S. patent application Ser. No. 16/672,168, filed on Nov. 1, 2019, which is a continuation of U.S. patent application Ser. No. 15/956,662, filed on Apr. 18, 2018, issued as U.S. Pat. No. 10,500,269, which is a continuation of U.S. patent application Ser. No. 15/200,837, filed on Jul. 1, 2016, issued as U.S. Pat. No. 9,974,851, which is a continuation of U.S. patent application Ser. No. 14/461,663, filed Aug. 18, 2014, issued as U.S. Pat. No. 9,498,526, which is a continuation of U.S. patent application Ser. No. 13/320,095, filed on Nov. 11, 2011, issued as U.S. Pat. No. 8,822,192, which is a § 371 U.S. national stage of International Application No. PCT/US2010/034537, filed on May 12, 2010, which claims priority U.S. Provisional Application No. 61/177,393 filed May 12, 2009. The entire contents of the prior applications are all incorporated herein by reference.

GOVERNMENT SPONSORSHIP

This invention was made by the Centers for Disease Control and Prevention, an agency of the United States Government. The U.S. government has certain rights in the invention.

FIELD OF THE INVENTION

The present invention relates generally to virus vaccine strains as well as vaccine compositions and methods relating thereto. More specifically, the present invention relates to human rotavirus A vaccine strains, vaccine compositions and methods of use to induce an immunological response against rotavirus A in a subject.

BACKGROUND OF THE INVENTION

Of the various enteric pathogenic viruses causing severe diarrhea in children, rotavirus is the most common causing an average of 611,000 deaths per year. Virtually all children are infected by rotavirus by age 5. The virus is believed to be highly contagious and has been described as a "democratic" virus since the infection affects no particular socioeconomic or geographic group disproportionately. While the majority of children having access to adequate supportive and palliative medical care survive infection with no significant long-term consequences, the number of deaths associated with severe diarrhea, vomiting, dehydration and shock is unacceptable and requires preventative intervention if possible.

Rotavirus A is an icosahedral virus in the family Reoviridae with a distinct hub-and-spoke morphology. Particular rotaviruses are classified by group, subgroup and serotype according to properties characteristic of the viral capsid proteins. Rotavirus particles contain 3 protein layers surrounding the viral genome which consists of 11 segments of double-stranded RNA, each segment encoding a protein. The viral proteins include structural proteins called VPs and nonstructural proteins designated NSPs. A number of the structural proteins are particularly important in eliciting an immune response in a host since these proteins are present on the outermost surface of the viral particles. In particular the proteins VP7 and VP4 both figure prominently in host immune response and therefore have also played a central role in development of rotavirus vaccines.

Variants of VP7 and VP4 structural proteins characterize distinct rotavirus A serotypes. In particular, variants of human VP7 are identified as "G" serotypes including at least serotypes G1, G2, G3, G4, as well as the less common G5, G6, G8, G9, G10, G11, G12, G13 and G14. Variants of the VP4 structural protein are identified as "P" serotypes including P1A, P1B, P2A, P3, P4, P5, P6 and P8. Because intact rotaviruses are characterized by both a VP7 protein and a VP4 protein, individual virus serotypes are named according to the identity of the variant of these two proteins contained in the particular virus. For example, a common rotavirus A contains both G1 and P[8] variants of VP7 and VP4, respectively. The G1, P[8] serotype of rotavirus A is one of the most common forms of the virus which cause disease worldwide. The G1 serotype of rotavirus A is the most common serotype associated with human disease worldwide. A number of vaccines have been developed which use rotavirus A G1 strains with the goal of developing immunity in a host against rotavirus A G1 strains as well as rotavirus A strains having other serotypes. However, this approach has been limited by important differences between the G1 and G2 serotypes. In particular, rotavirus A G2 strains are derived from a different lineage than most other rotavirus strains. This is demonstrated by nucleic acid hybridization experiments showing that labeled transcripts of the 11 gene segments of G2 strains, also known as the DS-1 genogroup, do not hybridize with corresponding nucleic acids from the strains known as the Wa genogroup of rotavirus A which includes G1, G3, G4, and G9. The lack of hybridization of these homologous genes indicates that differences in the encoded proteins, such as the outer capsid proteins VP4 and VP7 and inner capsid protein VP6, are substantial. These genetic differences support the observations that individuals infected or immunized using a G1 strain are less likely to show cross protection against G2 strains than other strains of the Wa genogroup.

In addition, to the common G1 and G2 rotavirus A strains, a diversity of human rotavirus types is increasingly recognized as contributing to acute severe diarrhea disease worldwide. This diversity underscores the need for robust vaccines capable of generating immunity against several strains. Recently, the United States Food and Drug Administration suspended the use of the ROTARIX vaccine citing contaminants in its preparation. Thus, the number of available vaccines for rotavirus is declining at a time when infections remain a serious worldwide problem. Another vaccine, RotaTeq®, appears safe and effective in preventing diarrhea among children in middle and high income countries and are currently licensed and recommended for use in infants throughout the world. However, the efficacy of this vaccine is reduced in low income countries of Africa and Asia.

Thus, there is a continuing need for vaccines against human rotavirus A of both common and less common types.

BRIEF DESCRIPTION OF THE DRAWINGS

FIG. 1A is a xerographic image of an electron micrograph showing intact isolated rotavirus A virions identified as strain CDC-9, having serotype P[8], G1;

FIG. 1B is a xerographic image of an electron micrograph showing intact isolated rotavirus A virions identified as strain CDC-66, having serotype P[4], G2;

FIG. 2 shows a xerographic reproduction of an image of a polyacrylamide gel illustrating RNA profiles of rotavirus A strain CDC-9 isolated from a stool sample (S) and Vero cells (V) and showing typical long (CDC-9) RNA electropherotypes for the rotavirus strain;

FIG. 3 shows a xerographic reproduction of an image of a polyacrylamide gel illustrating RNA profiles of the rotavirus A strain CDC-66 isolated from a stool sample and Vero cells and showing typical short RNA electropherotypes for this rotavirus strain;

FIG. 5A is a bar graph showing total antibody titers in response to thermally inactivated rotavirus in control and vaccinated mice;

FIG. 5B is a bar graph showing neutralizing antibody titers in response to thermally inactivated rotavirus in control and vaccinated mice;

Figure 4A:
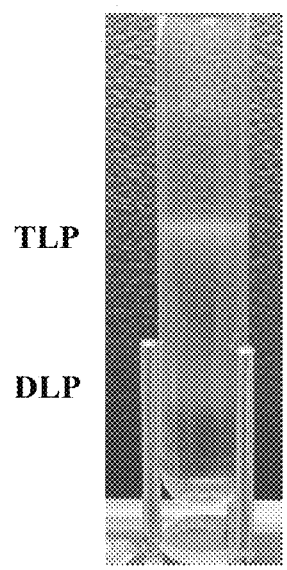
FIG. 4A shows bands of CsCl purified rotavirus particles of rotavirus A strain CDC-9.

FIG. 6 is a bar graph showing total serum antibody responses to thermally inactivated rotavirus formulated with $Al(OH)_3$ in control and vaccinated mice.

FIG. 7A shows virus shedding in fecal samples of piglets vaccinated with no antigen and with 750 micrograms of aluminum phosphate in 4 animals;

FIG. 7B shows virus shedding in fecal samples from piglets immunized with antigen and no adjuvant;

FIG. 7C shows virus shedding in fecal samples of piglets immunized with antigen and adjuvant;

FIG. 7D shows virus shedding measured in fecal samples of piglets immunized with buffer only;

FIG. 8A is a bar graph showing rotavirus specific IgG antibody response in sera of piglets vaccinated with no antigen and with 600 micrograms of aluminum phosphate (solid bars) or piglets vaccinated with 50 micrograms of antigen and with 600 micrograms of aluminum phosphate (hatched bars);

FIG. 8B is a bar graph showing neutralizing antibody response in sera of piglets vaccinated with no antigen and with 600 micrograms of aluminum phosphate or piglets vaccinated with 50 micrograms of antigen and with 600 micrograms of aluminum phosphate;

FIG. 9A shows virus shedding in fecal samples of piglets vaccinated with no antigen and with 600 micrograms of aluminum phosphate; and FIG. 9B shows virus shedding in fecal samples of piglets vaccinated with 50 micrograms of antigen and with 600 micrograms of aluminum phosphate.

SEQUENCE LISTING

The Sequence Listing is submitted as an ASCII text file [4239-98501-24_Sequence_Listing.txt, Apr. 11, 2021, 444 KB], which is incorporated by reference herein.

SUMMARY OF THE INVENTION

A vaccine composition is provided including one or more isolated rotavirus strains illustratively strain CDC-9 or CDC-66 in combination with a pharmaceutically acceptable carrier. An inventive vaccine optionally includes an adjuvant.

The CDC-9 or CDC-66 strains in an inventive vaccine are optionally live attenuated rotavirus or inactivated rotavirus.

It is appreciated that an inventive vaccine optionally includes at least two isolated rotavirus strains. The at least two isolated rotavirus strains each independently have a G group serotype of G1, G2, G3, G4, G5, G6, G7, G8, G9, G10, G11, G12, G13 or G14. Optionally, the at least two isolated rotavirus strains each independently have a P group serotype of P1A, P1B, P2A, P3, P4, P5, P6, P8, P11, or P12.

An inventive vaccine is optionally administered parenterally or orally.

An isolated rotavirus strain is also provided that is illustratively CDC-9 or CDC-66 strain.

An inventive vaccine is provided that includes a pharmaceutically acceptable carrier admixed with an isolated rotavirus strain characterized as having a G1 group serotype and an isolated rotavirus strain characterized as having a G2 group serotype. The G1 or G2 group serotype strains optionally each independently have a P group serotype of P1A, P1B, P2A, P3, P4, P5, P6, P8, P11 or P12. In some embodiments the human rotavirus strain characterized as having a G1 group serotype is CDC-9, or the human rotavirus strain characterized as having a G2 group serotype is CDC-66.

A method of inducing an immunological response to a rotavirus in a subject is provided including administering a vaccine composition including a pharmaceutically acceptable carrier admixed with an isolated human rotavirus strain of CDC-9 or CDC-66.

A method of inducing an immunological response to a rotavirus in a subject is provided including administering a vaccine composition including a pharmaceutically acceptable carrier admixed with an isolated human rotavirus strain characterized as having a G1 group serotype and an isolated human rotavirus strain characterized as having a G2 group serotype.

Also provided is a vaccine including a pharmaceutically acceptable carrier admixed with a portion of an isolated human rotavirus. The isolated human rotavirus portion is a peptide or polypeptide including an amino acid sequence of SEQ ID No. 2; SEQ ID No. 5; SEQ ID No. 8; SEQ ID No. 11; SEQ ID No. 14; SEQ ID No. 17; SEQ ID No. 20; SEQ ID No. 23; SEQ ID No. 26; SEQ ID No. 29; SEQ ID No. 32; SEQ ID No. 3; SEQ ID No. 6; SEQ ID No. 9; SEQ ID No. 12; SEQ ID No. 15; is SEQ ID No. 18; SEQ ID No. 21; SEQ ID No. 24; SEQ ID No. 27; SEQ ID No. 30; SEQ ID No. 33; SEQ ID No. 71; SEQ ID No. 77; SEQ ID No. 83; SEQ ID No. 89; SEQ ID No. 95; SEQ ID No. 101; SEQ ID No. 107; SEQ ID No. 113; SEQ ID No. 119; SEQ ID No. 125; SEQ ID No. 131; SEQ ID No. 72; SEQ ID No. 78; SEQ ID No. 84; SEQ ID No. 90; SEQ ID No. 96; SEQ ID No. 102; SEQ ID No. 108; SEQ ID No. 114; SEQ ID No. 120; SEQ ID No. 126; SEQ ID No. 132; a homolog thereof or a fragment thereof.

DETAILED DESCRIPTION OF THE PREFERRED EMBODIMENTS

Novel isolated human rotavirus A strains, vaccines including human rotavirus A strains, vaccines including a human rotavirus A polypeptide and/or an immunogenic fragment thereof, anti-rotavirus A antibodies and methods for vaccinating humans against rotavirus A disease are provided according to embodiments of the present invention.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B.

Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; Wild, D., The Immunoassay Handbook, 3rd Ed., Elsevier Science, 2005; Gosling, J. P., Immunoassays: A Practical Approach, Practical Approach Series, Oxford University Press, 2005; Antibody Engineering, Kontermann, R. and Dubel, S. (Eds.), Springer, 2001; Harlow, E. and Lane, D., Antibodies: A Laboratory Manual, Cold Spring Harbor Laboratory Press, 1988; Ausubel, F. et al., (Eds.), Short Protocols in Molecular Biology, Wiley, 2002; J. D. Pound (Ed.) Immunochemical Protocols, Methods in Molecular Biology, Humana Press; 2nd ed., 1998; B. K. C. Lo (Ed.), Antibody Engineering: Methods and Protocols, Methods in Molecular Biology, Humana Press, 2003; and Kohler, G. and Milstein, C., Nature, 256:495-497 (1975); the contents of each of which are incorporated herein by reference.

Human Rotaviruses

Novel human rotavirus A strains of the present invention are illustratively identified as CDC-9 and CDC-66, fragments thereof or homologues thereof.

The CDC-9 rotavirus A strain was isolated from a fecal specimen of a 5-month boy in Providence, R.I. Human rotavirus strain CDC-9 was characterized by RT-PCR using G and P type-specific primers. RT-PCR analysis indicates that isolated strain CDC-9 is a strain having a genotype P[8], G1. Particular characteristics of CDC-9, its identification, isolation, and passages in Vero cells are described by Esona, M D, et al., Human Vaccines, 2010; 6:1-7, the entire contents of which are incorporated herein by reference.

Following isolation from the fecal sample, isolated rotavirus strain CDC-9 was adapted to grow in MA104 cells that were prepared and frozen before 1980 and have complete documentation. The CDC-9 strain was then adapted to grow in Vero cells qualified for vaccine production. CDC-9 was purified by performing 3 rounds of limiting dilution and after amplification in Vero cells, was further purified by performing 3 rounds of plaque assays. The isolated strain CDC-9 was passaged 7 and 38 times in MA104 and Vero cells, respectively (total 45 passages). The adaptation and all passages are done using standard operation procedures and certified raw materials and reagents and under the Good Laboratory Practice Guidelines. Unlike other reference or laboratory strains, the isolated strain CDC-9 has complete passage history and documentation.

The titer of passaged human rotavirus strain CDC-9 is about $10^7$ ffu/ml.

Isolated human rotavirus strain CDC-9 was studied by electron microscopy using CDC-9 virions isolated from the medium of infected Vero cell cultures. FIG. 1A shows an electron micrograph of isolated CDC-9 virions. The micrograph shows the virions to have the morphology typical of human rotavirus A virions.

Isolated human rotavirus strain CDC-9 was further examined using polyacrylamide gel electrophoresis of RNA isolated from the strain. As shown in FIG. 2, CDC-9 has a typical long RNA electropherotype and the RNA profiles of both the original isolate from the stool and the Vero passaged rotavirus are identical. Also shown in FIG. 2 is a standard for comparison including an RNA profile of a Wa genogroup human rotavirus.

Isolated human rotavirus strain CDC-9 in stool and Vero cells (passage 27) was analyzed by sequence analysis of entire genome.

CDC9 amino acid sequences of proteins encoded by nucleic acids isolated from a stool sample: CDC9 NSP1 aa—stool is SEQ ID No. 2; CDC9 NSP 2 aa—stool is SEQ ID No. 5; CDC9 NSP 3 aa—stool is SEQ ID No. 8; CDC9 NSP 4 aa—stool is SEQ ID No. 11; CDC9 NSP 5 aa—stool is SEQ ID No. 14; CDC9 VP1 aa—stool is SEQ ID No. 17; CDC9 VP 2 aa—stool is SEQ ID No. 20; CDC9 VP 3 aa—stool is SEQ ID No. 23; CDC9 VP 4 aa—stool is SEQ ID No. 26; CDC9 VP 6 aa—stool is SEQ ID No. 29; and CDC9 VP 7 aa—stool is SEQ ID No. 32.

CDC9 nucleotide sequences of nucleic acids isolated from a stool sample: CDC9 NSP1 nt—stool is SEQ ID No. 35; CDC9 NSP 2 nt—stool is SEQ ID No. 38; CDC9 NSP 3 nt—stool is SEQ ID No. 41; CDC9 NSP 4 nt—stool is SEQ ID No. 44; CDC9 NSP 5 nt—stool is SEQ ID No. 47; CDC9 VP1 nt—stool is SEQ ID No. 50; CDC9 VP 2 nt—stool is SEQ ID No. 53; CDC9 VP 3 nt—stool is SEQ ID No. 56; CDC9 VP 4 nt—stool is SEQ ID No. 59; CDC9 VP 6 nt—stool is SEQ ID No. 62; and CDC9 VP 7 nt—stool is SEQ ID No. 65.

CDC9 amino acid sequences of proteins encoded by nucleic acids isolated from CDC9 rotavirus at passage 27 isolated from Vero cells: CDC9 NSP1 aa—Vero is SEQ ID No. 3; CDC9 NSP 2 aa—Vero is SEQ ID No. 6; CDC9 NSP 3 aa—Vero is SEQ ID No. 9; CDC9 NSP 4 aa—Vero is SEQ ID No. 12; CDC9 NSP 5 aa—Vero is SEQ ID No. 15; CDC9 VP1 aa—Vero is SEQ ID No. 18; CDC9 VP 2 aa—Vero is SEQ ID No. 21; CDC9 VP 3 aa—Vero is SEQ ID No. 24; CDC9 VP 4 aa—Vero is SEQ ID No. 27; CDC9 VP 6 aa—Vero is SEQ ID No. 30; and CDC9 VP 7 aa—Vero is SEQ ID No. 33.

CDC9 nucleotide sequences of nucleic acids isolated from CDC9 rotavirus at passage 27 isolated from Vero cells: CDC9 NSP1 nt—Vero is SEQ ID No. 36; CDC9 NSP 2 nt—Vero is SEQ ID No. 39; CDC9 NSP 3 nt—Vero is SEQ ID No. 42; CDC9 NSP 4 nt—Vero is SEQ ID No. 45; CDC9 NSP 5 nt—Vero is SEQ ID No. 48; CDC9 VP1 nt—Vero is SEQ ID No. 51; CDC9 VP 2 nt—Vero is SEQ ID No. 54; CDC9 VP 3 nt—Vero is SEQ ID No. 57; CDC9 VP 4 nt—Vero is SEQ ID No. 60; CDC9 VP 6 nt—Vero is SEQ ID No. 63; and CDC9 VP 7 nt—Vero is SEQ ID No. 66.

Nucleotide and amino acid sequences of entire genome from CDC-9 rotavirus isolated from stool and infected culture were compared with amino acid and nucleotide sequences of entire genome from reference KU or other G1P8 strains of rotavirus A, as shown herein.

Additionally, as shown in Table 2, CDC-9 genes (except for segment 3) share high sequence identity with the corresponding genes of the prototype P[8],G1 human KU strain.

| Gene | CDC-9 | |
|------|-------|------|
|      | % NT  | % AA |
| VP1  | 88    | 96   |
| VP2  | 95    | 98   |
| VP3  | 77    | 80   |
| VP4  | 91    | 94   |
| VP6  | 91    | 98   |
| VP7  | 93    | 96   |
| NSP1 | 83    | 81   |
| NSP2 | 90    | 94   |
| NSP3 | 93    | 95   |
| NSP4 | 93    | 94   |
| NSP5 | 93    | 94   |

In addition, changes in nt and aa sequences of entire genome of CDC-9 strain from stool to passage 27 in Vero cells have been documented, as shown in Table 3.

TABLE 3

Changes of nt and aa in genes of CDC-9 from stool to passage 27 in Vero cells

| Gene segment | # of nt changes | nt position | # of aa changes | aa position |
|---|---|---|---|---|
| NSP1 | 1 | 396 A→G | 1 | 122 Q→R |
| NSP2 | 0 | | 0 | |
| NSP3 | 0 | | 0 | |
| NSP4 | 0 | 0 | 0 | |
| NSP5 | 1 | 155C→T | 1 | 45 A→I |
| VP1 | 0 | | 0 | |
| VP2 | 0 | | 0 | |
| VP3 (DS-1) | 0 | | 0 | |
| VP4 | 6 | 161G→A, 1001C→T, 1101G→A, 1162G→C, 1171A→C, 2025T→C | 5 | 51G→-D, 331S→F, 364M→I, 385D→H, 388I→L |
| VP6 | 1 | 325C→T | 1 | 101A→V |
| VP7 | 1 | 678G→A | 0 | |
| Total: | 10 | | 8 | |

Isolated rotavirus CDC-9 in Vero cells is a reassortant that has all (except segment 3) genes from a KU-like strain. CDC-9 has as segment 3 derived from a DS-1 like strain as CDC-9 VP3 shares a high identity with the cognate gene of DS-1 strain. This reassortment might have occurred during natural infection or when G1P8 and G2P4 rotaviruses in the fecal specimen were adapted and passaged in cell culture. Rotavirus VP3 has been described to possess guanylyltransferase and may be involved in viral replication and morphogenesis.

The CDC-66 rotavirus A strain was isolated from a fecal specimen of an 11-month girl in Providence, R.I. Human rotavirus strain CDC-66 was characterized by RT-PCR using G and P type-specific primers. RT-PCR analysis indicates that isolated strain CDC-66 is a strain having a serotype P[4], G2.

Following isolation from the fecal sample, isolated rotavirus strain CDC-66 was adapted to grow in MA104 cells that were prepared and frozen before 1980 and have complete passage history and documentation. The CDC-66 strain was then adapted to grow in Vero cells qualified for vaccine production. CDC-66 was purified by performing 3 rounds of limiting dilution and after amplification in Vero cells, was further purified by performing 3 rounds of plaque assays. The isolated strain CDC-66 was passaged 5 and 40 times in MA104 and Vero cells, respectively (total 45 passages). The adaptation and all passages are done using standard operation procedures and certified raw materials and reagents and under the Good Laboratory Practice Guidelines. Unlike other reference and laboratory strains, the isolated strain CDC-66 has complete passage history and documentation.

The titer of passaged human rotavirus strain CDC-66 is about $10^7$ pfu/ml.

Isolated human rotavirus strain CDC-66 was studied by electron microscopy using CDC-66 virions isolated from the medium of infected Vero cell cultures. FIG. 1B shows an electron micrograph of isolated CDC-66 virions. The micrograph shows the virions to have the morphology typical of human rotavirus virions.

Isolated human rotavirus strain CDC-66 was further examined using polyacrylamide gel electrophoresis of RNA isolated from the strain. As shown in FIG. 3, CDC-66 has a typical short RNA electropherotype and the RNA profiles of both the original isolate from the stool and the Vero passaged rotavirus are identical. Also shown in FIG. 3 are standards for comparison including a DNA molecular weight marker III (Roche) in the far left lane and an RNA profile of rhesus rotavirus, RRV.

Isolated human rotavirus strain CDC-66 in stool and Vero cells (passage 27) was analyzed by sequence analysis of entire genome.

CDC66 amino acid sequences of proteins encoded by nucleic acids isolated from a stool sample: CDC66 NSP1 aa—stool is SEQ ID No. 71; CDC66 NSP 2 aa—stool is SEQ ID No. 77; CDC66 NSP 3 aa—stool is SEQ ID No. 83; CDC66 NSP 4 aa—stool is SEQ ID No. 89; CDC66 NSP 5 aa—stool is SEQ ID No. 95; CDC66 VP1 aa—stool is SEQ ID No. 101; CDC66 VP 2 aa—stool is SEQ ID No. 107; CDC66 VP 3 aa—stool is SEQ ID No. 113; CDC66 VP 4 aa—stool is SEQ ID No. 119; CDC66 VP 6 aa—stool is SEQ ID No. 125; and CDC66 VP 7 aa—stool is SEQ ID No. 131.

CDC-66 nucleotide sequences of proteins encoded by nucleic acids isolated from a stool sample: CDC66 NSP1 nt—stool is SEQ ID No. 68; CDC66 NSP 2 nt—stool is SEQ ID No. 74; CDC66 NSP 3 nt—stool is SEQ ID No. 80; CDC66 NSP 4 nt—stool is SEQ ID No. 86; CDC66 NSP 5 nt—stool is SEQ ID No. 92; CDC66 VP1 nt—stool is SEQ ID No. 98; CDC66 VP 2 nt—stool is SEQ ID No. 104; CDC66 VP 3 nt—stool is SEQ ID No. 110; CDC66 VP 4 nt—stool is SEQ ID No. 116; CDC66 VP 6 nt—stool is SEQ ID No. 122; and CDC66 VP 7 nt—stool is SEQ ID No. 128.

CDC-66 amino acid sequences of proteins encoded by nucleic acids isolated at passage 27 isolated from Vero cells: CDC66 NSP1 aa—Vero is SEQ ID No. 72; CDC66 NSP 2 aa—Vero is SEQ ID No. 78; CDC66 NSP 3 aa—Vero is SEQ ID No. 84; CDC66 NSP 4 aa—Vero is SEQ ID No. 90; CDC66 NSP 5 aa—Vero is SEQ ID No. 96; CDC66 VP1 aa—Vero is SEQ ID No. 102; CDC66 VP 2 aa—Vero is SEQ ID No. 108; CDC66 VP 3 aa—Vero is SEQ ID No. 114; CDC66 VP 4 aa—Vero is SEQ ID No. 120; CDC66 VP 6 aa—Vero is SEQ ID No. 126; and CDC66 VP 7 aa—Vero is SEQ ID No. 132.

CDC-66 nucleotide sequences of proteins encoded by nucleic acids isolated at passage 27 isolated from Vero cells: CDC66 NSP1 nt—Vero is SEQ ID No. 69; CDC66 NSP 2 nt—Vero is SEQ ID No. 75; CDC66 NSP 3 nt—Vero is SEQ ID No. 81; CDC66 NSP 4 nt—Vero is SEQ ID No. 87; CDC66 NSP 5 nt—Vero is SEQ ID No. 93; CDC66 VP1 nt—Vero is SEQ ID No. 99; CDC66 VP 2 nt—Vero is SEQ ID No. 105; CDC66 VP 3 nt—Vero is SEQ ID No. 111; CDC66 VP 4 nt—Vero is SEQ ID No. 117; CDC66 VP 6 nt—Vero is SEQ ID No. 123; and CDC66 VP 7 nt—Vero is SEQ ID No. 129.

Entire amino acid and nucleotide sequences from CDC-66 rotavirus isolated from stool and Vero cells are compared with entire amino acid and nucleotide sequences of a strain of rotavirus A considered to be the closest related known rotavirus A, human rotavirus DS-1 strain or another closely related strain, as shown herein.

As shown in Table 4, CDC-66 genes share high sequence identity with the corresponding genes of the prototype P[4],G2 strain DS-1.

TABLE 4

| Gene | nt % | aa % |
|---|---|---|
| VP1 | 90.85 | 97.24 |
| VP2 | 94.11 | 98.86 |
| VP3 | 92.9 | 95.69 |
| VP4 | 94.02 | 96.52 |

TABLE 4-continued

| Gene | nt % | aa % |
|---|---|---|
| VP6 | 87.98 | 98.74 |
| VP7 | 93.88 | 96.32 |
| NSP1 | 93.12 | 93.21 |
| NSP2 | 86.89 | 93.99 |
| NSP3 | 95.31 | 97.12 |
| NSP4 | 94.76 | 95.43 |
| NSP5 | 92.57 | 96.5 |

Changes in nt and aa sequences of entire genome of CDC-66 strain from stool to the pa

TABLE 5

Changes of nt and aa in genes of CDC-66 from stool to passage 27 in Vero cells

| Gene | nt change | aa change |
|---|---|---|
| NSP1 | none | none |
| NSP2 | 470 C→T | 142 H→Y |
| NSP3 | none | none |
| NSP4 | none | none |
| NSP5 | 126 T→C, 199 A→G | 60 I→V |
| VP1 | 440 A→G | 141 N→S |
| VP2 | none | none |
| VP3 | 760 T→C, 1143 T→C, 1882 A→G | 365 L→S |
| VP4 | 770C→A, 1109T→C, 1162G→A, 1184A→G | 254T→K, 367V→A, 385D→N, 392E→G |
| VP6 | none | none |
| VP7 | none | none |

Vaccines

Vaccines and methods for their use to induce active immunity and protection against rotavirus induced illness in a subject are provided according to the present invention.

In particular embodiments, vaccine compositions for enhancing immunological protection against a rotavirus-mediated disease in a subject are provided according to the present invention which includes a human rotavirus strain admixed with a pharmaceutically acceptable carrier.

The term "vaccine composition" is used herein to refers to a composition including a biological agent capable of inducing an immune response in a subject inoculated with the vaccine composition. In particular embodiments, the biological agent is a live attenuated and/or inactive rotavirus. In further embodiments, the biological agent is an antigenic portion of a rotavirus.

In particular embodiments, a human rotavirus strain included in a vaccine composition of the present invention is CDC-9 or CDC-66. Combinations of these human rotavirus strains are optionally included in vaccine compositions of the present invention. Additionally, a human rotavirus strain other than CDC-9 or CDC-66 is optionally included in a vaccine composition of the present invention.

In particular embodiments of a vaccine composition according to the present invention, at least two rotavirus strains are included. The two or more rotavirus strains each independently have a G1, G2, G3, G4, G5, G6, G7, G8, G9, G10, G11, G12, G13 or G14 G serotype. Thus, for example, at least one of CDC-9 or CDC-66 is present in a vaccine composition of the present invention along with at least a second human rotavirus strain which has a G1, G2, G3, G4, G5, G6, G7, G8, G9, G10, G11, G12, G13 or G14 G serotype.

Each of the at least two rotavirus strains included in a vaccine composition has a P serotype which is P1A, P1B, P2A, P3, P4, P5, P6, P8, P11, or P12 in particular embodiments.

A vaccine composition for enhancing immunological protection against a rotavirus-mediated disease in a subject includes a first human rotavirus strain characterized as having a G1 serotype and a second human rotavirus strain characterized as having a G2 serotype in particular embodiments of a vaccine composition of the present invention. Each of the two rotavirus strains independently has a P group serotype which is P1A, P1B, P2A, P3, P4, P5, P6, P8, P11 or P12.

In some embodiments, the human rotavirus strain having a G1 serotype is CDC-9.

In some embodiments, the human rotavirus strain having a G2 serotype is CDC-66.

Combinations of human rotavirus strains in particular embodiments of a vaccine composition of the present invention include CDC-9 and CDC-66.

A human rotavirus strain included in a vaccine composition according to the present invention is a live attenuated rotavirus or an inactivated rotavirus. The choice of live attenuated rotavirus or inactivated rotavirus depends on factors such as route of vaccine composition administration.

In a particular embodiment, a vaccine composition including a human rotavirus A strain CDC-9, and/or CDC-66, one or more rotavirus A CDC-9, and/or CDC-66 polypeptides and/or an immunogenic fragment of one or more rotavirus A CDC-9, and/or CDC-66 polypeptides, stimulates generation of neutralizing antibodies to a rotavirus A CDC-9, and/or CDC-66 strain.

Vaccine compositions are provided according to embodiments of the present invention which include one or more rotavirus A polypeptides and/or an immunogenic fragment of one or more rotavirus A polypeptides. In particular embodiments of an inventive vaccine composition, a CDC-9, and/or CDC-66 polypeptide, a homolog thereof, and/or an immunogenic fragment thereof is included.

The term "homolog" refers to a polypeptide characterized by amino acid sequence homology to a reference CDC-9 or CDC-66 rotavirus A polypeptide.

CDC-9 Sequences

Accordingly, the present invention provides a virus including an NSP1 having SEQ ID NO: 2 or a homolog having an amino acid sequence that is greater than 80%, is greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 2. Further, the present invention provides a virus including an NSP1 having SEQ ID NO: 3 or a homolog having an amino acid sequence that is greater than 80%, is greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 3.

The present invention provides a virus including an NSP2 having SEQ ID NO: 5 or a homolog having an amino acid sequence that is greater than 80%, is greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 5.

The present invention provides a virus including an NSP3 having SEQ ID NO: 8 or a homolog having an amino acid sequence that is greater than 80%, is greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 8.

The present invention provides a virus including an NSP4 having SEQ ID NO: 11 or a homolog having an amino acid sequence that is greater than 80%, is greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 11.

The present invention provides a virus including an NSP5 having SEQ ID NO: 14 or a homolog having an amino acid sequence that is greater than 80%, is greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 14. Further, the present invention provides a virus including an NSP5 having SEQ ID NO: 15 or a homolog having an amino acid sequence that is greater than 80%, is greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 15.

Accordingly, the present invention provides a virus including a VP1 having SEQ ID NO: 17 or a homolog having an amino acid sequence that is greater than 80%, is greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 17.

The present invention provides a virus including a VP2 having SEQ ID NO: 20 or a homolog having an amino acid sequence that is greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 20.

The present invention provides a virus including a VP3 having SEQ ID NO: 23 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 23.

The present invention provides a virus including a VP4 having SEQ ID NO: 26 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 26. Further, the present invention provides a virus including an VP4 having SEQ ID NO: 27 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 27.

The present invention provides a virus including a VP6 having SEQ ID NO: 29 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 29. Further, the present invention provides a virus including an VP6 having SEQ ID NO: 30 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 30.

The present invention provides a virus including a VP7 having SEQ ID NO: 32 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 32.

CDC-66 Sequences

The present invention provides a virus including an NSP1 having SEQ ID NO: 71 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 71.

The present invention provides a virus including an NSP2 having SEQ ID NO: 77 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 77. Further, the present invention provides a virus including an NSP2 having SEQ ID NO: 78 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 78.

The present invention provides a virus including an NSP3 having SEQ ID NO: 83 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 83.

The present invention provides a virus including an NSP4 having SEQ ID NO: 89 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 89.

The present invention provides a virus including an NSP5 having SEQ ID NO: 95 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 95. Further, the present invention provides a virus including an NSP5 having SEQ ID NO: 96 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 96.

Accordingly, the present invention provides a virus including a VP1 having SEQ ID NO: 101 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 101. Further, the present invention provides a virus including an VP1 having SEQ ID NO: 102 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 102.

The present invention provides a virus including a VP2 having SEQ ID NO: 107 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 107.

The present invention provides a virus including a VP3 having SEQ ID NO: 113 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 113. Further, the present invention provides a virus including an VP3 having SEQ ID NO: 114 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 114.

The present invention provides a virus including a VP4 having SEQ ID NO: 119 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 119. Further, the present invention provides a virus including an VP4 having SEQ ID NO: 120 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 120.

The present invention provides a virus including a VP6 having SEQ ID NO: 125 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 125.

The present invention provides a virus including a VP7 having SEQ ID NO: 131 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 131.

The present invention provides an isolated or purified NSP1, NSP2, NSP3, NSP4, NSP5, VP1, VP2, VP3, VP4, VP6, or VP7. The term "purified" or "isolated" as used herein, is intended to refer to a composition, isolatable from other components, wherein the compositions is purified to any degree relative to its naturally-obtainable state, i.e., in this case, relative to its purity within a cell, relative to is purity within a virion, or relative to its purity within an infective organism. An isolated composition, therefore, also refers to a protein, peptide, nucleic acid, or oligonucleotide, substantially free from the environment in which it may naturally occur.

It is recognized that numerous variants, analogues, or homologues are within the scope of the present invention including amino acid substitutions, alterations, modifications, or other amino acid changes that increase, decrease, or do not alter the function or immunogenic propensity of the inventive immunogen or vaccine. It is further appreciated that the inventive sequences are optionally modified by the addition of one or more amino acids, sugars, nucleotides, pendent groups, fluorophores, lumiphores, radioactive molecules, lipids, fatty acids, derivatives thereof, or other groups known in the art. Illustratively, an inventive immunogen is conjugated to a protein. Optionally, an inventive immunogen is conjugated to a protein that promotes the immunogenicity of an immunogen, illustratively, keyhole limpet hemocyanin (KLH), bovine serum albumin (BSA), or modifications thereof, as well as BLUE CARRIER immunogenic protein from Thermo Scientific, Rockford, Ill. Other sources of natural or artificial immunogenic protein conjugates are known in the art. Optionally, an inventive immunogen is conjugated to an antibody. Optionally, an inventive immunogen is conjugated to other regions of G-protein that may or may not also contain epitopes.

In some embodiments, the NSP1 has SEQ ID NO: 2 or SEQ ID No. 3, or is a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 2 or to SEQ ID No. 3. In a further embodiment, the NSP1 has SEQ ID NO: 71 or is a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 71.

The present invention provides an isolated or purified NSP2. In one embodiment, the NSP2 has SEQ ID NO: 5 or is a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 5. In a further embodiment, the NSP2 has SEQ ID NO: 77 or SEQ ID NO: 78 or is a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 77 or SEQ ID NO: 78.

The present invention provides an isolated or purified NSP3. In one embodiment, the NSP3 has SEQ ID NO: 8 or is a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 8. In a further embodiment, the NSP3 has SEQ ID NO: 83 or is a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 83.

The present invention provides an isolated or purified NSP4. In one embodiment, the NSP4 has SEQ ID NO: 11 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 11. In a further embodiment, the NSP4 has SEQ ID NO: 89 or a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 89

The present invention provides an isolated or purified NSP5. In one embodiment, the NSP5 has SEQ ID NO: 14 or SEQ ID NO. 15 or is a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 14 or SEQ ID NO. 15. In a further embodiment, the NSP5 has SEQ ID NO: 95 or SEQ ID NO: 96 or is a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 95 or SEQ ID NO: 96.

The present invention provides an isolated or purified VP1. In one embodiment, the VP1 has SEQ ID NO: 17 or is a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 17. In a further embodiment, the VP1 has SEQ ID NO: 101 or SEQ ID NO. 102 or is a homolog having an amino acid sequence that is greater than 80%, greater than 81%, greater than 82%, greater than 83%, greater than 84%, greater than 85%, greater than 86%, or greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 101 or SEQ ID NO. 102.

The present invention provides an isolated or purified VP2. In one embodiment, the VP2 has SEQ ID NO: 20 or is a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 20. In a further embodiment, the VP2 has SEQ ID NO: 107 or is a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 107.

The present invention provides an isolated or purified VP3. In one embodiment, the VP3 has SEQ ID NO: 23 or is a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 23. In a further embodiment, the VP3 has SEQ ID NO: 113 or SEQ ID NO. 114 or is a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 113 or SEQ ID NO. 114.

The present invention provides an isolated or purified VP4. In one embodiment, the VP4 has SEQ ID NO: 26 or SEQ ID NO. 27 or is a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 26 or SEQ ID NO. 27. In a further embodiment, the VP4 has SEQ ID NO: 119 or SEQ ID NO. 120 or is a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 119 or SEQ ID NO. 120.

The present invention provides an isolated or purified VP6. In one embodiment, the VP6 has SEQ ID NO: 29 or SEQ ID NO. 30 or is a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 29 or SEQ ID NO. 30. In a further embodiment, the VP6 has SEQ ID NO: 125 or is a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 125.

The present invention provides an isolated or purified VP7. In one embodiment, the VP7 has SEQ ID NO: 32 or is a homolog having an amino acid sequence that is greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98% or greater than 99% identical to SEQ ID NO: 32. In a further embodiment, the VP7 has SEQ ID NO: 131 or is a homolog having an amino acid sequence that is greater than 97%, greater than 98% or greater than 99% identical to SEQ ID NO: 131.

An isolated or purified nucleic acid encoding an above-described protein or fragment thereof is provided according to embodiments of the present invention. Optionally, the isolated or purified nucleic acid encoding an above-described protein or fragment thereof is included in a vector.

A nucleic acid encoding NSP1 includes the nucleotide sequence of SEQ ID NO: 35; SEQ ID NO: 36; SEQ ID NO: 68 or a fragment thereof encoding at least nine contiguous amino acids. A nucleic acid encoding NSP2 includes the nucleotide sequence of SEQ ID NO: 38; SEQ ID NO: 74; SEQ ID NO: 75; or a fragment thereof encoding at least nine contiguous amino acids. A nucleic acid encoding NSP3 includes the nucleotide sequence of SEQ ID NO: 41; SEQ ID NO: 80; or a fragment thereof encoding at least nine contiguous amino acids. A nucleic acid encoding NSP4 includes the nucleotide sequence of SEQ ID NO: 44; SEQ ID NO: 86; or a fragment thereof encoding at least nine contiguous amino acids. A nucleic acid encoding NSP5 includes the nucleotide sequence of SEQ ID NO: 47; SEQ ID NO: 48; SEQ ID NO: 92; SEQ ID NO: 93; or a fragment thereof encoding at least nine contiguous amino acids. A nucleic acid encoding VP1 includes the nucleotide sequence of SEQ ID NO: 50; SEQ ID NO: 98; SEQ ID NO: 99; or a fragment thereof encoding at least nine contiguous amino acids. A nucleic acid encoding VP2 includes the nucleotide sequence of SEQ ID NO: 53; SEQ ID NO: 104; or a fragment thereof encoding at least nine contiguous amino acids. A nucleic acid encoding VP3 includes the nucleotide sequence of SEQ ID NO: 23; SEQ ID NO: 110; SEQ ID NO: 111; or a fragment thereof encoding at least nine contiguous amino acids. A nucleic acid encoding VP4 includes the nucleotide sequence of SEQ ID NO: 59; SEQ ID NO: 60; SEQ ID NO: 116; SEQ ID NO: 117; or a fragment thereof encoding at least nine contiguous amino acids. A nucleic acid encoding VP6 includes the nucleotide sequence of SEQ ID NO: 62; SEQ ID NO: 63; SEQ ID NO: 122; or a fragment thereof encoding at least nine contiguous amino acids. A nucleic acid encoding VP7 includes the nucleotide sequence of SEQ ID NO: 65; SEQ ID NO: 128; SEQ ID NO: 129; or a fragment thereof encoding at least nine contiguous amino acids.

One of skill in the art will appreciate that, due to the degeneracy of the genetic code, a particular polypeptide or fragment thereof can be encoded by more than one nucleic acid sequence.

Mutations can be introduced using standard molecular biology techniques, such as site-directed mutagenesis and PCR-mediated mutagenesis. One of skill in the art will recognize that one or more amino acid mutations can be introduced without altering the functional properties of rotavirus polypeptides. For example, one or more amino acid substitutions, additions, or deletions can be made without altering the functional properties of rotavirus polypeptides. It is also appreciated that several mutations optionally increase, decrease, or do not change the immunogenicity of an inventive polypeptide.

Conservative amino acid substitutions can be made in rotavirus polypeptides to produce homologs. Conservative amino acid substitutions are art recognized substitutions of one amino acid for another amino acid having similar characteristics. For example, each amino acid may be described as having one or more of the following characteristics: electropositive, electronegative, aliphatic, aromatic, polar, hydrophobic and hydrophilic. A conservative substitution is a substitution of one amino acid having a specified structural or functional characteristic for another amino acid having the same characteristic. Acidic amino acids include aspartate, glutamate; basic amino acids include histidine, lysine, arginine; aliphatic amino acids include isoleucine, leucine and valine; aromatic amino acids include phenylalanine, glycine, tyrosine and tryptophan; polar amino acids include aspartate, glutamate, histidine, lysine, asparagine, glutamine, arginine, serine, threonine and tyrosine; and hydrophobic amino acids include alanine, cysteine, phenylalanine, glycine, isoleucine, leucine, methionine, proline, valine and tryptophan; and conservative substitutions include substitution among amino acids within each group. Amino acids may also be described in terms of relative size, alanine, cysteine, aspartate, glycine, asparagine, proline, threonine, serine, valine, all typically considered to be small.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly, where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

Rotavirus particles, nucleic acids, polypeptides and fragments thereof can be produced in recombinant host cells using well-known conventional techniques. Any nucleic acid construct, which is effective in producing the encoded protein or fragment thereof in a host cell, can be used to produce rotavirus particles, rotavirus polypeptides or fragments thereof.

One of ordinary skill in the art recognizes many ways to make the inventive CDC-9 or CDC-66 viruses for use in an inventive vaccine composition or in inventive processes. Illustratively, it is common practice for one to isolate a putative rotavirus from a stool or other biological sample optionally including passaging in cell culture such as in Vero cells similar to the methods illustrated in Esona, M D, et al., Human Vaccines, 2010; 6:1-7; the contents of which are incorporated herein by reference. One of skill in the art regularly isolates virus strains and characterizes the genome sequence by techniques well known in the art. It is common practice for one of skill in the art to sequence a viral genome and compare the output sequence to a model sequence such as the sequences of CDC-9 of CDC-66 disclosed herein to determine whether the isolated virus has the required genetic sequence to be CDC-9, CDC-66, or homologues thereof.

One of skill in the art also knows methods of modifying a model rotavirus such as KU or DS-1 to make CDC-9 or CDC-66 viruses. One such method uses the reverse genetics approach of Komoto, S., et al., *PNAS USA,* 2006; 103:4646-4651, the contents of which are incorporated herein by reference. Briefly, each of the genes of strain KU can be isolated and amplified by taking culture fluid from infected MA104 cells, extracting the viral dsRNA and synthesizing cDNA using with avian myeloblastosis virus reverse transcriptase (Seikagaku Kogyo, Tokyo, Japan) using a starting primer. It is well within the level of skill in the art to design primers for synthesizing cDNA. Numerous free and commercially available programs for primer synthesis are known to those of skill in the art. Illustratively, primers for the KU VP4 gene are described in Komoto, S., et al., *PNAS USA,* 2006; 103:4646-4651. Modification of the sequences of KU or any other strain to those of CDC-9 or CDC-66 are illustratively accomplished by establishing the sequence modifications such as by sequence alignments. Once the nucleotide substitutions are elucidated, modifications of the cDNA can be achieved by using the QUICKCHANGE XL site-directed mutagenesis kit available from Agilent Technologies, Santa Clara, Calif. Modified gene sequences to conform to that of CDC-9, CDC-66, or homologues thereof are optionally inserted into a cell line such as COS-7 cells along with a helper virus such as KU used to serve as a base for gene insertion into new viruses. The modified viruses are subsequently isolated by known techniques. An optional iterative process is used whereby each individual gene of CDC-9 or CDC-66 is substituted for the gene of the helper virus step wise whereby the isolated substituted virus strain from the substitution of the first gene is used as a helper virus for substitution of the second gene and so on until CDC-9 or CDC-66 is created from a source strain.

Illustrative examples of helper viruses or model rotaviruses can be found at GenBank Accession Nos: (a) VP3 strains: RV161-00 (DQ490547), RV176-00 (DQ490553), DRC88 (DQ005112), DRC86 (DQ005123), TB-Chen (AY787654), DS-1 (AY277914), AU-1 (DQ490537), T152 (DQ146701), Hosokawa (DQ870491), Hochi (AY277915), Wa (AY267335), L26 (AY277918), KU (AB022767), Dhaka25-02 (DQ146651), Dhaka12-03 (DQ146662), B4633-03 (DQ146640), PO-13 (AB009631).

(b) VP7 (G1) strains: SK417 (EU839907), DH415 (EU839906), MMC82 (EU839913), Dhaka18-02 (AY631051), MMC56 (EU839911), Matlab159-02 (AY631055), ISO-4 (AY098670), Thai-2104 (DQ512982), CMH042/04 (EF199713), 417 (D16328), T73 (AF450291), TE1 (D17721), K18 (D16319), Chi-87 (DQ512998), J-4825 (DQ512989), 88H249 (AB081795), 421 (D16326), RV-4 (M64666), AU007 (AB081799), HOU8697 (U88717), Mvd9607 (AF480295), 80 (D16325), DC03 (AF183859), KU (AB222788), K2 (D16323), K8 (D16344), Egy-8 (U26374), Brz-5 (U26367), Wa (K02033), D (AB118022), C95 (L24165), T449 (M92651), DS-1 (AB118023).

(c) VP4 P[8] strains: ITO (AB008280), D (EF672570), Wa (L34161), Hochi (AB008295), Odelia (AB008296), VA70 (AJ540229), CH32 (AB008274), MO (AB008278), KU (AB222784), Wi61 (EF672619), F45 (U30716) P (EF672598), AI-39 (AB008283), 90-544 (AB008304), B4633-03 (DQ146641), Dhaka25-02 (DQ146652), SK438 (EU839955), DH402 (EU839958), DH415 (EU839955), DS-1(AB118025).

(d) NSP4 strains: Dhaka16-03 (DQ492678), 1099 (AJ236759), Dhaka12-03 (DQ146669), Dhaka25-02 (DQ146658), KU (AB022772), Wa (AF093199), RMC321 (AF541921), OSU (D88831), AU-1 (D89873), CMH120/04 (DQ923799), B4106 (AY740732), C-11 (AF144793), DRC86 (DQ005116), DRC88 (DQ005105), DS-1 (AF174305), TB-Chen (AY787650), Ch-1 (AB065287).

Each of the files and sequences at the aforementioned accession numbers are incorporated herein by reference.

Other methods, primers, isolation techniques, sequencing techniques, and characterization techniques are known to those of skill in the art and are similarly operable herein. Illustratively, one can reconstitute CDC-9 or CDC-66 viruses de novo from isolated genes such as by assembly of virus particles with captured genes illustratively by the techniques of or modifications of Gonzalez, S A, and Affranchino, J L, J. Gen. Virol., 1995; 76:2357-2360, the contents of which are incorporated herein by reference.

Expression constructs and methods for their generation and use to express a desired protein are known in the art, as described, for example, in Sambrook et al., Molecular Cloning: A Laboratory Manual, Cold Spring Harbor Laboratory Press, 2001; Ausubel, F. et al., (Eds.), Short Protocols in Molecular Biology, Wiley, 2002; and S. J. Higgins and B. D. Hames (Eds.), Protein Expression: A Practical Approach, Oxford University Press, USA, 1999.

Illustratively, a nucleic acid molecule encoding one or more rotavirus polypeptides and/or rotavirus polypeptide fragments is operably linked to regulatory sequences that control transcriptional expression in an expression vector. The expression vector is introduced into a host cell and the produced rotavirus particles, one or more rotavirus polypeptides and/or rotavirus polypeptide fragments can then be isolated. Illustrative constructs include operably linking a rotavirus nucleic acid molecule into plasmid pT7 by first amplifying the nucleic acid molecule using primers including a T7 promoter sequence and ligating the amplified nucleic acids into the T7 expression vector pX8dT as described by Schnell, M J, et al., EMBO J, 1994; 13:4195-4203, the contents of which are incorporated herein by reference.

Non-limiting examples of regulatory sequences that control transcriptional expression in an expression vector illustratively include a promoter, an enhancer, a splicing signal, a transcription start site, a transcription termination signal, a polyadenylation signal, an internal ribosome entry site (IRES) and combinations of these or other regulatory sequences.

Expression vectors include, but are not limited to, viral vectors and bacterial vectors used to express a desired protein. Non-limiting examples of expression vectors include bacterial plasmids, bacteriophage, adenovirus, adeno-associated virus, herpes virus, vaccinia virus and lentivirus.

A host cell for expression of polypeptides and fragments thereof can be prokaryotic or eukaryotic, such as bacterial, plant, insect, fungus, yeast, and mammalian cells.

An expression vector is introduced into a host cell using well-known techniques such as infection or transfection, including calcium phosphate transfection, liposome-mediated transfection, electroporation and sonoporation.

In addition to recombinant methodology, chemical synthetic techniques can be used to produce polypeptides and fragments thereof. For example, solid phase synthesis, solution phase synthesis, partial solid phase synthesis or fragment condensation can be used.

The term "isolated" as used herein refers to a substance that has been separated from other cellular components associated with the substance in nature or when recombinantly produced not intended to be associated with the substance and that may interfere with use of the substance in therapeutic, prophylactic, diagnostic, research or other uses. Generally, an isolated substance described herein is at least about 80% pure, at least about 90% pure, at least about 95% pure, or greater than about 99% pure. Purification is achieved using well-known standard methodology such as fractionation and/or chromatography, such as ammonium sulfate precipitation and elution chromatography such as size exclusion chromatography, displacement chromatography, ion exchange chromatography and bioaffinity chromatography. Exemplary purification methodology is described in S. Doonan, Protein Purification Protocols Humana Press, 1996.

Percent identity is determined by comparison of amino acid or nucleic acid sequences, including a reference rotavirus A amino acid or nucleic acid sequence and a putative homologue amino acid or nucleic acid sequence. Algorithms used for determination of percent identity illustratively include the algorithms of S. Karlin and S. Altshul, PNAS, 90:5873-5877, 1993; T. Smith and M. Waterman, Adv. Appl. Math. 2:482-489, 1981, S. Needleman and C. Wunsch, J. Mol. Biol., 48:443-453, 1970, W. Pearson and D. Lipman, PNAS, 85:2444-2448, 1988 and others incorporated into computerized implementations such as, but not limited to, GAP, BESTFIT, FASTA, TFASTA; and BLAST, for example incorporated in the Wisconsin Genetics Software Package, Genetics Computer Group, 575 Science Drive, Madison, Wis. and publicly available from the National Center for Biotechnology Information.

Rotavirus A CDC-9, and/or CDC-66 polypeptides, a homolog thereof, and/or an immunogenic fragment thereof may be prepared by any of various methods, including isolation of virus particles from sources such as cultured cells or patient samples, isolation of one or more polypeptides and/or one or more polypeptide fragments from viral particles, recombinant production of viral polypeptides, fragments and/or viral particles, including intact and virus-like particles, and/or by chemical synthetic techniques. Methods of isolation of virus particles, virus polypeptides and/or one or more virus polypeptide fragments, recombinant production of virus polypeptides, virus polypeptide fragments and/or virus particles are described in detail herein, in references cited herein, and are known to those of skill in the art.

An antigen may be made more immunogenic if desired by linkage to a carrier molecule such bovine serum albumin or keyhole limpet hemocyanin and/or by use of an adjuvant. Carrier linkage may be accomplished by any of various techniques, illustratively including, but not limited to, conjugation and expression of a fusion protein.

Recombinantly expressed polypeptides or peptides may be tagged to allow for easier isolation. For instance, such polypeptides and peptides are optionally tagged illustratively, Fc-tagged, 6×HIS-tagged, FLAG-tagged, or by other tag suitable for isolation of a tagged polypeptide.

Vaccine Formulation

In particular embodiments of the invention, a rotavirus A strain for inclusion in a vaccine composition of the present invention is prepared by standard methods typically used for preparation of live or inactivated rotavirus. For example, generally a compatible cell type is inoculated with a rotavirus strain and the cells are maintained under conditions which allow for viral replication and production of infectious particles.

A particular example of a cell type which permits rotavirus infection, replication and particle production is a mammalian cell line such as a Vero cell line.

Rotavirus particles are harvested, typically from cell culture supernatant for inclusion in a vaccine composition. The rotavirus particles may be isolated from the cell culture supernatant, for example by filtration and/or centrifugation. The isolated rotavirus particles are optionally lyophilized, such as for later resuspension in a pharmaceutically acceptable carrier.

The term "pharmaceutically acceptable carrier" refers to a carrier which is substantially non-toxic to a subject and substantially inert to the rotavirus included in a vaccine composition. A pharmaceutically acceptable carrier is a solid, liquid or gel in form and is typically sterile and pyrogen free.

A vaccine composition of the present invention may be in any form suitable for administration to a subject.

A vaccine composition is administered by any suitable route of administration including oral and parenteral such as intravenous, intradermal, intramuscular, mucosal, nasal, or subcutaneous routes of administration.

For example, a vaccine composition for parenteral administration may be formulated as an injectable liquid including a rotavirus and a pharmaceutically acceptable carrier. Examples of suitable aqueous and nonaqueous carriers include water, ethanol, polyols such as propylene glycol, polyethylene glycol, glycerol, and the like, suitable mixtures thereof; vegetable oils such as olive oil; and injectable organic esters such as ethyloleate. Proper fluidity can be maintained, for example, by the use of a coating such as lecithin, by the maintenance of a desirable particle size in the case of dispersions, and/or by the use of a surfactant, such as sodium lauryl sulfate. A stabilizer is optionally included such as, for example, sucrose, EDTA, EGTA, and an antioxidant.

A solid dosage form for administration or for suspension in a liquid prior to administration illustratively includes capsules, tablets, powders, and granules. In such solid dosage forms, a rotavirus is admixed with at least one carrier illustratively including a buffer such as, for example, sodium citrate or an alkali metal phosphate illustratively including sodium phosphates, potassium phosphates and calcium phosphates; a filler such as, for example, starch, lactose, sucrose, glucose, mannitol, and silicic acid; a binder such as, for example, carboxymethylcellulose, alignates, gelatin, polyvinylpyrrolidone, sucrose, and acacia; a humectant such as, for example, glycerol; a disintegrating agent such as, for example, agar-agar, calcium carbonate, plant starches such as potato or tapioca starch, alginic acid, certain complex silicates, and sodium carbonate; a solution retarder such as, for example, paraffin; an absorption accelerator such as, for example, a quaternary ammonium compound; a wetting agent such as, for example, cetyl alcohol, glycerol monostearate, and a glycol; an adsorbent such as, for example, kaolin and bentonite; a lubricant such as, for example, talc, calcium stearate, magnesium stearate, a solid polyethylene glycol or sodium lauryl sulfate; a preservative such as an antibacterial agent and an antifungal agent, including for example, sorbic acid, gentamycin and phenol; and a stabilizer such as, for example, sucrose, EDTA, EGTA, and an antioxidant.

Solid dosage forms optionally include a coating such as an enteric coating. The enteric coating is typically a polymeric material. Preferred enteric coating materials have the characteristics of being bioerodible, gradually hydrolyzable and/or gradually water-soluble polymers. The amount of coating material applied to a solid dosage generally dictates the time interval between ingestion and drug release. A coating is applied having a thickness such that the entire coating does not dissolve in the gastrointestinal fluids at pH below 3 associated with stomach acids, yet dissolves above pH 3 in the small intestine environment. It is expected that any anionic polymer exhibiting a pH-dependent solubility profile is readily used as an enteric coating in the practice of the present invention to achieve delivery of the active agent to the lower gastrointestinal tract. The selection of the specific enteric coating material depends on properties such as resistance to disintegration in the stomach; impermeability to gastric fluids and active agent diffusion while in the stomach; ability to dissipate at the target intestine site; physical and chemical stability during storage; non-toxicity; and ease of application.

Suitable enteric coating materials illustratively include cellulosic polymers such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, hydroxypropylmethyl cellulose succinate and carboxymethylcellulose sodium; acrylic acid polymers and copolymers, preferably formed from acrylic acid, methacrylic acid, methyl acrylate, ammonium methylacrylate, ethyl acrylate, methyl methacrylate and/or ethyl; vinyl polymers and copolymers such as polyvinyl pyrrolidone, polyvinyl acetate, polyvinylacetate phthalate, vinylacetate crotonic acid copolymer, and ethylene-vinyl acetate copolymers; shellac; and combinations thereof. A particular enteric coating material includes acrylic acid polymers and copolymers described for example U.S. Pat. No. 6,136,345.

The enteric coating optionally contains a plasticizer to prevent the formation of pores and cracks that allow the penetration of the gastric fluids into the solid dosage form. Suitable plasticizers illustratively include, triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, a coating composed of an anionic carboxylic acrylic polymer typically contains approximately 10% to 25% by weight of a plasticizer, particularly dibutyl phthalate, polyethylene glycol, triethyl citrate and triacetin. The coating can also contain other coating excipients such as detackifiers, antifoaming agents, lubricants (e.g., magnesium stearate), and stabilizers (e.g. hydroxypropylcellulose, acids or bases) to solubilize or disperse the coating material, and to improve coating performance and the coated product.

Liquid dosage forms for oral administration include rotavirus and a pharmaceutically acceptable carrier formulated as an emulsion, solution, suspension, syrup, or elixir. A liquid dosage form of a vaccine composition of the present invention may include a wetting agent, an emulsifying agent, a suspending agent, a sweetener, a flavoring, or a perfuming agent.

Detailed information concerning customary ingredients, equipment and processes for preparing dosage forms is found in Pharmaceutical Dosage Forms: Tablets, eds. H. A. Lieberman et al., New York: Marcel Dekker, Inc., 1989; and in L. V. Allen, Jr. et al., Ansel's Pharmaceutical Dosage Forms and Drug Delivery Systems, 8th Ed., Philadelphia, Pa.: Lippincott, Williams & Wilkins, 2004, throughout and in chapter 16; A. R. Gennaro, Remington: The Science and Practice of Pharmacy, Lippincott Williams & Wilkins, $21^{st}$ ed., 2005, particularly chapter 89; and J. G. Hardman et al., Goodman & Gilman's The Pharmacological Basis of Therapeutics, McGraw-Hill Professional, 10th ed., 2001.

An adjuvant is optionally included in a virus composition according to embodiments of the present invention. Adjuvants are known in the art and illustratively include Freund's adjuvant, aluminum hydroxide, aluminum phosphate, aluminum oxide, saponin, dextrans such as DEAE-dextran, vegetable oils such as peanut oil, olive oil, and/or vitamin E acetate, mineral oil, bacterial lipopolysaccharides, peptidoglycans, and proteoglycans.

The term "subject" is used herein to refer to a human. Non-human animals, illustratively including other primates, cows, horses, sheep, goats, pigs, dogs, cats, birds, poultry, and rodents, are also referred to by the term subject in particular embodiments of the present invention.

The isolated rotavirus is treated to inactivate or attenuate the rotavirus. Thus, in particular embodiments a vaccine for human rotavirus includes a live attenuated human rotavirus or an inactivated human rotavirus.

The term "live attenuated rotavirus" refers to a rotavirus having the ability to infect an appropriate host or host cell and replicate and the term is used to distinguish an "inactivated" rotavirus. The term "live attenuated rotavirus" refers to a rotavirus characterized by substantially diminished virulence compared to wild type human rotavirus. The term "virulence" is used to describe the degree of pathogenicity of a rotavirus to a host cell or a host organism. Virulence is determined using any of various assays recognized in the art. For example, virulence may be assessed by exposing cultured host cells to an attenuated rotavirus and determining the number of cells which display a pathogenic response and/or the severity of pathogenic response elicited. Diminished virulence is present where an attenuated rotavirus has decreased capability to cause one or more pathogenic effects in a host cell and/or host organism.

The term "inactivated" rotavirus is used herein to refer to rotavirus that has been killed and which is therefore capable of neither replication nor infection of a host cell or host organism.

Inactivation is achieved by any of various techniques illustratively including inactivation using one or more chemical agents, thermal inactivation and/or UV light inactivation.

Chemical agents used to inactivate a rotavirus are known in the art and include such agents as ethyleneimines such as binary ethyleneimine; cross-linking aldehydes such as formaldehyde and glutaraldehyde; proteases illustratively including pronase, trypsin and/or chymotrypsin; and detergents such as octylphenol ethoxylates and alkyl trimethylammonium salts. Rotavirus may be inactivated by treatment with a base, for example by incubation of the rotavirus at a pH above pH 10.0.

Thermal inactivation may be achieved by heating at temperatures above 500 centigrade, for example.

Inactivation is assessed by techniques standard in the art, illustratively including sampling virus at various times during an inactivation procedure and observing cytopathic effects or infectivity of a sample on suitable cells, such as Vero cells.

It is appreciated that, in addition to live attenuated and inactivated rotavirus, an antigenic portion of a rotavirus is optionally included in a vaccine composition of the present invention. Thus, for example, a rotavirus-derived protein or peptide capable of inducing an immunological response in a subject is considered within the scope of the present invention. In particular, an antigenic portion of a human rotavirus strain identified as CDC-9 or CDC-66 is optionally included in a vaccine composition of the present invention.

Methods of inducing an immunological response against a rotavirus-mediated disease in a subject are provided according to embodiments of the present invention which include administering a therapeutic amount of a vaccine composition including at least one human rotavirus strain.

The phrase "therapeutically effective amount" is used herein to refer to an amount effective to induce an immunological response sufficient to prevent or ameliorate signs or symptoms of a rotavirus-mediated disease. Induction of an immunological response in a subject can be determined by any of various techniques known in the art, illustratively including detection of anti-rotavirus antibodies, measurement of anti-rotavirus antibody titer and/or lymphocyte proliferation assay. Illustrative methods for detection of anti-rotavirus antibodies are illustrated by Tsunemitsu, H, et al., *J. Clin. Microbiol.*, 1992; 30:2129-2134, the contents of which are incorporated herein by reference. Signs and symptoms of rotavirus-mediated disease may be monitored to detect induction of an immunological response to administration of a vaccine composition of the present invention in a subject. An immunological response is illustratively a reduction of clinical signs and symptoms of rotavirus-mediated disease such as reduction of the amount of virus shed in feces, reduction of the number of days on which virus is shed in feces, reduction in the number of days the subject has diarrhea, reduction in mortality, reduction in morbidity, reduction in weight loss or weight gain. An immunological response is illustratively, development of anti-rotavirus antibodies, activation of T-cells, B-cells, or other immune cells following administration of an inventive composition, or other immune responses known in the art.

In a particular embodiment, a method of inducing an immunological response against a rotavirus-mediated disease in a subject includes administering 104 to 108 ffu of live attenuated vaccine or 1 to 25 micrograms of inactivated virus in a typical vaccine composition.

In some embodiments, a method of inducing an immunological response against a rotavirus-mediated disease in a subject includes administering a therapeutically effective amount of a vaccine composition including a human rotavirus strain CDC-9 and/or CDC-66, polypeptide fragments thereof, homologues thereof, or combinations thereof.

In a further embodiment, a method of inducing an immunological response against a rotavirus-mediated disease in a subject includes administering a therapeutically effective amount of a vaccine composition including a G1 group serotype and a second human rotavirus strain characterized as having a G2 group serotype.

Administration of a vaccine composition according to a method of the present invention includes administration of one or more doses of a vaccine composition to a subject at one time in particular embodiments. Alternatively, two or more doses of a vaccine composition are administered at time intervals of days, weeks, or years. A suitable schedule for administration of vaccine composition doses depends on several factors including age and health status of the subject, type of vaccine composition used and route of administration, for example. One of skill in the art is able to readily determine a dose and schedule of administration to be administered to a particular subject.

Embodiments of inventive compositions and methods are illustrated in the following examples. These examples are provided for illustrative purposes and are not considered limitations on the scope of inventive compositions and methods.

EXAMPLES

Example 1—Adaptation and Passaging

One ml of a 10% virus suspension in DMEM is supplemented with neomycin in a 1.7 ml sterile low bind tube, mixed well and then centrifuged for 10 min at 3,000 rpm in an Eppendorf microcentrifuge. The supernatant is transferred to a new tube and centrifuged for 10 min at 10,000 rpm (8,000×g). The clarified supernatant is sterilized by passing though a 0.45 micron pore filter. The supernatant is tested by EIA (Rotaclone; Meridian Biosciences) and if OD value is >1.0, store it at 4° C. before use for infection. Stool extraction and Rotaclone testing can be done the day before infection.

The culture medium is removed from cell monolayers in individual roller tubes. Each roller tube is washed with 2 ml of maintenance medium, then 2 ml maintenance medium is added to each tube and incubated at 37° C. in a rolling apparatus until virus inoculum is ready.

An aliquot of 0.5 ml of supernatant is transferred to a sterile tube and 1 microliter of $CaCl_2$) stock (300 grams per liter) is added to make a final concentration of 800 micrograms per milliliter. The tube is incubated at room temperature for 30 min before adding 3 microliters of porcine trypsin stock (2.5 milligrams per milliliter)—final concentration of 15 micrograms per milliliter. The mixture is incubated for 60 min at 37° C. The same volume of MEM is treated in the same way as a mock inoculum. Separate pipette tips are used for pipetting virus suspension and trypsin solutions. All pipetting of virus should be done within the biological safety cabinet.

Medium is removed from each roller tube and 0.2 to 0.3 milliliter of trypsinized virus suspension or mock inoculums is added to each roller tube using separate sterile pipette. The caps are tightened and the tubes incubated at 37° C. on a roller tube apparatus located in an incubator. After 2 hrs incubation, inoculum is removed using a 1 ml pipette and washed gently with 2 ml maintenance medium.

Two milliliters of maintenance medium containing various concentrations (10, 20 or 30 micrograms per ml depending on strain) of trypsin is added into each tube and incubated for 2 hours at 37° C. on a roller tube apparatus located in an incubator.

The cells are observed daily for cytopathic effect (CPE), harvested at day 4 and stored at −70° C. The cells are subjected to freeze-thaw two times before the next passage.

The freeze-thawed cell lysates are treated with $CaCl_2$) and trypsin as described above and subsequent passages are performed as above. The cells are subjected to freeze-thaw at least once and assayed for rotavirus antigen by Rotaclone kit or virus titer is determined by FFA assays.

Example 2—Production and Purification of Rotavirus Strains

Production of rotavirus is accomplished by use of large scale production roller bottles. Briefly described, Vero cells are cultured in Dulbecco's Modified Eagle Medium supplemented with 5% fetal bovine serum (Invitrogen Corp., Grand Island, N.Y.) and 50 micrograms/milliliter of neomycin (Sigma Corp., St. Louis, Mo.). Confluent monolayers of Vero cells in roller bottles are infected with a particular rotavirus strain at a multiplicity of infection of 0.1.

Rotavirus obtained by large scale production is purified according to standard operating procedures. Briefly described, rotavirus is harvested from infected cultures of Vero cells at four days post-infection. Triple-layered rotavirus particles are purified from supernatants by centrifugation through 40% sucrose cushions in TNC buffer for 2 hours at 106,750×g using an SW32Ti rotor and then through isopycnic centrifugations in CsCl gradients for 17 hours at 111,160 g using an SW40Ti rotor. Rotavirus particles may also be purified using sucrose gradients. TNC buffer is 10 mM Tris, pH 8.0, 140 mM NaCl, and 10 mM $CaCl_2$). Purified rotavirus particles are resuspended in diluent buffer which is Hanks Balanced Salt Solution with $CaCl_2$) and $MgCl_2$, obtained from Invitrogen Corp., Grand Island, N.Y., supplemented with 10% sorbitol (Sigma Corp., St. Louis, Mo.). The resuspended isolated rotavirus is stored at −70° C. until it is inactivated and administered to a subject in this example.

Purified rotavirus is analyzed for purity and identity by any of various techniques, illustratively including SDS-PAGE followed by Coomassie blue staining, western blot using a rotavirus-specific antibody and/or electron microscopy. In addition, purity and identity of purified rotavirus strains is accomplished by identification of particular structural viral proteins.

Figure 4B:
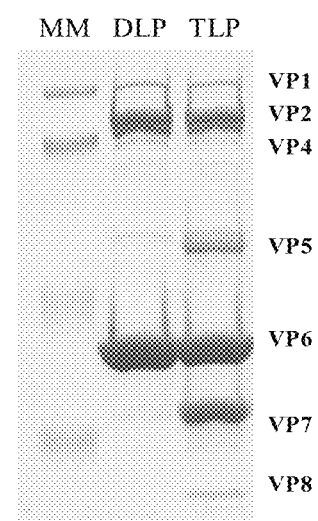
FIG. 4B shows identified structural viral proteins of rotavirus A strain CDC-9 analyzed by SDS-PAGE in comparison to molecular weight markers.

FIG. 4A shows CsCl purified rotavirus of strain CDC-9. FIG. 4B shows identified structural viral proteins of double- and triple-layered CDC-9 analyzed by SDS-PAGE in comparison to molecular weight markers.

Example 3—Immunogenicity of Inactivated Rotavirus (IRV)

Immunogenicity of rotavirus strains is tested in a mouse model. Purified killed rotavirus particles are administered intramuscularly to mice without an adjuvant. Animals are immunized with amounts of killed rotavirus protein in the range between 2 and 20 micrograms.

Immunogenicity is assayed by measuring immunoglobulin titers including IgM, IgA and IgG in blood samples obtained at various times after administration. Neutralizing antibody titers are measured by microneutralization assay as described in detail in Jiang, B., Vaccine, 17:1005-1013, 1999, the contents of which are incorporated herein by reference. Briefly described, mouse sera are serially diluted two-fold in duplicate wells and incubated with trypsin-inactivated RRV rotavirus. Activated rotavirus or similarly treated serum-free MEM medium is incubated in the absence of mouse serum and serve as positive and negative controls, respectively. MA104 cells in MEM medium supplemented with a final concentration of 10 micrograms/milliliter trypsin and 0.5% chick serum, obtained from Invitrogen Corp., Grand Island, N.Y., are added to each well. After incubation at 37° C. for 18 hours, cells are fixed with formalin. Rotavirus antigens in MA104 cells are detected by incubating cells with rabbit anti-RRV hyperimmune serum, HRP-labeled anti-rabbit IgG, and then tetramethyl benzidine. Neutralizing antibody titer in a serum is defined as the reciprocal of the highest dilution giving a 70% reduction in absorbance value compared to that in the virus control.

Antibody titers in mice injected with killed purified rotavirus particles are compared with antibody titers in control mice. Antibody titers in control mice are typically less than 100. FIGS. 5A and 5B illustrate total antibody and neutralizing antibody titers in control and vaccinated mice. Total serum antibody (FIG. 5A) and neutralizing antibody (FIG. 5B) responses to thermally inactivated rotavirus in mice. Mice are vaccinated I.M. twice with killed YK-1 and rotavirus-specific total (IgA, IgG, and IgM) and neutralizing antibodies are determined by EIA as described. For total antibody, each serum specimen is tested at an initial dilution of 1:100. Pre-bleed serum specimens have no detectable antibody at this dilution. A value of 20 is used for determining geometric mean titers and illustration. Neutralizing antibody is tested at an initial dilution of 1:20. Antibody titers are expressed as the geometric means for each group (n=7 or 6). Error bars represent 1 standard error.

Example 4—Adjuvant

In a further example, $Al(OH)_3$ is added as an adjutant to rotavirus particles in a vaccine administered to mice. Animals are immunized intramuscularly once with 2 micrograms or 0.2 micrograms of killed purified rotavirus particles in the presence or absence of 600 micrograms $Al(OH)_3$. AlOH dramatically enhances total antibody titers in mice at both concentrations of rotavirus administered. No antibody titers (less than 100 dilutions) are detected in control mice immunized with 600 micrograms of $Al(OH)_3$.

FIG. 6 is a bar graph showing total serum antibody responses to thermally inactivated rotavirus formulated with $Al(OH)_3$ in control and vaccinated mice. Mice are vaccinated I.M. once with killed YK-1 in the absence or presence of $Al(OH)_3$ and rotavirus-specific total (IgA, IgG, and IgM) antibodies are determined by EIA as described. For total antibody, each serum specimen is tested at an initial dilution of 1:100. Pre-bleed serum specimens have no detectable antibody at this dilution. A value of 20 is used for determining geometric mean titers and illustration. Antibody titers are expressed as the geometric means for each group (n=6). Error bars represent 1 standard error.

Example 5—Gnotobiotic Piglet Model

A gnotobiotic piglet model of rotavirus disease is used. This piglet model allows testing under defined conditions avoiding problems of environment exposure of animals and using disease as the outcome variable. This model also allows testing of an inactivated rotavirus vaccine having a G1 serotype against a homotypic Wa challenge. Gnotobiotic piglets are the best current animal model for infection and disease with human rotavirus strains. (See Saif L J, et al., *Archives of Virology*, 1996; 12:5153-61; and Iosef C, et al., Vaccine, 2002; 20:1741-53; the contents of each of which are incorporated herein by reference.)

Thirteen infant gnotobiotic piglets are selected and randomly assigned to 4 groups as indicated in Table 6.

TABLE 6

Piglet Study Design

| Group Name | Number of Piglets in Group | CDC-9 Antigen (micrograms) | Aluminum phosphate (micrograms) |
|---|---|---|---|
| AA | 4 | 0 | 750 |
| BB | 4 | 75 | 0 |
| CC | 3 | 75 | 750 |
| DD | 2 | 0 (buffer) | 0 (buffer) |

Each group of animals indicated in Table 6 is kept in separate isolators. Animals in groups BB and CC are vaccinated intramuscularly 3 times with an inactivated rotavirus vaccine without or with an adjuvant, respectively. The vaccine formulation in this example includes 75 micrograms of killed purified CDC-9 rotavirus in diluent mixed with 750 micrograms of aluminum phosphate. Animals in groups AA and DD are vaccinated with 750 micrograms of aluminum phosphate and buffer, respectively, in the same manner. Antigen adsorption is determined by the Bradford method which showed that about 50% of the antigen was bound to aluminum phosphate. Both bound and unbound antigen was injected in these immunizations.

Figure 7A:
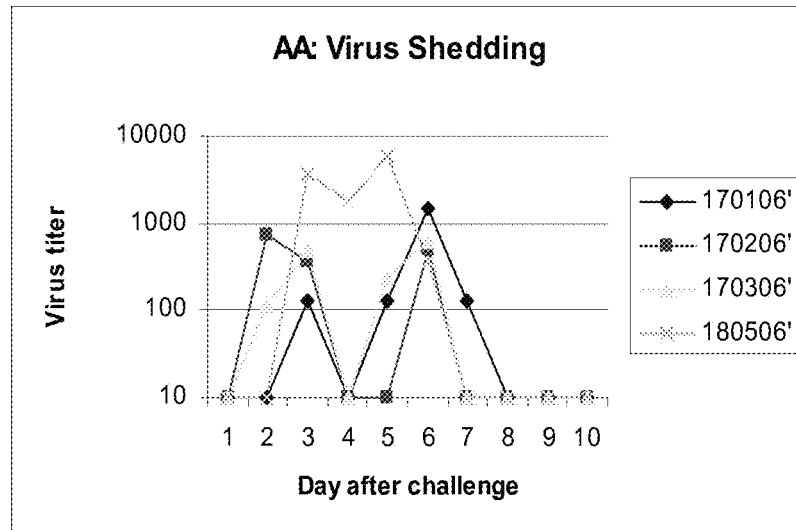
Figure 7B:
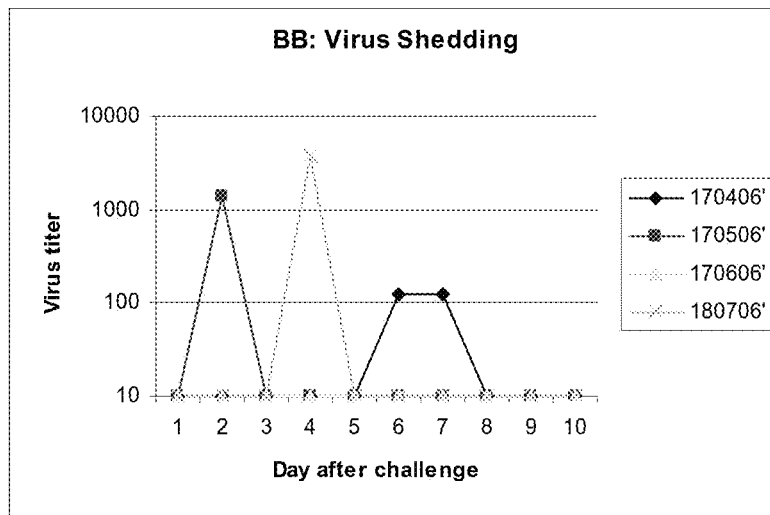
Figure 7C:
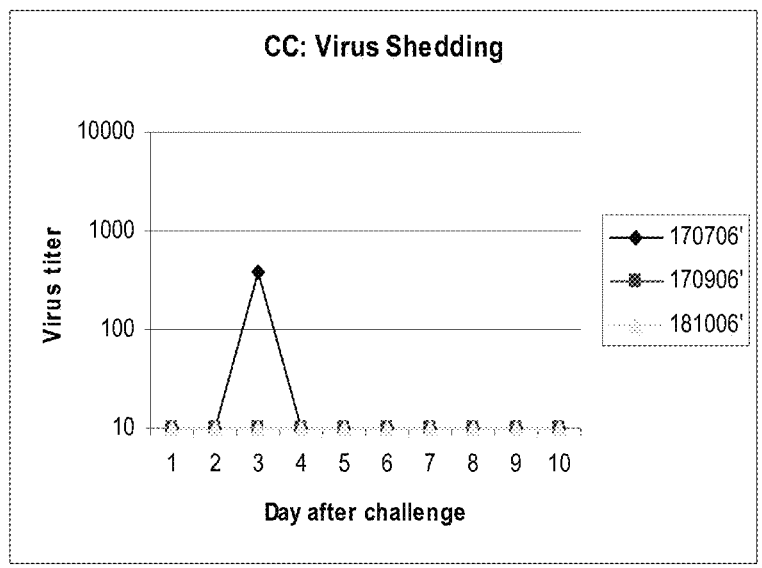
Figure 7D:
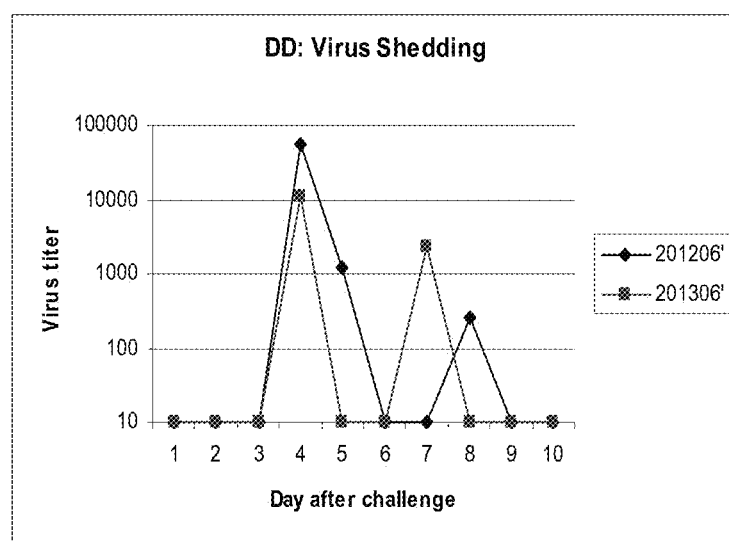

As shown in Table 6, piglets are immunized with a vaccine formulation including no antigen and 750 micrograms of aluminum phosphate; 75 micrograms of antigen and no aluminum phosphate; 75 micrograms of antigen and 750 micrograms of aluminum phosphate; or no antigen and no aluminum phosphate, that is buffer alone. Each vaccination is carried out by injecting 0.5 milliliters of the vaccine formulation into muscles of the hind legs of the piglets. After 3 doses of the vaccine formulation administered at intervals of 10-12 days, piglets are orally challenged with virulent Wa rotavirus. Prior to virus challenge, each piglet is inoculated with 3 milliliters of sodium bicarbonate to neutralize acids in the stomach. Fecal specimens are collected from the challenged piglets daily for 10 days. Blood samples are collected throughout the experiment at intervals of 7-14 days. FIG. 7A shows virus shedding in fecal samples of piglets vaccinated with no antigen and with 750 micrograms of aluminum phosphate in 4 animals. FIG. 7B shows virus shedding in fecal samples from piglets immunized with antigen and no adjuvant. FIG. 7C shows virus shedding in fecal samples of piglets immunized with antigen and adjuvant. FIG. 7D shows virus shedding measured in fecal samples of piglets immunized with buffer only. These illustrate that piglets that are mock vaccinated with aluminum phosphate only or diluent buffer only all shed rotavirus up to 5 days and at high titer. By contrast, piglets that are vaccinated with inactivated rotavirus without aluminum phosphate are partially protected, as evidenced by a shortened 1-day shedding or a delayed and reduced shedding. Of the 3 piglets that are vaccinated with inactivated rotavirus and aluminum phosphate, 2 are completely protected and 1 has only a short, 1-day, reduced shedding. Thus, these results show effectiveness of vaccine formulation according to embodiments of the present invention.

Example 6—Gnotobiotic Piglet Model—II

To repeat the experiment above, eleven infant gnotobiotic piglets are selected and randomly assigned to 2 groups as indicated in Table 7.

TABLE 7

Piglet Study Design

| Group Name | Number of Piglets in Group | CDC-9 Antigen (micrograms) | aluminum phosphate (micrograms) |
|---|---|---|---|
| GG | 5 | 0 | 600 |
| HH | 6 | 50 | 600 |

As shown in Table 7, and as described by Wang, Y, et al., Inactivated rotavirus vaccine induces protective immunity in gnotobiotic piglets, in press, the contents of which are incorporated herein by reference, piglets are immunized with a vaccine formulation including no antigen and 600 micrograms of aluminum phosphate or 50 micrograms of antigen and 600 micrograms of aluminum phosphate. Each vaccination is carried out by injecting 0.5 milliliters of the vaccine formulation into muscles of the hind legs of the piglets. After 3 doses of the vaccine formulation administered at intervals of 10-12 days, piglets are orally challenged with virulent Wa rotavirus. Prior to virus challenge, each piglet is inoculated with 3 milliliters of sodium bicarbonate to neutralize acids in the stomach. Fecal specimens are collected from the challenged piglets daily for 10 days. Blood samples are collected throughout the experiment at intervals of 7-14 days.

Figure 8A:
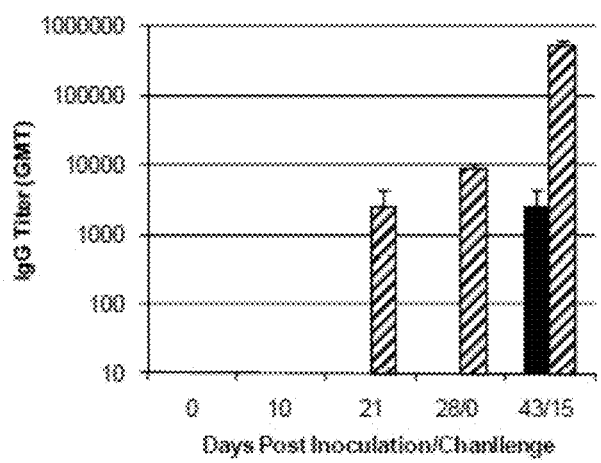
Figure 8B:
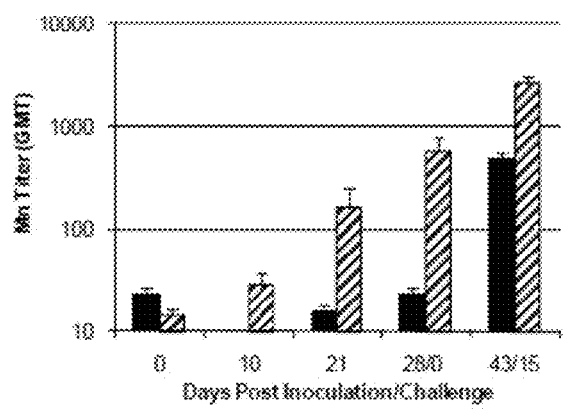

FIG. 8A shows the level of rotavirus specific IgG antibody response in sera of piglets vaccinated with no antigen and with 600 micrograms of aluminum phosphate (solid bars) or piglets vaccinated with 50 micrograms of antigen and with 600 micrograms of aluminum phosphate (hatched bars). FIG. 8B shows neutralizing antibody response in sera of piglets vaccinated with no antigen and with 600 micrograms of aluminum phosphate (solid bars) or piglets vaccinated with 50 micrograms of antigen and with 600 micrograms of aluminum phosphate (hatched bars). Piglets vaccinated with antigen develop significant levels of serum IgG. Oral challenge with rotavirus further enhances the serum IgG levels. The levels of neutralizing activity are significantly higher in piglets vaccinated with 50 micrograms of antigen and with 600 micrograms of aluminum phosphate than mock immunized animals.

Figure 9A:
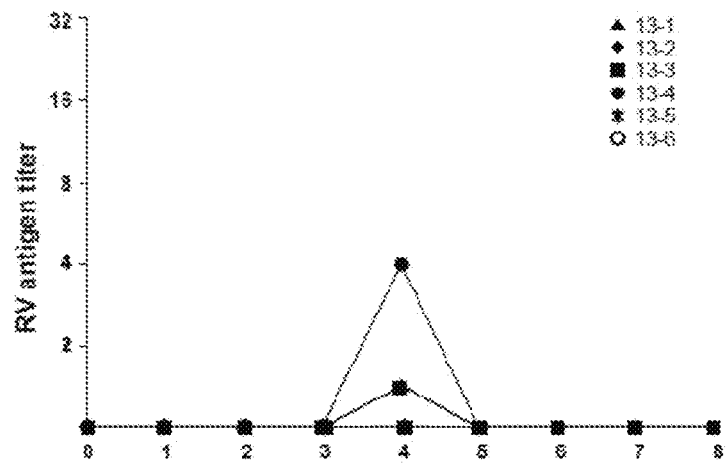
Figure 9B:
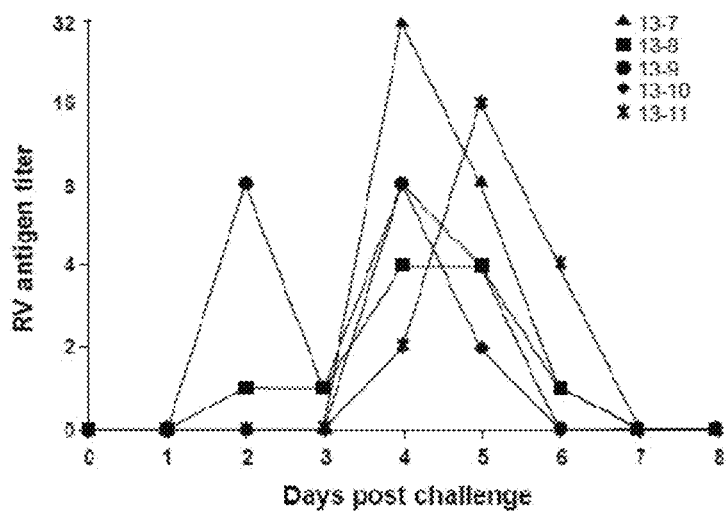

FIG. 9A shows virus shedding in fecal samples of piglets vaccinated with 50 micrograms of antigen and with 600 micrograms of aluminum phosphate. FIG. 9B shows virus shedding in fecal samples of piglets vaccinated with no antigen and with 600 micrograms of aluminum phosphate. These figures illustrate that piglets that are mock vaccinated with aluminum phosphate only or diluent buffer only all shed rotavirus up to 5 days and at high titer. By contrast, piglets that are vaccinated with inactivated rotavirus and aluminum phosphate are protected from shedding.

These results show effectiveness of vaccine formulation according to embodiments of the present invention and confirm the results in first piglet experiment. These results clearly demonstrate that IRV formulated with alum is highly immunogenic and protective against infection in piglets and consequently establish proof of concept for inactivated rotavirus vaccine.

Example 7—Gnotobiotic Piglet Model—III—
Immunization with CDC-66

To repeat the experiment above using CDC-66 rotavirus, eleven infant gnotobiotic piglets are selected and randomly assigned to 2 groups as indicated in Table 8.

TABLE 8

Piglet Study Design

| Group Name | Number of Piglets in Group | CDC-66 Antigen (micrograms) | aluminum phosphate (micrograms) |
|---|---|---|---|
| GG | 5 | 0 | 600 |
| HH | 6 | 50 | 600 |

As shown in Table 7, piglets are immunized with a vaccine formulation including no antigen and 600 micrograms of aluminum phosphate or 50 micrograms of antigen and 600 micrograms of aluminum phosphate ($AlPO_4$). Each vaccination is carried out by injecting 0.5 milliliters of the vaccine formulation into muscles of the hind legs of the piglets. After 3 doses of the vaccine formulation administered at intervals of 10-12 days, piglets are orally challenged with virulent DS-1 rotavirus. Prior to virus challenge, each piglet is inoculated with 3 milliliters of sodium bicarbonate to neutralize acids in the stomach. Fecal specimens are collected from the challenged piglets daily for 10 days. Blood samples are collected throughout the experiment at intervals of 7-14 days.

Piglets vaccinated with antigen develop significant levels of serum IgG. Oral challenge with rotavirus further enhances the serum IgG levels. The levels of neutralizing activity are significantly higher in piglets vaccinated with 50 micrograms of CDC-66 antigen and with 600 micrograms of aluminum phosphate than mock immunized animals.

Piglets that are mock vaccinated with aluminum phosphate only or diluent buffer only all shed rotavirus up to 5 days and at high titer. By contrast, piglets that are vaccinated with inactivated rotavirus CDC-66 and aluminum phosphate are protected from shedding.

These results show effectiveness of vaccine formulation according to embodiments of the present invention and confirm the results in first piglet experiment. These results clearly demonstrate that IRV formulated with alum is highly immunogenic and protective against infection in piglets and consequently establish proof of concept for inactivated rotavirus vaccine.

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

---

The invention claimed is:

1. An isolated nucleic acid molecule encoding a rotavirus non-structural protein (NSP) protein or a rotavirus VP4 protein, wherein
   a) the rotavirus NSP protein is a NSP1 protein that has greater than 95% identity to SEQ ID NO: 3, and wherein amino acid 122 is an arginine;
   b) the rotavirus NSP protein is a NSP5 protein that i) has greater than 95% identity to SEQ ID NO: 15, and wherein amino acid 45 is an isoleucine, or ii) has greater than 95% identity to SEQ ID NO: 96, and wherein amino acid 60 is a valine;
   c) the rotavirus NSP protein is a NSP2 protein that has greater than 95% identity to SEQ ID NO: 78, and wherein amino acid 142 is a tyrosine;
   d) the rotavirus VP4 protein has greater than 95% identity to SEQ ID NO: 27, and wherein amino acid 51 is an aspartic acid, amino acid 331 is a phenylalanine, amino acid 364 is an isoleucine, amino acid 385 is a histidine, and amino acid 388 is a leucine; or
   e) the rotavirus VP4 protein has greater than 95% identity to SEQ ID NO: 120, and wherein amino acid 254 is a lysine, amino acid 367 is an alanine, amino acid 385 is an asparagine, and amino acid 392 is a glycine.

2. The isolated nucleic acid molecule of claim 1, encoding the rotavirus NSP protein, wherein the NSP protein is the NSP1 protein, and wherein the NSP1 protein comprises the amino acid sequence of SEQ ID NO: 3.

3. The isolated nucleic acid molecule of claim 2, wherein the NSP1 protein consists of the amino acid sequence of SEQ ID NO: 3.

4. The isolated nucleic acid molecule of claim 1, encoding the rotavirus NSP protein, wherein the NSP protein is the NSP5 protein, and wherein the NSP5 protein comprises the amino acid sequence of SEQ ID NO: 15, wherein amino acid 45 is an isoleucine.

5. The isolated nucleic acid molecule of claim 4, wherein the NSP5 protein consists of the amino acid sequence of SEQ ID NO: 15, wherein amino acid 45 is an isoleucine.

6. The isolated nucleic acid molecule of claim 1, encoding the rotavirus NSP protein, wherein the NSP protein is the NSP5 protein, and wherein the NSP5 protein comprises the amino acid sequence of SEQ ID NO: 96.

7. The isolated nucleic acid molecule of claim 6, encoding the rotavirus NSP protein, wherein the NSP protein is the NSP5 protein, and wherein the NSP5 protein consists of the amino acid sequence of SEQ ID NO: 96.

8. The isolated nucleic acid molecule of claim 1, encoding the rotavirus NSP protein, wherein the NSP protein is the NSP2 protein, and wherein the NSP2 protein comprises the amino acid sequence of SEQ ID NO: 78.

9. The isolated nucleic acid molecule of claim 8, wherein the NSP2 protein consists of the amino acid sequence of SEQ ID NO: 78.

10. The isolated nucleic acid molecule of claim 1, encoding the rotavirus VP4 protein, wherein the rotavirusVP4 protein comprises the amino acid sequence of SEQ ID NO: 27.

11. The isolated nucleic acid molecule of claim 10, encoding the rotavirus VP4 protein, wherein the rotavirus VP4 protein consists of the amino acid sequence of SEQ ID NO: 27.

12. The isolated nucleic acid molecule of claim 1, encoding the rotavirus VP4 protein, wherein the rotavirusVP4 protein comprises the amino acid sequence of SEQ ID NO: 120.

13. The isolated nucleic acid molecule of claim 12, encoding the rotavirus VP4 protein, wherein the rotavirus VP4 protein consists of the amino acid sequence of SEQ ID NO: 120.

14. The isolated nucleic acid molecule of claim 1, operably linked to a promoter.

15. The isolated nucleic acid molecule of claim 14, wherein the promoter is a T7 promoter.

16. An expression vector comprising the isolated nucleic acid molecule of claim 1, operably linked to a promoter.

17. The expression vector of claim 16, wherein the expression vector is a viral vector.

18. An isolated host cell transfected with the expression vector of claim 16.

19. The isolated host cell of claim 18, wherein the host cell is a mammalian host cell.

20. A method of producing a rotavirus NSP protein or a rotavirus VP4 protein, comprising:
   culturing the isolated host cells of claim 18 in vitro, wherein the host cells produce the rotavirus NSP protein or the rotavirus VP4 protein; and
   isolating the rotavirus NSP protein or the rotavirus VP4 protein from the host cells.

* * * * *